(12) United States Patent
Khvorova et al.

(10) Patent No.: US 12,024,706 B2
(45) Date of Patent: Jul. 2, 2024

(54) MODIFIED OLIGONUCLEOTIDES TARGETING SNPS

(71) Applicant: UNIVERSITY OF MASSACHUSETTS, Boston, MA (US)

(72) Inventors: Anastasia Khvorova, Westborough, MA (US); Julia Alterman, Worcester, MA (US); Faith Conroy, Worcester, MA (US); Edith Pfister, Boxborough, MA (US); Neil Aronin, Newtonville, MA (US); Ken Yamada, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/988,391

(22) Filed: Aug. 7, 2020

(65) Prior Publication Data

US 2021/0071177 A1 Mar. 11, 2021

Related U.S. Application Data

(60) Provisional application No. 62/976,168, filed on Feb. 13, 2020, provisional application No. 62/885,066, filed on Aug. 9, 2019.

(51) Int. Cl.
*C12N 15/113* (2010.01)

(52) U.S. Cl.
CPC ........ *C12N 15/113* (2013.01); *C12N 2310/14* (2013.01); *C12N 2310/52* (2013.01)

(58) Field of Classification Search
CPC .............. C12N 15/113; C12N 2310/14; C12N 2310/352; C12N 2310/52
See application file for complete search history.

(56) References Cited

U.S. PATENT DOCUMENTS

| | | | |
|---|---|---|---|
| 4,522,811 A | 6/1985 | Eppstein et al. | |
| 5,194,596 A | 3/1993 | Tischer et al. | |
| 5,219,739 A | 6/1993 | Tischer et al. | |
| 5,240,848 A | 8/1993 | Keck et al. | |
| 5,328,470 A | 7/1994 | Nabel et al. | |
| 5,332,671 A | 7/1994 | Ferrara et al. | |
| 5,684,143 A | 11/1997 | Grayaznov et al. | |
| 5,814,014 A | 9/1998 | Elsberry et al. | |
| 5,858,988 A | 1/1999 | Wang | |
| 5,939,402 A | 8/1999 | Weis et al. | |
| 6,025,335 A | 2/2000 | Weis et al. | |
| 6,093,180 A | 7/2000 | Elsberry et al. | |
| 6,107,094 A | 8/2000 | Crooke | |
| 6,168,587 B1 | 1/2001 | Bellhouse et al. | |
| 6,177,403 B1 | 1/2001 | Stedman | |
| 6,194,389 B1 | 2/2001 | Johnston et al. | |
| 6,291,438 B1 | 9/2001 | Wang | |
| 6,312,900 B1 | 11/2001 | Dean et al. | |
| 6,383,814 B1 | 5/2002 | Lee et al. | |
| 6,447,768 B1 | 9/2002 | Van Zonneveld et al. | |
| 6,471,996 B1 | 10/2002 | Sokoll et al. | |
| 6,472,375 B1 | 10/2002 | Hoon et al. | |
| 6,489,464 B1 | 12/2002 | Agrawal et al. | |
| 7,250,496 B2 | 7/2007 | Bentwich | |
| 7,459,547 B2 | 12/2008 | Zamore et al. | |
| 7,691,997 B2 | 4/2010 | Khvorova et al. | |
| 7,723,512 B2 | 5/2010 | Manoharan et al. | |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 7,790,867 B2 | 9/2010 | Bentwich | |
| 7,834,171 B2 | 11/2010 | Leake et al. | |
| 8,013,136 B2 | 9/2011 | Manoharan et al. | |
| 8,097,752 B2 | 1/2012 | Calogeropolou et al. | |
| 8,304,530 B2 | 11/2012 | Zamore et al. | |
| 8,309,704 B2 | 11/2012 | Zamore et al. | |
| 8,309,705 B2 | 11/2012 | Zamore et al. | |
| 8,329,892 B2 | 12/2012 | Zamore et al. | |
| 8,431,544 B1 | 4/2013 | Agrawal et al. | |
| 8,501,706 B2 | 8/2013 | Yamada et al. | |
| 8,507,661 B2 | 8/2013 | Manoharan et al. | |
| 8,664,189 B2 | 3/2014 | Khvorova et al. | |
| 8,703,731 B2 | 4/2014 | Jimenez et al. | |
| 8,796,443 B2 | 8/2014 | Khvorova et al. | |
| 8,815,818 B2 | 8/2014 | Samarsky et al. | |

(Continued)

FOREIGN PATENT DOCUMENTS

| | | |
|---|---|---|
| CN | 104884618 A | 11/2015 |
| EP | 1752536 A1 | 2/2007 |

(Continued)

OTHER PUBLICATIONS

International Search Report & Written Opinion Received for PCT Application No. PCT/US2019/046013, dated Jan. 9, 2020, 18 Pages.

(Continued)

*Primary Examiner* — Brian Whiteman

(74) *Attorney, Agent, or Firm* — LATHROP GPM LLP; James H. Velema, Esq.; Michael J. Spellberg, Esq.

(57) ABSTRACT

Novel oligonucleotides that enhance silencing of the expression of a gene containing a single nucleotide polymorphism (SNP) relative to the expression of the corresponding wild-type gene are provided. Methods of using novel oligonucleotides that enhance silencing of the expression of a gene containing a SNP relative to the expression of the corresponding wild-type gene are provided.

20 Claims, 55 Drawing Sheets

Specification includes a Sequence Listing.

(56) References Cited

U.S. PATENT DOCUMENTS

| | | |
|---|---|---|
| 8,871,774 B2 | 10/2014 | Charifson et al. |
| 8,877,439 B2 | 11/2014 | Butora et al. |
| 8,906,874 B2 | 12/2014 | Rao et al. |
| 8,993,738 B2 | 3/2015 | Prakash et al. |
| 9,029,389 B2 | 5/2015 | No et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,796,756 B2 | 10/2017 | Hadwiger et al. |
| 9,809,817 B2 | 11/2017 | Khvorova et al. |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 10,844,377 B2 | 11/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 11,667,915 B2 | 6/2023 | Woolf et al. |
| 11,702,659 B2 | 7/2023 | Khvorova et al. |
| 2001/0027251 A1 | 10/2001 | Cook et al. |
| 2003/0045705 A1 | 3/2003 | Cook |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2004/0205839 A1 | 10/2004 | Doutriaux et al. |
| 2005/0096284 A1 | 5/2005 | McSwiggen |
| 2005/0220766 A1 | 10/2005 | Amalfitano et al. |
| 2005/0255487 A1 | 11/2005 | Khvorova et al. |
| 2006/0003322 A1 | 1/2006 | Bentwich et al. |
| 2006/0009409 A1 | 1/2006 | Woolf |
| 2006/0024715 A1 | 2/2006 | Liu et al. |
| 2006/0078542 A1 | 4/2006 | Mah et al. |
| 2006/0094032 A1 | 5/2006 | Fougerolles et al. |
| 2006/0105998 A1 | 5/2006 | Calogeropoulou et al. |
| 2007/0004664 A1 | 1/2007 | McSwiggen et al. |
| 2007/0004665 A1 | 1/2007 | McSwiggen et al. |
| 2007/0099860 A1 | 5/2007 | Sah et al. |
| 2007/0135372 A1 | 6/2007 | MacLachlan et al. |
| 2007/0160534 A1 | 7/2007 | Dennis et al. |
| 2007/0191273 A1 | 8/2007 | Ambat et al. |
| 2007/0259827 A1 | 11/2007 | Aronin et al. |
| 2008/0039415 A1 | 2/2008 | Stewart et al. |
| 2008/0108583 A1 | 5/2008 | Feinstein |
| 2008/0108801 A1 | 5/2008 | Manoharan |
| 2008/0113369 A1 | 5/2008 | Khvorova et al. |
| 2008/0119427 A1 | 5/2008 | Bhat et al. |
| 2008/0188429 A1 | 8/2008 | Iyer |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2009/0269332 A1 | 10/2009 | Gimeno et al. |
| 2009/0281299 A1 | 11/2009 | Manorahan et al. |
| 2009/0306178 A1 | 12/2009 | Bhat et al. |
| 2009/0318676 A1 | 12/2009 | Manoharan et al. |
| 2010/0015706 A1 | 1/2010 | Quay et al. |
| 2010/0093085 A1 | 4/2010 | Yamada et al. |
| 2010/0184209 A1 | 7/2010 | Vermeulen et al. |
| 2010/0186103 A1 | 7/2010 | Gao et al. |
| 2010/0240730 A1 | 9/2010 | Beigelman et al. |
| 2011/0039914 A1 | 2/2011 | Pavco et al. |
| 2011/0086905 A1 | 4/2011 | Glazer |
| 2011/0097716 A1 | 4/2011 | Natt et al. |
| 2011/0201006 A1 | 8/2011 | Roehl et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 | 3/2012 | Khvorova et al. |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0065298 A1 | 3/2013 | Davidson et al. |
| 2013/0131141 A1 | 5/2013 | Khvorova et al. |
| 2013/0131142 A1 | 5/2013 | Libertine et al. |
| 2013/0178513 A1 | 7/2013 | Dobie et al. |
| 2013/0196434 A1 | 8/2013 | Maier et al. |
| 2013/0197055 A1 | 8/2013 | Kamens et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0113950 A1 | 4/2014 | Khvorova et al. |
| 2014/0155387 A1 | 6/2014 | No et al. |
| 2014/0288148 A1 | 9/2014 | Biegelman et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0190525 A1 | 7/2015 | Tatro |
| 2015/0209441 A1 | 7/2015 | Carell |
| 2015/0232840 A1 | 8/2015 | Aronin et al. |
| 2015/0247142 A1 | 9/2015 | Esau et al. |
| 2015/0267200 A1 | 9/2015 | Mcswiggen et al. |
| 2015/0315584 A1 | 11/2015 | Macdonald et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1* | 12/2016 | Khvorova ............... A61P 43/00 |
| 2016/0355826 A1 | 12/2016 | Khvorova et al. |
| 2016/0376598 A1 | 12/2016 | Lee et al. |
| 2017/0009239 A1 | 1/2017 | Khvorova et al. |
| 2017/0009304 A1 | 1/2017 | Zhou |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1* | 2/2017 | Aronin ................. C12N 15/113 |
| 2017/0051286 A1 | 2/2017 | Smith |
| 2017/0067056 A1 | 3/2017 | Khvorova et al. |
| 2017/0183655 A1 | 6/2017 | Grabcysk et al. |
| 2017/0189541 A1 | 7/2017 | Foster |
| 2017/0281795 A1 | 10/2017 | Geall |
| 2017/0312367 A1 | 11/2017 | Alterman et al. |
| 2017/0327524 A1 | 11/2017 | Nanna et al. |
| 2017/0349903 A1 | 12/2017 | Wanqing et al. |
| 2017/0369882 A1 | 12/2017 | Khvorova et al. |
| 2018/0023082 A1 | 1/2018 | Stanek et al. |
| 2018/0087052 A1 | 3/2018 | Hung et al. |
| 2018/0094263 A1 | 4/2018 | Alterman et al. |
| 2018/0179546 A1 | 6/2018 | Khvorova et al. |
| 2018/0251764 A1 | 9/2018 | Albaek et al. |
| 2019/0002880 A1 | 1/2019 | Woolf et al. |
| 2019/0024082 A1 | 1/2019 | Khvorova et al. |
| 2019/0144860 A1 | 5/2019 | Konstantinova et al. |
| 2019/0185855 A1 | 6/2019 | Khvorova et al. |
| 2019/0211341 A1 | 7/2019 | Butler et al. |
| 2019/0225965 A1 | 7/2019 | Khvorova et al. |
| 2019/0247507 A1 | 8/2019 | Khvorova et al. |
| 2020/0087663 A1* | 3/2020 | Khvorova .......... C12N 15/1137 |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308578 A1 | 10/2020 | Woolf et al. |

(56) References Cited

U.S. PATENT DOCUMENTS

| | | |
|---|---|---|
| 2020/0308584 A1 | 10/2020 | Khvorova et al. |
| 2020/0339983 A1 | 10/2020 | Khvorova et al. |
| 2020/0362341 A1 | 11/2020 | Khvorova |
| 2020/0385737 A1 | 12/2020 | Khvorova |
| 2020/0385740 A1 | 12/2020 | Khvorova et al. |
| 2021/0024926 A1 | 1/2021 | Khvorova et al. |
| 2021/0071117 A9 | 3/2021 | Khvorova et al. |
| 2021/0071177 A1 | 3/2021 | Khvorova |
| 2021/0085793 A1 | 3/2021 | Khvorova et al. |
| 2021/0115442 A1 | 4/2021 | Khvorova et al. |
| 2021/0139901 A1 | 5/2021 | Khvorova et al. |
| 2021/0340535 A1 | 11/2021 | Khvorova |
| 2021/0355491 A1 | 11/2021 | Khvorova et al. |
| 2021/0363523 A1 | 11/2021 | Khvorova et al. |
| 2022/0010309 A1 | 1/2022 | Khvorova et al. |
| 2022/0090069 A1 | 3/2022 | Khvorova et al. |
| 2022/0228141 A2 | 7/2022 | Khvorova et al. |
| 2022/0251554 A1 | 8/2022 | Khvorova et al. |
| 2022/0251555 A1 | 8/2022 | Khvorova et al. |
| 2022/0364100 A1 | 11/2022 | Khvorova et al. |
| 2023/0021431 A1 | 1/2023 | Khvorova |
| 2023/0061751 A1 | 3/2023 | Khvorova et al. |
| 2023/0078622 A1 | 3/2023 | Khvorova et al. |
| 2023/0193281 A1 | 6/2023 | Khvorova et al. |
| 2023/0313198 A1 | 10/2023 | Khvorova et al. |
| 2023/0340475 A1 | 10/2023 | Khvorova et al. |
| 2023/0348907 A1 | 11/2023 | Khvorova et al. |
| 2023/0416735 A1 | 12/2023 | Khvorova et al. |

FOREIGN PATENT DOCUMENTS

| | | |
|---|---|---|
| EP | 2407539 A1 | 1/2012 |
| EP | 2601204 A2 | 6/2013 |
| EP | 2853597 A1 | 4/2015 |
| EP | 3277811 A1 | 2/2017 |
| EP | 3277814 A1 | 2/2018 |
| EP | 3277815 A1 | 2/2018 |
| EP | 3408391 A1 | 12/2018 |
| EP | 3550021 A1 | 10/2019 |
| EP | 3642341 A1 | 4/2020 |
| EP | 3929293 A2 | 12/2021 |
| EP | 3946369 A2 | 2/2022 |
| EP | 4126040 A2 | 2/2023 |
| JP | H06-41183 A | 2/1994 |
| JP | H6-504680 A | 6/1994 |
| JP | 2001-501614 A | 2/2001 |
| JP | 2009-504782 A | 2/2009 |
| JP | 2010-506598 A | 3/2010 |
| JP | 2012-502657 A | 2/2012 |
| JP | 2013-049714 A | 3/2013 |
| JP | 2015-061534 A | 4/2015 |
| JP | 2016-171815 A | 9/2016 |
| JP | 2016-526529 A | 9/2016 |
| JP | 2018-516091 A | 6/2018 |
| WO | WO 1992/013869 A1 | 8/1992 |
| WO | WO 1993/009239 A1 | 5/1993 |
| WO | WO 1993/024641 A2 | 12/1993 |
| WO | WO 1994/022890 A1 | 10/1994 |
| WO | WO 1996/003500 A1 | 2/1996 |
| WO | WO 1998/013526 A1 | 4/1998 |
| WO | WO 2003/029459 A2 | 4/2003 |
| WO | WO 2004/008946 A2 | 1/2004 |
| WO | WO 2004/013280 A2 | 2/2004 |
| WO | WO 2004/044136 A2 | 5/2004 |
| WO | WO 2004/061081 A2 | 7/2004 |
| WO | WO 2004/108956 A1 | 12/2004 |
| WO | WO 2006/019430 A2 | 2/2006 |
| WO | WO 2007/022470 A2 | 2/2007 |
| WO | WO 2007/022506 A2 | 2/2007 |
| WO | WO 2007/051045 A2 | 5/2007 |
| WO | WO 2007/091269 A2 | 8/2007 |
| WO | WO 2007/094218 A1 | 8/2007 |
| WO | WO 2007/112414 A2 | 10/2007 |
| WO | WO 2008/005562 A2 | 1/2008 |
| WO | WO 2008/154482 A2 | 12/2008 |
| WO | WO 2009/002944 A1 | 12/2008 |
| WO | WO 2009/054551 A2 | 4/2009 |
| WO | WO 2009/099991 A2 | 8/2009 |
| WO | WO 2009/102427 A2 | 8/2009 |
| WO | WO 2010/008582 A2 | 1/2010 |
| WO | WO 2010/011346 A1 | 1/2010 |
| WO | WO 2010/033246 A1 | 3/2010 |
| WO | WO 2010/033247 A2 | 3/2010 |
| WO | WO 2010/033248 A2 | 3/2010 |
| WO | WO 2010/048352 A2 | 4/2010 |
| WO | WO 2010/048585 A2 | 4/2010 |
| WO | WO 2010/059226 A2 | 5/2010 |
| WO | WO 2010/078536 A1 | 7/2010 |
| WO | WO 2010/090762 A1 | 8/2010 |
| WO | WO 2010/111503 A2 | 9/2010 |
| WO | WO 2011/109698 A1 | 9/2011 |
| WO | WO 2011/119852 A1 | 9/2011 |
| WO | WO 2011/119871 A1 | 9/2011 |
| WO | WO 2011/119887 A1 | 9/2011 |
| WO | WO 2011/125943 A1 | 10/2011 |
| WO | WO 2011/139702 A2 | 11/2011 |
| WO | WO 2011/158924 A1 | 12/2011 |
| WO | WO 2012/005898 A2 | 1/2012 |
| WO | WO 2012/058210 A1 | 5/2012 |
| WO | WO 2012/118911 A1 | 9/2012 |
| WO | WO 2012/131365 A1 | 10/2012 |
| WO | WO 2012/177906 A1 | 12/2012 |
| WO | WO 2013/165816 A2 | 11/2013 |
| WO | WO 2014/009429 A1 | 1/2014 |
| WO | WO 2014/043544 A1 | 3/2014 |
| WO | WO 2014/076195 A1 | 5/2014 |
| WO | WO 2014/089313 A1 | 6/2014 |
| WO | WO 2014/201306 A1 | 12/2014 |
| WO | WO 2014/203518 A1 | 12/2014 |
| WO | WO 2015/025122 A1 | 2/2015 |
| WO | WO 2015/113004 A2 | 7/2015 |
| WO | WO 2015/161184 A1 | 10/2015 |
| WO | WO 2015/200078 A1 | 12/2015 |
| WO | WO 2016/028649 A1 | 2/2016 |
| WO | WO 2016/077321 A1 | 5/2016 |
| WO | WO 2016/077349 A1 | 5/2016 |
| WO | WO 2016/149331 A2 | 9/2016 |
| WO | WO 2016/161374 A1 | 10/2016 |
| WO | WO 2016/161378 A1 | 10/2016 |
| WO | WO 2016/161388 A1 | 10/2016 |
| WO | WO 2016/164866 A1 | 10/2016 |
| WO | WO 2016/205410 A2 | 12/2016 |
| WO | WO 2017/015555 A1 | 1/2017 |
| WO | WO 2017/024239 A1 | 2/2017 |
| WO | WO 2017/030973 A1 | 2/2017 |
| WO | WO 2017/062862 A2 | 4/2017 |
| WO | WO 2017/132669 A1 | 8/2017 |
| WO | WO 2018/031933 A2 | 2/2018 |
| WO | WO 2018/041973 A1 | 3/2018 |
| WO | WO 2018/031933 A2 | 5/2018 |
| WO | WO 2018/185241 A1 | 10/2018 |
| WO | WO 2018/223056 A1 | 12/2018 |
| WO | WO 2018/237245 A1 | 12/2018 |
| WO | WO 2019/075418 A1 | 4/2019 |
| WO | WO 2019/075419 A1 | 4/2019 |
| WO | WO 2019/217459 A1 | 11/2019 |
| WO | WO 2019/232255 A1 | 12/2019 |
| WO | WO 2020/033899 A1 | 2/2020 |
| WO | WO 2020/041769 A1 | 2/2020 |
| WO | WO 2020/033899 A1 | 3/2020 |
| WO | WO 2020/150636 A1 | 7/2020 |
| WO | WO 2020/198509 A2 | 10/2020 |
| WO | WO 2021/216556 A2 | 10/2021 |
| WO | WO 2021/195533 A2 | 11/2021 |
| WO | WO 2021/242883 A1 | 12/2021 |

OTHER PUBLICATIONS

International Search Report and Written Opinion received for PCT Patent Application No. PCT/US2020/045487, dated Dec. 31, 2020, 26 Pages.

(56) References Cited

OTHER PUBLICATIONS

Alvarez-Erviti, et al., "Delivery of siRNA to the Mouse Brain by Systemic Injection of Targeted Exosomes", Nature Biotechnology, vol. 29, No. 4, pp. 341-345, Apr. 2011.
Andaloussi, et al., "Exosome-Mediated Delivery of siRNA In Vitro and In Vivo", Nature Protocols, vol. 7, No. 12, pp. 2112-2126, Nov. 15, 2012.
Andaloussi, et al., "Exosomes For Targeted siRNA Delivery Across Biological Barriers", Advanced Drug Delivery Reviews, vol. 65, pp. 391-397, 2013.
Andaloussi, et al., "Extracellular Vesicles: Biology and Emerging Therapeutic Opportunities", Nature Reviews Drug Discovery, vol. 12, pp. 347-357, May 2013.
Ausubel, et al., "Current Protocols in Molecular Biology", John Wiley & Sons, Inc., Sections 2.10 and 6.3-6.4, 1995.
Braasch, et al., "RNA Interference in Mammalian Cells by Chemically-Modified RNA", Biochemistry, vol. 42, No. 26, pp. 7967-7975, Jun. 11, 2003.
Chen et al., "Thermoresponsive polypeptides from pegylated poly-L-glutamates", Biomacromolecules 2011, 12: 2859-2863.
De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.
Egusquiaguirre, et al., "Nanoparticle Delivery Systems for Cancer Therapy: Advances in Clinical and Preclinical Research", Clinical and Translational Oncology, vol. 14, pp. 83-93, 2012.
Elmen, et al., "Locked Nucleic Acid (LNA) Mediated Improvements in siRNA Stability and Functionality", Nucleic Acids Research, vol. 33, Issue 1, pp. 439-447, Jan. 14, 2005.
Fattal, et al., "Biodegradable Polyalkylcyanoacrylate Nanoparticles for the Delivery of Oligonucleotides", Journal of Controlled Release, vol. 53, pp. 137-143, May 1998.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Herdewijn, Piet, "Heterocyclic Modifications of Oligonucleotides and Antisense Technology", Antisense and Nucleic Acid Drug Development, vol. 10, Issue 4, pp. 297-310, Jul. 8, 2004.
Lam, et al., "A New Type of Synthetic Peptide Library for Identifying Ligand-Binding Activity", Nature, vol. 354, pp. 82-84, Nov. 7, 1991.
Lambert, et al., "Nanoparticulate Systems for the Delivery of Antisense Oligonucleotides", Advanced Drug Delivery Reviews, vol. 47, pp. 99-112, 2001.
Lee, et al., "Recent Developments in Nanoparticle-Based siRNA Delivery for Cancer Therapy", BioMed Research International, vol. 2013, Article ID 782041, 10 Pages, Jun. 2013.
Nielsen, et al., "Sequence-Selective Recognition of DNA by Strand Displacement With a Thymine-Substituted Polyamide", Science, vol. 254, Issue 5037, pp. 1497-1500, Dec. 6, 1991.
Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.
Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.
Petersen, et al., "LNA: A Versatile Tool for Therapeutics and Genomics", Trends in Biotechnology, vol. 21, Issue 2, pp. 74-81, Feb. 2003.
Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.
Schwab, et al., "An Approach for New Anticancer Drugs:Oncogene-Targeted Antisense DNA", Annals of Oncology, vol. 5, Issue 4, pp. 55-58, 1994.

Wang, et al., "Nanoparticle-Based Delivery System for Application of siRNA In Vivo", Current Drug Metabolism, vol. 11, No. 2, pp. 182-196, 2010.
Yuan, et al., "Recent Advances of siRNA Delivery By Nanoparticles", Expert Opinion on Drug Delivery vol. 8, Issue 4, pp. 521-536, 2011.
Alexopoulou, et al., Recognition of Double-Stranded RNA and Activation of Nf-κB by Toll-like receptor 3, Nature, vol. 413, No. 6857, pp. 732-738, Oct. 18, 2001.
Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.
Allerson et al., "Fully 2'-modified oligonucleotide duplexes with improved in vitro potency and stability compared to unmodified small interfering RNA", J Med Chem., Feb. 24, 2005, 48(4): 901-904.
Alterman, et al., Hydrophobically Modified siRNAs Silence Huntingtin mRNA in Primary Neurons and Mouse Brain, Molecular Therapy-Nucleic Acids, vol. 4, pp. e266, Dec. 1, 2015.
Alves, et al., Selectivity, Cooperativity, and Reciprocity in the Interactions between the δ-Opioid Receptor, Its Ligands, and G-proteins, Journal of Biological Chemistry, vol. 279 No. 43, pp. 4673-44682, Aug. 17, 2004.
Amarzguioui, et al., "Tolerance for Mutations and Chemical Modifications in a siRNA", Nucleic Acids Research, Jan. 15, 2003, 31(2): 589-595.
Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).
Ambros, et al., MicroRNAs and Other Tiny Endogenous RNAs in C. elegans, Current Biology, vol. 13, Issue 10, pp. 807-818, May 13, 2003.
Ameres, et al., Molecular Basis for Target RNA Recognition and Cleavage by Human RISC, Cell, vol. 130, Issue 1, pp. 101-112, Jul. 13, 2007.
Anderson, et al., Experimental Validation of the Importance of Seed Complement Frequency to siRNA Specificity, RNA, vol. 14, No. 5, pp. 853-861, Mar. 26, 2008.
Anderson, et al., Identifying siRNA-Induced Off-Targets by Microarray Analysis, Methods in Molecular Biology, vol. 442, pp. 45-63, 2008.
Atwell, et al., Stable Heterodimers From Remodeling the Domain Interface of a Homodimer Using a Phage Display Library, Journal of Molecular Biology, vol. 270, Issue 1, pp. 26-35, Jul. 4, 1997.
Aubuchon, et al., "Preeclampsia: Animal Models for a Human Cure", Proceedings of the National Academy of Sciences, vol. 108, No. 4, pp. 1197-1198, Jan. 25, 2011.
Aureli, et al., GM1 Ganglioside: Past Studies and Future Potential, Molecular Neurobiology, vol. 53, Issue 3, pp. 1824-1842, Apr. 2016.
Avino, et al., Branched RNA: A New Architecture for RNA Interference, Journal of Nucleic Acids, Article IC586935, 7 pages, Mar. 6, 2011.
Bagella, et al., Cloning of Murine CDK9/PITALRE and Its Tissue-Specific Expression in Development, Journal of cellular physiology, vol. 177, No. 2, pp. 206-213, Dec. 7, 1998.
Bartlett, et al., Can Metastatic Colorectal Cancer be Cured?, Journal Oncology, Cancer Network, vol. 26, No. 3, pp. 266-275, Mar. 15, 2012.
Bartlett, et al., Insights Into the Kinetics of siRNA-Mediated Gene Silencing From Live-Cell and Live-Animal Bioluminescent Imaging, Nucleic Acids Research, vol. 34, Issue 1, pp. 322-333, Jan. 1, 2006.
Behlke, et al., Chemical Modification of siRNAs for In Vivo Use, Oligonucleotides, vol. 18, No. 4, pp. 305-320, Nov. 29, 2008.
Bell, et al., Liposomal Transfection Efficiency and Toxicity on Glioma Cell Lines: In Vitro and In Vitro Studies, Neuroreport, vol. 9, Issue 5, pp. 793-798, Mar. 30, 1998.
Billy, et al., Specific Interference With Gene Expression Induced by Long, Double- Stranded RNA in Mouse Embryonal Teratocarcinoma Cell Lines, Proceedings of the National Academy of Sciences, vol. 98, No. 25, pp. 14428-14433, Dec. 4, 2001.

(56) References Cited

OTHER PUBLICATIONS

Birmingham, et al., 3' UTR Seed Matches, But Not Overall Identity, Are Associated With RNAi Off-Targets, Nature Methods, vol. 3, No. 3, pp. 199-204, Feb. 17, 2006.
Birmingham, et al., A Protocol for Designing siRNAs With High Functionality and Specificity, Nature Protocols, vol. 2, No. 9, pp. 2068-2078, Aug. 23, 2007.
Boutla et al., "Short 5'-phosphorylated double-stranded RNAs induce RNA interference in *Drosophila*", Biology, 2001, 11: 1776-1780.
Brennecke, et al., Towards a Complete Description of the microRNA Complement of Animal Genomes, Genome Biology, vol. 4, No. 9, 3 Pages, Aug. 21, 2003.
Brummelkamp, et al., A System for Stable Expression of Short Interfering RNAs in Mammalian Cells, Science, vol. 296, Issue 5567, pp. 550-553, Apr. 19, 2002.
Burchard, et al., MicroRNA-Like Off-Target Transcript Regulation by siRNAs is Species Specific, RNA, vol. 15, No. 2, pp. 308-315, 2009.
Burke, et al., "Spiral Arterial Remodeling Is Not Essential for Normal Blood Pressure Regulation in Pregnant Mice", Hypertension, vol. 55, No. 3, pp. 729-737, Jan. 25, 2010.
Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.
Calegari, et al., Tissue-Specific RNA Interference in Postimplantation Mouse Embryos With Endoribonuclease-Prepared Short Interfering RNA, Proceedings of the National Academy of Sciences, vol. 99, No. 22, pp. 14236-14240, Oct. 29, 2002.
Carter, "Handbook of Parvoviruses", ed., P. Tijsser, CRC Press, pp. 155-168, 1990.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models For Study of the Pathogenesis of Huntington's Disease and Therapy, Drug design, development and therapy, vol. 9, pp. 2179-2188, Apr. 2015.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.
Charrier, et al., Inhibition of SRGAP2 Function by Its Human-Specific Paralogs Induces Neoteny during Spine Maturation, Cell, vol. 149, Issue 4, pp. 923-935, May 11, 2012.
Chen et al., "Lipophilic siRNAs mediate efficient gene silencing in oligodendrocytes with direct CNC delivery", Journal of Controlled Release, Elsevier, vol. 144, pp. 227-232. (Feb. 17, 2010).
Chen, et al., "Gene Therapy For Brain Tumors: Regression of Experimental Gliomas by Adenovirus-Mediated Gene Transfer In Vivo", Proceedings of the National Academy of Sciences, vol. 91, No. 8, pp. 3054-3057, 1994.
Cheng, et al., Enhanced Hepatic Uptake and Bioactivity of Type α1 (I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.
Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.
Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.
Choe, et al., Crystal Structure of Human Toll-Like Receptor 3 (TLR3) Ectodomain, Science, vol. 309, Issue 5734, pp. 581-585, Jun. 16, 2005.
Chung et al., "Reducible siRNA Dimeric Conjugates for Efficient Cellular Uptake and Gene Silencing", Bioconjugate Chem., 2011, 22(2): 299-306.
Coelho, et al., Safety and Efficacy of RNAi Therapy for Transthyretin Amyloidosis, New England Journal of Medicine, vol. 369, No. 9, pp. 819-829, Aug. 29, 2013.
Coles, et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.
Cui, et al., "Role of Corin in Trophoblast Invasion and Uterine Spiral Artery Remodelling in Pregnancy", Nature, vol. 484, No. 7393, pp. 246-250, Mar. 21, 2012.
Damha et al. (1990) "An improved procedure for derivatization of controlled-pore glass beads for solid-phase oligonucleotide synthesis," Nucleic Acids Research, 18(13):3813-3821.
Dass, Crispin R., Cytotoxicity Issues Pertinent to Lipoplex-Mediated Gene Therapy In-Vivo, Journal of Pharmacy and Pharmacology, vol. 54, Issue 5, pp. 593-601, Feb. 18, 2010.
Davidson, et al., A Model System For In Vivo Gene Transfer Into the Central Nervous System Using An Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types And Regions in the Mammalian Central Nervous System, Proceedings of the National Academy of Sciences, vol. 97, No. 7, pp. 3428-3432, Mar. 28, 2000.
De Fougerolles, et al., "Interfering With Disease: a Progress Report on siRNA- based Therapeutics", Nature Reviews Drug Discovery, vol. 6, pp. 443-453, Jun. 2007.
Deleavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.
Difiglia, et al., Therapeutic Silencing of Mutant Huntingtin With siRNA Attenuates Striatal and Cortical Neuropathology and Behavioral Deficits, Proceedings of the National Academy of Sciences, vol. 104, No. 43, pp. 17204-17209, Oct. 23, 2007.
Dinusha, Differnce Between Sterol and Steroid, Home / Health / Medicine / Nutrients & Drugs, Aug. 4, 2011.
Doench, et al., siRNAs Can Function as miRNAs, Genes & Development, vol. 17, pp. 438-442, 2003.
Dohmen et al., "Defined Folate-PEG-siRNA Conjugates for Receptor-specific Gene Slicing", Molecular Therapy-Nucleic Acids, 2012, 1(1): e7.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
El Andaloussi, et al., "Exosome-Mediated Delivery of siRNA In Vitro and In Vivo", Nature Protocols, vol. 7, No. 12, pp. 2112-2126, Nov. 15, 2012.
El Andaloussi, et al., "Exosomes for Targeted siRNA Delivery Across Biological Barriers", Advanced Drug Delivery Reviews, vol. 65, pp. 391-397, 2013.
El Andaloussi, et al., "Extracellular Vesicles: Biology and Emerging Therapeutic Opportunities", Nature Reviews Drug Discovery, vol. 12, pp. 347-357, May 2013.
EMBL Database, WO 2005116204-A/113070: Double Strand Polynucleotides Generating RNA Interference, EBI Accession No. Em PAT:FW706544, XP055753619, , Apr. 18, 2011.
Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Evers, et al., Antisense Oligonucleotides in Therapy for Neurodegenerative Disorders, Advanced Drug Delivery Reviews, vol. 87, pp. 90-103, Jun. 29, 2015.

(56) References Cited

OTHER PUBLICATIONS

Extended European Search Report for European Patent Application No. 16837593.9, dated Mar. 20, 2019.
Extended European Search Report for European Patent Application No. 17745083.0 , dated on Jul. 31, 2019.
Extended European Search Report for European Patent Application No. 17840367.1, dated Oct. 14, 2020.
Extended European Search Report for European Patent Application No. 20164108.1, dated on Dec. 3, 2020.
Extended European Search Report for European Patent Application No. 20216265.7, dated Feb. 10, 2022.
Extended European Search Report Received for EP Patent Application No. 18819571.3, dated May 14, 2021.
Fan, et al., Endometrial VEGF Induces Placental sFLT1 and Leads to Pregnancy Complications, The Journal of clinical investigation, vol. 124, No. 11, pp. 4941-4952, Oct. 20, 2014.
Fedorov, et al., Off-Target Effects by siRNA Can Induce Toxic Phenotype, RNA, vol. 12, No. 7, pp. 1188-1196, May 2006.
Felber, et al., The Interactions of Amphiphilic Antisense Oligonucleotides With Serum Proteins and Their Effects on In Vitro Silencing Activity, Biomaterials, vol. 33, Issue 25, pp. 5955-5965, Sep. 2012.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus For Gene Therapy Is Limited By Leading-Strand Synthesis, Journal of virology, vol. 70, No. 1, pp. 520-532, Jan. 1996.
Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.
Gaglione, et al., Recent Progress in Chemically Modified siRNAs, Mini Reviews in Medicinal Chemistry, vol. 10, No. 7, pp. pp. 578-595, 2010.
Gavrilov et al. (Jun. 2012) "Therapeutic siRNA: principles, challenges, and strategies", Yale Journal of Biology and Medicine, 85:187-200.
Geary, et al., Pharmacokinetics, Biodistribution and Cell Uptake of Antisense Oligonucleotides, Advanced Drug Delivery Reviews, vol. 87, pp. 46-51, Jun. 29, 2015.
Genbank, Mus Musculus Non-Coding RNA, Oocyte_Clustered_Small_RNA6599, Complete Sequence, GenBank Accession No. AB341398.1, May 24, 2008, 1 page.
Genbank, Rattus Norvegicus piRNApiR-182271, Complete Sequence, GenBank Accession No. DQ766949.1, Jul. 12, 2006, 1 Page.
Genbank, Signal Recognition Particle 54 kDa protein 2 [Perkinsus marinus ATCC 50983], NCBI Reference Sequence: XP_002784438.1.
Gilany, et al., The Proteome of the Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.

Grad, et al., Computational and Experimental Identification of C. elegans microRNAs, Molecular Cell, vol. 11, Issue 5, pp. 1253-1263, May 2003.
Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, San, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality in Mice Due to Oversaturation of Cellular MicroRNA/short Hairpin RNA Pathways, Nature, vol. 441, No. 7092, pp. 537-541, May 25, 2006.
Hamajima, et al., Intranasal Administration of HIV-DNA Vaccine Formulated with a Polymer, Carboxymethylcellulose, Augments Mucosal Antibody Production and Cell- Mediated Immune Response, Clinical Immunology and Immunopathology, vol. 88, Issue 2, pp. 205-210, Aug. 1998.
Haraszti, et al., "5'-Vinylphosphonate improves tissue accumulation and efficacy of conjugated siRNAs in vivo", Nucleic Acids Research, Jul. 27, 2017, 45(13): 7581-7592.
Heydarian, et al., Novel Splice Variants of sFlt1 are Upregulated in Preeclampsia, Placenta, vol. 30, Issue 3, pp. 250-255, Mar. 2009.
Heyer, et al., An Optimized Kit-Free Method For Making Strand-Specific Deep Sequencing Libraries From RNA Fragments, Nucleic Acids Research, vol. 43, Issue 1, pp. 1-14, Jan. 9, 2015.
Hirashima, et al., "Trophoblast Expression of Fms-like Tyrosine Kinase 1 Is Not Required for the Establishment of the Maternal-fetal Interface in the Mouse Placenta", Proceedings of the National Academy of Sciences of the United States of America, vol. 100, No. 26, p. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
International Search Report and Written Opinion received for PCT Patent Application No. PCT/US2016/025722, dated Aug. 12, 2016, 20 Pages.
International Search Report and Written Opinion received for PCT Patent Application No. PCT/US2016/025731, dated Sep. 9, 2016, 18 Pages.
International Search Report and Written Opinion received for PCT Patent Application No. PCT/US2016/025753, dated Sep. 14, 2016, 18 Pages.
International Search Report and Written Opinion received for PCT Patent Application No. PCT/US2016/046810, dated Nov. 29, 2016, 9 Pages.
International Search Report and Written Opinion received for PCT Patent Application No. PCT/US2017/015633, dated May 11, 2017, 12 Pages.
International Search Report and Written Opinion received for PCT Patent Application No. PCT/US2018/038952, dated Sep. 24, 2018.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iriyama et al., Hypoxia-independent up-regulation of placental HIF-1α gene expression contributes to the pathogenesis of preeclampsia, Hypertension, Jun. 2015, 65(6): 1307-1315.
Jackson, et al., Position-Specific Chemical Modification of siRNAs Reduces "Off-Target" Transcript Silencing, RNA, vol. 12, No. 7, pp. 1197-1205, May 8, 2006.
Jackson, et al., Recognizing and Avoiding siRNA Off-Target Effects For Target Identification and Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.

(56) References Cited

OTHER PUBLICATIONS

Janssen, et al., Long-Chain Polyunsaturated Fatty Acids (LCPUFA) From Genesis To Senescence: The Influence of LCPUFA on Neural Development, Aging, and Neurodegeneration, Progress in Lipid Research, vol. 53, pp. 1-17, Jan. 2014.

Jo, et al., Selection and Optimization of Asymmetric siRNA Targeting the Human c-MET Gene, Molecules and cells, vol. 32, No. 6, pp. 543-548, Dec. 31, 2011.

Judge, et al., Design of Noninflammatory Synthetic siRNA Mediating Potent Gene Silencing in Vivo, Molecular Therapy, vol. 13, Issue 3, pp. 494-505, Mar. 2006.

Kamba, et al., "VEGF-dependent Plasticity of Fenestrated Capillaries in the Normal Adult Microvasculature", American Journal of Physiology-Heart and Circulatory Physiology, vol. 29, pp. H560-H576, Feb. 1, 2006.

Karlin, et al., Applications and Statistics for Multiple High-Scoring Segments In Molecular Sequences, Proceedings of the National Academy of Sciences of the USA, vol. 90, pp. 5873-5877, Jun. 1993.

Karlin, et al., Methods for Assessing the Statistical Significance of Molecular Sequence Features by Using General Scoring Schemes, Proceedings of the National Academy of science of the USA, vol. 87, No. 6, pp. 2264-2268, Mar. 1990.

Karra, et al., Transfection Techniques for Neuronal Cells, Journal of Neuroscience, vol. 30, No. 18, pp. 6171-6177, May 5, 2010.

Kenski et al. (2012) "siRNA-optimized Modifications for Enhanced In Vivo Activity," Mol. Ther. Nucleic Acids. 1:e5. pp. 1-8.

Khvorova, et al., Abstract IA27: Advances in Oligonucleotide Chemistry for the Treatment of Neurodegenerative Disorders and Brain Tumors, Cancer Research, vol. 76, Issue 6, Abstract IA27, Mar. 2016.

Khvorova, et al., Functional siRNAs and miRNAs Exhibit Strand Bias, Cell, vol. 115, Issue 2, pp. 209-216, Oct. 17, 2003.

Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.

Kubo et al., "Lipid-Conjugated 27-Nucleotide Double-Stranded RNAs with Dicer- Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).

Kubo et al., "Palmitic Acid-Conjugated 21-Nucleotide siRNA Enhances Gene- Silencing Activity", Molecular Pharmaceutics, vol. 8, No. 6, pp. 2193-2203, DOI: 10.1021/mp200250f. (Oct. 10, 2011).

Lagos-Quintana, et al., Identification of Novel Genes Coding for Small Expressed RNAs, Science, vol. 294, Issue 5543, pp. 853-858, Oct. 26, 2001.

Lagos-Quintana, et al., Identification of Tissue-Specific MicroRNAs from Mouse, Current Biology, vol. 12, Issue 9, pp. 735-739, Apr. 30, 2002.

Lagos-Quintana, et al., New microRNAs From Mouse and Human, RNA, vol. 9, No. 2, pp. 175-179, 2003.

Lai, et al., Computational Identification of *Drosophila* microRNA Genes, Genome Biology, vol. 4, No. 7, pp. 1-20, Jun. 30, 2003.

Lan, et al., Neuroactive Steroid Actions at the GABAA Receptor, Hormones and Behavior, vol. 28, Issue 4, pp. 537-544, Dec. 1994.

Landis, et al., "A Call for Transparent Reporting to Optimize the Predictive Value of Preclinical Research", Nature, vol. 490, pp. 187-191, Oct. 10, 2012.

Lau, et al., An Abundant Class of Tiny RNAs with Probable Regulatory Roles in Caenorhabditis elegans, Science, vol. 294, Issue 5543, pp. 858-862, Oct. 26, 2001.

Lau, et al., Characterization of the piRNA Complex from Rat Testes, Science, vol. 313, Issue 5785, pp. 363-367, Jul. 21, 2006.

Laufer, et al., "Selected Strategies for the Delivery of siRNA In Vitro and In Vivo", RNA Technologies and Their Applications, 2010, pp. 29-58.

Lee, et al., An Extensive Class of Small RNAs in Caenorhabditis elegans, Science, vol. 294, Issue 5543, pp. 862-864, Oct. 26, 2001.

Lee, et al., Expression of Small Interfering RNAs Targeted Against HIV-1 rev Transcripts in Human Cells, Nature Biotechnology, vol. 20, No. 5, pp. 500-505, May 1, 2002.

Lee, et al., RNA Interference-Mediated Simultaneous Silencing of Four Genes Using Cross-Shaped RNA, Molecules and Cells, vol. 35, No. 4, pp. 320-326, Apr. 4, 2013.

Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.

Levine, et al., "Circulating Angiogenic Factors and the Risk of Preeclampsia", The New England Journal of Medicine, vol. 350, pp. 672-683, 2004.

Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.

Li, et al., Distribution of 5-Hydroxymethylcytosine in Different Human Tissues, "SAGE—Hindawi Access to Research, Journal of Nucleic Acids, vol. 2011", pp. 1-7, 2011.

Li, et al., Huntington's Disease Gene (IT15) Is Widely Expressed in Human and Rat Tissues, Neuron, vol. 11, No. 5, pp. 985-993, Nov. 1993.

Lim, et al., The microRNAs of Caenorhabditis elegans, Genes & Development, vol. 17, No. 8, pp. 991-1008, 2003.

Lim, et al., Vertebrate MicroRNA Genes, Science, vol. 299, Issue 5612, p. 1540, Mar. 7, 2003.

Lima, et al., Single-Stranded siRNAs Activate RNAi in Animals, Cell, vol. 150, Issue 5, pp. 883-894, Aug. 31, 2012.

Lopes, et al., Comparison Between Proliferative and Neuron-Like SH-SY5Y Cells as an In Vitro Model For Parkinson Disease Studies, Brain Research, vol. 1337, pp. 85-94, Jun. 14, 2010.

Lorenz, et al., Steroid and Lipid Conjugates of siRNAs to Enhance Cellular Uptake and Gene Silencing in Liver Cells, Bioorganic & Medicinal Chemistry Letters, vol. 14, Issue 19, pp. 4975-4977, Oct. 4, 2004.

Lundh, et al., Hypothalamic Expression of Mutant Huntingtin Contributes to the Development of Depressive-Like Behavior in the Bac Transgenic Mouse Model of Huntington's Disease, Human Molecular Genetics, vol. 22, Issue 17, pp. 3485-3497, Sep. 1, 2013.

Luo, et al., Photoreceptor Avascular Privilege Is Shielded By Soluble VEGF Receptor-1, Elife, vol. 2, pp. 1-22, Jun. 18, 2013.

Makris, et al., "Uteroplacental Ischemia Results in Proteinuric Hypertension and Elevated sFLT-1", Kidney International, vol. 71, Issue 1, pp. 977-984, May 2, 2007.

Maltepe, et al., "The Placenta: Transcriptional, Epigenetic, and Physiological Integration During Development", The Journal of Clinical Investigation, vol. 120, No. 4, pp. 1016-1025, Apr. 1, 2010.

Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.

Mantha, et al., Rnai-Based Therapies for Huntington's Disease: Delivery Challenges and Opportunities, Therapeutic Delivery, vol. 3, No. 9, pp. 1061-1076, Aug. 29, 2012.

Marcus, et al., FedExosomes: Engineering Therapeutic Biological Nanoparticles that Truly Deliver, Pharmaceuticals, vol. 6, No. 5, pp. 659-680, Apr. 29, 2013.

Marques, et al., A Structural Basis for Discriminating Between Self and Nonself Double-Stranded Rnas in Mammalian Cells, Nature biotechnology, vol. 23, No. 11, pp. 1399-1405, 2005.

Masotti, et al., Comparison of Different Commercially Available Cationic Liposome-DNA Lipoplexes: Parameters Influencing Toxicity and Transfection Efficiency, Colloids and Surfaces B: Biointerfaces, vol. 68, Issue 2, pp. 136-144, Feb. 1, 2009.

Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.

McCaffrey, et al., Gene Expression: RNA Interference in Adult Mice, Nature, vol. 418, No. 6893, pp. 38-39, Jul. 4, 2002.

McManus, et al., Gene Silencing Using Micro-RNA Designed Hairpins, RNA, vol. 8, Issue 6, pp. 842-850, Aug. 20, 2002.

(56) References Cited

OTHER PUBLICATIONS

Miyagishi, et al., U6 promoter-driven siRNAs With Four Uridine 3' Overhangs Efficiently Suppress Targeted Gene Expression in Mammalian Cells, Nature Biotechnology, vol. 20, No. 5, pp. 497-500, May 1, 2002.
Mok, et al., Multimeric small interfering ribonucleic acid for highly efficient sequence- specific gene silencing~, Nature Materials, vol. 9, pp. 272-278, Jan. 24, 2010.
Molitoris, et al., siRNA Targeted to p53 Attenuates Ischemic and Cisplatin- Induced Acute Kidney Injury, Journal of the American Society of Nephrology, vol. 20, Issue 8, pp. 1754-1764, Aug. 1, 2009.
Morrissey et al., "Activity of stabilized short interfering RNA in a mouse model of hepatitis B virus replication", Hepatology, 2005, 41: 1349-1356.
Mourelatos, et al., miRNPs: A Novel Class of Ribonucleoproteins Containing Numerous microRNAs, Genes & Development, vol. 16, No. 6, pp. 720-728, 2002.
Mullen, et al., NeuN, A Neuronal Specific Nuclear Protein In Vertebrates, Development, vol. 116, No. 1, pp. 201-211, 1992.
Myers, et al., Optimal Alignments in Linear Space, Computer Applications in the Biosciences, vol. 4, No. 1, pp. 11-17, Mar. 1988.
Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-4484, Nov. 1, 2004.
Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.
Nelson et al. (1992) "Oligonucleotide labeling methods 3. Direct labeling of oligonucleotides employing a novel, non-nucleosidic, 2-aminobutyl-1 ,3-propanediol backbone," 20(23):6253-6259.
Neufeld, et al., "Similarities and Differences Between the Vascular Endothelial Growth Factor (VEGF) Splice Variants", Cancer and Metastasis Reviews, vol. 15, pp. 153-158, Jun. 1996.
Nikan, et al., Docosahexaenoic Acid Conjugation Enhances Distribution and Safety of siRNA upon Local Administration in Mouse Brain, Molecular Therapy—Nucleic Acids, vol. 5, No. 8, pp. 1-11, Aug. 9, 2016.
Nishina et al., "Efficient In Vivo Delivery of siRNA to the Liver by Conjugation of α- Tocopherol", Mol Ther., Apr. 2008, 16(4): 734-740.
Ouimet, et al., DARPP-32, A Dopamine- and Adenosine 3':5'-Monophosphate-Regulated Phosphoprotein Enriched in Dopamine-Innervated Brain Regions. III. Immunocytochemical Localization, Journal of Neuroscience, vol. 4, No. 1, pp. 111-124, Jan. 1, 1984.
Owen, Morpholino-Mediated Increase in Soluble Flt-1 Expression Results in Decreased Ocular and Tumor Neovascularization, PLoS One, vol. 7, No. 3, pp. e33576, Mar. 15, 2012.
Paddison, et al., Short Hairpin RNAs (shRNAs) Induce Sequence-Specific Silencing In Mammalian Cells, Genes & Development, vol. 16, No. 8, pp. 948-958, 2002.
Partial European Search Report for European Patent Application No. 20216265.7, dated Nov. 10, 2021.
Partial European Search Report for European Patent Application No. 21197881.2, dated Mar. 14, 2022.
Pasquinelli, et al., Conservation of the Sequence and Temporal Expression of let-7 Heterochronic Regulatory RNA, Nature, vol. 408, No. 6808, pp. 86-89., Nov. 2, 2000.
Paul, et al., Effective Expression of Small Interfering RNA in Human Cells, Nature Biotechnology, vol. 20, No. 5, pp. 505-508, May 1, 2002.
Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.
Pei, et al., Quantitative Evaluation of siRNA Delivery in Vivo, RNA, vol. 16, No. 12, pp. 2553-2563, Oct. 12, 2010.

Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).
Posocco, et al., "Impact of siRNA Overhangs for Dendrimer-mediated siRNA Delivery and Gene Silencing", Molecular Pharmaceutics, Aug. 5, 2013, 10(8): 3262-3273.
Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.
Pubchem Database, Amino-TEG-Diol, National Institute or Biotechnology Information, PubChem Accession No. 22136768, 2003.
Pubchem Database, SCHEMBL867745, National Institute for Biotechnology Information, PubChem Accession No. 12454428, 12 pages, 2005.
Putnam, David A., Antisense Strategies and Therapeutic Applications, American Journal of Health System Pharmacy, vol. 53, No. 2, pp. 151-160, Jan. 15, 1996.
Raouane et al., "Lipid Conjugated Oligonucleotides: A Useful Strategy for Delivery", Chem., 2012, 23: 1091-1104.
Reinhart, et al., Small RNAs Correspond to Centromere Heterochromatic Repeats, Science, vol. 297, No. 5588, 1 Page., Sep. 13, 2002.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.
Rodriguez-Lebron, et al., Intrastriatal rAAV-Mediated Delivery of Anti-Huntingtin shRNAs Induces Partial Reversal of Disease Progression in R6/1 Huntington's Disease Transgenic Mice, Molecular Therapy, vol. 12, Issue 4, pp. 618-633, Oct. 2005.
Rupprecht, et al., Neuroactive Steroids: Mechanisms of Action and Neuropsychopharmacological Properties, Psychoneuroendocrinology, vol. 28, Issue 2, pp. 139-168, Feb. 2003.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Sah, et al., Oligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder and Declarative Memory Functioning: A Review, Dialogues in Clinical Neuroscience, vol. 13, No. 3, pp. 346-351, Sep. 2011.
Schirle, et al., Structural Basis for MicroRNA Targeting, Science, vol. 346, Issue 6209, pp. 608-613, Oct. 31, 2014.
Schwarz, et al., Asymmetry in the Assembly of the RNAi Enzyme Complex, Cell, vol. 115, Issue 2, pp. 199-208, Oct. 17, 2003.
Seq Id No. 1112 from U.S. Pat. No. 7,790,867. [Accessed Nov. 28, 2018, http://seqdata.uspto.gov/.psipsv?pageRequest=viewSequence&DocID=7790867&seq ID=1112.].
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Soutschek, et al., Therapeutic Silencing of an Endogenous Gene by Systemic Administration of Modified siRNAs, Nature, vol. 432, No. 7014, pp. 173-178, Nov. 11, 2004.
Stalder, et al., The Rough Endoplasmatic Reticulum Is a Central Nucleation Site of siRNA-Mediated RNA Silencing, The EMBO Journal, vol. 32, Issue 8, pp. 1115-1127, Mar. 19, 2013.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA in Targeting Protein Expression Iin Kidney Disease, Advanced Drug Delivery Reviews, vol. 62, Issue 14, pp. 1378-1389, Nov. 30, 2010.
Sui, et al., A DNA Vector-Based RNAi Technology to Suppress Gene Expression in Mammalian Cells, Proceedings of the National Academy of Sciences, vol. 99, No. 8, pp. 5515-5520, Apr. 16, 2002.

(56) References Cited

OTHER PUBLICATIONS

Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.
Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.
Tischer, et al., "The Human Gene for Vascular Endothelial Growth Factor. Multiple Protein Forms are Encoded Through Alternative Exon Splicing", The Journal of Biological Chemistry, vol. 266, p. 11947-11954, Jun. 25, 1991.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.US/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.
Uchida, et al., "An Integrated Approach for the Systematic Identification and Characterization of Heart-enriched Genes With Unknown Functions", BMC Genomics, vol. 10, No. 100, pp. 1-12, Mar. 2009.
Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 RNA Polymerase Transcription with 5-Position Modified UTP Derivatives, Journal of the American Chemical Society, vol. 126, No. 36, p. 11231-11237, Aug. 19, 2004.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal of Controlled Release, Elsevier, vol. 226, pp. 57-65, Doi: 10.1016/J.JCONREL.2016.02.007. (Feb. 5, 2016).
Watanabe, et al., Endogenous siRNAs From Naturally Formed dsRNAs Regulate Transcripts in Mouse Oocytes, Nature, vol. 453, No. 7194, pp. 539-543, Apr. 10, 2008.
Weyer, et al., Developmental and Cell Type-Specific Expression of the Neuronal Marker NeuN in the Murine Cerebellum, Journal of Neuroscience Research, vol. 73, Issue 3, pp. 400-409, May 23, 2003.
Whitehead, et al., "Knocking Down Barriers: Advances in siRNA Delivery", Nature Reviews Drug Discovery, vol. 8, No. 2, pp. 129-138, Feb. 2009.

Wolfrum et al., "Mechanisms and optimization of in vivo delivery of lipophilic siRNAs", Nature Biotechnology, Oct. 2007, 25(10): 1149-1157.
Wong, et al., Co-Injection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification of Factors That Contribute to Recombinant AAV2 Particle Aggregation and Methods to Prevent Its Occurrence During Vector Purification And Formulation, Molecular Therapy, vol. 12, Issue 1,, pp. 171-178, Jul. 2005.
Xia, et al., siRNA-Mediated Gene Silencing in Vitro and In Vivo, Nature Biotechnology, vol. 20, No. 10, pp. 1006-1010, Sep. 16, 2002.
Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression of Short-Interfering RNAs and Hairpin Rnas in Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones and Their Inhibition of Mutant SOD1-Dependent Protein Aggregation and Toxicity in PC12 Cells, Bioorganic & Medicinal Chemistry, vol. 20, Issue 2, pp. 1029-1045, Jan. 15, 2012.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.
Akinc et al., A Combinatorial Library of Lipid-like Materials for Delivery of RNAi Therapeutics, Nature Biotechnology, vol. 26, No. 5, 20 Pages, May 2008.
Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Alterman et al., "A divalent siRNA chemical scaffold for potent and sustained modulation of gene expression throughout the central nervous system", Nat Biotechnol., Aug. 2019, 37(8): 884-894.
Ämmälä, et al., Targeted Delivery of Antisense Oligonucleotides to Pancreatic β-cells, Science Advances, vol. 4, No. 10, eaat3386, pp. 1-11, Oct. 17, 2018.
Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.
Biscans et al., "Docosanoic acid conjugation to siRNA enables functional and safe delivery to skeletal and cardiac muscles", Molecular Therapy, Apr. 2021, vol. 29, No. 4, pp. 1382-1394.

(56) References Cited

OTHER PUBLICATIONS

Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.
Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.
Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.
Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.
Brown, et al., Effect of Phosphorothioate Modification of Oligodeoxynucleotides on Specific Protein Binding, Journal of Biological Chemistry, vol. 269, No. 43, p. 26801-26805, 1994.
Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.
Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.
Chen et al., Influence of Particle Size on the in Vivo Potency of Lipid Nanoparticle Formulations of siRNA, Journal of Controlled Release, vol. 235, pp. 236-244, Aug. 10, 2016.
Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.
Chu, et al., Potent RNAi by Short RNA Triggers, RNA, vol. 14, pp. 1714-1719, 2008.
Collis, "The synthesis of vinylphosphonate-linked RNA", Ph.D. Thesis, University of Nottingham, Feb. 2008.
Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide-Protein Interactions, Nucleic Acids Research, May 1, 2020, 48(10): 5235-5253.
Czauderna, et al., Structural Variations and Stabilising Modifications of Synthetic siRNAs in Mammalian Cells, Nucleic Acids Research, vol. 31, Issue 11, pp. 2705-2716, Jun. 2003.
Dahlman et al., In Vivo Endothelial siRNA Delivery using Polymeric Nanoparticles with Low Molecular Weight, Nature Nanotechnology, vol. 9, No. 8, 17 Pages, Aug. 2014.
De Paula et al., "Hydrophobization and bioconjugation for enhanced siRNA delivery and targeting", RNA, Feb. 28, 2007, vol. 13, No. 4, pp. 431-456.
Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.
Dowdy, Overcoming Cellular Barriers for RNA Therapeutics, Nature Biotechnology, vol. 35, pp. 222-229, Feb. 27, 2017.
Ducruix, et al., Crystallization of Nucleic Acids and Proteins: A Practical Approach, Second Edition, 1999, pp. 201-216.
Echevarría, et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Egli, et al., Re-engineering RNA Molecules Into Therapeutic Agents, Accounts of Chemical Research, vol. 52, pp. 1036-1047, 2019.
Elbashir, et al., RNA Interference Is Mediated By 21- and 22-Nucleotide RNAs, Genes & Development, vol. 15, No. 2, pp. 188-200, 2001.
Etzold et al., "The extension of the sugar chain of thymidine: a new route to 5'-deoxyhexose nucleosides", Chemical Communications (London), 1968, Issue 7.
Extended European Search Report for European Patent Application No. 19852320.1, dated May 2, 2022.
Extended European Search Report for European Patent Application No. 20741865.8, dated Apr. 26, 2023.
Extended European Search Report for European Patent Application No. 19847586.5, dated Jun. 21, 2023.
Fitzgerald, et al., A Highly Durable RNAi Therapeutic Inhibitor of PCSK9, New England Journal of Medicine, vol. 376, No. 1, pp. 41-51, Jan. 5, 2017.
Foster et al., "Advanced siRNA Designs Further Improve In Vivo Performance of GalNAc-siRNA Conjugates", Molecular Therapy, vol. 26, No. 3, pp. 709-717, Mar. 2018.
Frank et al., Structural Basis for 5'-Nucleotide Base-specific Recognition of Guide RNA by Human AGO2, Nature, vol. 465, pp. 818-822, Jun. 2010.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.
Geary, Antisense Oligonucleotide Pharmacokinetics and Metabolism, Expert Opinion on Drug Metabolism & Toxicology, vol. 5, pp. 381-391, Apr. 1, 2009.
Ghidini et al., "An RNA modification with remarkable resistance to RNase A", Chemical Communicaitons, Aug. 8, 2013, 49(79): 9036-9038.
Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Gvozdeva et al., "Noncanonical Synthetic RNAi Inducers InL RNA Interference", InTech, Apr. 6, 2016.
Haly et al., "An extended phosphate linkage: Synthesis, hybridization and modeling studies of modified oligonucleotides", Nucleosides and Nucleotides, 1996, 15(7-8): 1383-1395.
Hammerling et al., Monoclonal Antibodies and T-Cell Hybridomas, Research Monographs in Immunology, vol. 3, pp. 563-681, 1981.
Hanuš et al., "-CH2- lengthening of the internucleotide linkage in the ApA dimer can improve its conformational compatibility with its natural polynucleotide counterpart", Nucleic Acids Research, Dec. 15, 2001, 29(24): 5182-5194.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Hillier et al., yw97a12.r1 Soares_placenta_8to9weeks_2NbHP8to9W Homo sapiens cDNA clone Image:260158 5' similar to gb:X51602_cds1 Vascular Endothelial Growth Factor Receptor 1 (Human); contains element OFR repetitive element, mRNA sequence, NIH, Genbank Accession No. N47911.1, Feb. 14, 1996.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Preliminary Report on Patentability for PCT International Patent Application No. PCT/US2019/046013, dated Apr. 28, 2020.
International Preliminary Report on Patentability for PCT Patent Application No. PCT/US2020/025017, dated Sep. 28, 2021.

(56) References Cited

OTHER PUBLICATIONS

International Preliminary Report on Patentability for PCT Patent Application No. PCT/US2021/034290, dated Nov. 17, 2022.
International Search Report and Written Opinion for PCT International Patent Application No. PCT/US2019/048027 dated Nov. 15, 2019.
International Search Report and Written Opinion for PCT International Patent Application No. PCT/US2020/047492, dated Feb. 17, 2022.
International Search Report and Written Opinion for PCT International Patent Application No. PCT/US2020/025017, dated Sep. 18, 2020.
International Search Report and Written Opinion in related PCT Application No. PCT/US2021/024425, dated Oct. 15, 2021.
International Search Report and Written Opinion received for PCT Patent Application No. PCT/US2021/034290, dated Nov. 4, 2021.
International Search Report and Written Opinion received for PCT Patent Application No. PCT/US2021/041946, dated Oct. 29, 2021.
International Search Report and Written Opinion received for PCT Patent Application No. PCT/US2021/060356, dated Apr. 13, 2022.
Jebbink et al., "Expression of Placental FLT1 Transcript Variants Relates to Both Gestational Hypertensive Disease and Fetal Growth", Hypertension, Apr. 25, 2011, 58(1): 70-76.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kachare et al., "Phospho-carboxylic anhydride of a homologated nucleoside leads to primer degradation in the presence of a polymerase", Bioorg Med Chem Letters, Jun. 15, 2014, 24(12): 2720-2723.
Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.
Khan et al., Silencing Myostatin using Cholesterol-Conjugated siRNAs Induces Muscle Growth, Molecular Therapy, Nucleic Acids, vol. 5, 9 Pages, Jan. 1, 2016.
Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.
Khvorova, Oligonucleotide Therapeutics—A New Class of Cholesterol-Lowering Drugs, The New England Journal of Medicine, vol. 376, No. 1, pp. 4-7, Jan. 5, 2017.
Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.
Kim et al., "PEG conjugated VEGF siRNA for anti-angiogenic gene therapy", Journal of Controlled Release, Jun. 3, 2006, vol. 116, No. 2, pp. 123-129.
Kofoed et al., "Oligodeoxynucleotides with Extended 3'- and 5'-Homologous Internucleotide Linkages", Acta Chemica Scandanavia, 1997, 51: 318-324.
Kubo, et al., Modified 27-nt dsRNAs With Dramatically Enhanced Stability in Serum and Long-term RNAi Activity, Oligonucleotides, vol. 17, No. 4, pp. 445-464, 2007.
Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.
Lebedeva et al., "Phosphorothioate oligodeoxynucleotides as inhibitors of gene expression: antisense and non-antisense effects", Applications of Antisense therapies to restenosis, 1999, p. 101.
Lee et al., "Current preclinical small interfering RNA (siRNA)-based conjugate systems for RNA therapeutics", Advanced Drug Delivery Reviews, Oct. 27, 2015, vol. 104, pp. 78-92.
Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.
Liu et al., Snapshot Pk: A Rapid Rodent in Vivo Preclinical Screening Approach, Drug Discovery Today, vol. 13, No. 7-8, pp. 360-367, Apr. 1, 2008.
Loy et al., "Allele-Specific Gene Silencing in Two Mouse Models of Autosomal Dominant Skeletal Myopathy", PLoS One, Nov. 2012, 7(11): e49757, 11 pages.
Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis For 5'-End-Specific Recognition of Guide RNA by the A. Fulgidus Piwi Protein, Nature, vol. 434, No. 7033, pp. 666-670, Mar. 31, 2005.
Ma, et al., Structural Basis for Overhang-Specific Small Interfering RNA Recognition by the PAZ Domain, Nature, vol. 429, No. 6989, pp. 318-322, May 20, 2004.
Magner et al., "Influence of mismatched and bulged nucleotides on SNP-preferential RNase H cleavage of RNA-antisense gapmer heteroduplexes", Scientific Reports, Oct. 2017, 7(12532), 16 pages.
Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.
Mazur et al., "Isosteres of natural phosphates. 11. Synthesis of a phosphonic acid analogue of an oligonucleotide", Tetrahedron, 1984, 40(20): 3949-3956.
Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.
Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.
Monteys et al., "Artificial miRNAs Targeting Mutant Huntingtin Show Preferential Silencing In Vitro and In Vivo", Molecular Therapy, Nucleic Acids, 2015, 4: E234, 11 pages.
Nair, et al., Impact of Enhanced Metabolic Stability on Pharmacokinetics and Pharmacodynamics of GalNAc-siRNA Conjugates, Nucleic Acids Research, vol. 45, Issue 19, pp. 10969-10977, Nov. 2, 2017.
Nallagatla et al., Nucleoside Modifications Modulate Activation of the Protein Kinase PKR in an RNA Structure-Specific Manner, RNA, vol. 14, pp. 1201-1213, Jun. 1, 2008.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Oberbauer et al., Renal Uptake of an 18-mer Phosphorothioate Oligonucleotide, Kidney International, vol. 48, pp. 1226-1232, 1995.
Ohtsuka et al., "Joining of synthetic ribotrinucleotides with defined catalyzed by T4 Rna ligase", European Journal of Biochemistry, 1977, 81(2): 285-291.
Osborn et al., Hydrophobicity Drives the Systemic Distribution of Lipid-Conjugated siRNAs Via Lipid Transport Pathways, Nucleic Acids Research, vol. 47, No. 3, pp. 1070-1081, Dec. 8, 2018.
Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.
Padiukova et al., "Synthesis of 5'-derivatives of thymidine", Bioorg Khim., 1990, 16(5): 668-673 [Article in Russian—No. abstract available].
Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.

(56) References Cited

OTHER PUBLICATIONS

Partial Supplementary European Search Report for European Patent Application No. 20741865.8, dated Dec. 20, 2022.
Partial Supplementary European Search Report for European Patent Application No. 20777915.8, dated Apr. 5, 2023.
Pokholenko et al., Lipid Oligonucleotide Conjugates as Responsive Nanomaterials for Drug Delivery, Journal of Materials Chemistry B, vol. 1, 6 Pages, 2013.
Prakash et al., Targeted Delivery of Antisense Oligonucleotides to Hepatocytes Using Triantennary N-Acetyl Galactosamine Improves Potency 10-Fold in Mice, Nucleic Acids Research, vol. 42, Issue 13, pp. 8796-8807, Jul. 29, 2014.
Prakash, et al., Identification of Metabolically Stable 5'-Phosphate Analogs That Support Single-Stranded siRNA Activity, Nucleic Acids Research, Mar. 9, 2015, 43(6): 2993-3011.
PubChem Detabase, CID-16131506, Compund Summary: dGTGGGTGGGT, Jul. 3, 2007, Retrieved from url: https://pubchem.ncbi.nlm.nih.gov/compound/16131506.
Raal, et al., Inclisiran for the Treatment of Heterozygous Familial Hypercholesterolemia, New England Journal of Medicine, vol. 382, No. 16, pp. 1520-1530, Apr. 16, 2020.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Reed et al., Forty Mouse Strain Survey of Body Composition, Physiology & Behavior, vol. 91, No. 5, 15 Pages, Aug. 15, 2007.
Reynolds, A, et al., Rational siRNA Design for RNA Interference, Nature Biotechnology, vol. 22, No. 3, pp. 326-330, Apr. 2004.
Roy et al., "Synthesis of DNA/RNA and Their Analogs via Phosphoramidite and H-Phosphonate Chemistries", Molecules, 2013, 18(11): 14268-14284.
Rozners et al., "Synthesis and Properties of RNA Analogues Having Amides as Interuridine Linkages at Selected Positions", JACS Articles, Sep. 6, 2003, 125: 12125-12136.
Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Schlegal et al., "Chirality Dependent Potency Enhancement and Structural Impact of Glycol Nucleic Acid Modification on siRNA", JACS, Jun. 1, 2017, pp. 1-28.
Schoch, et al., Antisense Oligonucleotides: Translation From Mouse Models to Human Neurodegenerative Diseases, Neuron, vol. 94, Issue 6, pp. 1056-1070, Jun. 21, 2017.
Setten, et al., The Current State and Future Directions of RNAi-based Therapeutics, Nature Reviews Drug Discovery, vol. 18, pp. 421-446, Mar. 7, 2019.
Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.
Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.
Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.
Shukla et al., "Exploring Chemical Modifications for siRNA Therapeutics: A Structural and Functional Outlook", ChemMedChem, Feb. 19, 2010, 5(3): 328-349.
Sipova et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Stein, et al., Physicochemical Properties of Phosphorothioate Oligodeoxynucleotides, Nucleic Acids Research, vol. 16, No. 8, pp. 3209-3221, Apr. 25, 1988.
Sugo et al., "Development of antibody-siRNA conjugate targeted to cardiac and skeletal muscles", Journal of Controlled Release, Jun. 29, 2016, vol. 237, pp. 1-13.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Sun, et al., Asymmetric RNA Duplexes Mediate RNA Interference in Mammalian Cells, Nature Biotechnology, vol. 26, pp. 1379-1382, Dec. 2008.
Tan et al., "Allele-Specific Targeting of microRNAs to HLA-G and Risk of Asthma", American Journal of Human Genetics, Oct. 2007, 81(4): 829-834.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Teng et al., "A GDF15 3' UTR variant, rs1054564, results in allele-specific translational repression of GDF15 by hsa-miR-1233-3p", PLoS One, Aug. 2017, 12(8): e0183187, 15 pages.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Vickers, et al., Development of a Quantitative BRET Affinity Assay for Nucleic Acid-protein Interactions, PLoS One, vol. 11, No. 8, p. e0161930, pp. 1-17, Aug. 29, 2016.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Whitehead et al., Degradable Lipid Nanoparticles with Predictable in Vivo siRNA Delivery Activity, Nature Communications, vol. 5, pp. 1-10, Jun. 27, 2014.
Wickstrom, Oligodeoxynucleotide Stability in Subcellular Extracts and Culture Media, Journal of Biochemical and Biophysical Methods, vol. 13, Issue 2, pp. 97-102, Sep. 1986.
Yamana, et al., 2'-Pyrene Modified Oligonucleotide Provides a Highly Sensitive Fluorescent Probe of RNA, Nucleic Acids Research, 1999, 27(11): 2387-2392.
Yekta, et al., MicroRNA-Directed Cleavage of HOXB8 mRNA, Science, Apr. 23, 2004, 304(5670): 594-596.
Zamore, et al., Ancient Pathways Programmed by Small RNAs, Science, May 17, 2002, 296(5571): 1265-1269.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Zlatev, et al., Reversal of siRNA-mediated Gene Silencing in Vivo, Nature Biotechnology, vol. 36, No. 6, pp. 509-511, 2018.
Bertram et al., "Vinylphosphonate Internucleotide Linkages Inhibit the Activity of PcrA DNA Helicase", Biochemistry, Jun. 18, 2002, 41(24): 7725-7731.
Extended Supplementary European Search Report for European Patent Application No. 20777915.8, mailed Sep. 15, 2023.
Flower et al., MSH3 Modifies Somatic instability and Disease Severity in Huntington's and Myotonic Dystrophy Type 1, Brain, A Journal of Neurology, Jul. 2019, 142(7): 1876-1886.

(56) References Cited

OTHER PUBLICATIONS

Ghosh et al., "Comparing 2-nt 3' overhangs against blunt-ended siRNAs: a systems biology based study", BMC Genomics, 2009, 10(Suppl. 1):S17.
Harlow et al., "Antibodies: A Laboratory Manual", Cold Spring Harbor Laboratory Chapter 14, Second Edition, 2013.
International Search Report & Written Opinion Received for PCT Application No. PCT/US2021/028166, mailed on Nov. 26, 2021.
International Search Report & Written Opinion Received for PCT Application No. PCT/US2021/044158, dated Jan. 31, 2022.
International Search Report & Written Opinion Received for PCT Application No. PCT/US2022/039047, dated Mar. 3, 2023.
Khorev et al., Trivalent, Gal//GalNAc-containing ligands designed for the asialoglycoprotein receptor, Bioorgan. & Medicin. Chem., 2008, 16: 5216-5231.
Lee et al., A Novel Approach to Investigate Tissue-specific Trinucleotide Repeat Instability, BMC Systems Biology, Mar. 19, 2010, 4(29): 1-16.
Lee et al., Adeno-associated virus (AAV) vectors: Rational design strategies for capsid engineering, Current Opinion in Biomed. Eng., 2018, 58-63.
Miller et al., Adaptable Synthesis of C-Glycosidic Multivalent Carbohydrates and Succinamide-Linked Derivization, Org. Letter., 2010, 12(22): 5262-5265.
Moss et al., Identification of Genetic Variants Associated with Huntington's Disease Progression: A Genome-wide Association Study, The Lancet, Neurology, Sep. 2017, 16(9): 701-711.
Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.
Old et al., "Cloning in Yeast and Microbial Eukaryotes", Principles of Gene Manipulation: An Introduction to Genetic Engineering, Studies in Microbiology, 1989, 2(11): 199-221.
Østergaard et al., "Conjugation of hydrophobic moieties enhances potency of antisense oligonucleotides in the muscle of rodents and non-human primates", Nucleic Acids Research, 2019, 47(12): 6045-6058.
Partial Supplementary European Search Report for European Patent Application No. 20852443.9, mailed Aug. 25, 2023.
Partial Supplementary European Search Report for European Patent Application No. 20856904.6, mailed Sep. 13, 2023.
Supplementary European Search Report for European Patent Application No. 20856904.6, mailed Jan. 2, 2024.
Tome et al., MSH3 Polymorphisms and Protein Levels Affect CAG Repeat Instability in Huntington's Disease Mice, PLOS Genetics, Feb. 28, 2013, 9(2): el003280, 1-16.
Zeng et al., "RNA Interference in human cells is restricted to the cytoplasm", RNA, Jul. 1, 2002, 8(7): 855-860.

\* cited by examiner

FIG. 9
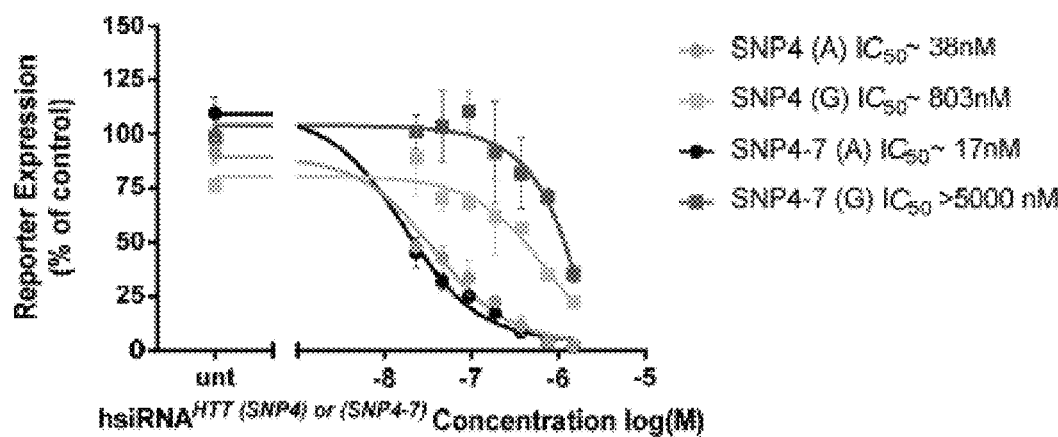
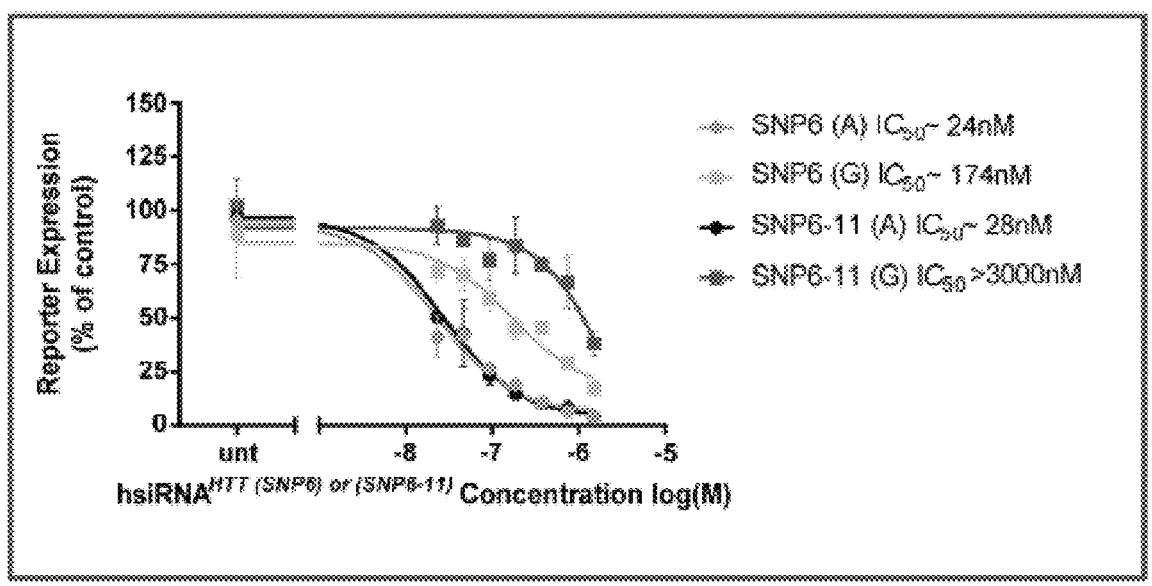

FIG. 10
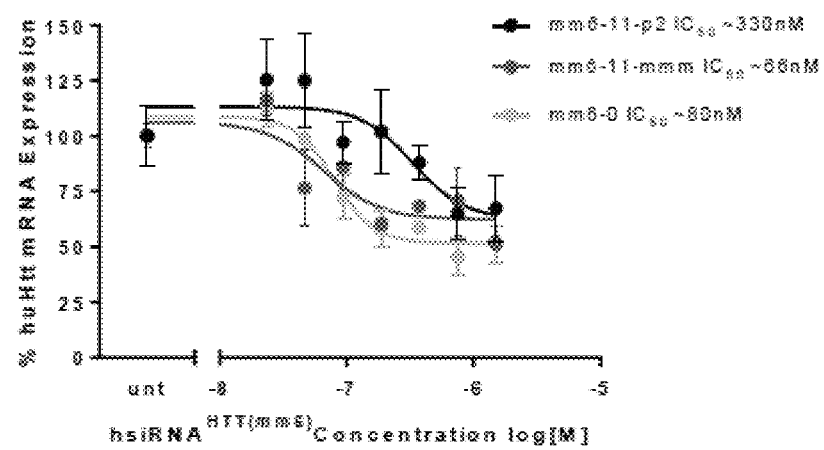
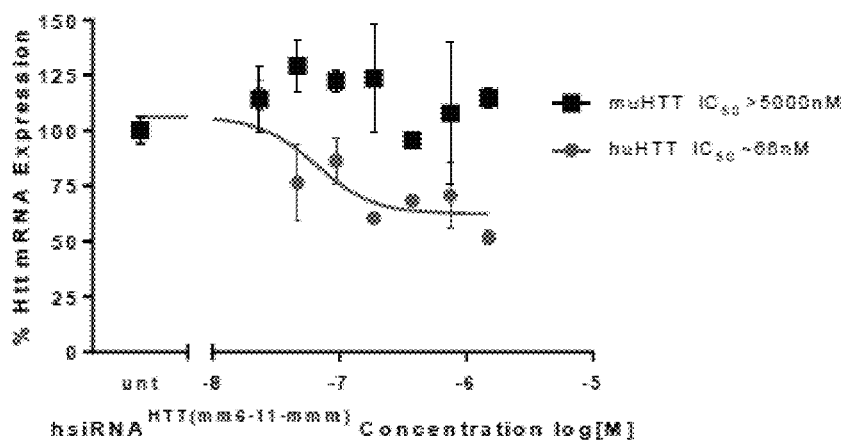

FIG. 12A

| mm2-3G | P(mU)#(fU)#(mG)(fG)(mC)(fA)(mG)(fC)(mA)(fG)(mC)(fU)(mU)#(C)#(mU)#(C)#(mG)#(fU)#(mG)#(fG) |
|---|---|
| mm2-3U | P(mU)#(fU)#(mU)(fG)(mC)(fA)(mG)(fC)(mA)(fG)(mC)(fU)(mU)#(C)#(mU)#(C)#(mG)#(fU)#(mG)#(fG) |
| mm2-3C | P(mU)#(fU)#(mC)(fG)(mC)(fA)(mG)(fC)(mA)(fG)(mC)(fU)(mU)#(C)#(mU)#(C)#(mG)#(fU)#(mG)#(fG) |
| mm2-4 | P(mU)#(fU)#(mA)(fU)(mC)(fA)(mG)(fC)(mA)(fG)(mC)(fU)(mU)#(C)#(mU)#(C)#(mG)#(fU)#(mG)#(fG) |
| mm2-5 | P(mU)#(fU)#(mA)(fG)(mU)(fA)(mG)(fC)(mA)(fG)(mC)(fU)(mU)#(C)#(mU)#(C)#(mG)#(fU)#(mG)#(fG) |
| mm2-6 | P(mU)#(fU)#(mA)(fG)(mC)(fU)(mG)(fC)(mA)(fG)(mC)(fU)(mU)#(C)#(mU)#(C)#(mG)#(fU)#(mG)#(fG) |
| mm2-7 | P(mU)#(fU)#(mA)(fG)(mC)(fA)(mU)(fC)(mA)(fG)(mC)(fU)(mU)#(C)#(mU)#(C)#(mG)#(fU)#(mG)#(fG) |
| mm2-8 | P(mU)#(fU)#(mA)(fG)(mC)(fA)(mG)(fU)(mA)(fG)(mC)(fU)(mU)#(C)#(mU)#(C)#(mG)#(fU)#(mG)#(fG) |
| mm2-9 | P(mU)#(fU)#(mA)(fG)(mC)(fA)(mG)(fC)(mU)(fG)(mC)(fU)(mU)#(C)#(mU)#(C)#(mG)#(fU)#(mG)#(fG) |
| mm2-10 | P(mU)#(fU)#(mA)(fG)(mC)(fA)(mG)(fC)(mA)(fU)(mC)(fU)(mU)#(C)#(mU)#(C)#(mG)#(fU)#(mG)#(fG) |
| mm2-11 | P(mU)#(fU)#(mA)(fG)(mC)(fA)(mG)(fC)(mA)(fG)(mU)(fU)(mU)#(C)#(mU)#(C)#(mG)#(fU)#(mG)#(fG) |
| mm2-12 | P(mU)#(fU)#(mA)(fG)(mC)(fA)(mG)(fC)(mA)(fG)(mC)(fA)(mU)#(C)#(mU)#(C)#(mG)#(fU)#(mG)#(fG) |
| mm2-13 | P(mU)#(fU)#(mA)(fG)(mC)(fA)(mG)(fC)(mA)(fG)(mC)(fU)(mA)#(C)#(mU)#(C)#(mG)#(fU)#(mG)#(fG) |
| mm2-14 | P(mU)#(fU)#(mA)(fG)(mC)(fA)(mG)(fC)(mA)(fG)(mC)(fU)(mU)#(U)#(mU)#(C)#(mG)#(fU)#(mG)#(fG) |
| mm2-15 | P(mU)#(fU)#(mA)(fG)(mC)(fA)(mG)(fC)(mA)(fG)(mC)(fU)(mU)#(C)#(mA)#(C)#(mG)#(fU)#(mG)#(fG) |
| mm2-16 | P(mU)#(fU)#(mA)(fG)(mC)(fA)(mG)(fC)(mA)(fG)(mC)(fU)(mU)#(C)#(mU)#(U)#(mG)#(fU)#(mG)#(fG) |

FIG. 12B

| mm4-2 | P(mU)#(fA)#(mG)(fU)(mA)(fG)(mC)(fA)(mG)(fC)(mA)(fG)(mC)(fU)#(mU)#(fC)#(mU)#(fC)#(mG)#(fU) |
|---|---|
| mm4-3U | P(mU)#(fU)#(mU)(fU)(mA)(fG)(mC)(fA)(mG)(fC)(mA)(fG)(mC)#(fU)#(mU)#(fC)#(mU)#(fC)#(mG)#(fU) |
| mm4-3A | P(mU)#(fU)#(mA)(fU)(mA)(fG)(mC)(fA)(mG)(fC)(mA)(fG)(mC)#(fU)#(mU)#(fC)#(mU)#(fC)#(mG)#(fU) |
| mm4-5C | P(mU)#(fU)#(mG)(fU)(mC)(fG)(mC)(fA)(mG)(fC)(mA)(fG)(mC)#(fU)#(mU)#(fC)#(mU)#(fC)#(mG)#(fU) |
| mm4-5G | P(mU)#(fU)#(mG)(fU)(mG)(fG)(mC)(fA)(mG)(fC)(mA)(fG)(mC)#(fU)#(mU)#(fC)#(mU)#(fC)#(mG)#(fU) |
| mm4-6 | P(mU)#(fU)#(mG)(fU)(mA)(fU)(mC)(fA)(mG)(fC)(mA)(fG)(mC)#(fU)#(mU)#(fC)#(mU)#(fC)#(mG)#(fU) |
| mm4-7 | P(mU)#(fU)#(mG)(fU)(mA)(fG)(mU)(fA)(mG)(fC)(mA)(fG)(mC)#(fU)#(mU)#(fC)#(mU)#(fC)#(mG)#(fU) |
| mm4-8 | P(mU)#(fU)#(mG)(fU)(mA)(fG)(mC)(fU)(mG)(fC)(mA)(fG)(mC)#(fU)#(mU)#(fC)#(mU)#(fC)#(mG)#(fU) |
| mm4-9 | P(mU)#(fU)#(mG)(fU)(mA)(fG)(mC)(fA)(mU)(fC)(mA)(fG)(mC)#(fU)#(mU)#(fC)#(mU)#(fC)#(mG)#(fU) |
| mm4-10 | P(mU)#(fU)#(mG)(fU)(mA)(fG)(mC)(fA)(mG)(fU)(mA)(fG)(mC)#(fU)#(mU)#(fC)#(mU)#(fC)#(mG)#(fU) |
| mm4-11 | P(mU)#(fU)#(mG)(fU)(mA)(fG)(mC)(fA)(mG)(fC)(mU)(fG)(mC)#(fU)#(mU)#(fC)#(mU)#(fC)#(mG)#(fU) |
| mm4-12 | P(mU)#(fU)#(mG)(fU)(mA)(fG)(mC)(fA)(mG)(fC)(mA)(fU)(mC)#(fU)#(mU)#(fC)#(mU)#(fC)#(mG)#(fU) |
| mm4-13 | P(mU)#(fU)#(mG)(fU)(mA)(fG)(mC)(fA)(mG)(fC)(mA)(fG)(mU)#(fU)#(mU)#(fC)#(mU)#(fC)#(mG)#(fU) |
| mm4-14 | P(mU)#(fU)#(mG)(fU)(mA)(fG)(mC)(fA)(mG)(fC)(mA)(fG)(mC)#(fA)#(mU)#(fC)#(mU)#(fC)#(mG)#(fU) |
| mm4-15 | P(mU)#(fU)#(mG)(fU)(mA)(fG)(mC)(fA)(mG)(fC)(mA)(fG)(mC)#(fU)#(mA)#(fC)#(mU)#(fC)#(mG)#(fU) |
| mm4-16 | P(mU)#(fU)#(mG)(fU)(mA)(fG)(mC)(fA)(mG)(fC)(mA)(fG)(mC)#(fU)#(mU)#(fU)#(mU)#(fC)#(mG)#(fU) |

FIG. 12C

| mm6-2 | P(mU)#(mA)#(mC)(fU)(mG)(fU)(mA)(fG)(mC)(fA)(mG)(fC)(mA)#(fG)#(mC)#(fU)#(mU)#(fC)#(mU)#(fC) |
|---|---|
| mm6-3 | P(mU)#(fU)#(mU)(fU)(mG)(fU)(mA)(fG)(mC)(fA)(mG)(fC)(mA)#(fG)#(mC)#(fU)#(mU)#(fC)#(mU)#(fC) |
| mm6-4 | P(mU)#(fU)#(mC)(fA)(mG)(fU)(mA)(fG)(mC)(fA)(mG)(fC)(mA)#(fG)#(mC)#(fU)#(mU)#(fC)#(mU)#(fC) |
| mm6-5U | P(mU)#(fU)#(mC)(fU)(mU)(fU)(mA)(fG)(mC)(fA)(mG)(fC)(mA)#(fG)#(mC)#(fU)#(mU)#(fC)#(mU)#(fC) |
| mm6-5A | P(mU)#(fU)#(mC)(fU)(mA)(fU)(mA)(fG)(mC)(fA)(mG)(fC)(mA)#(fG)#(mC)#(fU)#(mU)#(fC)#(mU)#(fC) |
| mm6-7C | P(mU)#(fU)#(mC)(fU)(mG)(fU)(mC)(fG)(mC)(fA)(mG)(fC)(mA)#(fG)#(mC)#(fU)#(mU)#(fC)#(mU)#(fC) |
| mm6-7G | P(mU)#(fU)#(mC)(fU)(mG)(fU)(mG)(fG)(mC)(fA)(mG)(fC)(mA)#(fG)#(mC)#(fU)#(mU)#(fC)#(mU)#(fC) |
| mm6-8 | P(mU)#(fU)#(mC)(fU)(mG)(fU)(mA)(fU)(mC)(fA)(mG)(fC)(mA)#(fG)#(mC)#(fU)#(mU)#(fC)#(mU)#(fC) |
| mm6-9 | P(mU)#(fU)#(mC)(fU)(mG)(fU)(mA)(fG)(mU)(fA)(mG)(fC)(mA)#(fG)#(mC)#(fU)#(mU)#(fC)#(mU)#(fC) |
| mm6-10 | P(mU)#(fU)#(mC)(fU)(mG)(fU)(mA)(fG)(mC)(fU)(mG)(fC)(mA)#(fG)#(mC)#(fU)#(mU)#(fC)#(mU)#(fC) |
| mm6-11 | P(mU)#(fU)#(mC)(fU)(mG)(fU)(mA)(fG)(mC)(fA)(mU)(fC)(mA)#(fG)#(mC)#(fU)#(mU)#(fC)#(mU)#(fC) |
| mm6-12 | P(mU)#(fU)#(mC)(fU)(mG)(fU)(mA)(fG)(mC)(fA)(mG)(fU)(mA)#(fG)#(mC)#(fU)#(mU)#(fC)#(mU)#(fC) |
| mm6-13 | P(mU)#(fU)#(mC)(fU)(mG)(fU)(mA)(fG)(mC)(fA)(mG)(fC)(mU)#(fG)#(mC)#(fU)#(mU)#(fC)#(mU)#(fC) |
| mm6-14 | P(mU)#(fU)#(mC)(fU)(mG)(fU)(mA)(fG)(mC)(fA)(mG)(fC)(mA)#(fU)#(mC)#(fU)#(mU)#(fC)#(mU)#(fC) |
| mm6-15 | P(mU)#(fU)#(mC)(fU)(mG)(fU)(mA)(fG)(mC)(fA)(mG)(fC)(mA)#(fG)#(mU)#(fU)#(mU)#(fC)#(mU)#(fC) |
| mm6-16 | P(mU)#(fU)#(mC)(fU)(mG)(fU)(mA)(fG)(mC)(fA)(mG)(fC)(mA)#(fG)#(mC)#(fA)#(mU)#(fC)#(mU)#(fC) |

FIG. 13

| description of hsiRNA | | | sequence/modification pattern | |
|---|---|---|---|---|
| compound name | snp position | additional mismatch position | antisense strand | sense strand |
| mm2-7 | 2 | 7 | [illegible sequence] | [illegible sequence] |
| mm4-7 | 4 | 7 | [illegible sequence] | [illegible sequence] |
| mm4-8 | 4 | 8 | [illegible sequence] | [illegible sequence] |
| mm4-15 | 4 | 15 | [illegible sequence] | [illegible sequence] |
| mm6-5A | 6 | 5 | [illegible sequence] | [illegible sequence] |
| mm6-8 | 6 | 8 | [illegible sequence] | [illegible sequence] |
| mm6-11 | 6 | 11 | [illegible sequence] | [illegible sequence] |
| mm6-14 | 6 | 14 | [illegible sequence] | [illegible sequence] |
| mm6-16 | 6 | 16 | [illegible sequence] | [illegible sequence] | red = SNP position
blue = additional mismatch position

Vinyl phosphonate walk on Guide strand

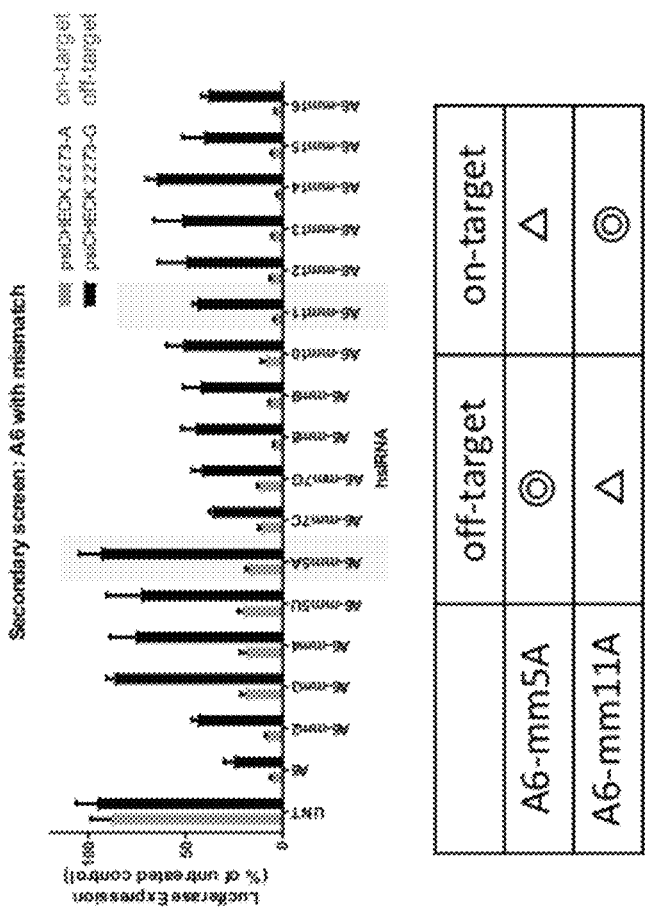
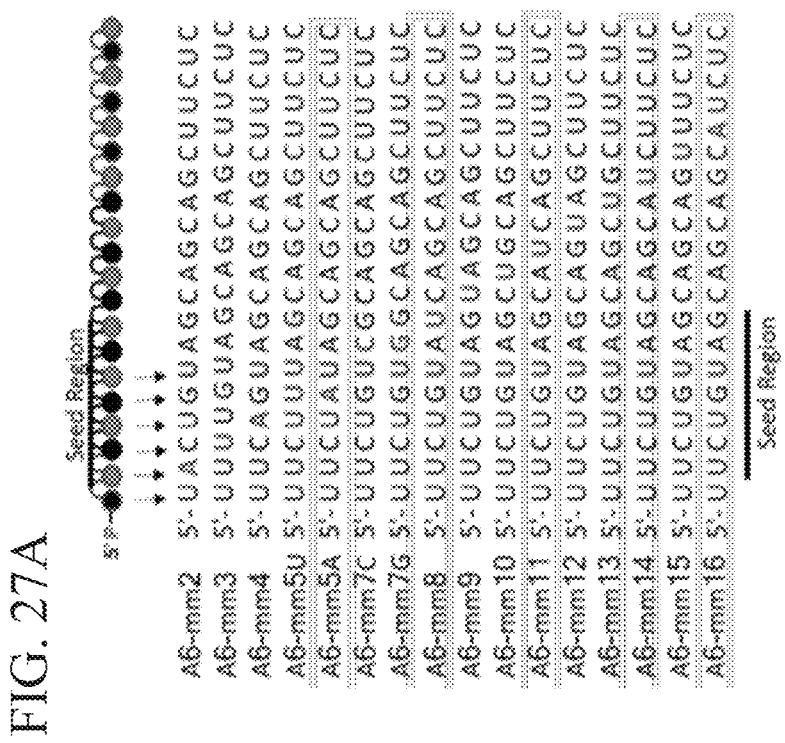
FIG. 27A

Where X is (C)n or (CO)n or (COC)n or (CONH)n or mixture of therein
Where Y is (C)n or (CO)n or (COC)n or (CONH)n or mixture of therein or spacer or divider, cleavable or not
Where W is a bioactive conjugate (right)

FIG. 38
Linkers and Spacers
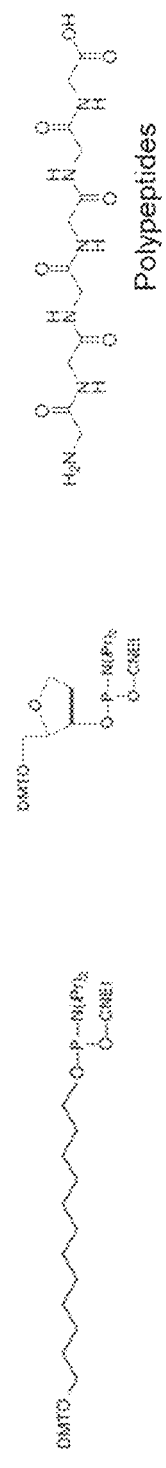
Branching Moieties
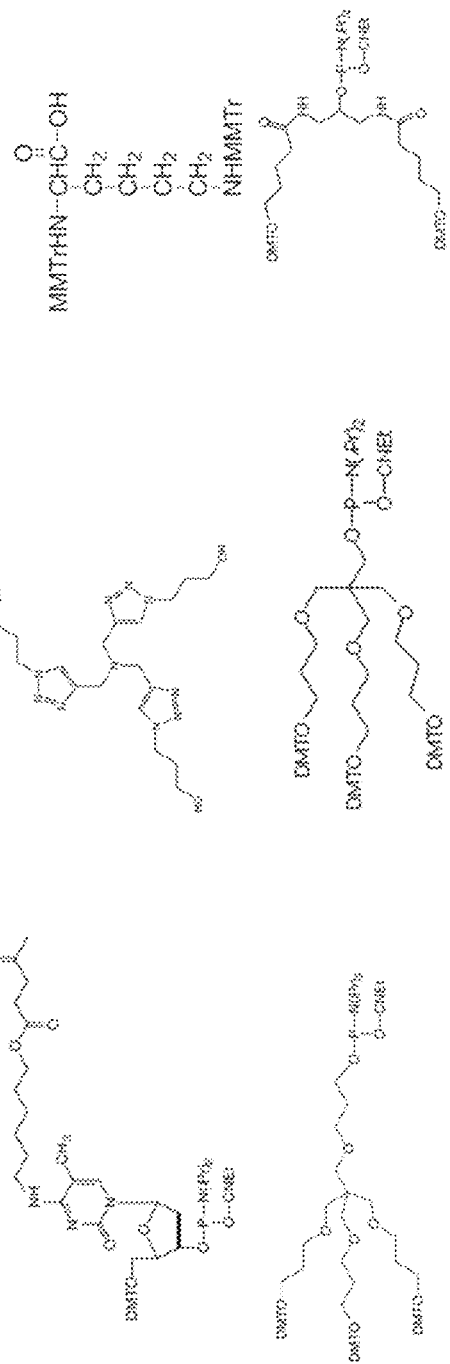

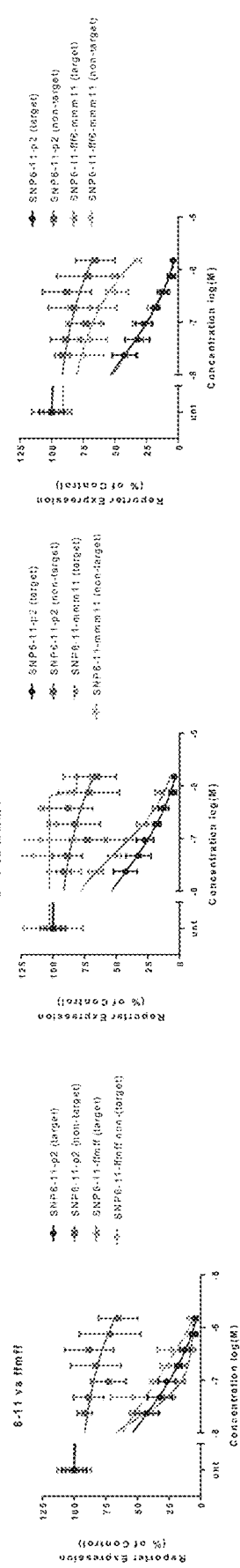

MODIFIED OLIGONUCLEOTIDES TARGETING SNPS

RELATED APPLICATIONS

This application claims priority to U.S. Provisional Patent Application No. 62/885,066 filed Aug. 9, 2019, and U.S. Provisional Patent Application No. 62/976,168 filed Feb. 13, 2020. The entire contents of these applications are incorporated herein by reference.

STATEMENT OF FEDERALLY SPONSORED RESEARCH

This invention was made with government support under Grant Nos. NS104022 and GM108803 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 19, 2021, is named 708008_UM9-227CIP_SL.txt and is 90,782 bytes in size.

BACKGROUND

RNA interference represents a simple and effective tool for inhibiting the function of genes. RNA silencing agents have received particular interest as research tools and therapeutic agents for their ability to knock down expression of a particular protein with a high degree of sequence specificity. The sequence specificity of RNA silencing agents is particularly useful for the treatment of diseases caused by dominant mutations in heterozygotes bearing one mutant and one wild-type copy of a particular gene. However, there remains a need for RNA silencing agents that can preferentially silence mutant, disease-causing allele expression while not (or only minimally) effecting expression of the wild-type allele.

SUMMARY

The present disclosure is based, at least in part, on the surprising discovery of novel oligonucleotides that enhance silencing of the expression of a gene containing a single nucleotide polymorphism (SNP) (e.g., a heterozygous SNP) relative to the expression of the corresponding wild-type gene in a heterozygote, e.g., by up to more than 100-fold. In certain aspects, an oligonucleotide (e.g., a dsRNA) is provided that preferentially targets a SNP-containing nucleic acid for degradation, wherein the oligonucleotide (e.g., a double-stranded RNA (dsRNA)) does not target, or targets to a lesser degree, the corresponding wild-type (non-SNP-containing) nucleic acid for degradation. In certain aspects, an oligonucleotide (e.g., a dsRNA) of the disclosure is: 1) complementary to a SNP position in a target nucleic acid; and 2) contains a mismatch at a particular position of the target nucleic acid relative to the SNP. In certain embodiments, an oligonucleotide (e.g., a dsRNA) contains two mismatches relative to the corresponding wild-type target nucleic acid sequence: 1) at the wild-type SNP position; and 2) at the particular position of the target nucleic acid sequence relative to the wild-type SNP position. Accordingly, an exemplary oligonucleotide (e.g., dsRNA) contains one mismatch relative to a SNP-containing target and two mismatches relative to the corresponding wild-type sequence, thus resulting in preferential cleavage of the SNP-containing target relative to the corresponding wild-type sequence.

In one aspect, a nucleic acid having a 5' end, a 3' end and a seed region, that is complementary to a region of a gene comprising an allelic polymorphism, wherein the nucleic acid comprises a single nucleotide polymorphism (SNP) position nucleotide at a position within the seed region, wherein the SNP position nucleotide is complementary to the allelic polymorphism, a mismatch (MM) position that is a mismatch with a nucleotide in the gene, and at least one modified nucleotide (X) on either side of the SNP position nucleotide, wherein each X is located within four, three or two nucleotides from the SNP position nucleotide, is provided. In some embodiments, each X is located within four nucleotides from the SNP position nucleotide. In some embodiments, each X is located within three nucleotides from the SNP position nucleotide In some embodiments, each X is located within two nucleotides from the SNP position nucleotide.

In certain exemplary embodiments, each X independently comprises a sugar modification selected from the group consisting of 2'-O-methyl (2'-OMe), 2'-fluoro (2'-F), 2'-ribo, 2'-deoxyribo, 2'-F-4'-thioarabino (2'-F-ANA), 2'-O-(2-methoxyethyl) (2'-MOE), 4'-S-RNA, locked nucleic acid (LNA), 4'-S-F-ANA, 2'-O-allyl, 2'-O-ethylamine, 2'-O-cyanoethyl-RNA (CNet-RNA), tricyclo-DNA, cyclohexenyl nucleic acid (CeNA), arabino nucleic acid (ANA), and hexitol nucleic acid (HNA).

In certain exemplary embodiments, an X is positioned immediately 5' to the SNP position nucleotide or immediately 3' to the SNP position nucleotide. In certain exemplary embodiments, an X is positioned immediately 5' to the SNP position nucleotide and immediately 3' to the SNP position nucleotide.

In certain exemplary embodiments, the SNP position nucleotide is present at from position 2 to position 6 from the 5' end (e.g., at position 2 from the 5' end, at position 3 from the 5' end, at position 4 from the 5' end, at position 5 from the 5' end, or at position 6 from the 5' end). In certain exemplary embodiments, the SNP position nucleotide is present at from position 3 to position 6 from the 5' end (e.g., at position 3 from the 5' end, at position 4 from the 5' end, at position 5 from the 5' end, or at position 6 from the 5' end). In some embodiments, the SNP position nucleotide is present at from position 4 to position 6 from the 5' end (e.g., at position 4 from the 5' end, at position 5 from the 5' end, or at position 6 from the 5' end). In some embodiments, the SNP position nucleotide is present at from position 2 to position 5 from the 5' end (e.g., at position 2 from the 5' end, at position 3 from the 5' end, at position 4 from the 5' end, or at position 5 from the 5' end). In some embodiments, the SNP position nucleotide is present at from position 3 to position 5 from the 5' end (e.g., at position 3 from the 5' end, at position 4 from the 5' end, or at position 5 from the 5' end). In some embodiments, the SNP position nucleotide is present at from position 2 to position 4 from the 5' end (e.g., at position 2 from the 5' end, at position 3 from the 5' end, or at position 4 from the 5' end).

In some embodiments, the MM position nucleotide is located from 2 to 11 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide. In some embodiments, the MM position is located 7 nucleotides from the SNP position nucleotide. In some embodiments, the MM position is located 8 nucleotides from the SNP position nucleotide. In some embodiments, the MM position is located 9 nucleotides from the SNP position nucleotide. In some embodiments, the MM position is located 10 nucleotides from the SNP position nucleotide. In some embodiments, the MM position is located 11 nucleotides from the SNP position nucleotide.

In some embodiments, the MM position nucleotide is located from 2 to 6 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide.

In another aspect, a nucleic acid having a 5' end, a 3' end and a seed region, that is complementary to a region of a gene comprising an allelic polymorphism, wherein the nucleic acid comprises a SNP position nucleotide at a position within the seed region, wherein the SNP position nucleotide is complementary to the allelic polymorphism, a MM position that is a mismatch with a nucleotide in the gene, and at least one modified nucleotide (Y) on either side of the MM position nucleotide, wherein each Y is located within four, three or two nucleotides from the MM position nucleotide, is provided. In some embodiments, each Y is located within four nucleotides from the MM position nucleotide. In some embodiments, each Y is located within three nucleotides from the MM position nucleotide. In some embodiments, each Y is located within two nucleotides from the MM position nucleotide.

In some embodiments, each Y independently comprises a sugar modification selected from the group consisting of 2'-OMe, 2'-F, 2'-ribo, 2'-deoxyribo, 2'-F-ANA, 2'-MOE, 4'-S-RNA, LNA, 4'-S-F-ANA, 2'-O-allyl, 2'-O-ethylamine, CNet-RNA, tricyclo-DNA, CeNA, ANA, and HNA.

In some embodiments, a Y is positioned immediately 5' to the MM position nucleotide or immediately 3' to the MM position nucleotide. In certain exemplary embodiments, a Y is positioned immediately 5' to the MM position nucleotide and immediately 3' to the MM position nucleotide.

In certain exemplary embodiments, the SNP position nucleotide is present at position 2 to position 6 from the 5' end (e.g., at position 2 from the 5' end, at position 3 from the 5' end, at position 4 from the 5' end, at position 5 from the 5' end, or at position 6 from the 5' end). In some embodiments, the SNP position nucleotide is present at from position 3 to position 6 from the 5' end (e.g., at position 3 from the 5' end, at position 4 from the 5' end, at position 5 from the 5' end, or at position 6 from the 5' end). In some embodiments, the SNP position nucleotide is present at from position 4 to position 6 from the 5' end (e.g., at position 4 from the 5' end, at position 5 from the 5' end, or at position 6 from the 5' end). In some embodiments, the SNP position nucleotide is present at from position 2 to position 5 from the 5' end (e.g., at position 2 from the 5' end, at position 3 from the 5' end, at position 4 from the 5' end, or at position 5 from the 5' end). In some embodiments, the SNP position nucleotide is present at from position 3 to position 5 from the 5' end (e.g., at position 3 from the 5' end, at position 4 from the 5' end, or at position 5 from the 5' end). In some embodiments, the SNP position nucleotide is present at from position 2 to position 4 from the 5' end (e.g., at position 2 from the 5' end, at position 3 from the 5' end, or at position 4 from the 5' end).

In some embodiments, the MM position nucleotide is located from 2 to 11 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide. In some embodiments, the MM position is located 7 nucleotides from the SNP position nucleotide. In some embodiments, the MM position is located 8 nucleotides from the SNP position nucleotide. In some embodiments, the MM position is located 9 nucleotides from the SNP position nucleotide. In some embodiments, the MM position is located 10 nucleotides from the SNP position nucleotide. In some embodiments, the MM position is located 11 nucleotides from the SNP position nucleotide.

In some embodiments, the MM position nucleotide is located from 2 to 6 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide.

In another aspect, a nucleic acid having a 5' end, a 3' end and a seed region, that is complementary to a region of a gene comprising an allelic polymorphism, wherein the nucleic acid comprises a SNP position nucleotide at a position within the seed region, wherein the SNP position nucleotide is complementary to the allelic polymorphism, a MM position that is a mismatch with a nucleotide in the gene, and at least one modified nucleotide (X) on either side of the SNP position nucleotide, wherein each X is located within four, three or two nucleotides from the SNP position nucleotide, and at least one modified nucleotide (Y) on either side of the MM position nucleotide, wherein each Y is located within four, three or two nucleotides from the MM position nucleotide, is provided. In some embodiments, each X is located within four nucleotides from the SNP position nucleotide. In some embodiments, each X is located within three nucleotides from the SNP position nucleotide. In some embodiments, each X is located within two nucleotides from the SNP position nucleotide. In some embodiments, each Y is located within four nucleotides from the MM position nucleotide. In some embodiments, each Y is located within three nucleotides from the MM position nucleotide. In some embodiments, each Y is located within two nucleotides from the MM position nucleotide.

In some embodiments, each X independently comprises a sugar modification selected from the group consisting of 2'-OMe, 2'-F, 2'-ribo, 2'-deoxyribo, 2'-F-ANA, 2'-MOE, 4'-S-RNA, LNA, 4'-S-F-ANA, 2'-O-allyl, 2'-O-ethylamine, CNet-RNA, tricyclo-DNA, CeNA, ANA, and HNA. In some embodiments, each Y independently comprises a sugar modification selected from the group consisting of 2'-OMe, 2'-F, 2'-ribo, 2'-deoxyribo, 2'-F-ANA, 2'-MOE, 4'-S-RNA, LNA, 4'-S-F-ANA, 2'-O-allyl, 2'-O-ethylamine, CNet-RNA, tricyclo-DNA, CeNA, ANA, and HNA.

In certain exemplary embodiments, an X is positioned immediately 5' to the SNP position nucleotide or immediately 3' to the SNP position nucleotide. In certain exemplary embodiments, an X is positioned immediately 5' to the SNP position nucleotide and immediately 3' to the SNP position nucleotide.

In certain exemplary embodiments, a Y is positioned immediately 5' to the MM position nucleotide or immediately 3' to the MM position nucleotide. In certain exemplary embodiments, a Y is positioned immediately 5' to the MM position nucleotide and immediately 3' to the MM position nucleotide.

In certain exemplary embodiments, the SNP position nucleotide is present from position 2 to position 6 from the 5' end (e.g., at position 2 from the 5' end, at position 3 from the 5' end, at position 4 from the 5' end, at position 5 from the 5' end, or at position 6 from the 5' end). In some embodiments, the SNP position nucleotide is present at from position 3 to position 6 from the 5' end (e.g., at position 3 from the 5' end, at position 4 from the 5' end, at position 5 from the 5' end, or at position 6 from the 5' end). In some embodiments, the SNP position nucleotide is present at from position 4 to position 6 from the 5' end (e.g., at position 4 from the 5' end, at position 5 from the 5' end, or at position 6 from the 5' end). In some embodiments, the SNP position nucleotide is present at from position 2 to position 5 from the 5' end (e.g., at position 2 from the 5' end, at position 3 from the 5' end, at position 4 from the 5' end, or at position 5 from the 5' end). In some embodiments, the SNP position nucleotide is present at from position 3 to position 5 from the 5' end (e.g., at position 3 from the 5' end, at position 4 from the 5' end, or at position 5 from the 5' end). In some embodiments, the SNP position nucleotide is present at from position 2 to position 4 from the 5' end (e.g., at position 2 from the 5' end, at position 3 from the 5' end, or at position 4 from the 5' end).

In some embodiments, the MM position nucleotide is located from 2 to 11 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide. In some embodiments, the MM position is located 7 nucleotides from the SNP position nucleotide. In some embodiments, the MM position is located 8 nucleotides from the SNP position nucleotide. In some embodiments, the MM position is located 9 nucleotides from the SNP position nucleotide. In some embodiments, the MM position is located 10 nucleotides from the SNP position nucleotide. In some embodiments, the MM position is located 11 nucleotides from the SNP position nucleotide.

embodiments, the MM position nucleotide is located from 2 to 6 nucleotides from the SNP position nucleotide. For example, in some embodiments, the MM position is located 2 nucleotides from the SNP position nucleotide. In some embodiments, the MM position is located 3 nucleotides from the SNP position nucleotide. In some embodiments, the MM position is located 4 nucleotides from the SNP position nucleotide. In some embodiments, the MM position is located 5 nucleotides from the SNP position nucleotide. In some embodiments, the MM position is located 6 nucleotides from the SNP position nucleotide.

In some embodiments, X and Y are the same.

In another aspect, a nucleic acid having a 5' end and a 3' end that is complementary to a region of a gene comprising an allelic polymorphism, wherein the nucleic acid comprises a SNP position nucleotide that is complementary to the allelic polymorphism, a MM position nucleotide that is a mismatch with a nucleotide in the gene, at least one 2'-fluoro-ribonucleotide on either side of the SNP position nucleotide, wherein each 2'-fluoro-ribonucleotide is located within four, three or two nucleotides from the SNP position nucleotide, and at least one 2'-methoxy-ribonucleotide on either side of the MM position nucleotide, wherein each 2'-methoxy-ribonucleotide is located within four, three or two nucleotides from the MM position nucleotide, is provided.

In certain exemplary embodiments, a 2'-fluoro-ribonucleotide is positioned immediately 5' to the SNP position nucleotide or a 2'-fluoro-ribonucleotide is positioned immediately 3' to the SNP position nucleotide.

In certain exemplary embodiments, a 2'-fluoro-ribonucleotide is positioned immediately 5' to the SNP position nucleotide and a 2'-fluoro-ribonucleotide is positioned immediately 3' to the SNP position nucleotide.

In certain exemplary embodiments, a 2'-methoxy-ribonucleotide is positioned immediately 5' to the MM position nucleotide or a 2'-methoxy-ribonucleotide is positioned immediately 3' to the MM position nucleotide. In certain exemplary embodiments, a 2'-methoxy-ribonucleotide is positioned immediately 5' to the MM position nucleotide and a 2'-methoxy-ribonucleotide is positioned immediately 3' to the MM position nucleotide.

In certain exemplary embodiments, the SNP position nucleotide is present in a seed region, and the MM position nucleotide is located from 2 to 11 nucleotides from the SNP position nucleotide (e.g., 2 nucleotides from the SNP position nucleotide, 3 nucleotides from the SNP position nucleotide, 4 nucleotides from the SNP position nucleotide, 5 nucleotides from the SNP position nucleotide, 6 nucleotides from the SNP position nucleotide, 7 nucleotides from the SNP position nucleotide, 8 nucleotides from the SNP position nucleotide, 9 nucleotides from the SNP position nucleotide, 10 nucleotides from the SNP position nucleotide, or 11 nucleotides from the SNP position nucleotide).

In certain exemplary embodiments, the SNP position nucleotide is present from position 2 to position 6 from the 5' end, and the MM position nucleotide is located 2-6 nucleotides from the SNP position nucleotide.

In certain exemplary embodiments, the nucleic acid comprises three, four, five or six 2'-fluoro-ribonucleotides. In certain exemplary embodiments, the nucleic acid comprises three, four, five or six 2'-methoxy-ribonucleotides.

In another aspect, a nucleic acid having a 5' end and a 3' end that is complementary to a region of a gene comprising an allelic polymorphism, wherein the nucleic acid comprises a SNP position nucleotide that is complementary to the allelic polymorphism, a MM position nucleotide that is a mismatch with a nucleotide in the gene, at least three 2'-fluoro-ribonucleotides located within four, three or two nucleotides from the SNP position nucleotide, and at least three 2'-methoxy-ribonucleotides located within four, three or two nucleotides from the MM position nucleotide, is provided.

In certain exemplary embodiments, a 2'-fluoro-ribonucleotide is positioned immediately 5' to the SNP position nucleotide or a 2'-fluoro-ribonucleotide is positioned immediately 3' to the SNP position nucleotide. In certain exemplary embodiments, a 2'-fluoro-ribonucleotide is positioned immediately 5' to the SNP position nucleotide and a 2'-fluoro-ribonucleotide is positioned immediately 3' to the SNP position nucleotide.

In certain exemplary embodiments, a 2'-methoxy-ribonucleotide is positioned immediately 5' to the MM position nucleotide or a 2'-methoxy-ribonucleotide is positioned immediately 3' to the MM position nucleotide.

In certain exemplary embodiments, a 2'-methoxy-ribonucleotide is positioned immediately 5' to the MM position nucleotide and a 2'-methoxy-ribonucleotide is positioned immediately 3' to the MM position nucleotide.

In certain exemplary embodiments, the SNP position nucleotide is present in a seed region, and the MM position nucleotide is located 2-11 nucleotides from the SNP position nucleotide.

In certain exemplary embodiments, the SNP position nucleotide is present from position 2 to position 6 from the 5' end, and wherein the MM position nucleotide is located 2-6 nucleotides from the SNP position nucleotide.

In a further aspect, an siRNA molecule comprises a sense strand having complementarity to a target gene and an antisense strand having complementarity to the sense strand, wherein the antisense strand comprises the nucleic acid of any one of the foregoing aspects or embodiments, is provided.

In some embodiments, the sense strand has a length of from 13 nucleotides or nucleotide analogs to 17 nucleotides or nucleotide analogs (e.g., a length of 13, 14, 15, 16, or 17 nucleotides or nucleotide analogs).

In some embodiments, the antisense strand has a length of from 18 nucleotides or nucleotide analogs to 22 nucleotides or nucleotide analogs (e.g., a length of 18, 19, 20, 21, or 22 nucleotides or nucleotide analogs).

In some embodiments, the sense strand has a length of 15 nucleotides or nucleotide analogs and the antisense strand has a length of 20 nucleotides or nucleotide analogs.

In some embodiments, the sense strand has a length of 16 nucleotides or nucleotide analogs and the antisense strand has a length of 20 nucleotides or nucleotide analogs.

In a further aspect, a branched oligonucleotide comprising two or more siRNA molecules covalently bound to one another, wherein each siRNA molecule is, independently, an siRNA molecule of any one of the preceding aspects or embodiments, is provided.

In some embodiments, the branched oligonucleotide comprises two of the siRNA molecules covalently bound to one another.

In some embodiments, the siRNA molecules are covalently bound to one another by way of a linker.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 1 discloses SEQ ID NOS 265-268, respectively, in order of appearance.

FIG. 9 depicts dose response curves comparing silencing effects of SNP4 or SNP6 hsiRNAs with an additional mismatch (SNP4-7 and SNP6-11, respectively), compared to the same hsiRNAs without an additional mismatch (SNP4-0 and SNP4-11). HeLa cells transfected with one of two reporter plasmids were revers transfected with hsiRNAs by passive uptake, and treated for 72 hours. reporter expression was measured with a dual luciferase assay.

FIG. 10 depicts dose response curves of htt mRNA expression that measures silencing efficacy of hsiRNAs with additional mismatches.

FIG. 12A-FIG. 12C depict the SNP2, SNP4 and SNP6 hsiRNA libraries, respectively. Antisense strands are depicted 5' to 3', with the SNP site in red and the mismatch in blue. FIG. 12A discloses SEQ ID NOS 269-284, respectively, in order of appearance. FIG. 12B discloses SEQ ID NOS 285-300, respectively, in order of appearance. FIG. 12C discloses SEQ ID NOS 301-316, respectively, in order of appearance.

FIG. 13 depicts antisense and sense strand sequences and modification patterns for various hsiRNA constructs according to certain embodiments. mm4-7 and mm6-11 demonstrated superior SNP discrimination, and were selected for further screening. FIG. 13 discloses SEQ ID NOS 317, 291-292, 299, 305, 308, 311, 314, 316, 318, 319, 319, 319, 320, 320, 320, 320 and 320, respectively, in order of columns.

FIG. 14 discloses SEQ ID NOS 321-322 and 321-322, respectively, in order of appearance.

FIG. 15 depicts backbone linkages according to certain exemplary embodiments. Oligonucleotide backbones may comprise one or any combination of phosphates, phosphorothioates (a racemic mixture or stereospecific), diphosphorothioates, phosphoramidates, peptide nucleic acids (PNAs), boranophosphates, 2'-5'-phosphodiesters, amides, phosphonoacetates, morpholinos and the like FIG. 16 depicts sugar modifications according to certain exemplary embodiments. Sugar modifications include one or any combination of 2'-O-methyl, 2'-fluoro, 2'-ribo, 2'-deoxyribo, 2'-F-ANA, MOE, 4'-S-RNA, LNA, 4'-S-F-ANA, 2'-O-allyl, 2'-O-ethylamine, CNet-RNA, tricyclo-DNA, CeNA, ANA, HNA and the like.

FIG. 18 depicts 5' stabilization modifications according to certain exemplary embodiments. A suitable 5' stabilization modification can be a phosphate, no phosphate, a vinyl phosphonate, a C5-methyl (R or S or racemic), a C5-methyl on vinyl, reduced vinyl (e.g., three carbon alkyl) or the like.

FIG. 19 depicts conjugates moieties according to certain exemplary embodiments. A suitable conjugated moiety can be any length alkyl chain, a vitamin, a ligand, a peptide or a bioactive conjugate, e.g., a glycosphingolipid, a polyunsaturated fatty acid, a secosteroid, a steroid hormone, a steroid lipid, or the like.

FIG. 24 discloses SEQ ID NOS 323-342, respectively, in order of appearance.

FIGS. 27A and 27B illustrate the effect of adding a mismatch in the siRNA sequence improves allelic discrimination without impairing the silencing of the mutant allele. FIG. 27A discloses SEQ ID NOS 343-346, 234, 347-348, 235, 349-350, 236, 351-352, 237, 353 and 238, respectively, in order of appearance.

FIG. 28A discloses SEQ ID NOS 354-360, respectively, in order of appearance. FIG. 28B discloses SEQ ID NOS 361-364, 355-360, respectively, in order of appearance.

FIG. 34 discloses SEQ ID NOS 343-346, 234, 348, 235, 349-350, 236, 351-352, 237, 353, 238, respectively, in order of appearance.

FIG. 35 discloses SEQ ID NOS 365, 386 and 366-373, respectively, in order of columns.

FIG. 38 shows exemplary amidite linkers, spacers and branching moieties.

FIG. 47 discloses SEQ ID NOS 374-385, respectively, in order of appearance.

FIG. 48A-FIG. 48D graphically depict efficacy and discrimination of target and non-target binding and cleavage mediated by altering the 2'-fluoro/2'-methoxy content adjacent to the SNP position nucleotide and the MM position nucleotide of an siRNA. FIG. 48A depicts results for a variety of SNP 6-11 variants. FIG. 48B depicts results for 6-11 vs. 6-11 having a modified ffmff pattern (four 2'-fluoro-ribonucleotides and a 2'-methoxy-ribonucleotide near the SNP at position 6). FIG. 48C depicts results for 6-11 vs. 6-11 having a modified mmm11 pattern (three 2'-methoxy-ribonucleotides near the MM at position 11). FIG. 48D depicts results for 6-11 vs. 6-11 having a modified fff6mmm11 pattern (three 2'-fluoro-ribonucleotides near the SNP at position 6, and three 2'-methoxy-ribonucleotides near the MM at position 11). HeLa cells were transfected with one of two reporter plasmids, were reverse-transfected with siR- NAs by passive uptake, and treated for 72 hours. Reporter expression was measured using a dual-luciferase assay.

DETAILED DESCRIPTION

Figure 1:
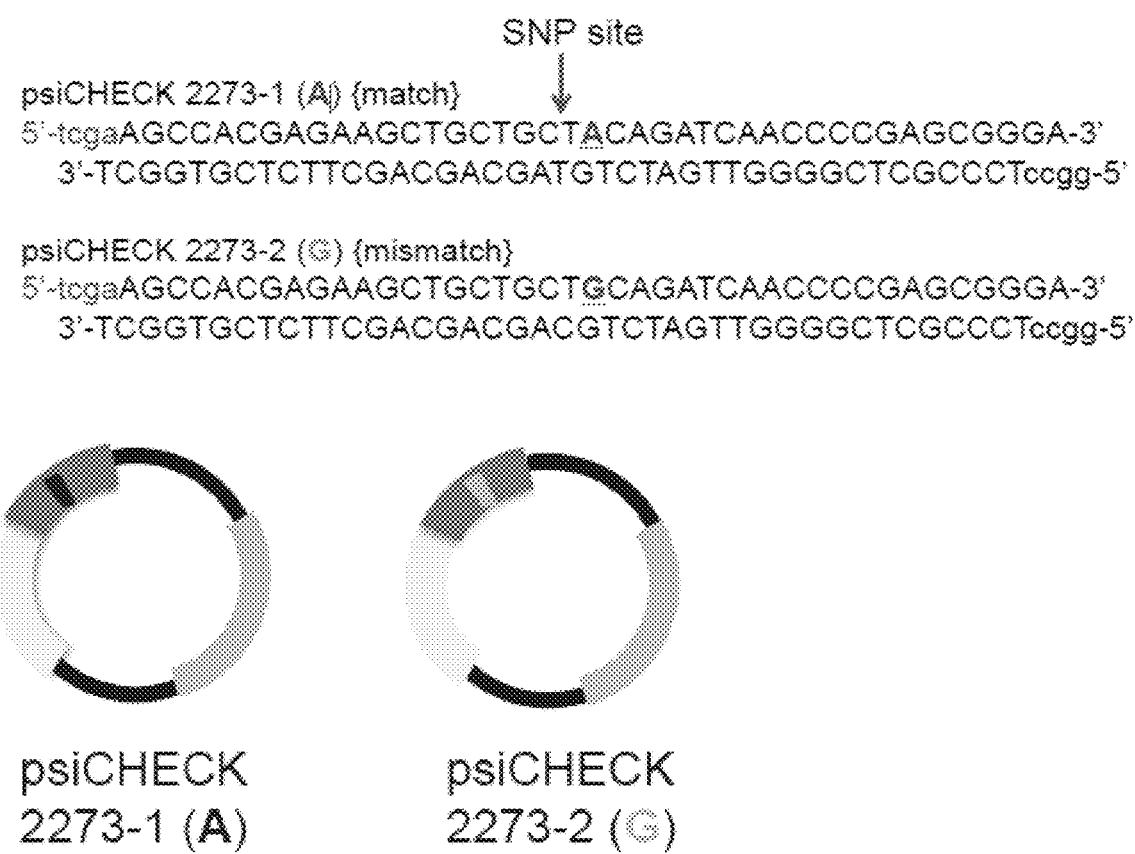
FIG. 1 depicts psiCHECK reporter plasmids containing either a wild-type region of htt or the same region of htt with the SNP, rs362273.

The present disclosure relates to compositions comprising oligonucleotide, e.g., RNA, silencing agents, e.g., RNAs such as double-stranded RNAs ("dsRNAs"), antisense oligonucleotides ("ASOs") and the like, that are useful for silencing allelic polymorphisms located within a gene encoding a mutant protein. In a particular aspect, an oligonucleotide, e.g., an RNA, silencing agent is a dsRNA agent provided herein, that destroys a corresponding mutant mRNA (e.g., a SNP-containing mRNA) with nucleotide specificity and selectivity. Oligonucleotide, e.g., RNA, silencing agents, e.g., dsRNA agents disclosed herein target mRNA corresponding to polymorphic regions of a mutant gene, resulting in cleavage of mutant mRNA, and preventing synthesis of the corresponding mutant protein e.g., a gain of function mutant protein, such as the huntingtin protein.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base adenine (e.g., cytidine or a chemically-modified derivative thereof), As used herein, the term "capping group" refers to a chemical moiety that replaces a hydrogen atom in a functional group such as an alcohol (ROH), a carboxylic acid ($RCO_2H$), or an amine ($RNH_2$). Non-limiting examples of capping groups include: alkyl (e.g., methyl, tertiary-butyl); alkenyl (e.g., vinyl, allyl); carboxyl (e.g., acetyl, benzoyl); carbamoyl; phosphate; and phosphonate (e.g., vinylphosphonate). Other suitable capping groups are known to those of skill in the art.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, and the like; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs, such as those described in Herdewijn, Antisense Nucleic Acid Drug Dev., 2000 Aug. 10(4):297-310.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages, which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. In particular embodiments, RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, exemplary oligonucleotides include, but are not limited to, siRNAs, miRNAs, shRNAs, CRISPR guides, DNA oligonucleotides, antisense oligonucleotides, AAV oligonucleotides, gapmers, mixmers, miRNA inhibitors, SSOs, PMOs, PNAs and the like.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

As used herein, the term "hsiRNA" refers to an embodiment of the double-stranded RNAs provided herein, wherein the RNA molecule is fully chemically modified, including one or more hydrophobic modifications, as described herein.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, translational repression and the like) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence, e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g., promoter or enhancer elements) of a target gene. In other embodiments, the target polynucleotide sequence is a target mRNA encoded by a target gene.

A gene "involved" in a disease or disorder includes a gene, the normal or aberrant expression or function of which effects or causes the disease or disorder or at least one symptom of said disease or disorder.

As used herein, the term "target gene" (e.g., the mutant allele of a heterozygous polymorphism, e.g., a heterozygous SNP) is a gene whose expression is to be substantially inhibited or "silenced." This silencing can be achieved by RNA silencing, e.g., by cleaving the mRNA of the target gene or translational repression of the target gene. The term "non-target gene" (e.g., the wild-type allele) is a gene whose expression is not to be substantially silenced. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., single nucleotide polymorphisms or SNPs). In another embodiment, the target and non-target genes can share less than 100% sequence identity. In another embodiment, the non-target gene may be a homolog (e.g., an ortholog or paralog) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele (e.g., the corresponding wild-type allele) whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism," as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared.

In particular embodiments, the polymorphism is a single nucleotide polymorphism (SNP). A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP, also referred to herein as a heterozygous SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In particular embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g. a SNP allele) is at least 10% (e.g., at least 15%, 20%, 25%, 30%, 35%, 40% or more) in a sample population.

The term "gain-of-function mutation," as used herein, refers to any mutation in a gene in which the protein encoded by said gene (i.e., the mutant protein) acquires a function not normally associated with the protein (i.e., the wild-type protein) causes or contributes to a disease or disorder. The gain-of-function mutation can be a deletion, addition, or substitution of a nucleotide or nucleotides in the gene, which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "gain-of-function disorder" refers to a disorder characterized by a gain-of-function mutation. In one embodiment, the gain-of-function disorder is a neurodegenerative disease caused by a gain-of-function mutation, e.g., polyglutamine disorders and/or trinucleotide repeat diseases, for example, Huntington's disease. In another embodiment, the gain-of-function disorder is caused by a gain-of-function in an oncogene, the mutated gene product being a gain-of-function mutant, e.g., cancers caused by a mutation in the ret oncogene (e.g., ret-1), for example, endocrine tumors, medullary thyroid tumors, parathyroid hormone tumors, multiple endocrine neoplasia type2, and the like. Additional exemplary gain-of-function disorders include, but are not limited to, Alzheimer's disease, amyotrophic lateral sclerosis (ALS), human immunodeficiency disorder (HIV), and slow channel congenital myasthenic syndrome (SCCMS).

The term "trinucleotide repeat diseases," as used herein, refers to any disease or disorder characterized by an expanded trinucleotide repeat region located within a gene, the expanded trinucleotide repeat region being causative of the disease or disorder. Examples of trinucleotide repeat diseases include, but are not limited to, spino-cerebellar ataxia type 12 spino-cerebellar ataxia type 8, fragile X syndrome, fragile XE Mental Retardation, Friedreich's ataxia and myotonic dystrophy. Exemplary trinucleotide repeat diseases for treatment according to the present disclosure are those characterized or caused by an expanded trinucleotide repeat region at the 5' end of the coding region of a gene, the gene encoding a mutant protein, which causes or is causative of the disease or disorder. Certain trinucleotide diseases, for example, fragile X syndrome, where the mutation is not associated with a coding region may not be suitable for treatment according to the methodologies of the present disclosure, as there is no suitable mRNA to be targeted by RNAi. By contrast, disease such as Friedreich's ataxia may be suitable for treatment according to the methodologies of this disclosure because, although the causative mutation is not within a coding region (i.e., lies within an intron), the mutation may be within, for example, an mRNA precursor (e.g., a pre-spliced mRNA precursor).

The term "polyglutamine disorder," as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include, but are not limited to, Huntington's disease, spino-cerebellar ataxia type 1, spino-cerebellar ataxia type 2, spino-cerebellar ataxia type 3 (also known as Machado-Joseph disease), and spino-cerebellar ataxia type 6, spino-cerebellar ataxia type 7, dentatoiubral-pallidoluysian atrophy and the like.

The term "single nucleotide polymorphism disorder" or "SNP disorder" refers to a disorder characterized by the presence of an SNP, e.g., a heterozygous SNP. SNP disorders include, but are not limited to, phenylketonuria, cystic fibrosis, sickle-cell anemia, albinism, Huntington's disease, myotonic dystrophy type 1, hypercholesterolemia (autosomal dominant, type B), neurofibromatosis (type 1), polycystic kidney disease (1 and 2), hemophilia A, Duchenne's muscular dystrophy, X-linked hypophosphatemic rickets, Rett's syndrome, non-obstructive spermatogenic failure and the like. An exemplary heterozygous SNP disorder is Huntington's disease.

In certain aspects, a double-stranded RNA (dsRNA) is provided comprising a first strand of about 15-35 nucleotides that is complementary to a region of a gene comprising an allelic polymorphism, and a second strand of about 15-35 nucleotides that is complementary to at least a portion of the first strand, wherein the first strand comprises a single nucleotide polymorphism (SNP) position nucleotide at a position 2 to 7 from the 5' end that is complementary to the allelic polymorphism; and a mismatch (MM) position nucleotide located 2-11 nucleotide from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide.

As used herein, a "single nucleotide polymorphism position nucleotide" or a "SNP position nucleotide" refers to the position of an RNA described herein (e.g., the first strand of a dsRNA) that corresponds to the polymorphic position of a target nucleic acid sequence (i.e., either the mutant nucleotide corresponding to the SNP allele or the wild-type nucleotide corresponding to the wild-type allele). For example, a strand may be labeled "SNP2," "SNP3," or "SNP4" to denote the position of the SNP as being 2, 3, or 4 nucleotides from the 5' end of the strand.

In certain exemplary embodiments, a SNP position nucleotide is within a seed region. In certain exemplary embodiments, a SNP position nucleotide is located between position 2 and position 7 from the 5' end, between position 2 and position 6 from the 5' end, or between position 2 and position 5 from the 5' end. In certain exemplary embodiments, a SNP position nucleotide is located at position 2 from the 5' end, at position 3 from the 5' end, at position 4 from the 5' end, at position 5 from the 5' end, at position 6 from the 5' end, or at position 7 from the 5' end of an RNA described herein (e.g., the first strand of a dsRNA). In certain exemplary embodiments, a SNP position nucleotide is located at a position set forth in Tables 5-7.

As used herein, the term "seed region" refers to a six-nucleotide stretch corresponding to positions 2-7 from the 5' end of an RNA strand. siRNA recognition of the target mRNA is believed to be conferred by the seed region of its antisense strand.

As used herein, a "mismatch position nucleotide" or a "MM position nucleotide" refers to the position of an RNA described herein (e.g., the first strand of a dsRNA) that is in a position that does not correspond to the SNP position nucleotide. A MM position nucleotide can be defined by its position from the 5' end or the 3' end of an RNA described herein (e.g., the 5' or the 3' end of first strand of a dsRNA), or defined by its position relative to a SNP position nucleotide of an RNA described herein (e.g., a first strand of a dsRNA).

In certain exemplary embodiments, a MM position nucleotide is located 2-11 nucleotides, 2-10 nucleotides, 2-9 nucleotides, 2-8 nucleotides, 2-7 nucleotides, or 2-6 nucleotides from a SNP position nucleotide. In certain exemplary embodiments, a MM position nucleotide is located 11 nucleotides, 10 nucleotides, 9 nucleotides, 8 nucleotides, 7 nucleotides, 6 nucleotides, 5 nucleotides, 4 nucleotides, 3 nucleotides or 2 nucleotides from a SNP position nucleotide. In certain exemplary embodiments, a MM position nucleotide is located at a position set forth in Tables 5-7.

In one embodiment, an RNA described herein (e.g., the first strand of a dsRNA) is homologous to an allelic polymorphism except for one mismatched oligonucleotide at a particular position relative to the nucleotide corresponding to the allelic polymorphism. In certain embodiments, the mismatch is within about 6 nucleotides of the SNP position nucleotide, within about 5 nucleotides of the SNP position nucleotide, within about 4 nucleotides of the SNP position nucleotide, within about 3 nucleotide of the SNP position nucleotide, within about 2 nucleotide of the SNP position nucleotide, or within about 1 nucleotide of the SNP position nucleotide. In particular embodiments, the mismatch is not adjacent to a SNP position nucleotide.

In another embodiment, a SNP position nucleotide is at position 2, 3, 4, 5, or 6 from the 5' end. In an embodiment, a SNP position nucleotide is at position 2 from the 5' end. In an embodiment, is at position 3 from the 5' end. In an embodiment, a SNP position nucleotide is at position 4 from the 5' end. In an embodiment, a SNP position nucleotide is at position 5 from the 5' end. In an embodiment, a SNP position nucleotide is at position 6 from the 5' end.

In certain exemplary embodiments, an RNA described herein (e.g., the first strand of a dsRNA) comprises a MM position nucleotide at position 5, 7, 8, 11, 14, 15 or 16 from the 5' end. In certain exemplary embodiments, an RNA described herein (e.g., the first strand of a dsRNA) comprises a MM position nucleotide 1, 2, 3, 4, 5, 8, 9, 10 or 11 nucleotides from the SNP position nucleotide.

In certain exemplary embodiments, an RNA described herein (e.g., the first strand of a dsRNA) comprises a SNP position nucleotide (referenced from the 5' end)—MM position nucleotide (referenced from the 5' end) combination selected from the group consisting of 2-7, 4-7, 4-8, 4-15, 6-5, 6-8, 6-11, 6-14, 6-16, 3-5, 3-7 and 3-8.

In a particularly exemplary embodiment, an RNA described herein (e.g., the first strand of a dsRNA) comprises an SNP position nucleotide at position 6 from the 5' end and a MM position nucleotide at position 11 from the 5' end. In another particularly exemplary embodiment, an RNA described herein (e.g., the first strand of a dsRNA) comprises an SNP position nucleotide at position 4 from the 5' end and a mismatch at position 7 from the 5' end.

In one aspect, the double-stranded RNAs provided herein selectively silence a mutant allele having an allelic polymorphism. In an embodiment, the double-stranded RNAs provided herein silence a mutant allele having an allelic polymorphism and do not affect the wild-type allele of the same gene. In another embodiment, the double-stranded RNAs provided herein silence a mutant allele having an allelic polymorphism and silence the wild-type allele of the same gene to a lesser extent than the mutant allele.

Accordingly, in one aspect, the present disclosure provides a method of treating a subject having or at risk of having a disease characterized or caused by a mutant protein associated with an allelic polymorphism by administering to the subject an effective amount of an RNAi agent targeting an allelic polymorphism within a gene encoding a mutant protein (e.g., huntingtin protein), such that sequence-specific interference of a gene occurs resulting in an effective treatment for the disease.

In one aspect, RNA silencing agents disclosed herein preferentially silence a mutant allele comprising a polymorphism more efficiently than the corresponding wild-type allele. In certain exemplary embodiments, dsRNAs disclosed herein silence the allele comprising a polymorphism about 20%, about 30%, about 40%, about 50%, about 60%, about 70%, about 80%, or about 90% more than the corresponding wild-type allele. In an embodiment, RNA silencing agents disclosed herein silence the allele comprising a polymorphism at least about 50% more than the corresponding wild-type allele. In certain exemplary embodiments, dsRNAs disclosed herein silence the allele comprising a polymorphism at least about 5 times, about 10 times, about 15 times, about 20 times, about 25 times, about 30 times, about 35 times, about 40 times, about 45 times, about 50 times, about 55 times, about 60 times, about 65 times, about 70 times, about 75 times, about 80 times, about 85 times, about 90 times, about 95 times, about 100 times, about 110 times, about 120 times, about 130 times, about 140 times, about 150 times, about 160 times, about 170 times, about 180 times, about 190 times, about 200 times, about 250 times, about 300 times, about 350 times, about 400 times, about 450 times, or up to about 500 times the level of silencing of the corresponding wild-type allele.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "antisense oligonucleotide" or "ASO" refers to a nucleic acid (e.g., an RNA), having sufficient sequence complementarity to a target an RNA (e.g., a SNP-containing mRNA or a SNP-containing pre-mRNA) in order to block a region of a target RNA in an effective manner, e.g., in a manner effective to inhibit translation of a target mRNA and/or splicing of a target pre-mRNA. An antisense oligonucleotide having a "sequence sufficiently complementary to a target RNA" means that the antisense agent has a sequence sufficient to mask a binding site for a protein that would otherwise modulate splicing and/or that the antisense agent has a sequence sufficient to mask a binding site for a ribosome and/or that the antisense agent has a sequence sufficient to alter the three-dimensional structure of the targeted RNA to prevent splicing and/or translation.

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

Linkers useful in conjugated compounds of the disclosure include glycol chains (e.g., polyethylene glycol), alkyl chains, peptides, RNA, DNA, and combinations thereof. As used herein, the abbreviation "TEG" refers to triethylene glycol.

Design of Oligonucleotides

In certain embodiments, an oligonucleotide, e.g., an siRNA, of the disclosure is a duplex containing a sense strand and complementary antisense strand, the antisense strand having sufficient complementary to a target mRNA containing an allelic polymorphism to mediate RNAi. In exemplary embodiments, the siRNA molecule has a length from about 10-50 or more nucleotides, i.e., each strand comprises 10-50 nucleotides (or nucleotide analogs). In particularly exemplary embodiments, the siRNA molecule has a length from about 15-35, e.g., about 15, about 16, about 17, about 18, about 19, about 20, about 21, about 22, about 23, about 24, about 25, about 26, about 27, about 28, about 29, about 30, about 31, about 32, about 33, about 34 or about 35 nucleotides in each strand, wherein one of the strands is sufficiently complementary to a target region.

In exemplary embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In exemplary embodiments, the siRNA molecule has a length from about 10-50 or more nucleotides, i.e., each strand comprises 10-50 nucleotides (or nucleotide analogs). In particularly exemplary embodiments, the siRNA molecule has a length from about 15-35, e.g., about 15, about 16, about 17, about 18, about 19, about 20, about 21, about 22, about 23, about 24, about 25, about 26, about 27, about 28, about 29, about 30, about 31, about 32, about 33, about 34 or about 35 nucleotides in each strand, wherein one of the strands is substantially complementary to a target sequence containing an allelic polymorphism, and the other strand is complementary or substantially complementary to the first strand. In an embodiment, the siRNA molecule in fully complementary to a target sequence containing an allelic polymorphism except for one additional mismatch, also known as secondary mismatch.

In some embodiments, each strand contains from 10 to 50 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, 45 nucleotides or nucleotide analogs, 46 nucleotides or nucleotide analogs, 47 nucleotides or nucleotide analogs, 48 nucleotides or nucleotide analogs, 49 nucleotides or nucleotide analogs, or 50 nucleotides or nucleotide analogs). In some embodiments, each strand contains from 10 to 49 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, 45 nucleotides or nucleotide analogs, 46 nucleotides or nucleotide analogs, 47 nucleotides or nucleotide analogs, 48 nucleotides or nucleotide analogs, or 49 nucleotides or nucleotide analogs). In some embodiments, each strand contains from 10 to 48 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, 45 nucleotides or nucleotide analogs, 46 nucleotides or nucleotide analogs, 47 nucleotides or nucleotide analogs, or 48 nucleotides or nucleotide analogs). In some embodiments, each strand contains from 10 to 47 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, 45 nucleotides or nucleotide analogs, 46 nucleotides or nucleotide analogs, or 47 nucleotides or nucleotide analogs). In some embodiments, each strand contains from 10 to 46 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, 45 nucleotides or nucleotide analogs, or 46 nucleotides or nucleotide analogs). In some embodiments, each strand contains from 10 to 45 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, 44 nucleotides or nucleotide analogs, or 45 nucleotides or nucleotide analogs). In some embodiments, each strand contains from 10 to 44 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, 43 nucleotides or nucleotide analogs, or 44 nucleotides or nucleotide analogs). In some embodiments, each strand contains from 10 to 43 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, 42 nucleotides or nucleotide analogs, or 43 nucleotides or nucleotide analogs). In some embodiments, each strand contains from 10 to 42 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, 41 nucleotides or nucleotide analogs, or 42 nucleotides or nucleotide analogs). In some embodiments, each strand contains from 10 to 41 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, 40 nucleotides or nucleotide analogs, or 41 nucleotides or nucleotide analogs). In some embodiments, each strand contains from 10 to 40 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, 39 nucleotides or nucleotide analogs, or 40 nucleotides or nucleotide analogs). In some embodiments, each strand contains from 10 to 39 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, 38 nucleotides or nucleotide analogs, or 39 nucleotides or nucleotide analogs). In some embodiments, each strand contains from 10 to 38 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, 37 nucleotides or nucleotide analogs, or 38 nucleotides or nucleotide analogs). In some embodiments, each strand contains from 10 to 37 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, 36 nucleotides or nucleotide analogs, or 37 nucleotides or nucleotide analogs). In some embodiments, each strand contains from 10 to 36 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, 35 nucleotides or nucleotide analogs, or 36 nucleotides or nucleotide analogs). In some embodiments, each strand contains from 10 to 35 nucleotides or nucleotide analogs (e.g., 10 nucleotides or nucleotide analogs, 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs). In some embodiments, each strand contains from 11 to 35 nucleotides or nucleotide analogs (e.g., 11 nucleotides or nucleotide analogs, 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs). In some embodiments, each strand contains from 12 to 35 nucleotides or nucleotide analogs (e.g., 12 nucleotides or nucleotide analogs, 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs). In some embodiments, each strand contains from 13 to 35 nucleotides or nucleotide analogs (e.g., 13 nucleotides or nucleotide analogs, 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs). In some embodiments, each strand contains from 14 to 35 nucleotides or nucleotide analogs (e.g., 14 nucleotides or nucleotide analogs, 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs). In some embodiments, each strand contains from 15 to 35 nucleotides or nucleotide analogs (e.g., 15 nucleotides or nucleotide analogs, 16 nucleotides or nucleotide analogs, 17 nucleotides or nucleotide analogs, 18 nucleotides or nucleotide analogs, 19 nucleotides or nucleotide analogs, 20 nucleotides or nucleotide analogs, 21 nucleotides or nucleotide analogs, 22 nucleotides or nucleotide analogs, 23 nucleotides or nucleotide analogs, 24 nucleotides or nucleotide analogs, 25 nucleotides or nucleotide analogs, 26 nucleotides or nucleotide analogs, 27 nucleotides or nucleotide analogs, 28 nucleotides or nucleotide analogs, 29 nucleotides or nucleotide analogs, 30 nucleotides or nucleotide analogs. 31 nucleotides or nucleotide analogs, 32 nucleotides or nucleotide analogs, 33 nucleotides or nucleotide analogs, 34 nucleotides or nucleotide analogs, or 35 nucleotides or nucleotide analogs).

In some embodiments, the siRNA contains a sense strand and an antisense strand (e.g., as described above), and the antisense strand has a length of from 15 to 25 nucleotides or nucleotide analogs, such as a length of from 16 to 24 nucleotides or nucleotide analogs, a length of from 17 to 23 nucleotides or nucleotide analogs, a length of from 18 to 22 nucleotides or nucleotide analogs, or a length of 19 to 21 nucleotides or nucleotide analogs. In some embodiments, the antisense strand has a length of 15 nucleotides or nucleotide analogs. In some embodiments, the antisense strand has a length of 16 nucleotides or nucleotide analogs. In some embodiments, the antisense strand has a length of 17 nucleotides or nucleotide analogs. In some embodiments, the antisense strand has a length of 18 nucleotides or nucleotide analogs. In some embodiments, the antisense strand has a length of 19 nucleotides or nucleotide analogs. In some embodiments, the antisense strand has a length of 20 nucleotides or nucleotide analogs. In some embodiments, the antisense strand has a length of 21 nucleotides or nucleotide analogs. In some embodiments, the antisense strand has a length of 22 nucleotides or nucleotide analogs. In some embodiments, the antisense strand has a length of 23 nucleotides or nucleotide analogs. In some embodiments, the antisense strand has a length of 24 nucleotides or nucleotide analogs. In some embodiments, the antisense strand has a length of 25 nucleotides or nucleotide analogs.

In some embodiments, the siRNA contains a sense strand and an antisense strand (e.g., as described above), and the sense strand has a length of from 10 to 20 nucleotides or nucleotide analogs, such as a length of from 11 to 19 nucleotides or nucleotide analogs, a length of from 12 to 18 nucleotides or nucleotide analogs, a length of from 13 to 17 nucleotides or nucleotide analogs, or a length of from 14 to 16 nucleotides or nucleotide analogs. In some embodiments, the sense strand has a length of 10 nucleotides or nucleotide analogs. In some embodiments, the sense strand has a length of 11 nucleotides or nucleotide analogs. In some embodiments, the sense strand has a length of 12 nucleotides or nucleotide analogs. In some embodiments, the sense strand has a length of 13 nucleotides or nucleotide analogs. In some embodiments, the sense strand has a length of 14 nucleotides or nucleotide analogs. In some embodiments, the sense strand has a length of 15 nucleotides or nucleotide analogs. In some embodiments, the sense strand has a length of 16 nucleotides or nucleotide analogs. In some embodiments, the sense strand has a length of 17 nucleotides or nucleotide analogs. In some embodiments, the sense strand has a length of 18 nucleotides or nucleotide analogs. In some embodiments, the sense strand has a length of 19 nucleotides or nucleotide analogs. In some embodiments, the sense strand has a length of 20 nucleotides or nucleotide analogs.

In some embodiments, the siRNA contains a sense strand and an antisense strand (e.g., as described above), wherein the antisense strand has a length of from 15 to 25 nucleotides or nucleotide analogs and the sense strand has a length of from 10 to 20 nucleotides or nucleotide analogs. In some embodiments, the antisense strand has a length of from 16 to 24 nucleotides or nucleotide analogs and the sense strand has a length of from 11 to 19 nucleotides or nucleotide analogs. In some embodiments, the antisense strand has a length of from 17 to 23 nucleotides or nucleotide analogs and the sense strand has a length of from 12 to 18 nucleotides or nucleotide analogs. In some embodiments, the antisense strand has a length of from 18 to 22 nucleotides or nucleotide analogs and the sense strand has a length of from 13 to 17 nucleotides or nucleotide analogs. In some embodiments, the antisense strand has a length of from 19 to 21 nucleotides or nucleotide analogs and the sense strand has a length of from 14 to 16 nucleotides or nucleotide analogs.

In some embodiments, the siRNA contains a sense strand and an antisense strand (e.g., as described above), wherein the antisense strand has a length of 20 nucleotides or nucleotide analogs and the sense strand has a length of 15 nucleotides or nucleotide analogs.

In some embodiments, the siRNA contains a sense strand and an antisense strand (e.g., as described above), wherein the antisense strand has a length of 21 nucleotides or nucleotide analogs and the sense strand has a length of 15 nucleotides or nucleotide analogs.

In some embodiments, the siRNA contains a sense strand and an antisense strand (e.g., as described above), wherein the antisense strand has a length of 20 nucleotides or nucleotide analogs and the sense strand has a length of 16 nucleotides or nucleotide analogs.

In some embodiments, the siRNA contains a sense strand and an antisense strand (e.g., as described above), wherein the antisense strand has a length of 21 nucleotides or nucleotide analogs and the sense strand has a length of 16 nucleotides or nucleotide analogs.

Generally, siRNAs can be designed by using any method known in the art, for instance, by using the following protocol:

1. The siRNA may be specific for a target sequence which contains an allelic polymorphism. In exemplary embodiments, the first strand is substantially complementary to the target sequence containing an allelic polymorphism having one mismatch to the target sequence containing an allelic polymorphism, and the other strand is substantially complementary to the first strand. In an embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus, in one embodiment, the disclosure includes nucleic acid molecules having 35-55% G/C content.

2. The sense strand of the siRNA is designed based on the sequence of the selected target site and the position of the allelic polymorphism. In exemplary embodiments, the RNA silencing agents of the disclosure do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the disclosure have sufficient complementarity with the target sequence such that the siRNA can mediate RNAi. In general, siRNA containing nucleotide sequences sufficiently identical to a target sequence portion of the target gene to effect RISC-mediated cleavage of the target gene are used. Accordingly, in an exemplary embodiment, the sense strand of the siRNA is designed have to have a sequence sufficiently identical to a portion of the target which contains an allelic polymorphism. The disclosure has the advantage of being able to tolerate certain sequence variations to enhance efficiency and specificity of RNAi. In an aspect, the sense strand has 1 mismatched nucleotide with a target region containing an allelic polymorphism, such as a target region that differs by at least one base pair between a wild-type and mutant allele, e.g., a target region comprising the gain-of-function mutation, and the other strand is identical or substantially identical to the first strand. In some embodiments, the mismatch is 4 nucleotides upstream, 3 nucleotides upstream nucleotide corresponding to the allelic polymorphism, 2 nucleotides upstream nucleotide corresponding to the allelic polymorphism, 1 nucleotide upstream, 1 nucleotide downstream nucleotide corresponding to the allelic polymorphism, 2 nucleotides downstream nucleotide corresponding to the allelic polymorphism, 3 nucleotides downstream nucleotide corresponding to the allelic polymorphism, 4 nucleotides downstream nucleotide corresponding to the allelic polymorphism, or 5 nucleotides downstream nucleotide corresponding to the allelic polymorphism. In some embodiments, the mismatch is not adjacent to the nucleotide corresponding to the allelic polymorphism. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). An exemplary, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). An exemplary, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant: wild-type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet the criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6 (log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference in its entirety for all purposes.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}P$, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

Sites of siRNA-mRNA complementation are selected, which result in optimal mRNA specificity and maximal mRNA cleavage.

siRNA-Like Molecules siRNA-like molecules of the present disclosure have a sequence (i.e., have a strand having a sequence) that is "sufficiently complementary" to a target sequence of an mRNA (e.g. an htt mRNA) to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g., within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected, such that it forms a wobble base pair (e.g., G:U) or a mismatched base pair (G:A, C:A, C:U, G:G, A:A, C:C, U:U). In a further exemplary embodiment, the "bulge" is centered at nucleotide positions 12 and 13 from the 5' end of the miRNA molecule.

Modified RNA Silencing Agents

In certain aspects of the disclosure, an RNA silencing agent (or any portion thereof) of the disclosure as described supra may be modified such that the activity of the agent is further improved. For example, the RNA silencing agents described in above may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the disclosure may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain exemplary embodiments, the RNA silencing agents of the disclosure are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is typically utilized because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-0-methoxyethyl-inosine, and 2'-OMe-inosine. In particularly exemplary embodiments, the universal nucleotide is an inosine residue or a naturally occurring analog thereof.

In certain embodiments, the RNA silencing agents of the disclosure are modified by the introduction of at least one destabilizing nucleotide within 11 nucleotides from a specificity-determining nucleotide (e.g., within 11 nucleotides from the nucleotide which recognizes the disease-related polymorphism (e.g., a SNP position nucleotide)). For example, the destabilizing nucleotide may be introduced at a position that is within 11, 10, 9, 8, 7, 6, 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g., siRNAs and shRNAs), the destabilizing nucleotide may be introduced in the strand or strand portion that does not contain the specificity-determining nucleotide. In particular exemplary embodiments, the destabilizing nucleotide is introduced in the same strand or strand portion that contains the specificity-determining nucleotide.

In certain embodiments, the RNA silencing agents of the disclosure are modified by the introduction of a modified intersubunit linkage of Formula 1:

wherein:

D is selected from the group consisting of O, OCH$_2$, OCH, CH$_2$, and CH;

C is selected from the group consisting of O$^-$, OH, OR$^1$, NH$^-$, NH$_2$, S$^-$, and SH;

A is selected from the group consisting of O and CH$_2$;

R$^1$ is a protecting group;

=== is an optional double bond; and the intersubunit is bridging two optionally modified nucleosides.

In an embodiment, when C is O$^-$, either A or D is not O.

In an embodiment, D is CH$_2$. In another embodiment, the modified intersubunit linkage of Formula VIII is a modified intersubunit linkage of Formula 2:

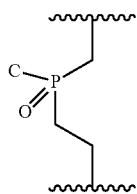

(2)

In an embodiment, D is O. In another embodiment, the modified intersubunit linkage of Formula VIII is a modified intersubunit linkage of Formula 3:

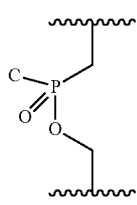

(3)

In an embodiment, D is CH. In another embodiment, the modified intersubunit linkage of Formula VIII is a modified intersubunit linkage of Formula 4:

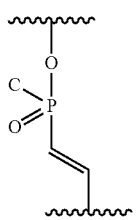

(4)

In another embodiment, the modified intersubunit linkage is a modified intersubunit linkage of Formula 5:

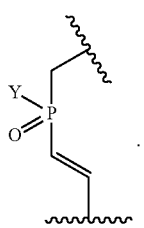

(5)

In an embodiment, D is OCH$_2$. In another embodiment, the modified intersubunit linkage is a modified intersubunit linkage of Formula 6:

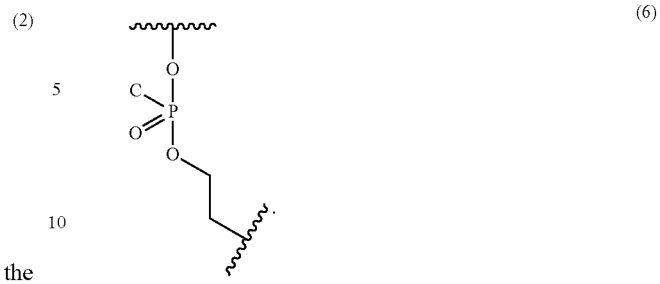

(6)

In another embodiment, the modified intersubunit linkage of Formula VII is a modified intersubunit linkage of Formula 7:

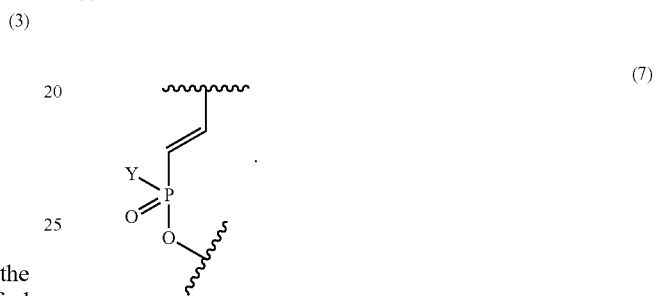

(7)

Figure 43:
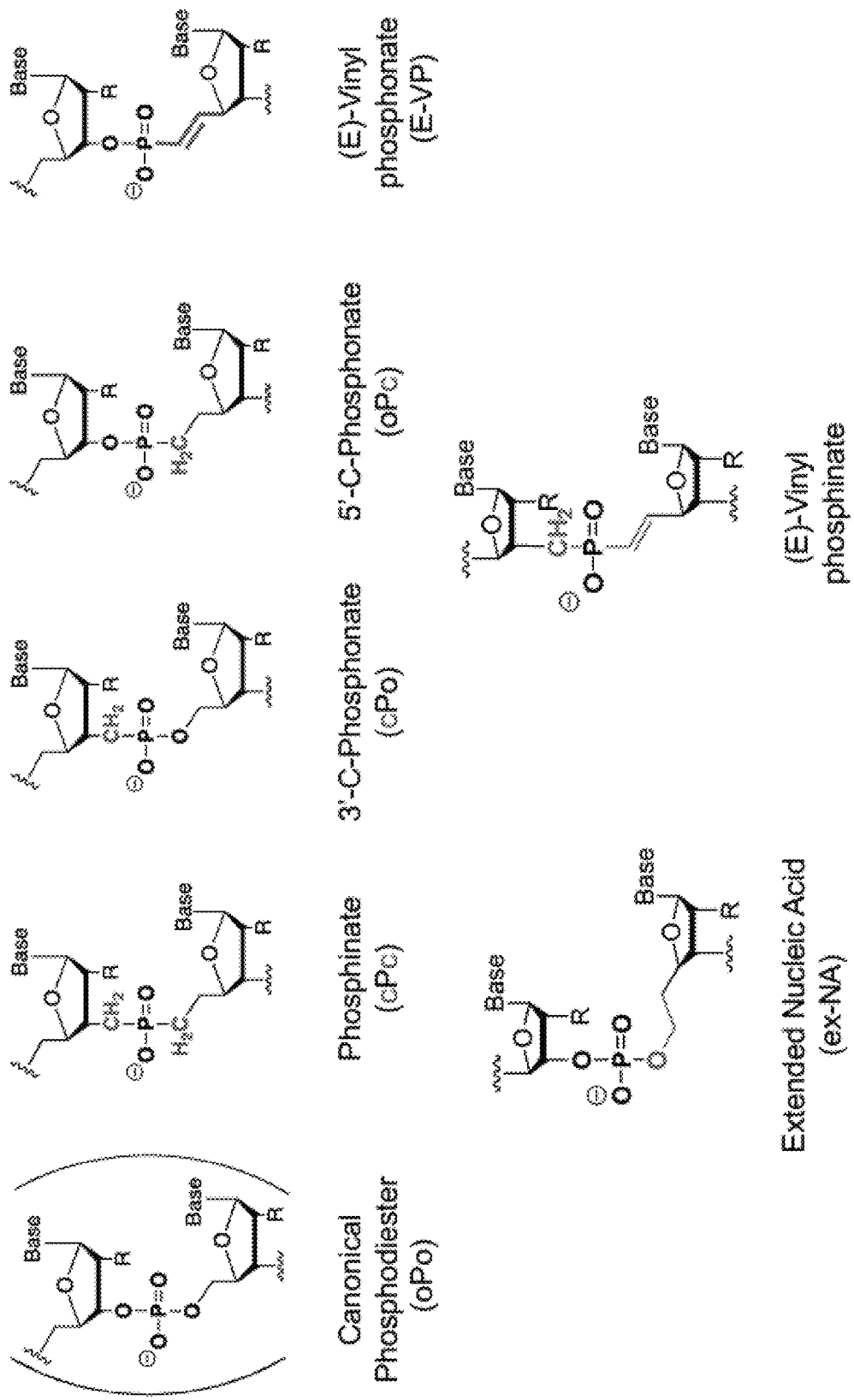
FIG. 43 illustrates example modified intersubunit linkers.

In certain embodiments, the RNA silencing agents of the disclosure are modified by the introduction of one or more of the intersubunit linkers of FIG. 43. In an exemplary embodiment, an intersubunit linker of FIG. 43 is inserted between the SNP position nucleotide and a nucleotide at a position directly adjacent to and on either side of the SNP position nucleotide of the antisense strand.

In certain embodiments, the RNA silencing agents of the disclosure are modified by the introduction of one or more vinyl phosphonate (VP) motifs in the intersubunit linker having the following formula:

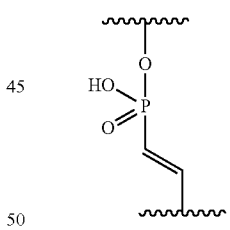

In certain embodiments, a VP motif is inserted at any position(s) of an oligonucleotide, e.g., an RNA. For example, for an oligonucleotide having a length of 20 nucleotides, a VP motif can be inserted at position 1-2, 2-3, 3-4, 4-5, 5-6, 6-7, 7-8, 8-9, 9-10, 10-11, 11-12, 12-13, 13-14, 14-15, 15-16, 16-17, 17-18, 18-19 or 19-20 and at any combinations of these.

In certain exemplary embodiments, a VP motif is inserted at one or more of positions 1-2, 5-6, 6-7, 10-11, 18-19 and/or 19-20 of the antisense strand.

In other exemplary embodiments, a VP motif is inserted at one or more of positions 1-2, 6-7, 10-11 and/or 19-20 of the antisense strand.

In an exemplary embodiment, a VP motif is inserted next to (i.e., between a SNP position nucleotide and a nucleotide at a position directly adjacent to and on either side of) the SNP position nucleotide of the antisense strand. In another exemplary embodiment, a VP motif is inserted next to (i.e., between a MM position nucleotide and a nucleotide at a position directly adjacent to and on either side of) the MM position nucleotide of the antisense strand.

2) Modifications to Enhance Efficacy and Specificity

In certain embodiments, the RNA silencing agents of the disclosure may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the disclosure or an siRNA produced from a shRNA) into RISC in favor of the sense strand, such that the antisense strand preferentially guides cleavage or translational repression of a target mRNA, and thus increasing or improving the efficiency of target cleavage and silencing. In exemplary embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the disclosure may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the disclosure may be enhanced such that there is at least one mismatched base pair between the 5' end of the first or antisense strand and the 3' end of the sense strand portion. In an exemplary embodiment, the mismatched base pair is selected from the group consisting of G:A, C:A, C:U, G:G, A:A, C:C and U:U. In another embodiment, the asymmetry of an RNA silencing agent of the disclosure may be enhanced such that there is at least one wobble base pair, e.g., G:U, between the 5' end of the first or antisense strand and the 3' end of the sense strand portion. In another embodiment, the asymmetry of an RNA silencing agent of the disclosure may be enhanced such that there is at least one base pair comprising a rare nucleotide, e.g., inosine (I). In exemplary embodiments, the base pair is selected from the group consisting of an I:A, I:U and I:C. In yet another embodiment, the asymmetry of an RNA silencing agent of the disclosure may be enhanced such that there is at least one base pair comprising a modified nucleotide. In particular embodiments, the modified nucleotide is selected from the group consisting of 2-amino-G, 2-amino-A, 2,6-diamino-G, and 2,6-diamino-A.

In certain embodiments, the RNA silencing agents of the disclosure are altered at one or more intersubunit linkages in an oligonucleotide by the introduction of a vinyl phosphonate (VP) motif having the following formula:

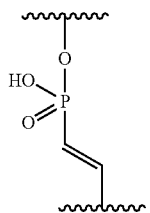

3) RNA Silencing Agents with Enhanced Stability

The RNA silencing agents of the present disclosure can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a particular aspect, the disclosure features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a particular embodiment of the present disclosure, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Particularly, the ends may be stabilized by incorporating modified nucleotide analogues.

In certain embodiments, the RNA silencing agents of the disclosure are altered at one or more intersubunit linkages in an oligonucleotide by the introduction of a vinyl phosphonate (VP) motif having the following formula:

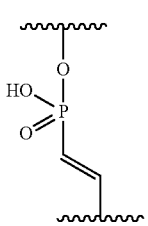

A variety of oligonucleotide types (e.g., gapmers, mixmers, miRNA inhibitors, splice-switching oligonucleotides ("SSOs"), phosphorodiamidate morpholino oligonucleotides ("PMOs"), peptide nucleic acids ("PNAs") and the like) can be used in the oligonucleotides described herein, optionally utilizing various combinations of modifications (e.g., chemical modifications) and/or conjugations described herein and in, e.g., U.S. Ser. No. 15/089,423; U.S. Ser. No. 15/236,051; U.S. Ser. No. 15/419,593; U.S. Ser. No. 15/697,120 and U.S. Pat. No. 9,809,817; and U.S. Ser. No. 15/814,350 and U.S. Pat. No. 9,862,350, each of which is incorporated herein by reference in its entirety for all purposes.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant disclosure. Additional modified residues include, deoxy-abasic, inosine, N3-methyl-uridine, N6,N6-dimethyl-adenosine, pseudouridine, purine ribonucleoside and ribavirin. In a particularly exemplary embodiment, the 2' moiety is a methyl group such that the linking moiety is a 2'-O-methyl oligonucleotide.

In an exemplary embodiment, the RNA silencing agent of the disclosure comprises locked nucleic acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol. 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the disclosure comprises peptide nucleic acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

In certain exemplary embodiments, nucleobase-modified ribonucleotides, i.e., ribonucleotides, containing at least one non-naturally occurring nucleobase instead of a naturally occurring nucleobase, are used. Bases may be modified to block the activity of adenosine deaminase. Exemplary modified nucleobases include, but are not limited to, uridine and/or cytidine modified at the 5-position, e.g., 5-(2-amino) propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the disclosure includes RNA silencing agents having two complementary strands of nucleic acid, wherein the two strands are crosslinked. The disclosure also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2'-OMe moiety on a U in a sense or antisense strand, but especially on a sense strand, or provision of a 2'-OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (in most cases, sequence changes are located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2'-OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the disclosure includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a modification to the RNA silencing agents of the disclosure comprise a vinyl phosphonate (VP) motif in one or more intersubunit linkers of an oligonucleotide, wherein the VP motif has the following formula:

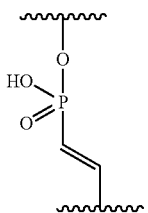

In a particular embodiment, an RNA silencing agent of disclosure is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl) cholenic acid, dimethoxytrityl, or phenoxazine.

5) Tethered Ligands

Other entities can be tethered to an RNA silencing agent of the disclosure. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. In certain exemplary embodiments, these are located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, typically covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon.

In one aspect, the ligand is a lipid or lipid-based molecule. Such a lipid or lipid-based molecule typically binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. In a particular embodiment, the lipid based ligand binds HSA. However, it is desired that the affinity not be so strong that the HSA-ligand binding cannot be reversed. In another exemplary embodiment, the lipid based ligand binds HSA weakly or not at all.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, typically a helical cell-permeation agent. In certain exemplary embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an alpha-helical agent, which typically has a lipophilic face and a lipophobic face.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

6) Hydrophobic Moieties

In certain embodiments of the double-stranded RNAs provided herein, the RNA molecule is conjugated to one or more hydrophobic moieties (see PCT Pub. No. WO 2018/031933, which is incorporated herein by reference). In an embodiment, the hydrophobic moiety has an affinity for low density lipoprotein and/or intermediate density lipoprotein. In a related embodiment, the hydrophobic moiety is a saturated or unsaturated moiety having fewer than three double bonds.

In another embodiment, the hydrophobic moiety has an affinity for high density lipoprotein. In a related embodiment, the hydrophobic moiety is a polyunsaturated moiety having at three or more double bonds (e.g., having three, four, five, six, seven, eight, nine or ten double bonds). In a particular embodiment, the hydrophobic moiety is a polyunsaturated moiety having three double bonds. In a particular embodiment, the hydrophobic moiety is a polyunsaturated moiety having four double bonds. In a particular embodiment, the hydrophobic moiety is a polyunsaturated moiety having five double bonds. In a particular embodiment, the hydrophobic moiety is a polyunsaturated moiety having six double bonds.

In another embodiment, the hydrophobic moiety is selected from the group consisting of fatty acids, steroids, secosteroids, lipids, gangliosides and nucleoside analogs, and endocannabinoids.

In another embodiment, the hydrophobic moiety is a neuromodulatory lipid, e.g., an endocannabinoid. Non-limiting examples of endocannabinoids include: anandamide, arachidonoylethanolamine, 2-Arachidonyl glyceryl ether (noladin ether), 2-Arachidonyl glyceryl ether (noladin ether), 2-Arachidonoylglycerol, and N-Arachidonoyl dopamine.

In another embodiment, the hydrophobic moiety is an omega-3 fatty acid. Non-limiting examples of omega-3 fatty acids include, but are not limited to: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, Timnodonic acid), heneicosapentaenoic acid (HPA), docosapentaenoic acid (DPA, clupanodonic acid), docosahexaenoic acid (DHA, cervonic acid), tetracosapentaenoic acid, and tetracosahexaenoic acid (nisinic acid).

In another embodiment, the hydrophobic moiety is an omega-6 fatty acid. Non-limiting examples of omega-6 fatty acids include, but are not limited to: linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (osbond acid), tetracosatetraenoic acid, and tetracosapentaenoic acid.

In another embodiment, the hydrophobic moiety is an omega-9 fatty acid. Non-limiting examples of omega-9 fatty acids include, but are not limited to: oleic acid, eicosenoic acid, Mead acid, erucic acid, and nervonic acid.

In another embodiment, the hydrophobic moiety is a conjugated linolenic acid. Non-limiting examples of conjugated linolenic acids include, but are not limited to: α-calendic acid, β-calendic acid, jacaric acid, α-eleostearic acid, β-eleostearic acid, catalpic acid, and punicic acid.

In another embodiment, the hydrophobic moiety is a saturated fatty acid. Non-limiting examples of saturated fatty acids include, but are not limited to: caprylic acid, capric acid, docosanoic acid, lauric acid, myristic acid, palmitic acid, stearic acid, arachidic acid, behenic acid, lignoceric acid, and cerotic acid.

In another embodiment, the hydrophobic moiety is an acid selected from the group consisting of: rumelenic acid, α-parinaric acid, β-parinaric acid, bosseopentaenoic acid, pinolenic acid, and podocarpic acid.

In another embodiment, the hydrophobic moiety is selected from the group consisting of: docosanoic acid (DCA), docosahexaenoic acid (DHA), and eicosapentaenoic acid (EPA). In a particular embodiment, the hydrophobic moiety is docosanoic acid (DCA). In another particular embodiment, the hydrophobic moiety is DHA. In another particular embodiment, the hydrophobic moiety is EPA.

In another embodiment, the hydrophobic moiety is a secosteroid. In a particular embodiment, the hydrophobic moiety is calciferol. In another embodiment, the hydrophobic moiety is a steroid other than cholesterol.

In a particular embodiment, the hydrophobic moiety is not cholesterol.

In another embodiment, the hydrophobic moiety is an alkyl chain, a vitamin, a peptide, or a bioactive conjugate, including but not limited to: glycosphingolipids, polyunsaturated fatty acids, secosteroids, steroid hormones, or sterol lipids.

In an embodiment, a double-stranded RNA provided herein comprises one or more chemically-modified nucleotides. In a particular embodiment, the double-stranded RNA comprises alternating 2'-methoxy-nucleotides and 2'-fluoro-nucleotides. In another particular embodiment, one or more nucleotides of the double-stranded RNA are connected to adjacent nucleotides via phosphorothioate linkages. In certain embodiments of the dsRNAs disclosed herein, the mismatch nucleotide and the nucleotide(s) adjacent to the mismatch nucleotide are 2'-methoxy-ribonucleotides.

In another particular embodiment, the nucleotides at positions 1 and 2 from the 3' end of the double-stranded RNAs provided herein are connected to adjacent nucleotides via phosphorothioate linkages. In yet another particular embodiment, the nucleotides at positions 1 and 2 from the 3' end of the double-stranded RNAs and the nucleotides at positions 1 and 2 from the 5' end of the double-stranded RNAs are connected to adjacent nucleotides via phosphorothioate linkages.

In one embodiment of a double-stranded RNA, the first oligonucleotide comprises at least 16 contiguous nucleotides, a 5' end, a 3' end, and has complementarity to a target, wherein:
  (1) the first oligonucleotide comprises alternating 2'-methoxy-nucleotides and 2'-fluoro-nucleotides;
  (2) the nucleotides at positions 2 and 14 from the 5' end are not 2'-methoxy-nucleotides;
  (3) the nucleotides are connected via phosphodiester or phosphorothioate linkages; and
  (4) the nucleotides at positions 1-6 from the 3' end, or positions 1-7 from the 3' end, are connected to adjacent nucleotides via phosphorothioate linkages.

7) Advanced Stabilization Pattern

In one embodiment of the double-stranded RNAs provided herein:
  (1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides;

(2) the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides;

(3) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and (4) the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

In one embodiment of the double-stranded RNAs, the first oligonucleotide has 3-7 more ribonucleotides than the second oligonucleotide.

In one embodiment, the double-stranded RNA comprises 11-16 base pair duplexes, wherein the nucleotides of each base pair duplex have different chemical modifications (e.g., one nucleotide has a 2'-fluoro modification and the other nucleotide has a 2'-methoxy).

In one embodiment of the double-stranded RNAs, the first oligonucleotide has 3-7 more ribonucleotides than the second oligonucleotide. In another embodiment.

In one embodiment, the first oligonucleotide is the antisense strand and the second oligonucleotide is the sense strand. See PCT Pub. No. WO 2016/161388, which is incorporated herein by reference.

In one embodiment, the first or second oligonucleotide comprises one or more VP intersubunit modifications having the following formula:

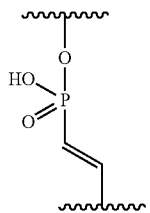

8) Branched Oligonucleotides

Figure 31:
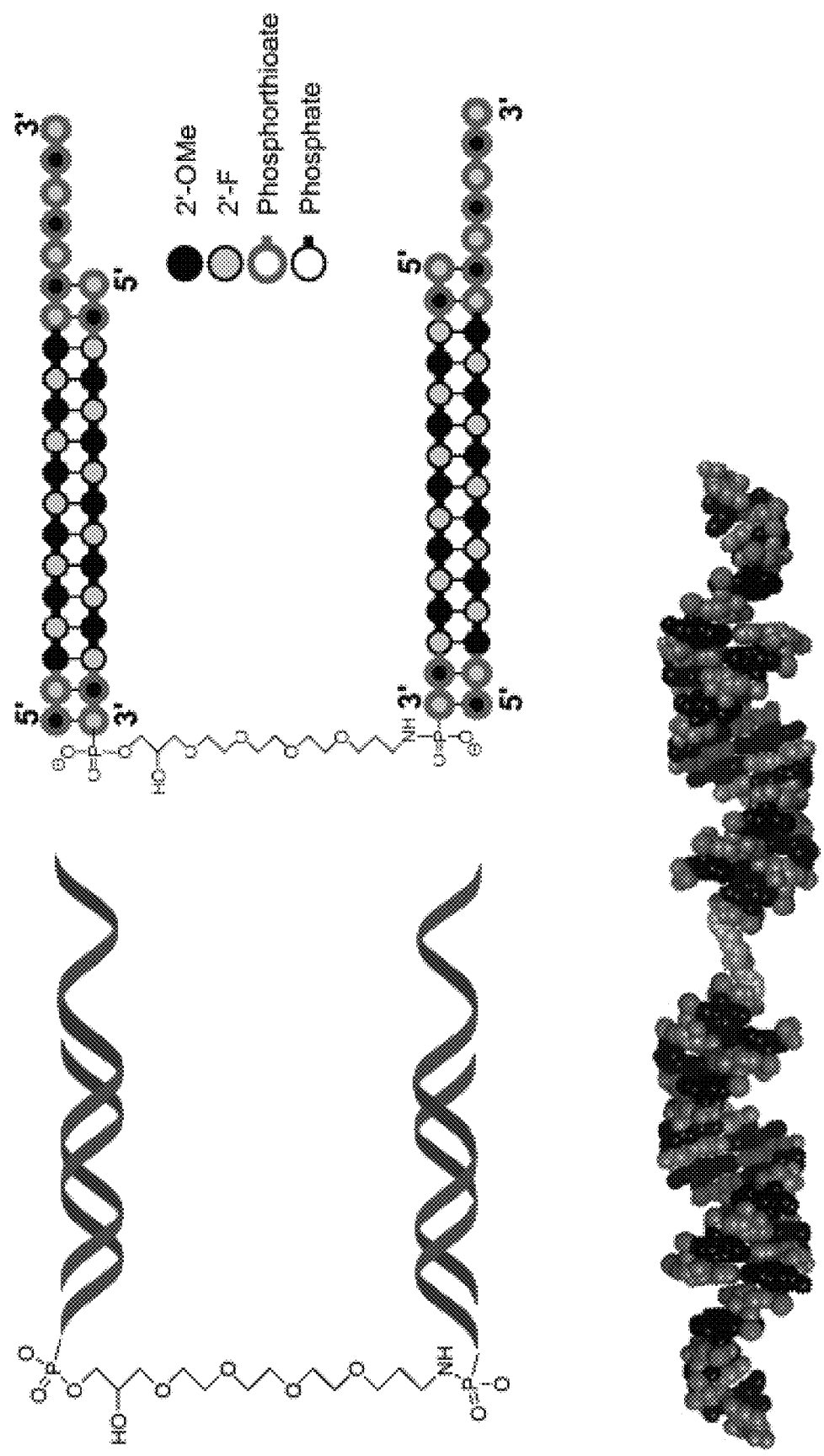
FIG. 31 illustrates an example di-branched siRNA chemical scaffold.

Two or more RNA silencing agents as disclosed above, for example oligonucleotide constructs such as siRNAs, may be connected to one another by one or more moieties independently selected from a linker, a spacer and a branching point, forming a branched oligonucleotide containing two or more RNA silencing agents. FIG. 31 illustrates an exemplary di-siRNA di-branched scaffolding for delivering two siRNAs. In representative embodiments, the nucleic acids of the branched oligonucleotide each comprise an antisense strand (or portions thereof), wherein the antisense strand has sufficient complementary to a heterozygous single nucleotide polymorphism to mediate an RNA-mediated silencing mechanism (e.g. RNAi). In other embodiments, there is provided a second type of branched oligonucleotides featuring nucleic acids that comprise a sense strand (or portions thereof) for silencing antisense transcripts, where the sense strand has sufficient complementarity to an antisense transcript to mediate an RNA-mediated silencing mechanism. In further embodiments, there is provided a third type of branched oligonucleotides including nucleic acids of both types, that is, a nucleic acid comprising an antisense strand (or portions thereof) and an oligonucleotide comprising a sense strand (or portions thereof).

In exemplary embodiments, the branched oligonucleotides may have two to eight RNA silencing agents attached through a linker. The linker may be hydrophobic. In a particular embodiment, branched oligonucleotides of the present application have two to three oligonucleotides. In one embodiment, the oligonucleotides independently have substantial chemical stabilization (e.g., at least 40% of the constituent bases are chemically-modified). In a particular embodiment, the oligonucleotides have full chemical stabilization (i.e., all of the constituent bases are chemically-modified). In some embodiments, branched oligonucleotides comprise one or more single-stranded phosphorothioated tails, each independently having two to twenty nucleotides. In a particular embodiment, each single-stranded tail has eight to ten nucleotides.

In certain embodiments, branched oligonucleotides are characterized by three properties: (1) a branched structure, (2) full metabolic stabilization, and (3) the presence of a single-stranded tail comprising phosphorothioate linkers. In a specific embodiment, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Figure 36:
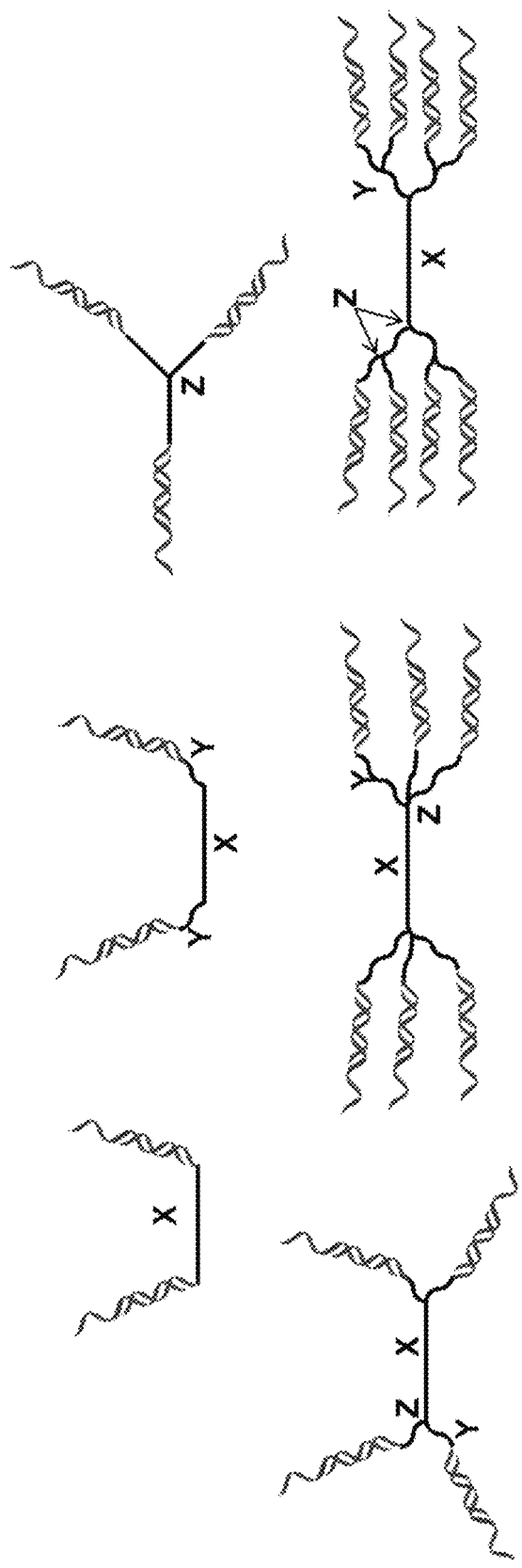
FIG. 36 shows oligonucleotide branching motifs according to certain exemplary embodiments. The double-helices represent oligonucleotides. The combination of different linkers, spacer(s) and branching points allows generation of a wide diversity of branched hsiRNA structures.

Branched oligonucleotides are provided in various structurally diverse embodiments. As shown in FIG. 36, for example, in some embodiments nucleic acids attached at the branching points are single stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature ($T_m$ ~37° C.) for fast dissociation upon internalization of the branched structure into the cell.

Figure 37:
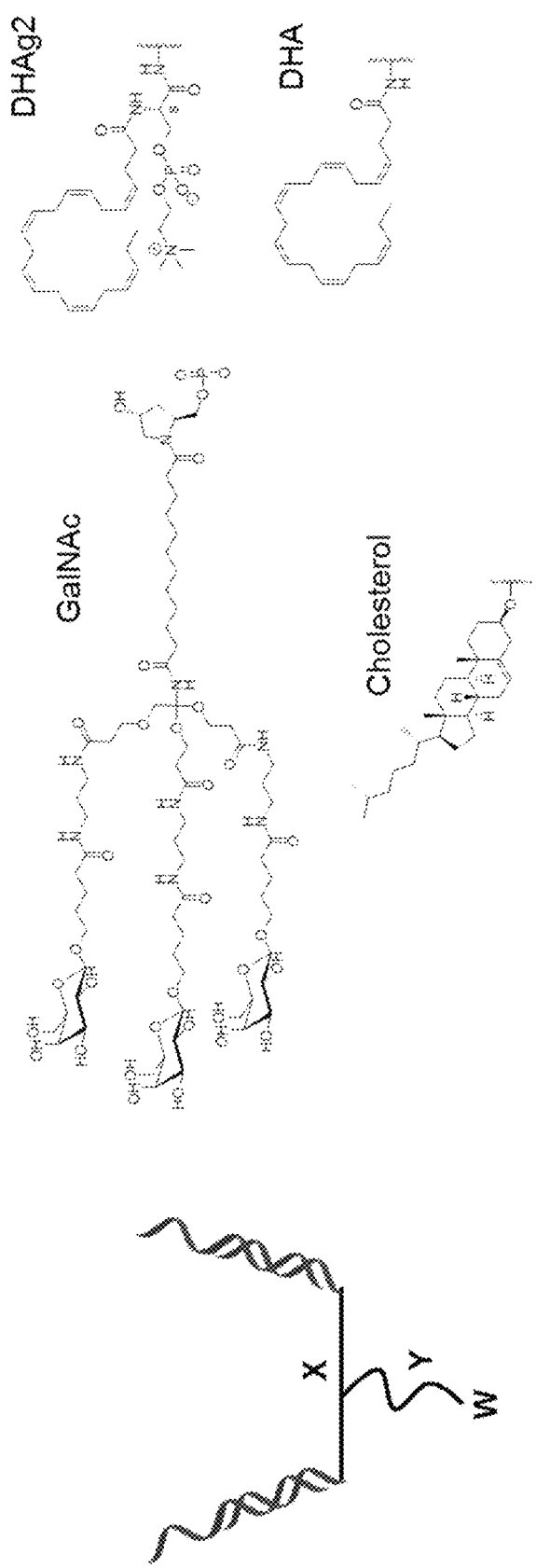
FIG. 37 shows exemplary branched oligonucleotides with conjugated bioactive moieties.

As shown in FIG. 37, Di-siRNA branched oligonucleotides may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof, wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole. In another embodiment, each linker is a structure selected from the formulas of FIG. 37.

9) Compound of Formula (I)

In another aspect, provided herein is a branched oligonucleotide compound of formula (I):

$$L\text{-}(N)_n \qquad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof, S is independently for each occurrence selected from an ethylene glycol chain, an alkyl chain, a peptide, RNA, DNA, a phosphate, a phosphonate, a phosphoramidate, an ester, an amide, a triazole, and combinations thereof, N is an RNA duplex comprising a sense strand and an antisense strand, wherein the antisense strand comprises a region of complementarity which is substantially complementary to a region of a gene comprising an allelic polymorphism, wherein the antisense strand comprises: a single nucleotide polymorphism (SNP) position nucleotide at a position 2 to 7 from the 5' end that is complementary to the allelic polymorphism; and a mismatch (MM) position nucleotide located 2-11 nucleotides from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide.

The sense strand and antisense strand each independently comprise one or more chemical modifications; and n is 2, 3, 4, 5, 6, 7 or 8.

In an embodiment, the compound of formula (I) has a structure selected from formulas (I-1)-(I-9) of Table 1.

TABLE 1

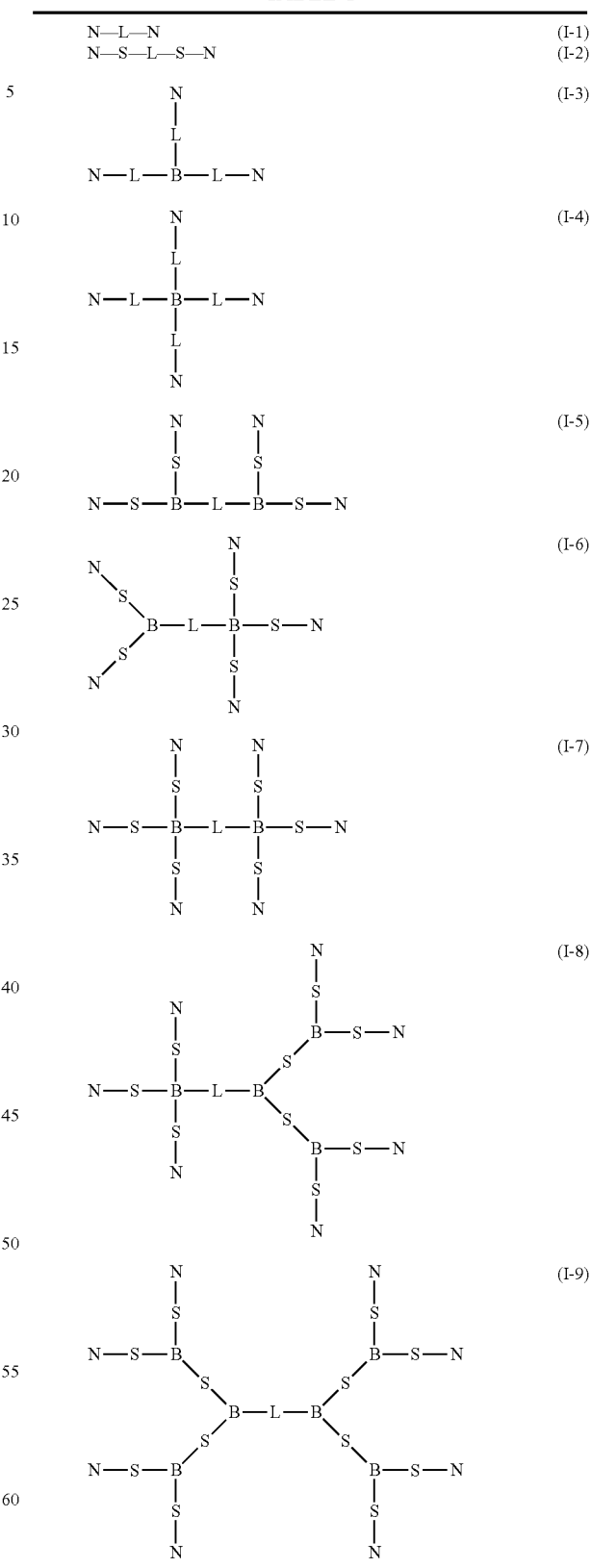

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof, wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole. In another embodiment of the compound of formula (I), each linker is a structure selected from the formulas of FIG. 36 and FIG. 38.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of FIG. 38.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2:

TABLE 2

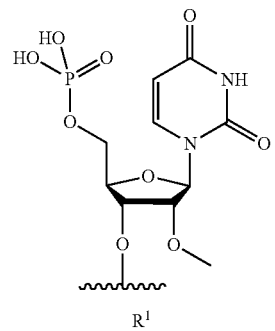

$R^1$

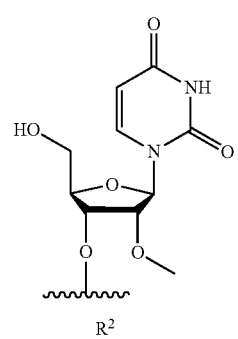

$R^2$

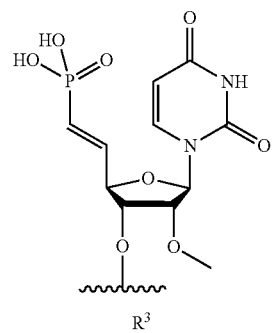

$R^3$

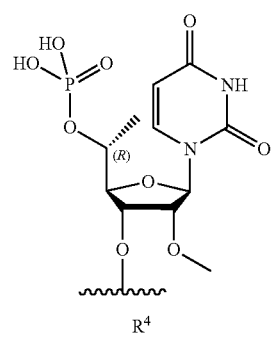

$R^4$

TABLE 2-continued

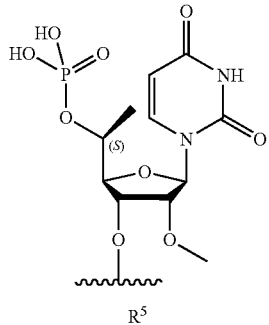

R⁵

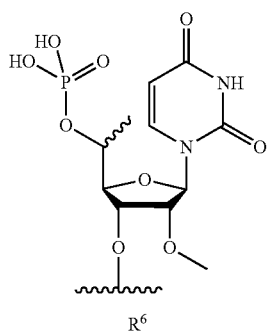

R⁶

TABLE 2-continued

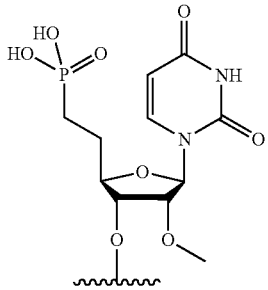

R⁷

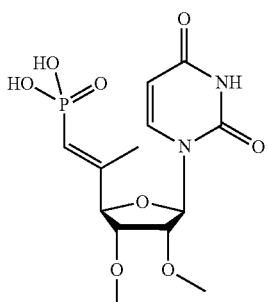

R⁸

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) the structure of formula (II):

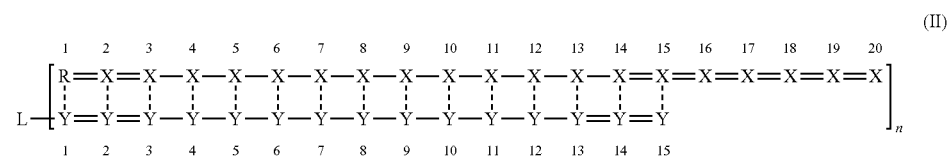

(II)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; = represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III):

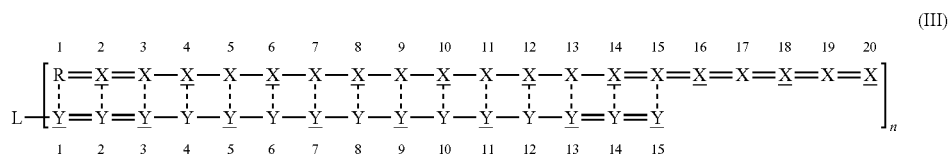

(III)

wherein $\underline{X}$, for each occurrence, independently, is a nucleotide comprising a 2'-deoxy-2'-fluoro modification; X, for each occurrence, independently, is a nucleotide comprising a 2'-O-methyl modification; $\underline{Y}$, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

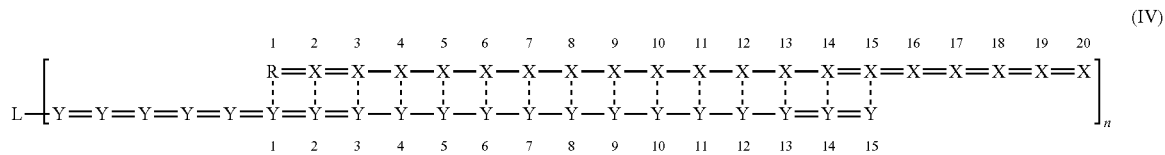

(IV)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; = represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (V)

In an embodiment, the compound of formula (I) has the structure of formula (V):

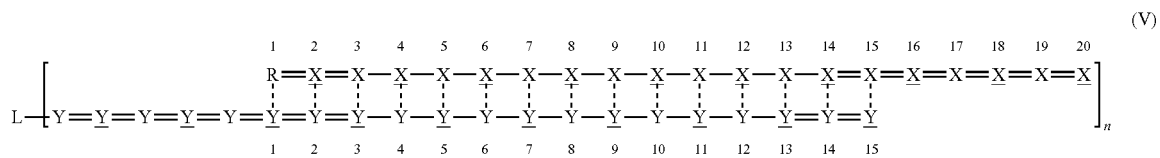

wherein $\underline{X}$, for each occurrence, independently, is a nucleotide comprising a 2'-deoxy-2'-fluoro modification; X, for each occurrence, independently, is a nucleotide comprising a 2'-O-methyl modification; $\underline{Y}$, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

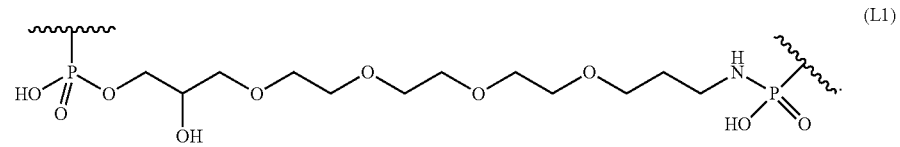 [SMILES: *P(=O)(O)NCCCOCCOCCOCCOCC(O)COP(*)(=O)O]

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

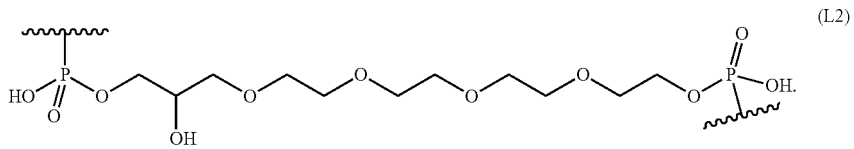 [SMILES: *P(=O)(O)OCCOCCOCCOCCOCC(O)COP(*)(=O)O]

(L2)

In an embodiment of L2, R is $R^3$ and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

10) Delivery System

In a further aspect, provided herein is a delivery system for therapeutic nucleic acids having the structure of formula (VI):

(VI)

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof, S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VI) has a structure selected from formulas (VI-1)-(VI-9) of Table 3:

TABLE 3

| | |
|---|---|
| ANc—L—cNA | (VI-1) |
| ANc—S—L—S—cNA | (VI-2) |
| ![structure] ANc—L—B—L—cNA with cNA branch via L | (VI-3) |
| ![structure] ANc—L—B—L—cNA with cNA branches via L above and below | (VI-4) |
| ![structure] ANc—S—B—L—B—S—cNA with cNA—S branches | (VI-5) |
| ![structure] Two ANc—S branches to B—L—B—S—cNA with cNA and S—cNA branches | (VI-6) |

TABLE 3-continued

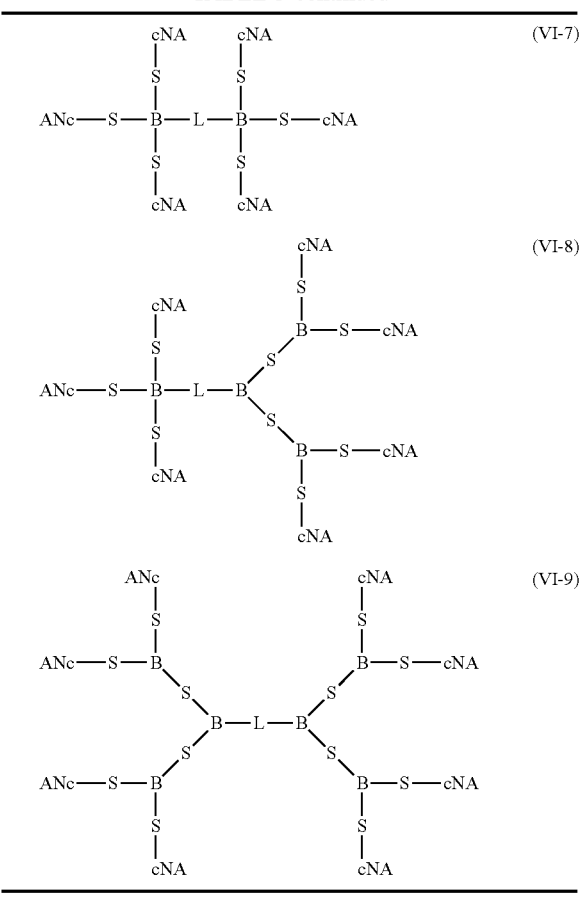

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI) (including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a region of complementarity which is substantially complementary to a region of a gene comprising an allelic polymorphism, wherein the antisense strand comprises: a single nucleotide polymorphism (SNP) position nucleotide at a position 2 to 7 from the 5' end that is complementary to the allelic polymorphism; and a mismatch (MM) position nucleotide located 2-11 nucleotide from the SNP position nucleotide that is a mismatch with a nucleotide in the gene. In exemplary embodiments, the SNP position nucleotide is at a position 2, 4 or 6 from the 5' end and the mismatch (MM) position nucleotide is located 2-6 nucleotides from the SNP position nucleotide. Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 16 contiguous nucleotides. In an embodiment, each NA independently comprises 16-20 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L 1 or L2 wherein R is R3 and n is 2. In another embodiment, the delivery system has a structure selected from formulas (I), (II), (III), (IV), (V), (VI), further comprising a linker of structure L1 wherein R is R3 and n is 2. In another embodiment, the delivery system has a structure selected from formulas (I), (II), (III), (IV), (V), (VI), further comprising a linker of structure L2 wherein R is R3 and n is 2.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier. In one embodiment, the pharmaceutical composition comprises one or more double-stranded, chemically-modified nucleic acid as described herein, and a pharmaceutically acceptable carrier. In a particular embodiment, the pharmaceutical composition comprises one double-stranded, chemically-modified nucleic acid as described herein, and a pharmaceutically acceptable carrier. In another particular embodiment, the pharmaceutical composition comprises two double-stranded, chemically-modified nucleic acids as described herein, and a pharmaceutically acceptable carrier.

In a particular embodiment, the pharmaceutical composition comprises a double-stranded RNA molecule comprising about 15-35 nucleotides complementary to a region of a gene encoding a heterozygous SNP mutant protein, said region comprising an allelic polymorphism, and a second strand comprising about 15-35 nucleotides complementary to the first strand, wherein the dsRNA molecule comprises a mismatch that is not in the position of the allelic polymorphism; and the mismatch and the nucleotide corresponding to the polymorphism are not in the center of the dsRNA molecule.

In an embodiment, the mismatch is 4 nucleotides upstream, 3 nucleotides upstream nucleotide corresponding to the allelic polymorphism, 2 nucleotides upstream nucleotide corresponding to the allelic polymorphism, 1 nucleotide upstream, 1 nucleotide downstream nucleotide corresponding to the allelic polymorphism, 2 nucleotides downstream nucleotide corresponding to the allelic polymorphism, 3 nucleotides downstream nucleotide corresponding to the allelic polymorphism, 4 nucleotides downstream nucleotide corresponding to the allelic polymorphism, or 5 nucleotides downstream nucleotide corresponding to the allelic polymorphism. In certain embodiments, the mismatch is not adjacent to the nucleotide corresponding to the allelic polymorphism.

In another embodiment of the pharmaceutical composition, the double-stranded RNA comprises a nucleotide corresponding to the allelic polymorphism which is in position 2, 3, 4, 5, or 6 from the 5' end. In an embodiment, the nucleotide corresponding to the allelic polymorphism is in position 2 from the 5' end. In an embodiment, the nucleotide corresponding to the allelic polymorphism is in position 3 from the 5' end. In an embodiment, the nucleotide corresponding to the allelic polymorphism is in position 4 from the 5' end. In an embodiment, the nucleotide corresponding to the allelic polymorphism is in position 5 from the 5' end. In an embodiment, the nucleotide corresponding to the allelic polymorphism is in position 6 from the 5' end.

In an embodiment of the pharmaceutical composition, the double-stranded RNA selectively silences a mutant allele having an allelic polymorphism, e.g., a heterozygous SNP. In an embodiment of the pharmaceutical composition, the double-stranded RNA silences a mutant allele having an allelic polymorphism and does not affect the wild-type allele of the same gene. In another embodiment of the pharmaceutical composition, the double-stranded RNA provided herein silences a mutant allele having an allelic polymorphism and silences the wild-type allele of the same gene to a lesser extent than the mutant allele.

A pharmaceutical composition of the disclosure is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desired to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, typical methods of preparation are vacuum drying and freeze-drying which yields a powder of the active ingredient plus any additional desired ingredient from a previously sterile-filtered solution thereof.

The data obtained from the cell culture assays and animal studies can be used in formulating a range of dosage for use in humans. The dosage of such compounds should typically lie within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

The present disclosure provides for both prophylactic and therapeutic methods of treating a subject at risk of (or susceptible to) a disease or disorder caused, in whole or in part, by an allelic polymorphism (e.g., a heterozygous SNP). In one embodiment, the disease or disorder is a trinucleotide repeat disease or disorder. In another embodiment, the disease or disorder is a polyglutamine disorder. In an embodiment, the methods comprise administering a therapeutically effective amount of a double-stranded RNA molecule provided herein. In an embodiment, the disease or disorder is a disorder associated with the expression of huntingtin and in which alteration of huntingtin, especially the amplification of CAG repeat copy number, leads to a defect in the huntingtin gene (structure or function) or huntingtin protein (structure or function or expression), such that clinical manifestations include those seen in Huntington's disease patients.

In embodiments of the methods, the double-stranded RNAs disclosed herein are homologous to an allelic polymorphism except for one mismatched oligonucleotide at a particular position relative to the nucleotide corresponding to the allelic polymorphism. In certain embodiments, the mismatch is within about 6 nucleotides of the nucleotide corresponding to the allelic polymorphism, within about 5 nucleotides of the nucleotide corresponding to the allelic polymorphism, within about 4 nucleotides of the nucleotide corresponding to the allelic polymorphism within about 3 nucleotide of the nucleotide corresponding to the allelic polymorphism, within about 2 nucleotide of the nucleotide corresponding to the allelic polymorphism, or within about 1 nucleotides of the nucleotide corresponding to the allelic polymorphism. In particularly exemplary embodiments, the mismatch is not adjacent to the nucleotide corresponding to the allelic polymorphism.

In another embodiment of the methods, the double-stranded RNA comprises a nucleotide corresponding to the allelic polymorphism which is in position 2, 3, 4, 5, or 6 from the 5' end. In an embodiment, the nucleotide corresponding to the allelic polymorphism is in position 2 from the 5' end. In an embodiment, the nucleotide corresponding to the allelic polymorphism is in position 3 from the 5' end. In an embodiment, the nucleotide corresponding to the allelic polymorphism is in position 4 from the 5' end. In an embodiment, the nucleotide corresponding to the allelic polymorphism is in position 5 from the 5' end. In an embodiment, the nucleotide corresponding to the allelic polymorphism is in position 6 from the 5' end.

In an embodiment of the methods, the dsRNA comprises a nucleotide corresponding to a polymorphism at position 6 from the 5'end and a mismatch at position 11 from the 5' end. In an embodiment of the methods, the dsRNA comprises a nucleotide corresponding to a polymorphism at position 4 from the 5' end and a mismatch at position 7 from the 5' end.

In another embodiment of the methods, the double-stranded RNA selectively silences a mutant allele having an allelic polymorphism. In an embodiment, the double-stranded RNA silences a mutant allele having an allelic polymorphism and does not affect the wild-type allele of the same gene. In another embodiment, the double-stranded RNA silences a mutant allele having an allelic polymorphism and silences the wild-type allele of the same gene to a lesser extent than the mutant allele.

In an embodiment of the methods, the dsRNA comprises one or more VP intersubunit linkage modifications wherein the intersubunit linkage has the following formula:

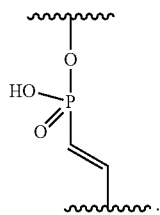 [SMILES: */C=C/P(=O)(O)O*]

In additional embodiments, the dsRNA comprises one or more of the intersubunit linkage modifications depicted in FIG. 43.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the disclosure provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the disclosure pertains to methods treating subjects therapeutically, i.e., alter onset of symptoms of the disease or disorder. In an exemplary embodiment, the modulatory method of the disclosure involves contacting a cell expressing a gain-of-function mutant with a therapeutic agent (e.g., a RNAi agent or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An RNA silencing agent modified for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075 or 0.00015 nmole of RNA silencing agent per kg of bodyweight. The unit dose, for example, can be administered by injection (e.g., intravenous or intramuscular, intrathecally, or directly into the brain), an inhaled dose, or a topical application. In exemplary embodiments, dosages are less than 2, 1 or 0.1 mg/kg of body weight.

Delivery of an RNA silencing agent directly to an organ (e.g., directly to the brain) can be at a dosage on the order of about 0.00001 mg to about 3 mg per organ, or about 0.0001-0.001 mg per organ, about 0.03-3.0 mg per organ, about 0.1-3.0 mg per organ or about 0.3-3.0 mg per organ. The dosage can be an amount effective to treat or prevent a neurological disease or disorder (e.g., Huntington's disease). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In particular embodiments, the dosage may be delivered no more than once per day, e.g., no more than once per 24, 36, 48 or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

Huntington's Disease

In certain aspects of the disclosure, RNA silencing agents are designed to target polymorphisms (e.g., heterozygous single nucleotide polymorphisms) in the mutant human huntingtin protein (htt) for the treatment of Huntington's disease. Accordingly, in another aspect, provided herein is a method of treating or managing Huntington's disease comprising administering to a patient in need of such treatment or management a therapeutically effective amount of a compound, oligonucleotide, or nucleic acid as described herein, or a pharmaceutical composition comprising said compound, oligonucleotide, or nucleic acid.

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. The CAG repeat varies in number from 8 to 35 copies in normal individuals (Kremer et al., 1994). The genetic mutation (e.g., an increase in length of the CAG repeats from less than 36 in the normal huntingtin gene to greater than 36 in the disease) is associated with the synthesis of a mutant huntingtin protein, which has greater than 36 consecutive polyglutamine residues (Aronin et al., 1995). In general, individuals with 36 or more CAG repeats will get Huntington's disease. Prototypic for as many as twenty other diseases with a lengthened CAG as the underlying mutation, Huntington's disease still has no effective therapy. A variety of interventions—such as interruption of apoptotic pathways, addition of reagents to boost mitochondrial efficiency, and blockade of NMDA receptors—have shown promise in cell cultures and mouse model of Huntington's disease. However, at best these approaches reveal a short prolongation of cell or animal survival.

The disease gene linked to Huntington's disease is termed Huntingtin or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Mutant huntingtin (protein) likely accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome-loss of mutant huntingtin.

Huntington SNPs

Exemplary SNPs in the huntingtin gene sequence suitable for targeting according to certain exemplary embodiments are disclosed in Table 4 below. Genomic sequence for each SNP site can be found in, for example, the publicly available "SNP Entrez" database maintained by the NCBI. The frequency of heterozygosity for each SNP site for HD patient and control DNA is further illustrated in Table 4. Targeting combinations of frequently heterozygous SNPs allows the treatment of a large percentage of the individuals in a HD population using a relatively small number of allele-specific RNA silencing agents.

TABLE 4 htt SNPs.

| | | | | |
|---|---|---|---|---|
| rs363125 | ORF, exon 39 | 11.00% | GTTAAGAGATGGGGAC AGTA[A/C]TTCAACG CTAGAAGAACACA (SEQ ID NO: 1) | |
| rs362273 | ORF, exon 57 | 35.20% | AGCCACGAGAAGCTGC TGCT[A/G]CAGATCA ACCCCGAGCGGGA (SEQ ID NO: 2) | |
| rs362307 | 3' UTR, exon 67 | 48.60% | CCGGAGCCTTTGGAAG TCTG[C/T]GCCCTTG TGCCCTGCCTCCA (SEQ ID NO: 3) | |
| rs362336 | ORF, exon 48 | 37.40% | CAGCCCGAGCTGCCTG CAGA[A/G]CCGGCGG CCTACTGGAGCAA (SEQ ID NO: 4) | |
| rs362331 | ORF, exon 50 | 39.40% | CCCACGCCTGCTCCCT CATC[C/T]ACTGTGT GCACTTCATCCTG (SEQ ID NO: 5) | |
| rs362272 | ORF, exon 61 | 36.10% | GGGTTGGAGCCCTGCA CGGC[A/G]TCCTCTA TGTGCTGGAGTGC (SEQ ID NO: 6) | |
| rs362306 | 3' UTR, exon 67 | 35.80% | CTGCTGGTTGTTGCCA GGTT[A/G]CAGCTGC TCTTGCATCTGGG (SEQ ID NO: 7) | |
| rs362268 | 3' UTR, exon 67 | 35.80% | TCCTCCCTCCTGCAGG CTGG[C/G]TGTTGGC CCCTSTGCTGTCC (SEQ ID NO: 8) | |

TABLE 4-continued htt SNPs.

| | | | | |
|---|---|---|---|---|
| rs362267 | 3' UTR, exon 67 | 35.50% | GATTTGGGAGCTCTGC TTGC[C/T]GACTGGC TGTGAGACGAGGC (SEQ ID NO: 9) | |
| rs363099 | ORF, exon 29 | 35.80% | GAAAAGTTTGGAGGGT TTCT[C/T]CGCTCAG CCTTGGATGTTCT (SEQ ID NO: 10) | |

In one embodiment, RNA silencing agents of the disclosure are capable of targeting one or more of the SNP sites listed in Table 4. In one embodiment, RNA silencing agents of the disclosure are capable of targeting rs363125 SNP site of the Huntingtin mRNA. In another embodiment, RNA silencing agents of the disclosure are capable of targeting rs362273 SNP site of the Huntingtin mRNA. In another embodiment, RNA silencing agents of the disclosure are capable of targeting rs362307 SNP site of the Huntingtin mRNA. In another embodiment, RNA silencing agents of the disclosure are capable of targeting rs362336 SNP site of the Huntingtin mRNA. In another embodiment, RNA silencing agents of the disclosure are capable of targeting rs362331 SNP site of the Huntingtin mRNA. In another embodiment, RNA silencing agents of the disclosure are capable of targeting rs362272 SNP site of the Huntingtin mRNA. In another embodiment, RNA silencing agents of the disclosure are capable of targeting rs362306 SNP site of the Huntingtin mRNA. In another embodiment, RNA silencing agents of the disclosure are capable of targeting rs362268 SNP site of the Huntingtin mRNA. In another embodiment, RNA silencing agents of the disclosure are capable of targeting rs362267 SNP site of the Huntingtin mRNA. In another embodiment, RNA silencing agents of the disclosure are capable of targeting rs363099 SNP site of the Huntingtin mRNA. In some embodiments, SNP sites targeted by RNA silencing agents are associated with Huntington's Disease. In particularly exemplary embodiments, SNP sites targeted by RNA silencing agents are significantly associated with Huntington's Disease.

In additional exemplary embodiments, the RNA silencing agents include one or more of the sequences of Tables 5-7:

TABLE 5

| | | | | sequence | | | |
|---|---|---|---|---|---|---|---|
| HTT SNP | compound name | sup position | additional mismatch position | antisense strand | SEQ ID NO: | sense strand | SEQ ID NO: |
| rs362273 | SNP2-7 | 2 | 7 | UUAGCAUCAGCUUCUCGUGG | 230 | AGAAGCUGCUGCUAA | 242 |
| rs362273 | SNP4-7 | 4 | 7 | UUGUAGUAGCAGCUUCUCGU | 231 | AAGCUGCUGCUACAA | 243 |
| rs362273 | SNP4-8 | 4 | 8 | UUGUAGCUGCAGCUUCUCGU | 232 | AAGCUGCUGCUACAA | 243 |
| rs362273 | SNP4-15 | 4 | 15 | UUGUAGCAGCAGCUACUCGU | 233 | AAGCUGCUGCUACAA | 243 |
| rs362273 | SNP6-5A | 6 | 5 | UUCUAUAGCAGCAGCUUCUC | 234 | GCUGCUGCUACAGAA | 244 |
| rs362273 | SNP6-8 | 6 | 8 | UUCUGUAUCAGCAGCUUCUC | 235 | GCUGCUGCUACAGAA | 244 |
| rs362273 | SNP6-11 | 6 | 11 | UUCUGUAGCAUCAGCUUCUC | 236 | GCUGCUGCUACAGAA | 244 |
| rs362273 | SNP6-14 | 6 | 14 | UUCUGUAGCAGCAUCUUCUC | 237 | GCUGCUGCUACAGAA | 244 |
| rs362273 | SNP6-16 | 6 | 16 | UUCUGUAGCAGCAGCAUCUC | 238 | GCUGCUGCUACAGAA | 244 |
| rs362307 | SNP3-5G | 3 | 5 | UCGCGGACUUCCAAAGGCUC | 239 | UUUGGAAGUCCGCGA | 245 |

TABLE 5-continued

| HTT SNP | compound name | sup position | additional mismatch position | antisense strand | SEQ ID NO: | sense strand | SEQ ID NO: |
|---|---|---|---|---|---|---|---|
| rs362307 | SNP3-7G | 3 | 7 | UCGCAGGCUUCCAAAGGCUC | 240 | UUUGGAAGCCUGCGA | 246 |
| rs362307 | SNP3-8 | 3 | 8 | UCGCAGAUUUCCAAAGGCUC | 241 | UUUGGAAAUCUGCGA | 247 |

U can be replaced with T

TABLE 6

| SNP of interest SNP | compound name | snp position | additional mismatch position | antisense strand | SEQ ID NO: | sense strand | SEQ ID NO: |
|---|---|---|---|---|---|---|---|
| rs362273 (A) | SNP2-7 | 2 | 7 | UUAGCAUCAGCUUCUCGUGG | 230 | AGAAGCUGCUGCUAA | 242 |
| rs362273 (A) | SNP4-7 | 4 | 7 | UUGUAGUAGCAGCUUCUCGU | 231 | AAGCUGCUGCUACAA | 243 |
| rs362273 (A) | SNP4-8 | 4 | 8 | UUGUAGCUGCAGCUUCUCGU | 232 | AAGCUGCUGCUACAA | 243 |
| rs362273 (A) | SNP4-15 | 4 | 15 | UUGUAGCAGCAGCUACUCGU | 233 | AAGCUGCUGCUACAA | 243 |
| rs362273 (A) | SNP6-5A | 6 | 5 | UUCUAUAGCAGCAGCUUCUC | 234 | GCUGCUGCUACAGAA | 244 |
| rs362273 (A) | SNP6-8 | 6 | 8 | UUCUGUAUCAGCAGCUUCUC | 235 | GCUGCUGCUACAGAA | 244 |
| rs362273 (A) | SNP6-11 | 6 | 11 | UUCUGUAGCAUCAGCUUCUC | 236 | GCUGCUGCUACAGAA | 244 |
| rs362273 (A) | SNP6-14 | 6 | 14 | UUCUGUAGCAGCAUCUUCUC | 237 | GCUGCUGCUACAGAA | 244 |
| rs362273 (A) | SNP6-16 | 6 | 16 | UUCUGUAGCAGCAGCAUCUC | 238 | GCUGCUGCUACAGAA | 244 |
| rs362307 (C') | SNP3-5G | 3 | 5 | UCGCGGACUUCCAAAGGCUC | 239 | UUUGGAAGUCCGCGA | 245 |
| rs362307 (C') | SNP3-7G | 3 | 7 | UCGCAGGCUUCCAAAGGCUC | 240 | UUUGGAAGCCUGCGA | 246 |
| rs362307 (C') | SNP3-8 | 3 | 8 | UCGCAGAUUUCCAAAGGCUC | 241 | UUUGGAAAUCUGCGA | 247 |

TABLE 7

| SNP of interest SNP | compound name | snp position | additional mismatch position | antisense strand | SEQ ID NO: | sense strand | SEQ ID NO: |
|---|---|---|---|---|---|---|---|
| rs362273 (G) | SNP2-7 | 2 | 7 | UCAGCAUCAGCUUCUCGUGG | 248 | AGAAGCUGCUGCUGA | 259 |
| rs362273 (G) | SNP4-7 | 4 | 7 | UUGCAGUAGCAGCUUCUCGU | 249 | AAGCUGCUGCUGCAA | 260 |
| rs362273 (G) | SNP4-8 | 4 | 8 | UUGCAGCUGCAGCUUCUCGU | 250 | AAGCUGCUGCUGCAA | 260 |
| rs362273 (G) | SNP4-15 | 4 | 15 | UUGCAGCAGCAGCUACUCGU | 251 | AAGCUGCUGCUGCAA | 260 |
| rs362273 (G) | SNP6-5A | 6 | 5 | UUCUACAGCAGCAGCUUCUC | 252 | GCUGCUGCUGCAGAA | 261 |
| rs362273 (G) | SNP6-8 | 6 | 8 | UUCUGCAUCAGCAGCUUCUC | 253 | GCUGCUGCUGCAGAA | 261 |

TABLE 7-continued

| SNP of interest SNP | compound name | description of siRNA sequence flanking snp | | sequence | | | |
|---|---|---|---|---|---|---|---|
| | | snp position | additional mismatch position | antisense strand | SEQ ID NO: | sense strand | SEQ ID NO: |
| rs362273 (G) | SNP6-11 | 6 | 11 | UUCUGCAGCAUCAGCUUCUC | 254 | GCUGCUGCUGCAGAA | 261 |
| rs362273 (G) | SNP6-14 | 6 | 14 | UUCUGCAGCAGCAUCUUCUC | 255 | GCUGCUGCUGCAGAA | 261 |
| rs362307 (T) | SNP3-5G | 3 | 5 | UCACGGACUUCCAAAGGCUC | 256 | UUUGGAAGUCCGUGA | 262 |
| rs362307 (T) | SNP3-7G | 3 | 7 | UCACAGGCUUCCAAAGGCUC | 257 | UUUGGAAGCCUGUGA | 263 |
| rs362307 (T) | SNP3-8 | 3 | 8 | UCACAGAUUUCCAAAGGCUC | 258 | UUUGGAAAUCUGUGA | 264 |

In certain embodiments of Tables 5-7, a U nucleotide may be replaced with a T nucleotide.

Methods of Delivering Nucleic Acids

RNA silencing agents of the disclosure may be directly introduced into a cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the disclosure can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-IS mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly), or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double-stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, fluorescence activated cell analysis (FACS) and the like.

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Depending on the assay, quantitation of the amount of gene expression allows one to determine a degree of inhibition which is greater than 10%, 33%, 50%, 90%, 95% or 99% as compared to a cell not treated according to the present disclosure. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell. mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In a particular aspect, the efficacy of an RNAi agent of the disclosure (e.g., an siRNA targeting a polymorphism in a mutant gene) is tested for its ability to specifically degrade mutant mRNA (e.g., mutant htt mRNA and/or the production of mutant huntingtin protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild-type or mutant cDNAs (e.g., human wild-type or mutant huntingtin cDNA). Standard siRNA, modified siRNA or vectors able to produce siRNA from U-looped mRNA are co-transfected. Selective reduction in mutant mRNA (e.g., mutant huntingtin mRNA) and/or mutant protein (e.g., mutant huntingtin) is measured. Reduction of mutant mRNA or protein can be compared to levels of normal mRNA or protein. Exogenously-introduced normal mRNA or protein (or endogenous normal mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

In certain exemplary embodiments, a composition that includes an RNA agent, e.g., a dsRNA agent, of the disclosure can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA agents, e.g., dsRNA agents, to peripheral neurons. An exemplary route of delivery is directly to the brain, e.g., into the ventricles or the hypothalamus of the brain, or into the lateral or dorsal areas of the brain. The RNA agents, e.g., dsRNA agents, for neural cell delivery can be incorporated into pharmaceutical compositions suitable for administration.

For example, compositions can include one or more species of an RNA agent, e.g., a dsRNA agent, and a pharmaceutically acceptable carrier. The pharmaceutical compositions of the present disclosure may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the disclosure is delivered across the Blood-Brain-Barrier (BBB) suing a variety of suitable compositions and methods described herein.

The route of delivery can be dependent on the disorder of the patient. For example, a subject diagnosed with Huntington's disease can be administered an anti-htt RNA agent, e.g., a dsRNA agent, of the disclosure directly into the brain (e.g., into the globus pallidus or the corpus striatum of the basal ganglia, and near the medium spiny neurons of the corpus striatum). In addition to an RNA silencing agent of the disclosure, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). For the treatment of Huntington's disease, for example, symptomatic therapies can include the drugs haloperidol, carbamazepine, or valproate. Other therapies can include psychotherapy, physiotherapy, speech therapy, communicative and memory aids, social support services, and dietary advice.

An RNA agent, e.g., a dsRNA agent, can be delivered to neural cells of the brain. Delivery methods that do not require passage of the composition across the blood-brain barrier can be utilized. For example, a pharmaceutical composition containing an RNA agent, e.g., a dsRNA agent, can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA agent, e.g., a dsRNA agent, can be delivered into multiple regions of the central nervous system (e.g., into multiple regions of the brain, and/or into the spinal cord). The RNA agent, e.g., a dsRNA agent, can be delivered into diffuse regions of the brain (e.g., diffuse delivery to the cortex of the brain).

In one embodiment, the RNA agent, e.g., a dsRNA agent, can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA agent, e.g., dsRNA agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is affected by a conduit leading from the pump or reservoir to the site of release. Devices for delivery to the brain are described, for example, in U.S. Pat. Nos. 6,093,180, and 5,814,014.

An RNA agent, e.g., a dsRNA agent, of the disclosure can be further modified such that it is capable of traversing the blood brain barrier. For example, the RNA agent, e.g., a dsRNA agent, can be conjugated to a molecule that enables the agent to traverse the barrier. Such modified RNA agents, e.g., dsRNA agents, can be administered by any desired method, such as by intraventricular or intramuscular injection, or by pulmonary delivery, for example.

In certain embodiments, exosomes are used to deliver an RNA agent, e.g., a dsRNA agent, of the disclosure. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mäger I, Wood M J. (2013). Exosomes for targeted siRNA delivery across biological barriers. Adv. Drug Deliv Rev. 2013 March; 65(3):391-7. doi: 10.1016/j.addr.2012.08.008).

In certain embodiments, one or more lipophilic molecules are used to allow delivery of an RNA agent, e.g., a dsRNA agent, of the disclosure past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the disclosure. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA agent, e.g., a dsRNA agent, of the disclosure across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide)(PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA agent, e.g., a dsRNA agent, of the disclosure can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA agent, e.g., a dsRNA agent, of the disclosure can be administered by any suitable method. As used herein, topical delivery can refer to the direct application of an RNA agent, e.g., a dsRNA agent, to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA agent, e.g., a dsRNA agent, to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration typically do not include a transfection reagent or an additional lipophilic moiety besides, for example, the lipophilic moiety attached to the RNA agent, e.g., a dsRNA agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA agent, e.g., a dsRNA agent, of the disclosure can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA agent, e.g., a dsRNA agent, administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are exemplary. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. An exemplary group of carbohydrates includes lactose, trehalose, raffinose maltodextrins, and mannitol. Suitable polypeptides include aspartame. Amino acids include alanine and glycine, with glycine being exemplary.

Suitable pH adjusters or buffers include organic salts prepared from organic acids and bases, such as sodium citrate, sodium ascorbate, and the like; sodium citrate is exemplary.

An RNA agent, e.g., a dsRNA agent, of the disclosure can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA agents, e.g., dsRNA agents, are dispensed by an implanted device. The device can include a sensor that monitors a parameter within a subject. For example, the device can include a pump, such as an osmotic pump and, optionally, associated electronics.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1: SNP Discrimination Varies According to the Position of the Mismatch

Figure 46:
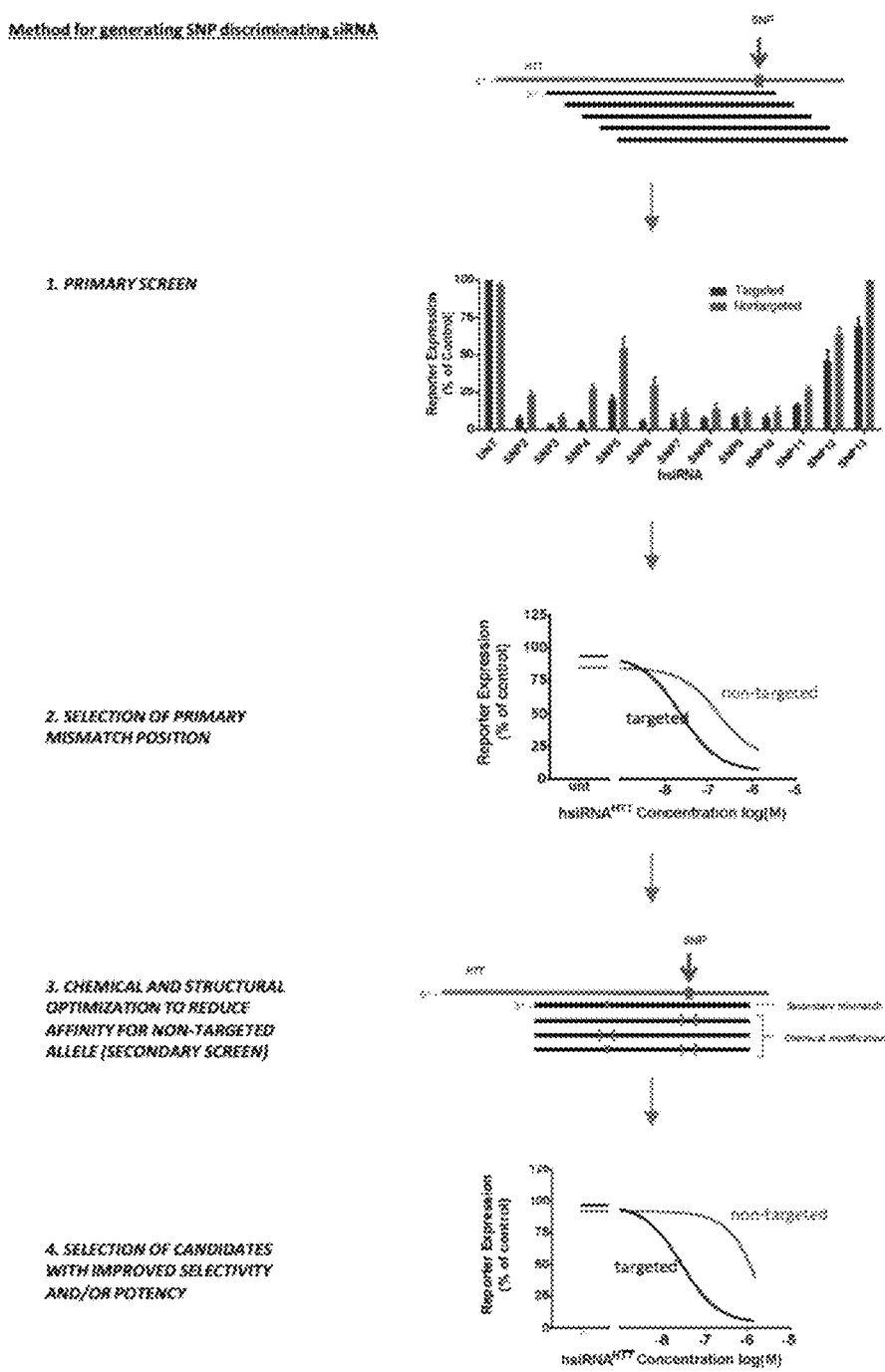
FIG. 46 is a flow chart illustrating a methodology for generating and selecting SNP-discriminating siRNAs.

FIG. 46 is a flow chart illustrating a methodology for generating and selecting SNP-discriminating siRNAs that was implemented in the instance of HTT, but is also applicable to SNPs in other genes. A primary screen is conducted to determine which position the SNP is placed at causes the greatest discrimination. Then, the mismatch position(s) yielding best results are selected, and affinity for non-target alleles is further reduced in a secondary screening where chemical and structural optimizations to the siRNA molecule with improved selectivity and/or potency are selected.

Figure 45:
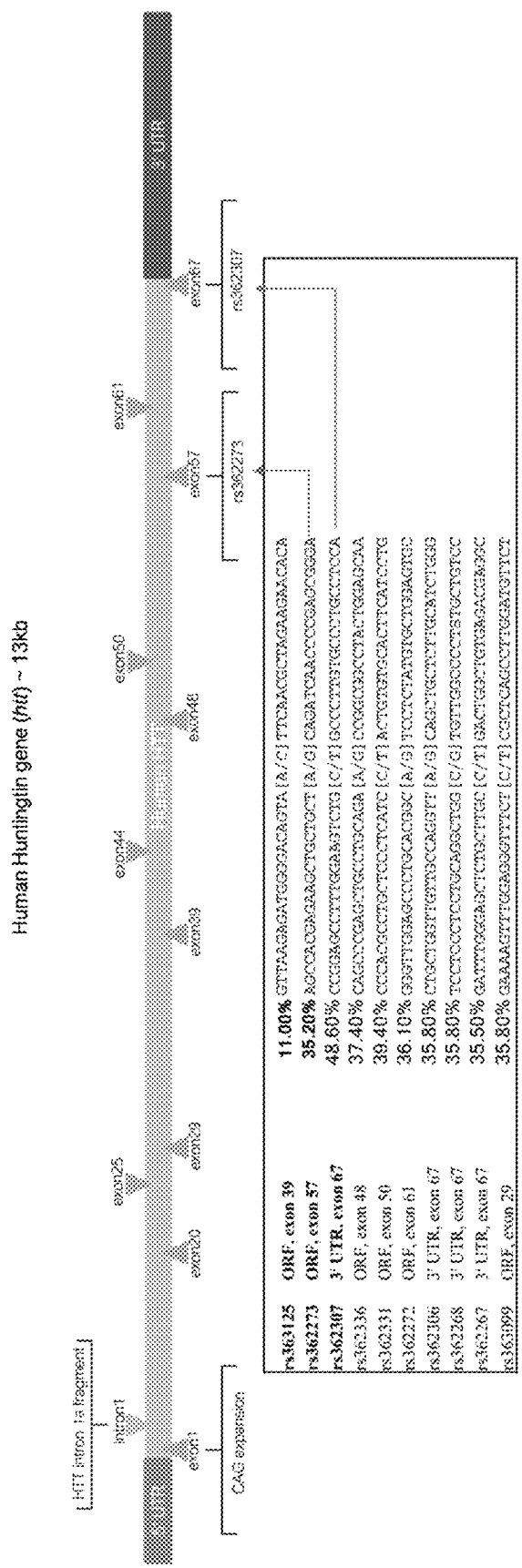
FIG. 45 illustrates exemplary SNPs within the HTT gene (SEQ ID NOs: 1-10 (numbered from top to bottom)).

There are several SNPs within the HTT gene that have high rates of heterozygosity in HD patients (FIG. 45). For optimization of SNP-specific RNAi-mediated silencing of huntingtin, SNP rs362273 in exon 57 of HTT mRNA was used as model target for optimization of SNP selective silencing. This SNP heterozygosity occurs in 35% of the HD patient population.

The psiCHECK reporter plasmid described herein contains SNP rs362273 and a partial flanking region from exon 57 of htt, within a Rluc 3' UTR. The wild-type psiCHECK reporter plasmid contains the same region of htt without the SNP (FIG. 1).

Figure 2:
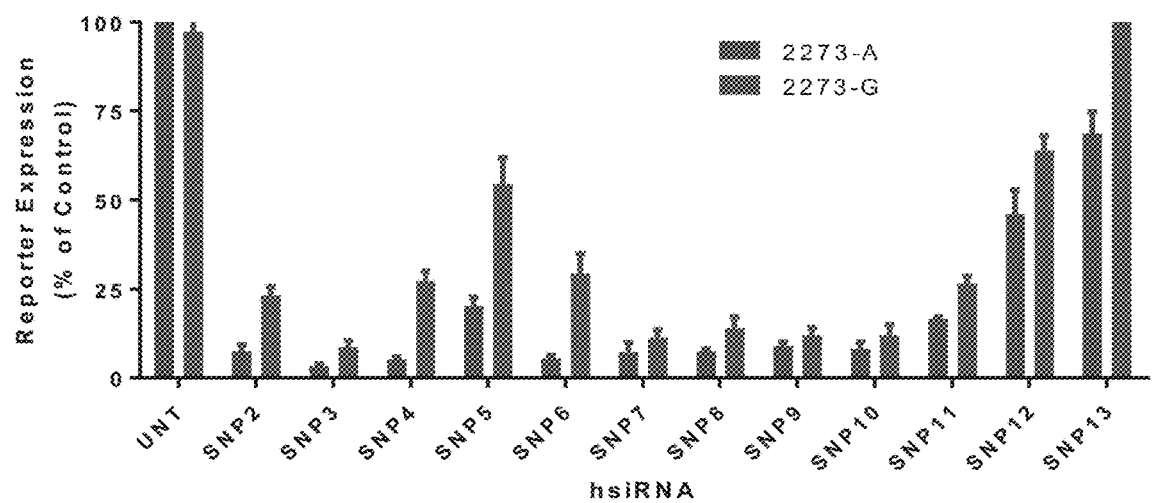
FIG. 2 depicts a bar graph showing luciferase activity following a psiCHECK reporter plasmid assay in HeLa cells transfected with hsiRNAs with the SNP nucleotide at varying positions. This primary screen yielded multiple efficacious hydrophobically modified siRNA (hsiRNA) sequences.
Figure 47:
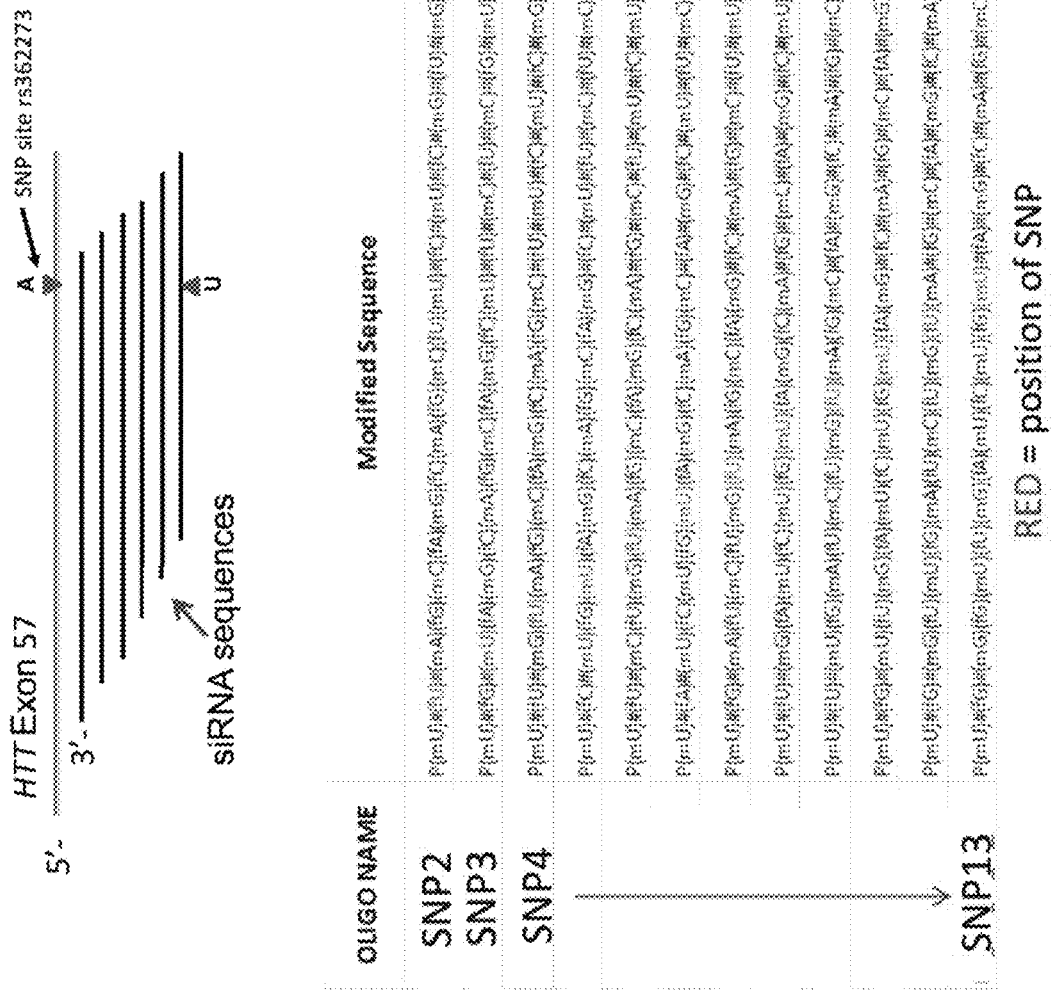
FIG. 47 illustrates a naming convention denoting the position of an SNP within an siRNA.
Figure 48A:
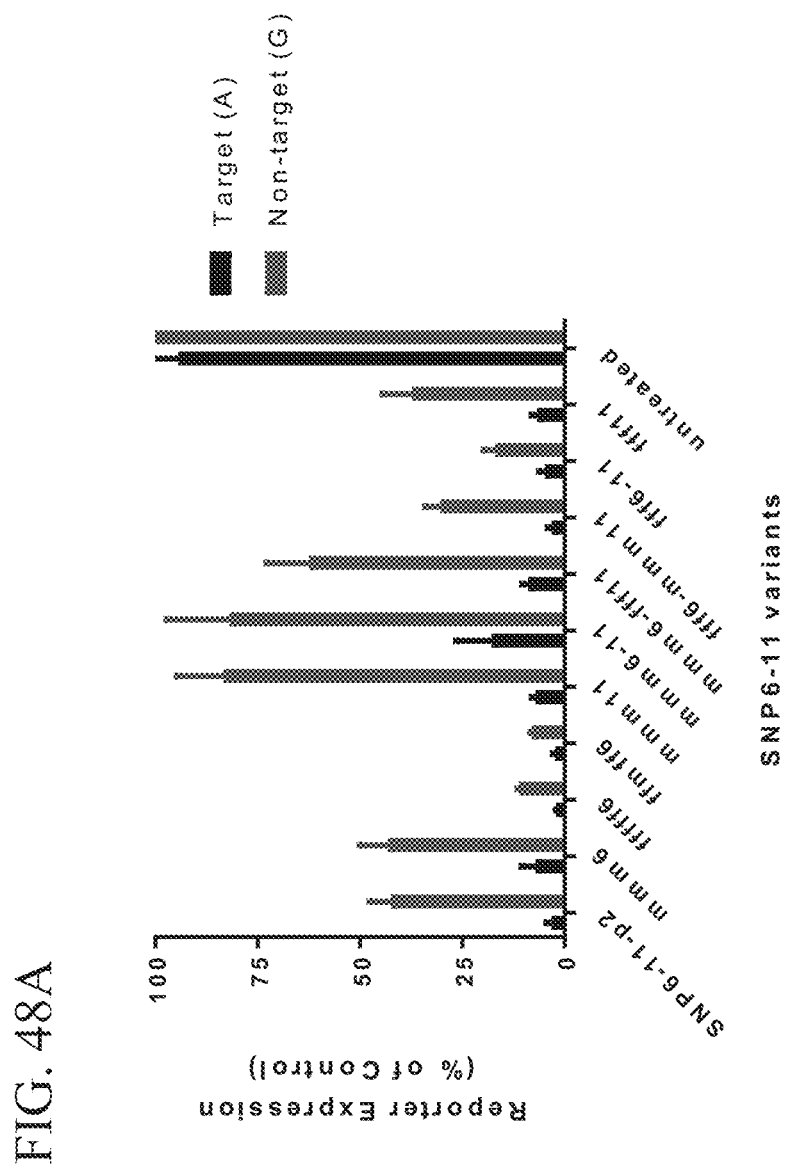

Hydrophobically modified RNAs (hsiRNAs) designed to be complimentary to the Huntingtin (htt) mRNA containing the mutant SNP (2273-1 (A)) were screened for efficacy with the psiCheck reporter plasmid system. The number following SNP represents the position of the SNP in the siRNA (FIG. 47). FIG. 2 shows that placing the SNP in position 2, 4 or 6 provided the greatest SNP discrimination, without losing efficacy against the mutant allele. HeLa cells transfected with one of two reporter plasmids were reverse transfected with 1.5 μM hsiRNAs by passive uptake, and treated for 72 hours. Luciferase activity was measured at 72 hours post transfection (FIG. 2).

Figure 3:
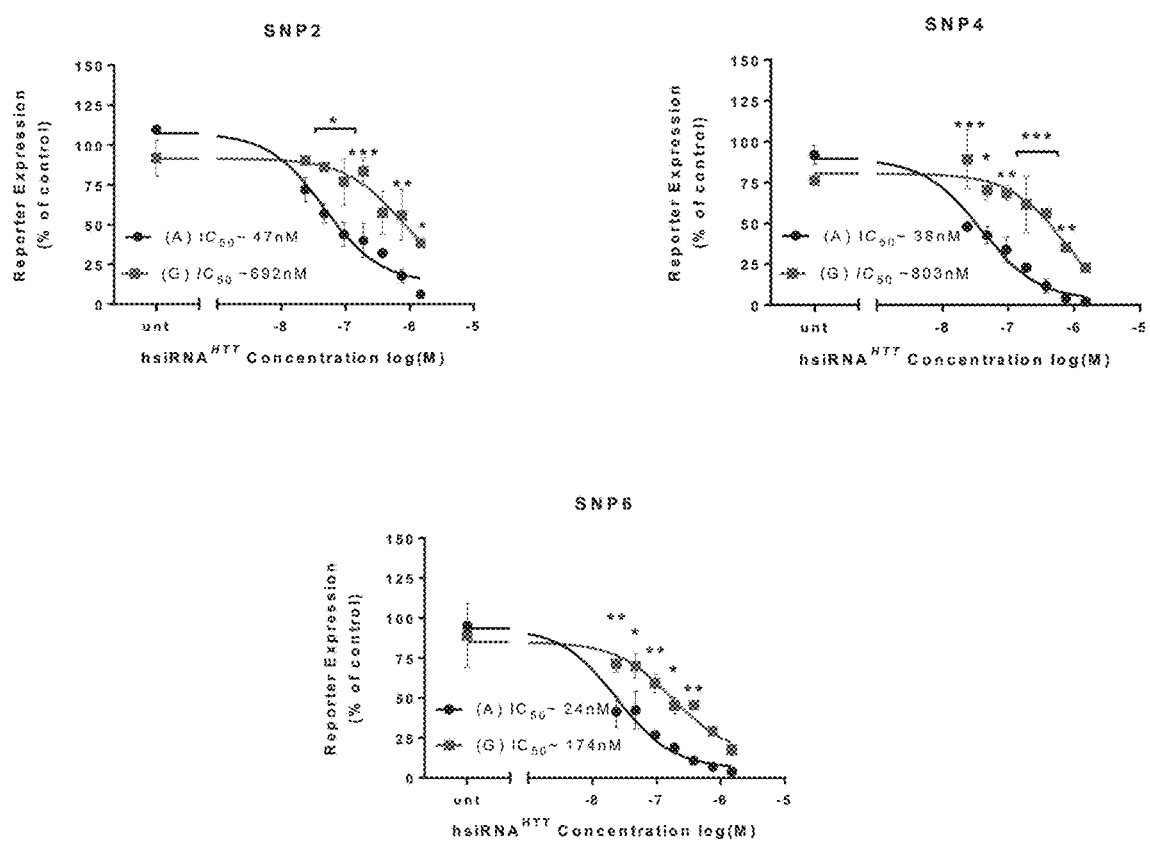
FIG. 3 depicts dose response curves showing the silencing effects of three exemplary hsiRNAs on psiCHECK reporter plasmids.

The hsiRNAs were further tested for allelic discrimination in a dose response dual luciferase assay in HeLa cells (FIG. 3). Multiple hsiRNAs preferentially silenced the reporter plasmid containing the mutant SNP as compared to the wild-type reporter plasmid. HeLa cells transfected with one of two reporter plasmids were reverse transfected with 1.5 μM hsiRNAs by passive uptake, and treated for 72 hours. Reporter plasmid expression was measured at 72 hours post transfection (FIG. 3).

Example 2: SNP Discrimination in the Endogenous Hit mRNA

Figure 4:
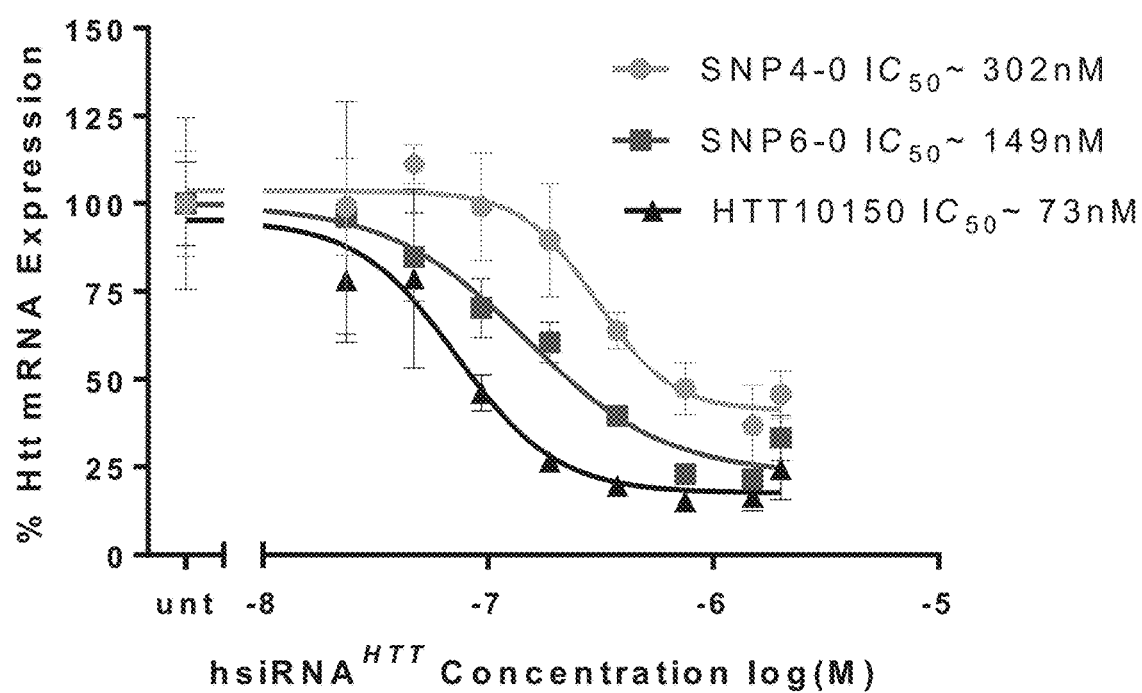
FIG. 4 depicts a dose response curve showing the efficacy of two hsiRNAs on silencing htt mRNA.

The hsiRNAs were tested for efficacy against the endogenous Huntingtin mRNA containing a homozygous rs362273 SNP. As HeLa cells are homozygous at rs362273, with an A on each allele, allelic discrimination was not assessed with this assay. Instead, FIG. 4 shows that two hsiRNAs, SNP4-0 and SNP6-0, were highly effective at silencing the htt mRNA containing the correct SNP. The mRNA levels were measured using Quantigene 2.0 bDNA assay after treating HeLa cells with hsiRNAs via passive uptake for 72 hours. Human htt mRNA levels were normalized to human HPRT.

Figure 34:
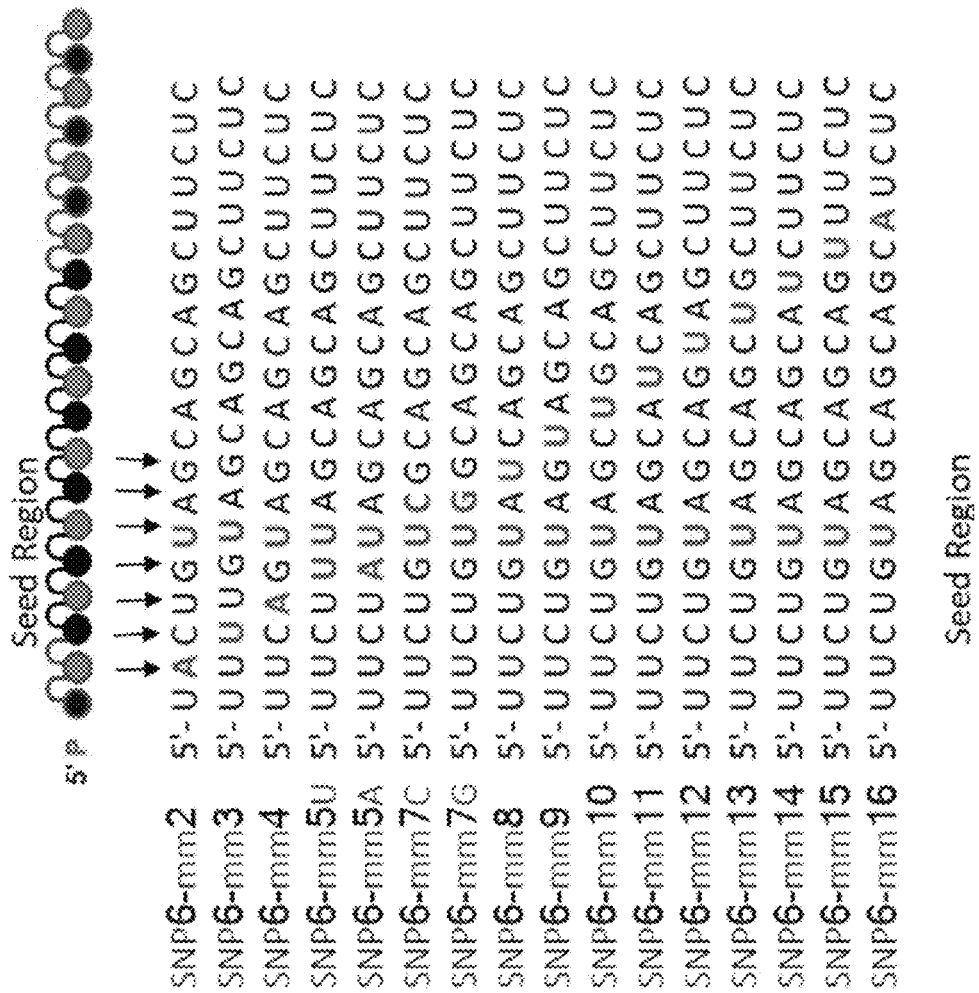
FIG. 34 illustrates example sequences introducing single mismatches in sequences previously chosen for dose response.

Example 3: Designing hsiRNAs with a Second Mismatch for Greater Allelic Discrimination For each of the three hsiRNAs (SNP2-0, SNP4-0, and SNP6-0, also named mm2, mm4, and mm6, respectively) previously chosen for dose response, 16 new hsiRNAs were designed and synthesized with slight sequence modifications (FIG. 34). These sequences introduced a single mismatch at every possible position along the original sequence, in order to test if the second mismatch impairs silencing of the off-target SNP more significantly than before, with little effect on silencing the target SNP. Antisense strand sequences shown 5' to 3', with the SNP site in red, and the new mismatch in blue (FIG. 12).

Figure 5:
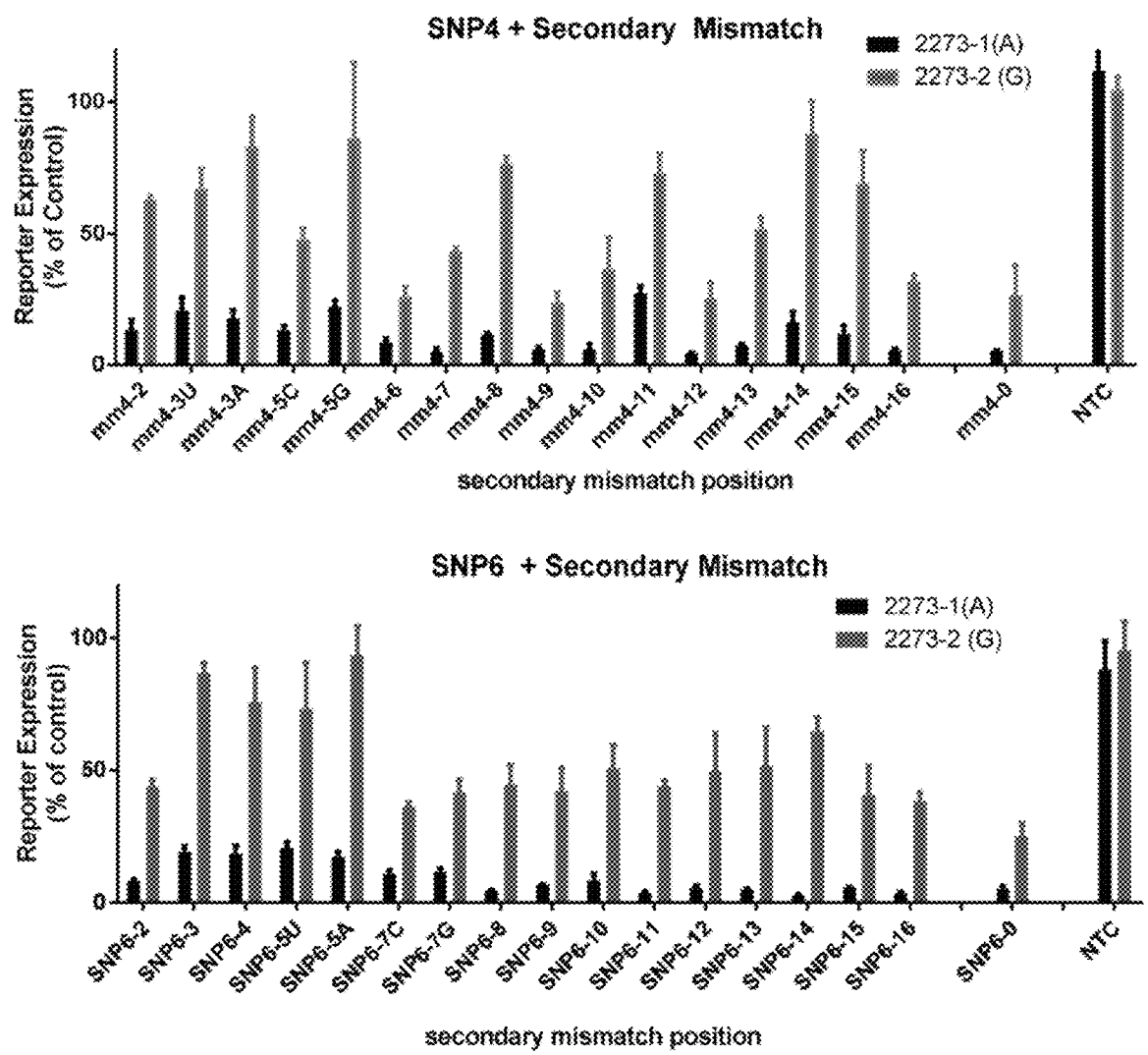
FIG. 5 depicts bar graphs showing luciferase activity following a psiCHECK reporter plasmid assay in HeLa cells transfected with hsiRNAs having a second mismatch at varying positions.

A primary screen of the efficacy of the hsiRNAs in FIG. 12 showed that the position of the second mismatch, relative to the position of the nucleotide corresponding to the SNP, resulted in varying levels of SNP discrimination in HeLa cells. HeLa cells transfected with one of two psiCHECK reporter plasmids were reverse transfected with 1.5 μM hsiRNAs by passive uptake, and treated for 72 hours. Luciferase activity was measured at 72 hours post transfection. FIG. 5 shows that multiple hsiRNAs discriminately silenced the reporter plasmid containing the SNP mutation as compared to the wild-type reporter plasmid.

Figure 6:
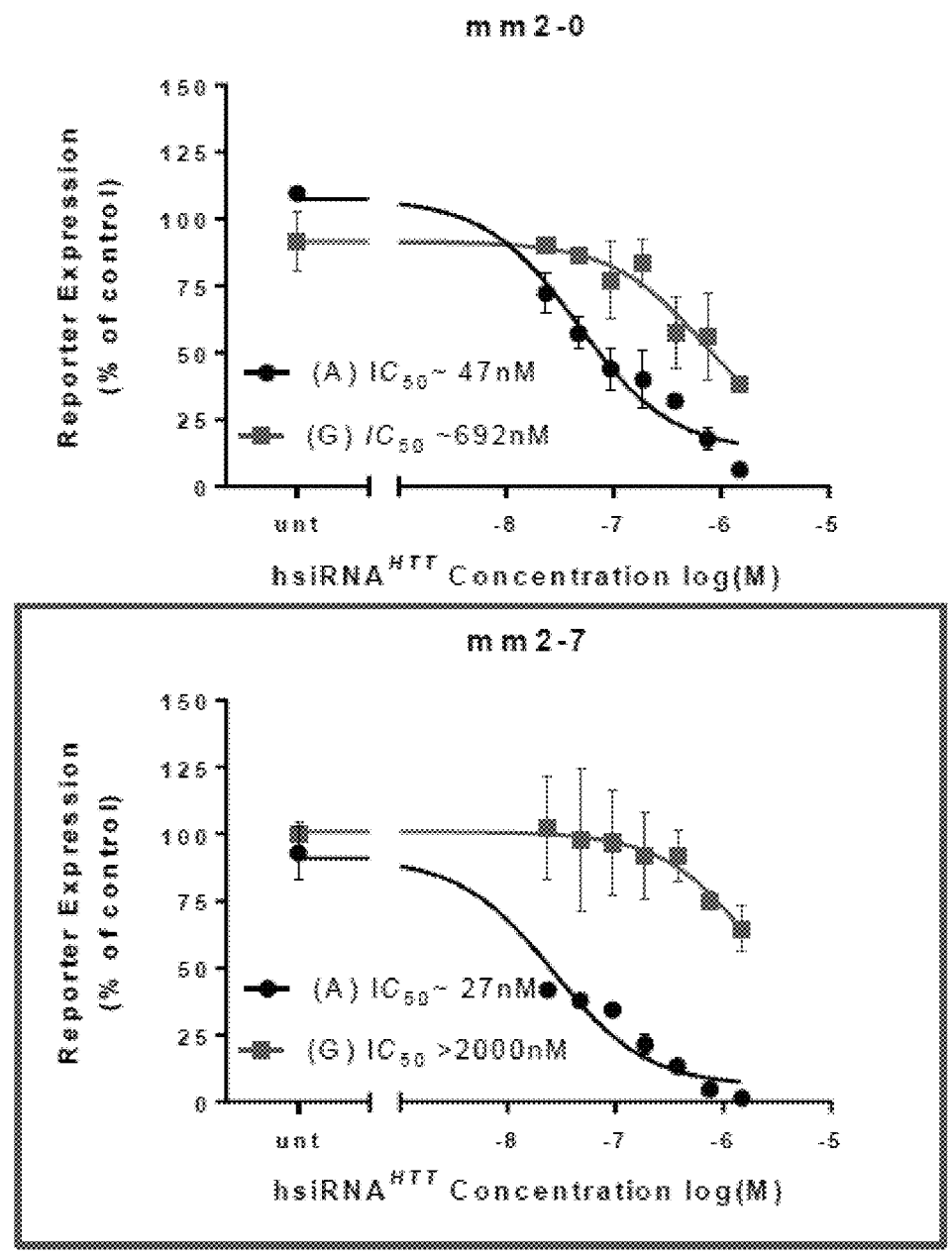
FIG. 6 depicts dose response curves comparing silencing effects of SNP2 hsiRNA with (mm2-7) or without (mm2-0) an additional mismatch.
Figure 7:
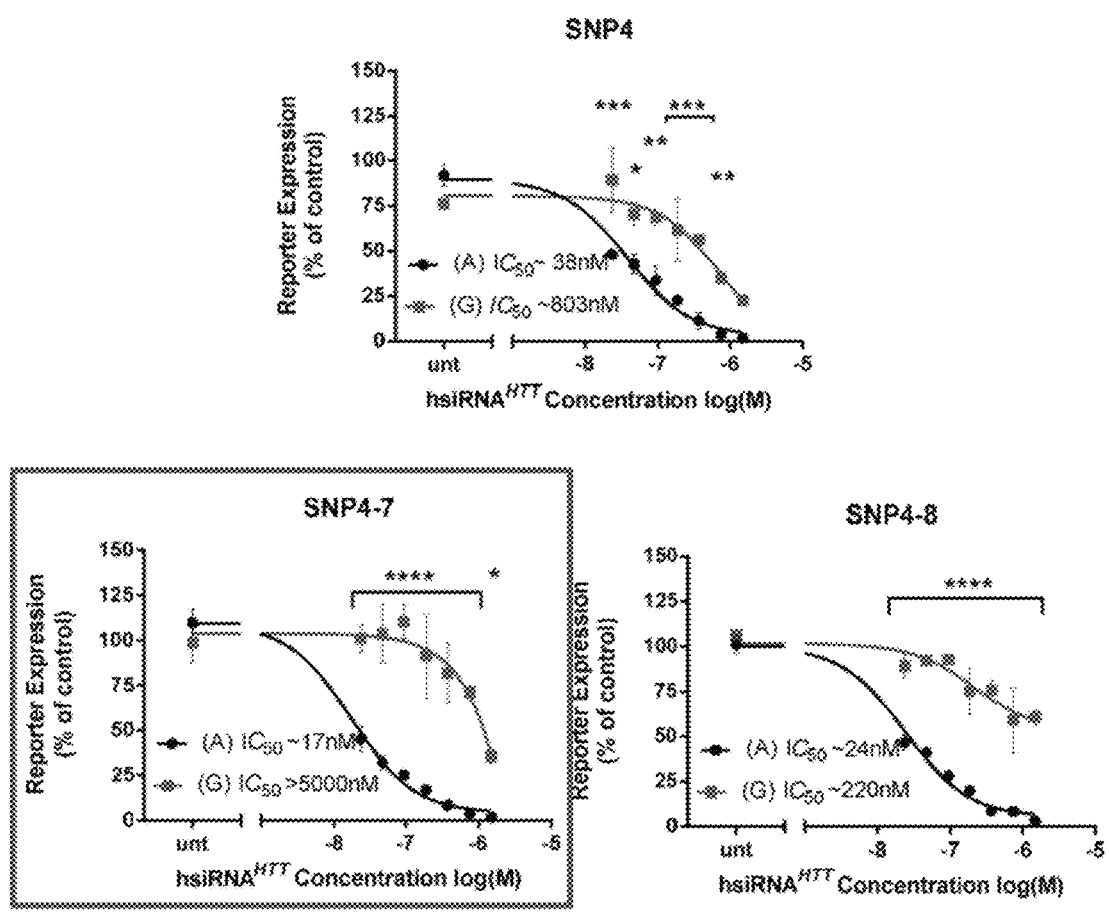
FIG. 7 depicts dose response curves comparing silencing effects of SNP4 hsiRNAs with or without an additional mismatch.
Figure 8:
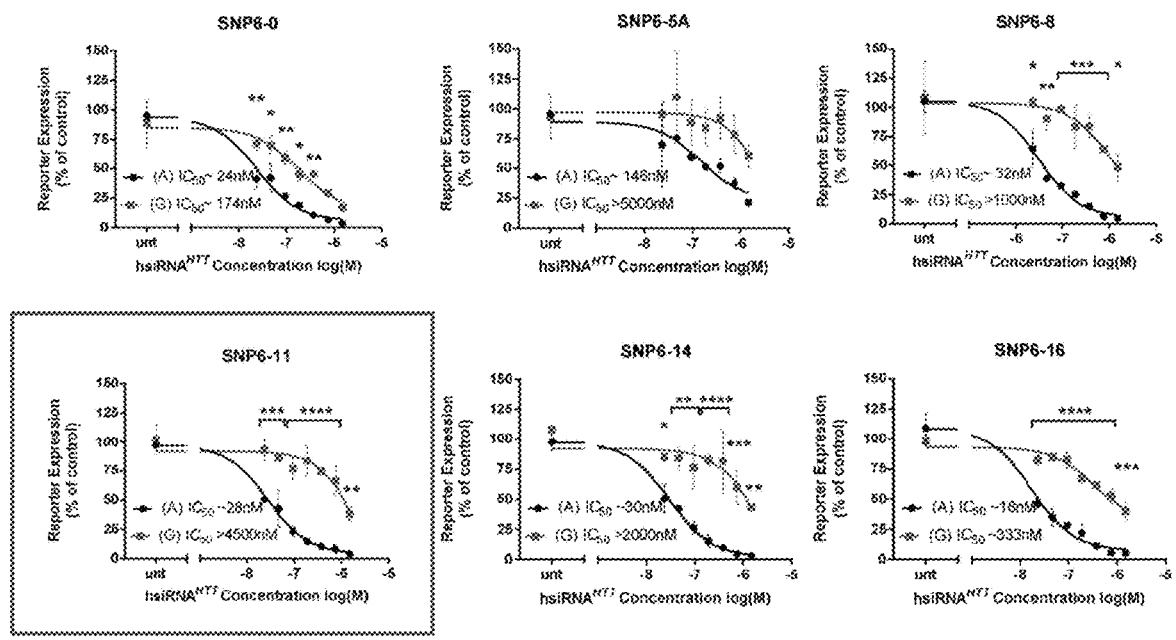
FIG. 8 depicts dose response curves comparing silencing effects of SNP6 hsiRNAs with or without an additional mismatch.
Figure 11:
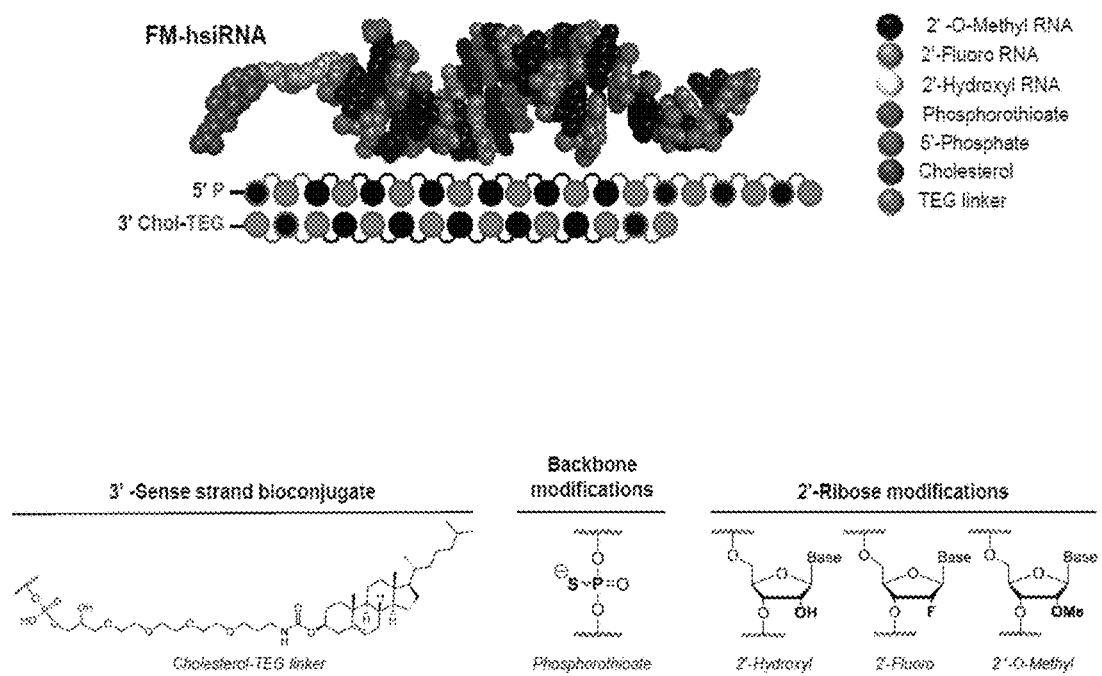
FIG. 11 schematically depicts an hsiRNA and exemplary modifications according to some embodiments.

The most efficacious hsiRNAs, containing the second mismatch, were further tested in a dose response curve to verify improved SNP discrimination. HeLa cells transfected with one of two reporter plasmids were reverse transfected with hsiRNAs by passive uptake, and treated for 72 hours. Reporter expression measured with a dual-luciferase assay. FIGS. 6-8 show the IC50 values of the hsiRNAs with two mismatches for silencing the reporter plasmid containing the SNP mutation versus the wild-type reporter plasmid. The SNP6-11 hsiRNA (hsiRNA molecule with the nucleotide corresponding to the polymorphism at position 6 from the 5' end and the mismatch at position 11 from the 5' end) and the SNP4-7 hsiRNA (hsiRNA molecule with the nucleotide corresponding to the polymorphism at position 4 from the 5'end and the mismatch at position 7 from the 5' end) were shown to be the most efficacious (see FIGS. 7-9). Surprisingly, altering the modification pattern around the SNP rescues efficacy lost by introducing the second mismatch without impairing discrimination. The SNP6-11 hsiRNA was altered so that it had 2'O-methyl modifications flanking the mismatch nucleotide (as well as the mismatch nucleotide itself having the 2'O-methyl modification) (see FIG. 10).

Example 4: Additional Modifications

A variety of oligonucleotide types (e.g., gapmers, mixmers, miRNA inhibitors, splice-switching oligonucleotides ("SSOs"), phosphorodiamidate morpholino oligonucleotides ("PMOs"), peptide nucleic acids ("PNAs") and the like) can be used in the oligonucleotides described herein, optionally utilizing various combinations of modifications (e.g., chemical modifications) and/or conjugations described herein and in, e.g., U.S. Ser. No. 15/089,423; U.S. Ser. No. 15/236,051; U.S. Ser. No. 15/419,593; U.S. Ser. No. 15/697,120 and U.S. Pat. No. 9,809,817; and U.S. Ser. No. 15/814,350 and U.S. Pat. No. 9,862,350, each of which is incorporated herein by reference in its entirety for all purposes.

Figure 14:
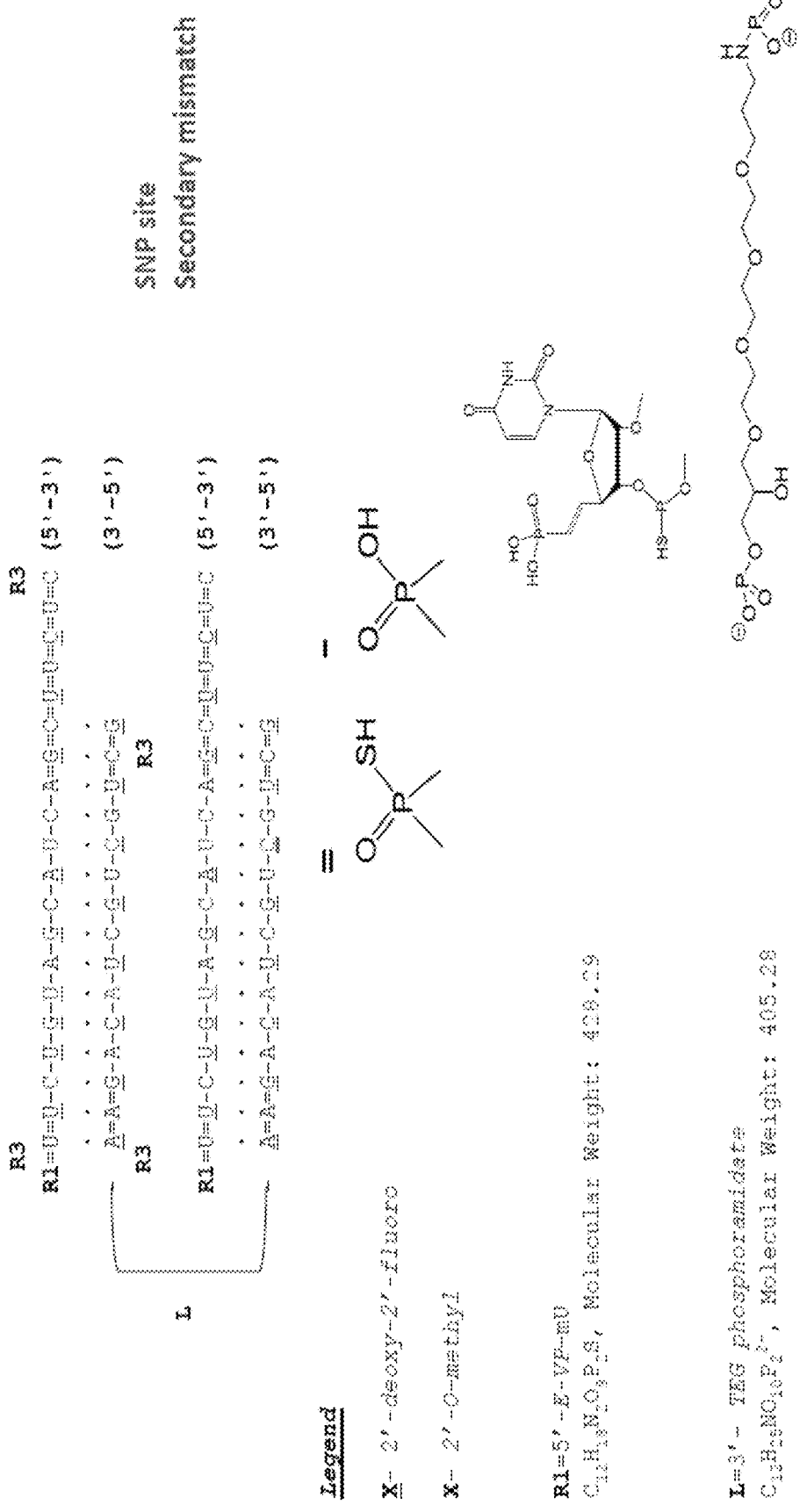
FIG. 14 depicts an exemplary SNP-selective compound designed as a di-siRNA.
Figure 15:
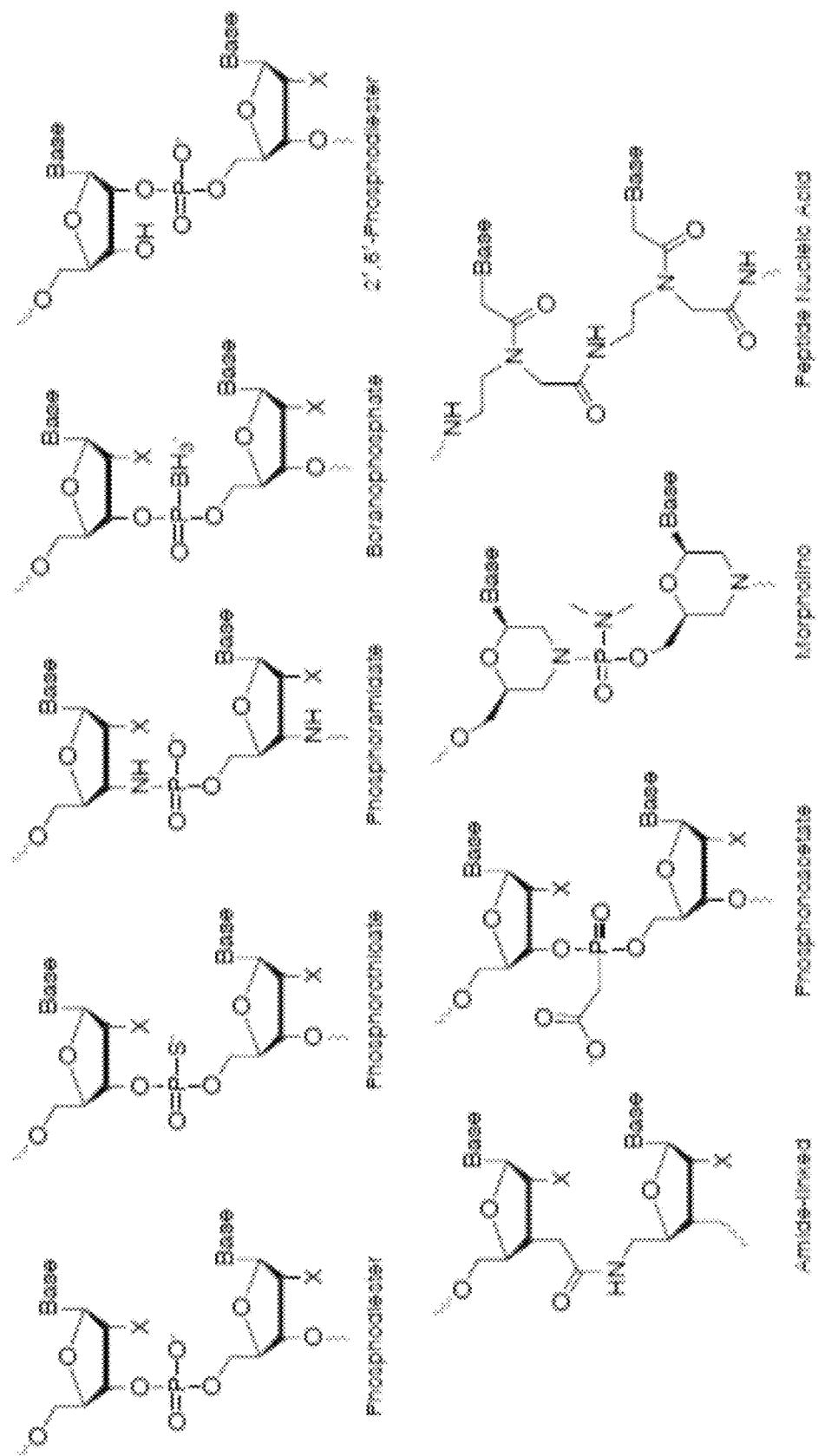
Figure 16:
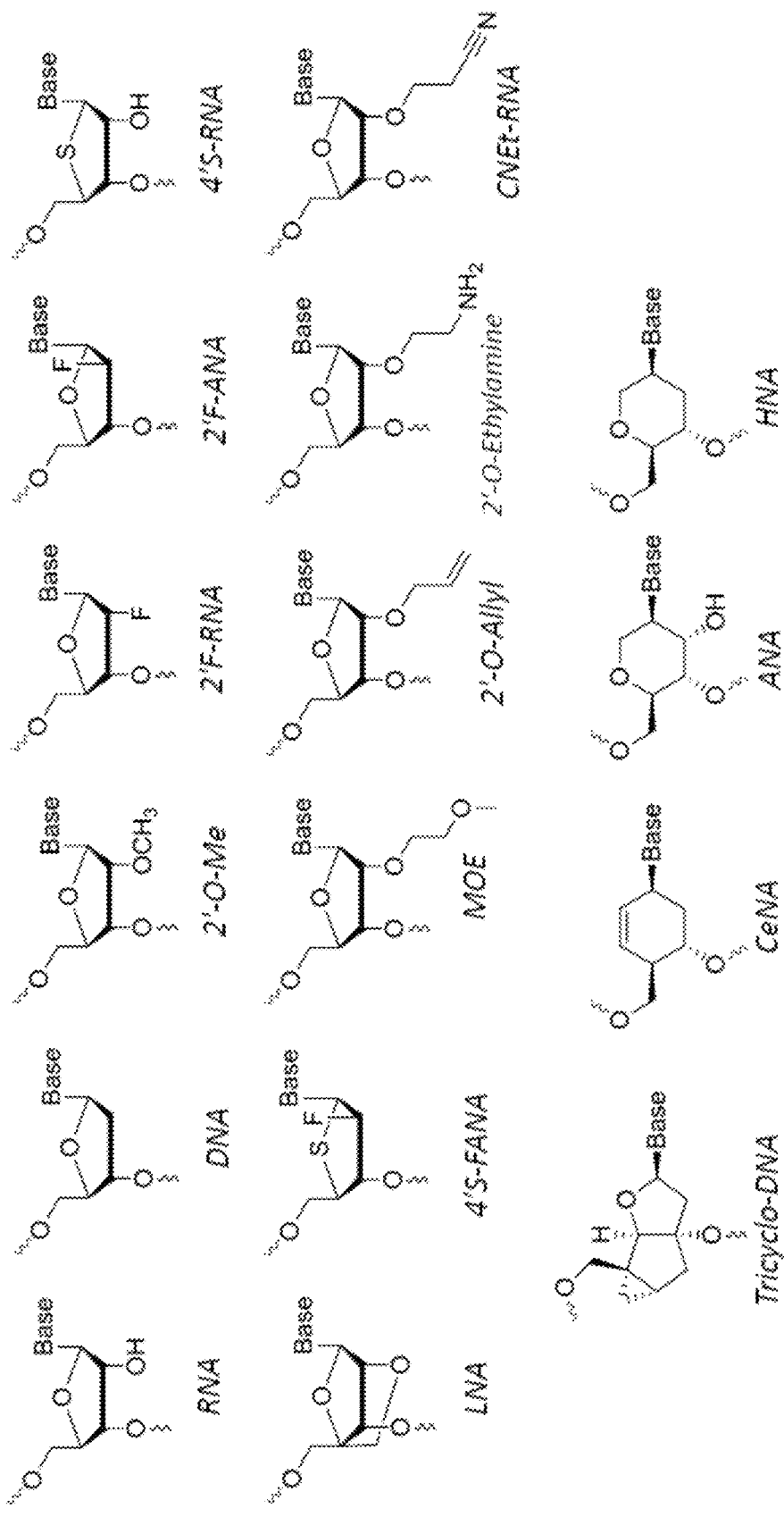
Figure 17:
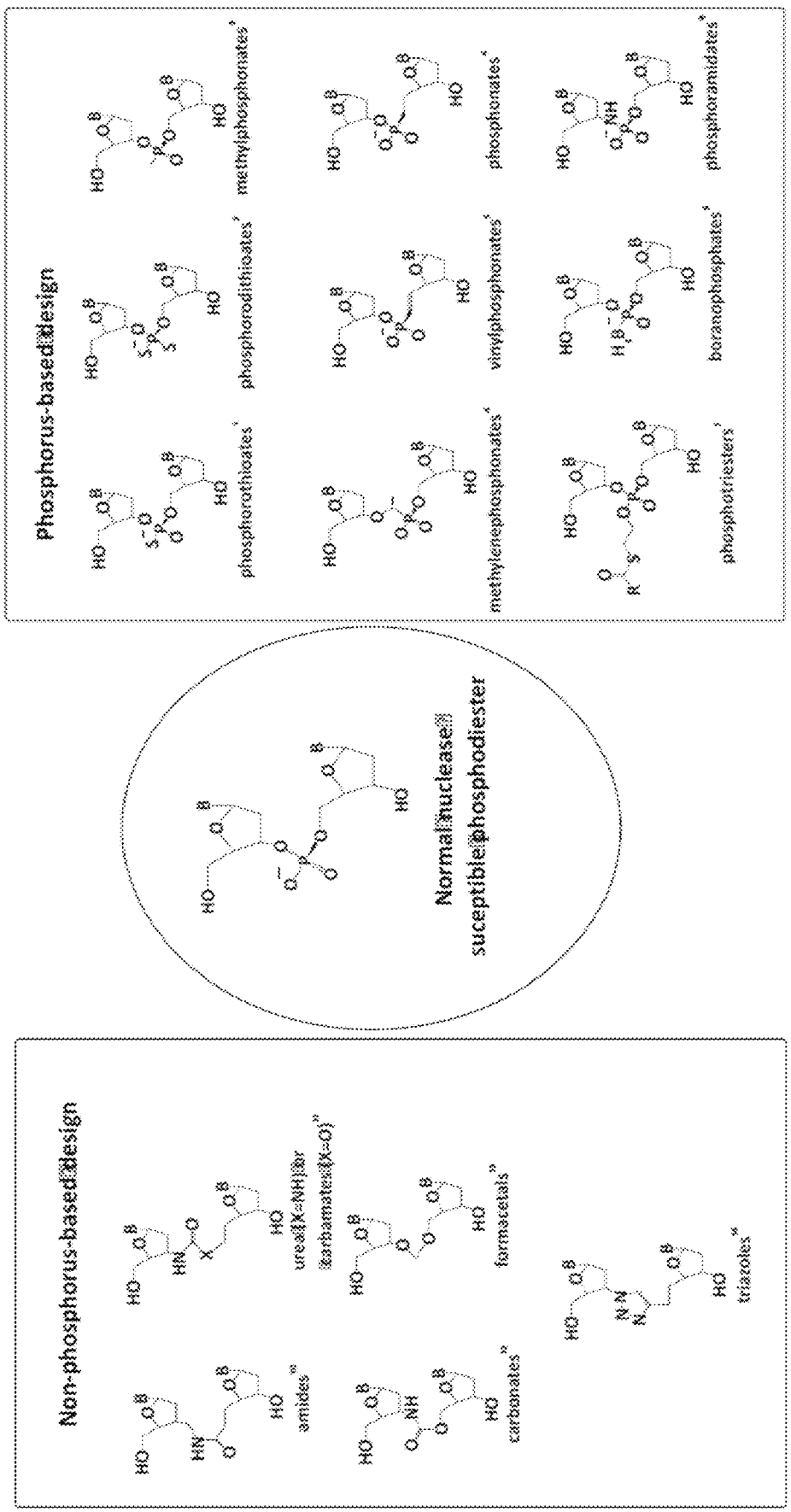
FIG. 17 depicts internucleotide bonds according to certain exemplary embodiments. Potential internucleotide bonds can be between the first two nucleotides at the 5' or 3' ends of any given oligonucleotide strand can be stabilized with any of the moieties depicted.
Figure 18:
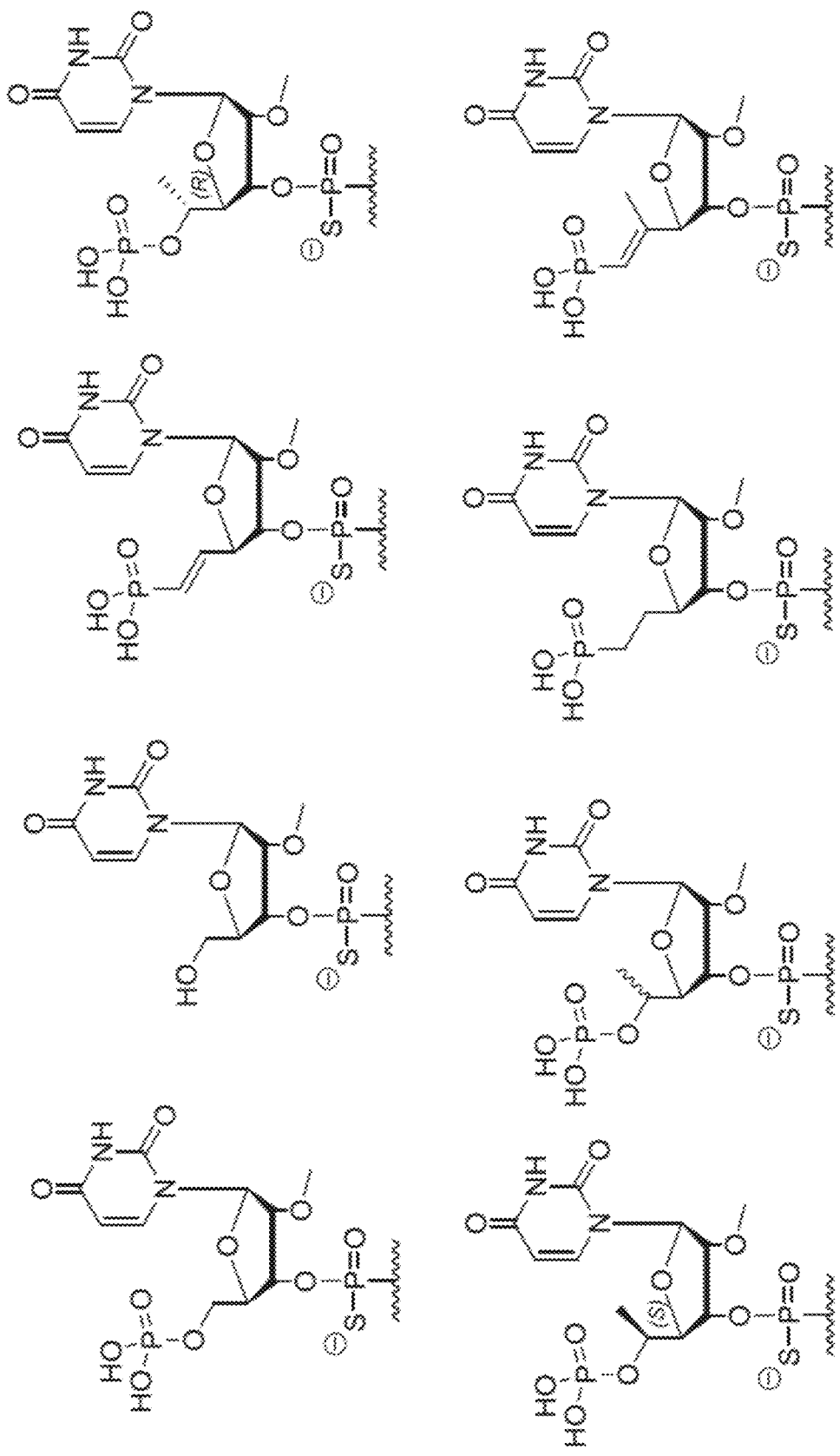
Figure 19:
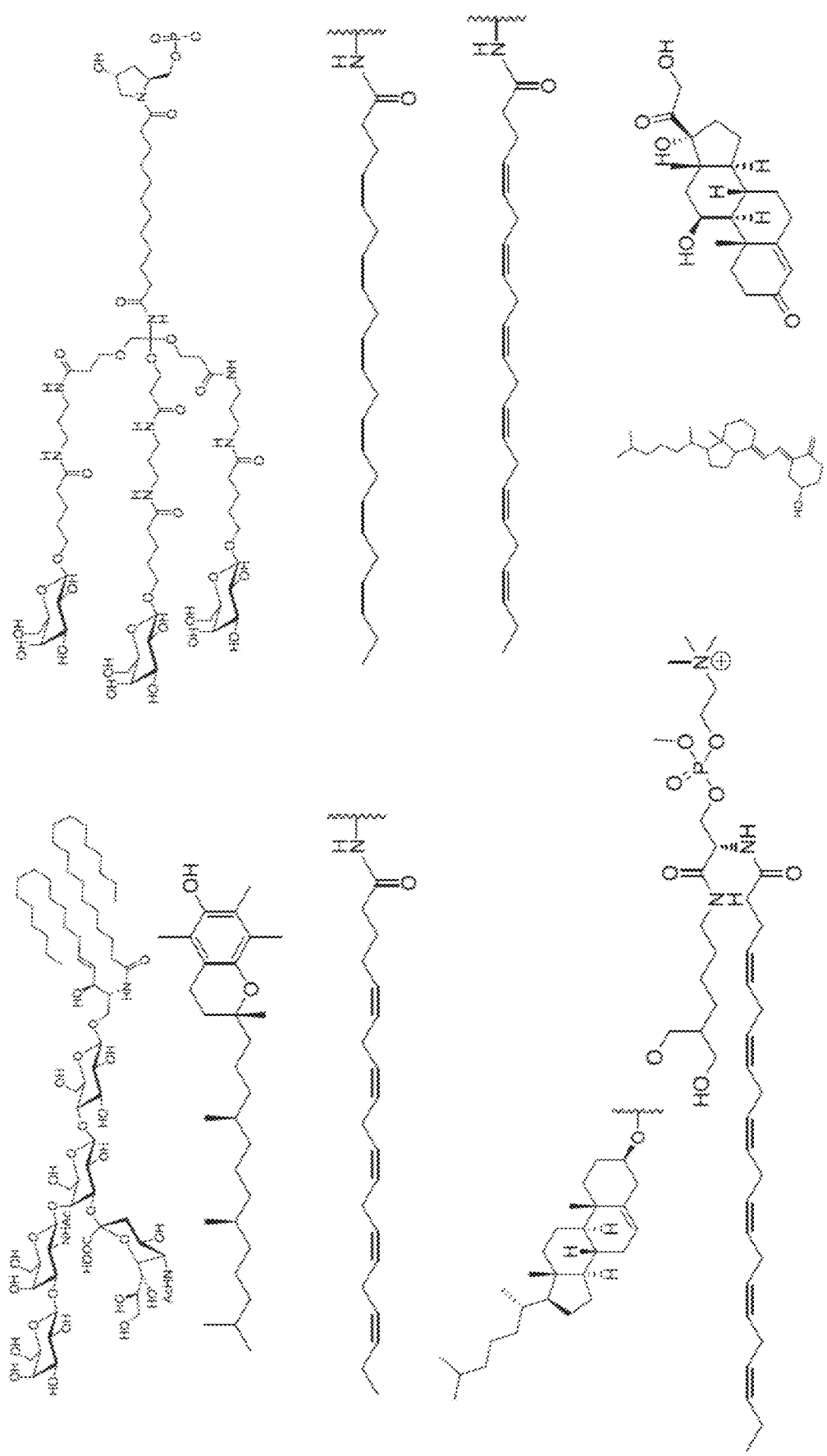
Figure 35:
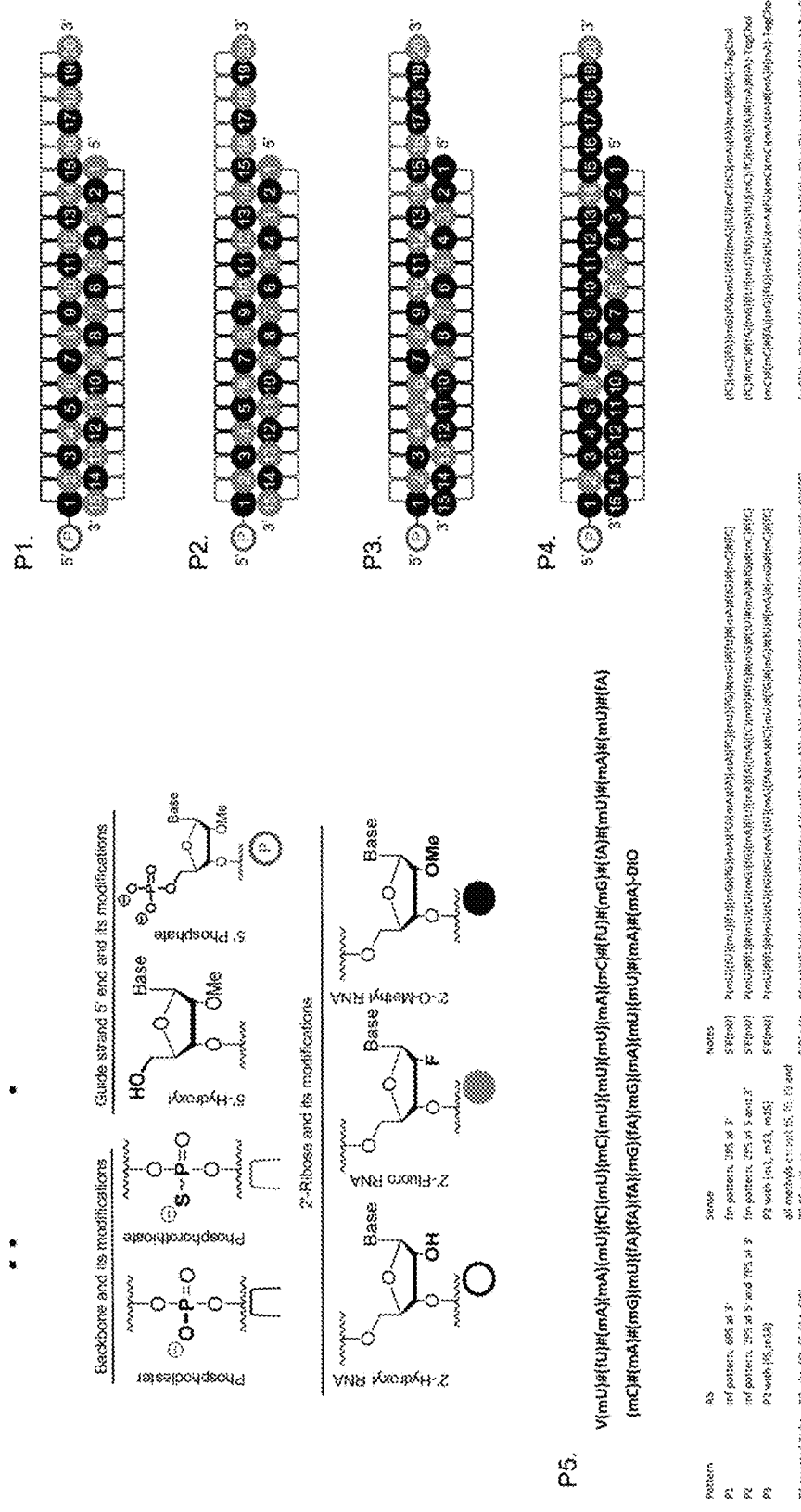
FIG. 35 illustrates a number of exemplary oligonucleotide backbone modifications.

For example, an oligonucleotide described herein may be designed as a di-siRNA (see, e.g., FIG. 14). An oligonucleotide described herein may include one or more different backbone linkages (see, e.g., FIG. 15). An oligonucleotide described herein may include a variety of sugar modifications (see, e.g., FIG. 16). An oligonucleotide described herein may include a variety of internucleotide bonds (see, e.g., FIG. 17). An oligonucleotide described herein may include one or more 5' stabilization modifications (see, e.g., FIG. 18). An oligonucleotide described herein may include one or more conjugated moieties (see, e.g., FIG. 19). Illustrated in FIG. 35 are a number of exemplary oligonucleotide backbone modifications.

Figure 33:
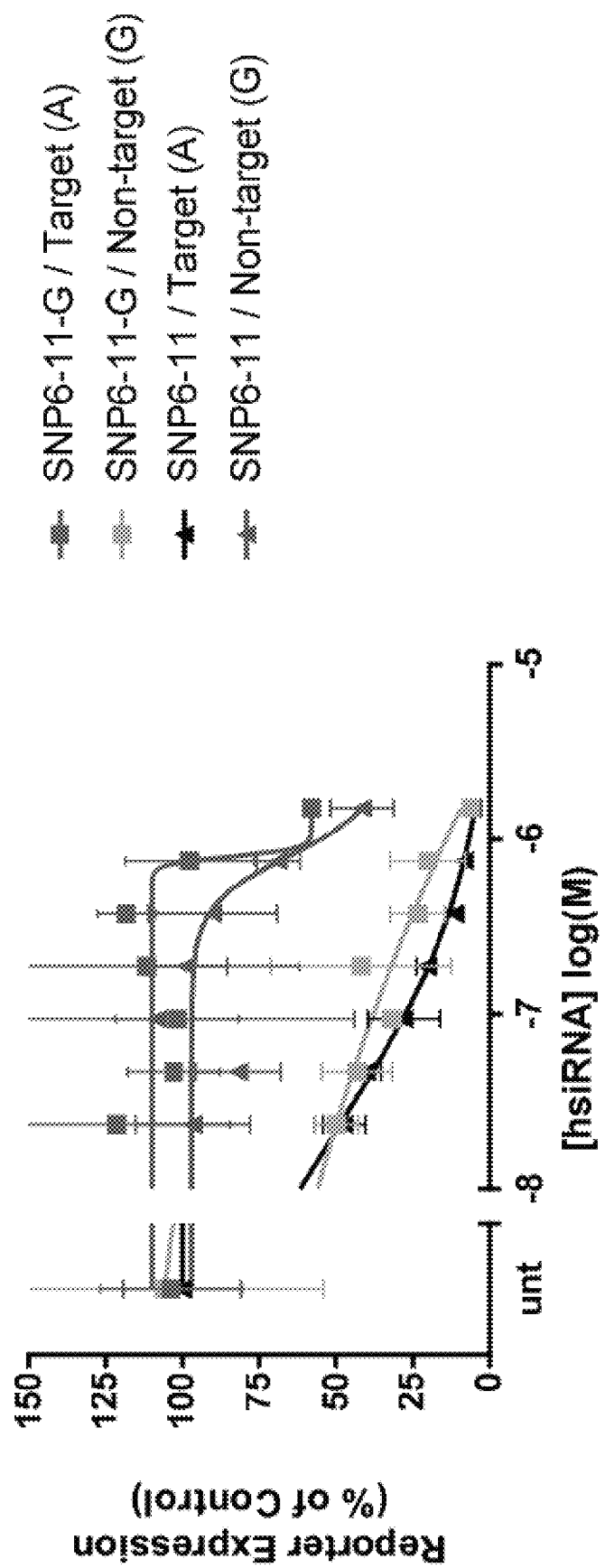
FIG. 33 depicts dose response curves comparing silencing effects for oligonucleotides targeting G at the SNP site instead of A.

An oligonucleotide described herein can effectively be used to target a G at the SNP site simply by changing the base at the SNP position. As seen in FIG. 33, compound SNP6-11 was synthesized a second time, this time to target a G at the SNP site instead of an A. This allowed for selectively silencing either allele, a strategy that is very useful for patients with different heterozygosities at the same SNP site.

In certain exemplary embodiments, one or more abasic nucleotides are utilized at an SNP position nucleotide, at a MM position nucleotide, at the 5' end, at the 3' end, or any combination of these.

In certain exemplary embodiments, hsiRNAs are synthesized with varying sugar modifications around the mismatch to improve allele specificity, e.g., 2'FANA instead of 2'F; triple 2'F or triple 2'OMe around SNP/mismatch position.

Example 5: HTT Mouse Model

BAC97-HD refer to a transgenic mouse comprising a human bacterial artificial chromosome (BAC) transgenic insert containing the entire pathogenic 170 kb human Huntingtin (htt) genomic locus that was modified by replacing the human htt exon 1 with a loxP-flanked human mutant htt exon 1 sequence containing 97 mixed CAA-CAG repeats encoding a continuous polyglutamine (polyQ) stretch.

Lead compound (SNP6-11) was synthesized into the di-branched chemical scaffold having the structure illustrated in FIG. 31 and subsequently tested in vivo via 40 nmol bilateral intracerebroventricular (ICV) injection (20 nmols to each side) in BAC97-HD female mice at 8 weeks of age. The mice had two copies of normal mouse htt gene with a G at SNP rs362273 and a transgenic insert of pathogenic human htt gene with an A at SNP rs362273A. A nonsense sequence with no target matches in the RNA transcriptome was also synthesized into the same di-branched scaffold and injected in the mice as a negative control (NTC).

Figure 32A:
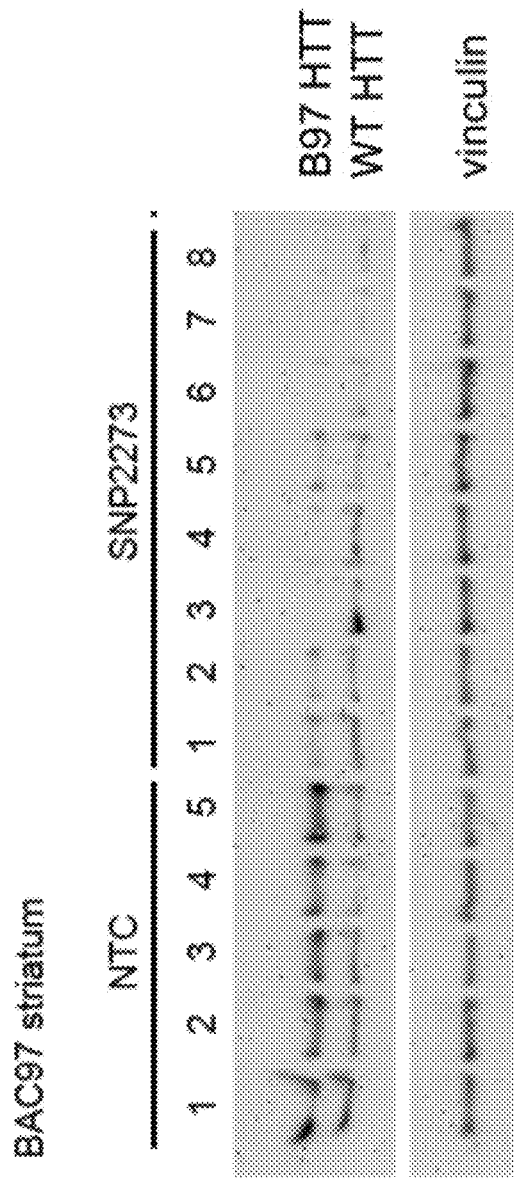
FIG. 32A is a western blot performed to measure HTT protein levels.
Figure 32B:
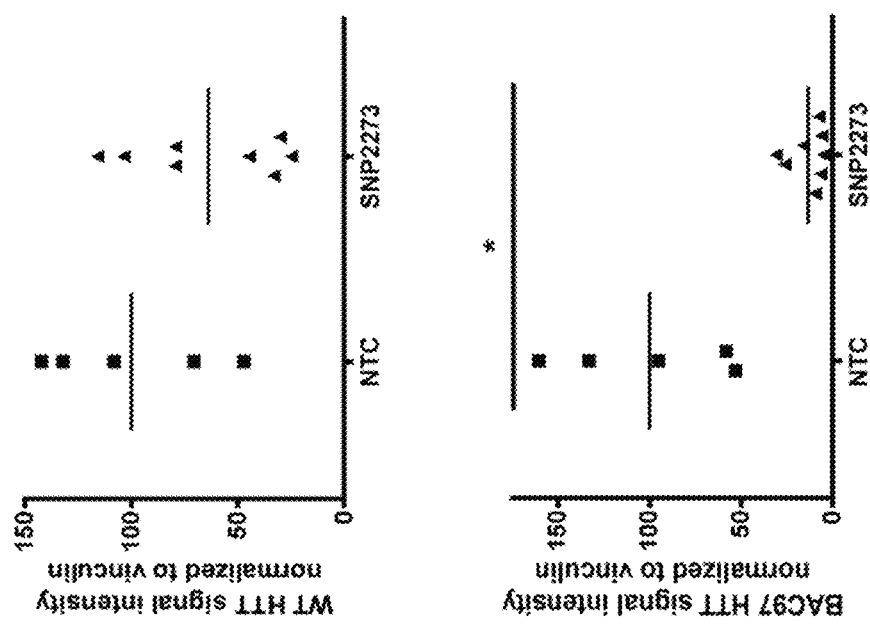
FIG. 32B shows protein levels normalized to vinculin.

Several brain regions were collected from the mice for RNA and protein analysis 1 month post injection, and HTT protein levels were measured by western blot using Ab1 antibody. FIG. 32A is a western blot performed on collected striatum tissue, and protein levels normalized to vinculin are presented in FIG. 32B.

Example 6: SNP Targeting is Sequence-Independent

Figure 20:
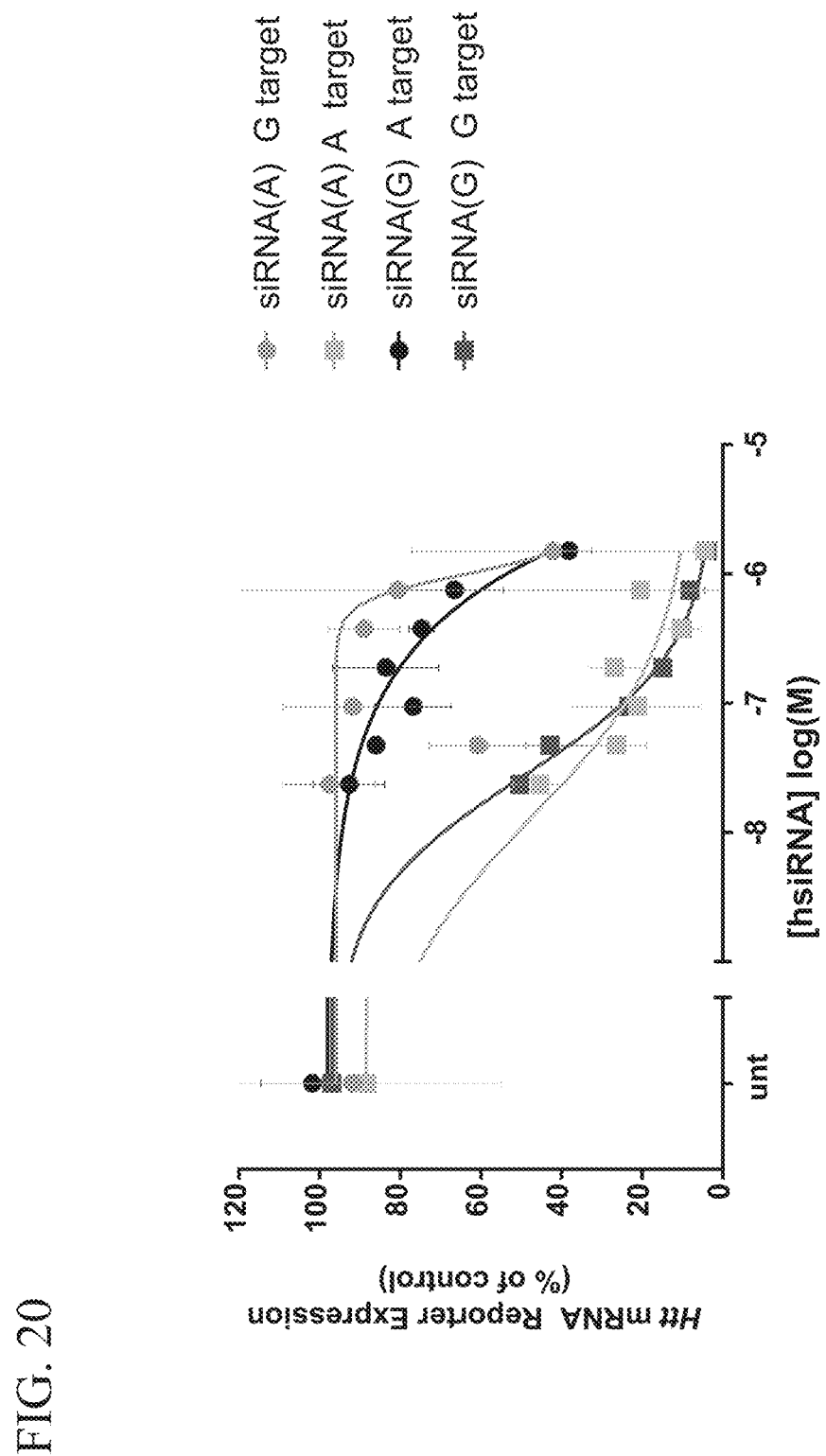
FIG. 20 graphically depicts that the activity of a SNP discriminating scaffold that comprises a SNP position nucleotide at position 6 from the 5' end, and a mismatch position nucleotide located at position 11 from the 5' end, is sequence-independent.

Whether SNP discrimination of lead compounds was sequence-dependent was assessed. Hydrophobically modified RNAs (hsiRNAs) designed to be complimentary to the Huntingtin (htt) mRNA containing a U to G mismatch or a C to A mismatch in rs362273 were used. Both the 6-11 hsiRNA complementary to a U to G mismatch and the 6-11 hsiRNA complementary to a C to A mismatch preferentially cleaved the target SNP (FIG. 20).

Example 7: Synthesis of Vinyl Phosphonate Modified Intersubunit Linkages

Figure 21:
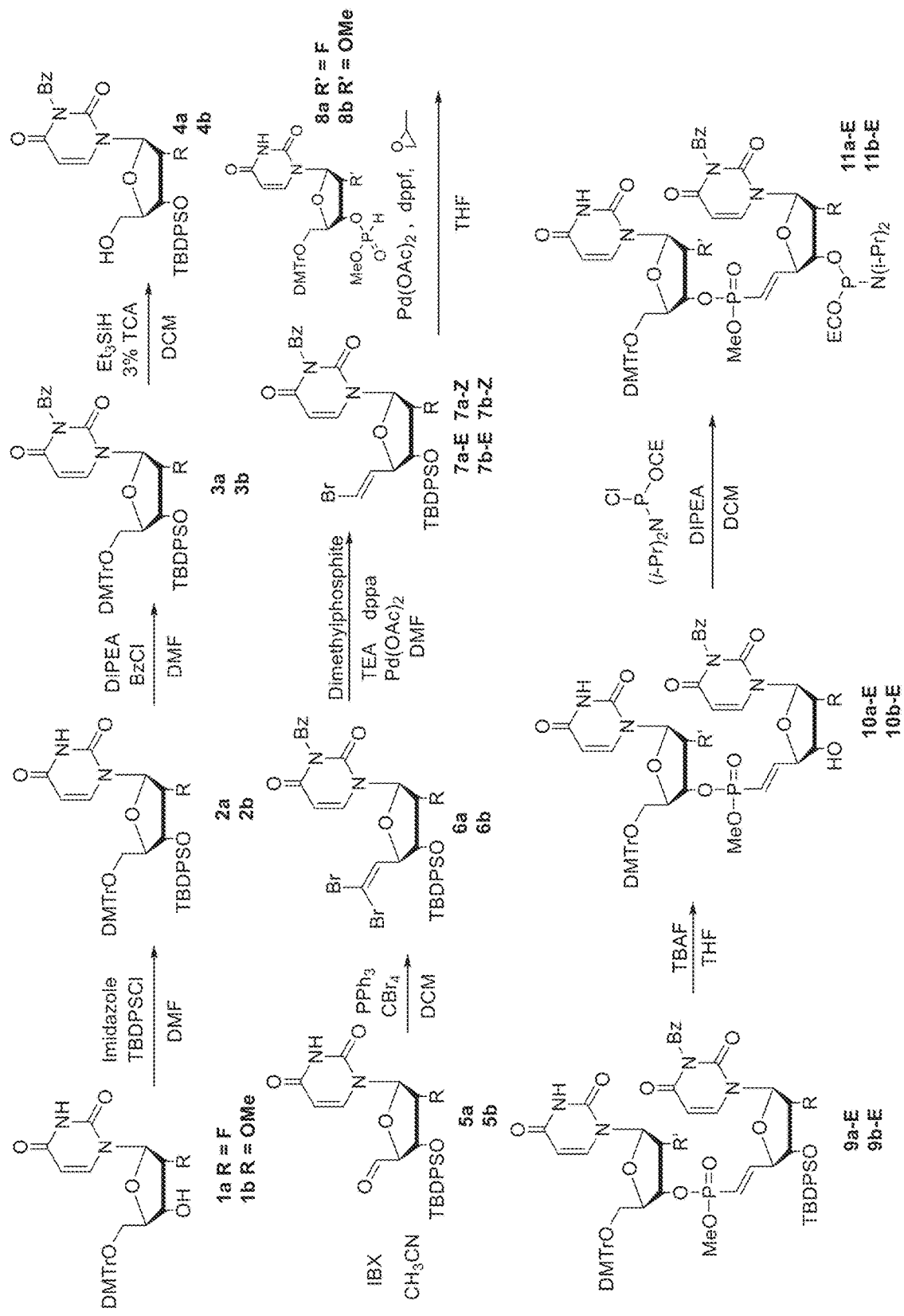
FIG. 21 illustrates a representative synthesis of the vinyl phosphonate (VP)-modified intersubunit linkage described herein.
Figure 29:
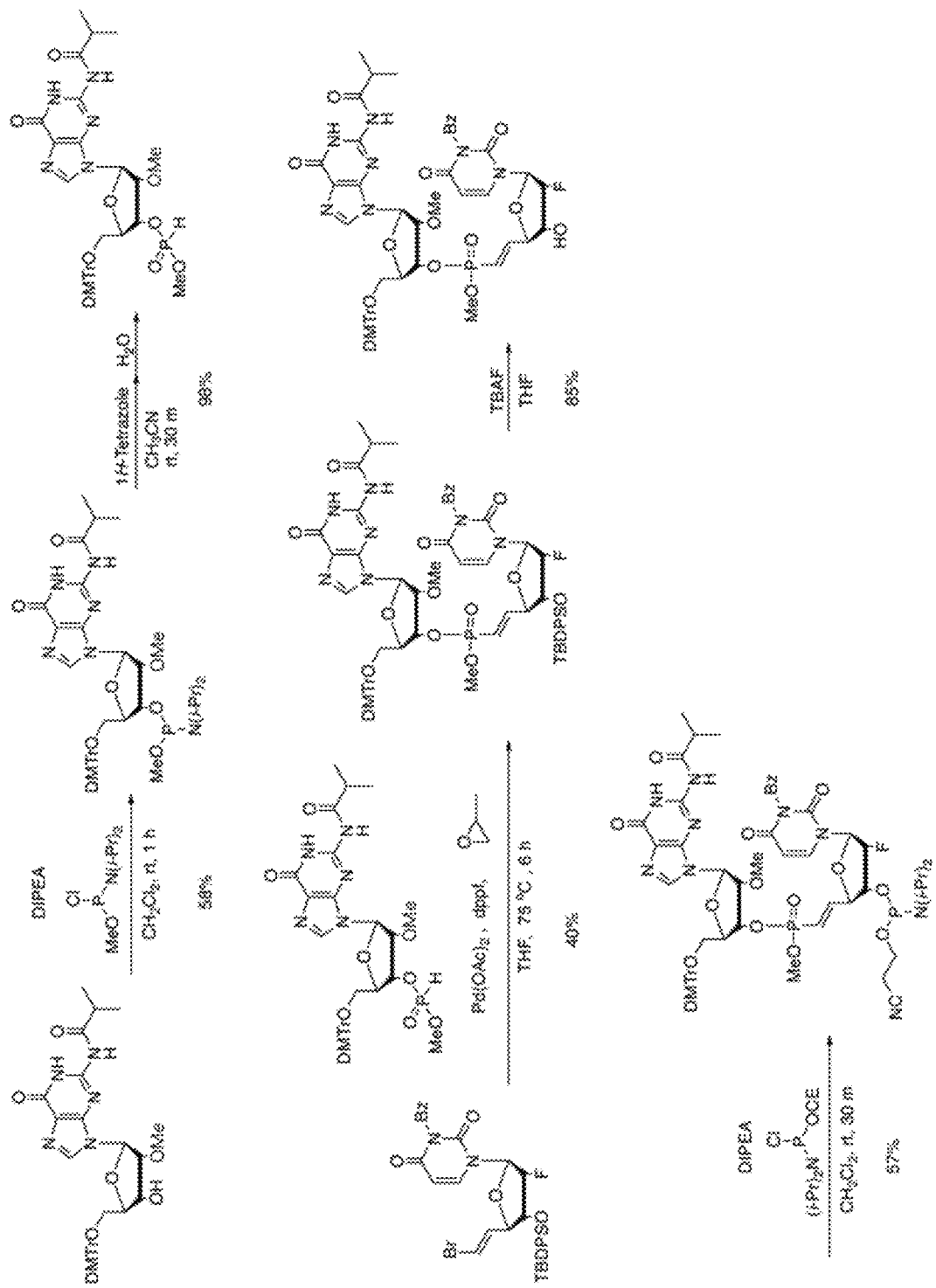
FIG. 29 demonstrates another method for preparing the VP-modified oligonucleotides provided herein.

Representative syntheses of the vinyl phosphinate modified intersubunit linkages discussed herein are illustrated in FIGS. 21 and 29. The synthetic procedure of FIG. 21 is detailed below.

Synthesis of Compound 3a

Anhydrous solution of compound 2a (16.6 g, 20.8 mmol) in pyridine (100 mL) was added anhydrous DIPEA (6.5 mL, 37.4 mmol) and benzoyl chloride (3.6 mL, 31.2 mmol). After the mixture was stirred for 4 hours at room temperature, excess pyridine was evaporated and diluted with $CH_2Cl_2$. The organic solution was washed by sat. aq. $NaHCO_3$. The organic layer was collected, dried over $MgSO_4$, filtered and evaporated. Obtained crude material was purified by silica gel column chromatography (hexane-ethyl acetate, 4:1 to 1:1) yielding compound 3a as a slightly yellow foam (14.5 g, 78%); $^1$H NMR (500 MHz, CDCl$_3$) δ 7.88-7.87 (m, 2H), 7.84 (d, 1H, J=8.3 Hz), 7.67-7.58 (m, 5H), 7.48-7.45 (m, 4H), 7.39-7.32 (m, 4H), 7.25-7.23 (m, 3H), 7.18-7.17 (m, 2H), 7.12-7.07 (m, 4H), 6.80-6.75 (m, 4H), 6.08 (dd, 1H, $J_{HH}$=1.5 Hz, $J_{HF}$=15.2 Hz), 5.14, (d, 1H, $J_{HH}$=8.3 Hz), 4.59 (ddd, 1H, $J_{HH}$=3.7, 1.5 Hz, $J_{HF}$=51.9 Hz), 4.43 (ddd, 1H, $J_{HH}$=7.4, 4.0 Hz, $J_{HF}$=19.1 Hz), 4.24-4.23 (m, 1H), 3.79 (s, 6H), 3.62 (dd, 1H, $J_{HH}$=11.2, 2.0 Hz), 3.35 (dd, 1H, $J_{HH}$=11.1, 2.0 Hz), 1.00 (s, 9H); $^{13}$C NMR (126 Hz, CDCl$_3$) δ 168.4, 161.8, 158.72, 158.66, 148.9, 143.9, 139.4, 135.71. 135.70, 135.1, 134.8, 134.7, 132.3, 132.2, 131.3, 130.4, 130.2, 130.1, 129.1, 128.2, 128.0, 127.91, 127.89, 127.2, 113.19, 113.16, 102.2, 92.5 (d, JCF=194.4 Hz), 87.7 (d, $J_{CF}$=34.5 Hz), 87.2, 82.4, 70.0 (d, $J_{CF}$=15.4 Hz), 60.7, 60.4, 55.2, 26.6.

Synthesis of Compound 4a

Compound 3a (14.5 g, 16.3 mmol) was dissolved into 3% trichloroacetic acid/CH$_2$Cl$_2$ solution (200 mL) containing triethylsilane (8.0 mL, 50.1 mmol) and stirred for 1 hour at room temperature. After the solution was washed by sat. aq. NaHCO$_3$ three times, collected organic layer was dried over MgSO$_4$, filtered, and evaporated. Obtained crude material was purified by silica gel column chromatography (hexane/ethyl acetate, 4:1 to 3:7) yielding compound 4a as a white foam (8.67 g, 91%); $^1$H NMR (500 MHz, CDCl$_3$) δ 7.89-7.88 (m, 2H), 7.68-7.64 (6H, m), 7.51-7.45 (m, 4H), 7.42-7.38 (4H, m), 5.93 (dd, 1H, $J_{HH}$=2.9 Hz, $J_{HF}$=15.1 Hz), 5.73 (d, 1H, $J_{HH}$=8.2 Hz), 4.74 (ddd, 1H, $J_{HH}$=4.1, 3.2 Hz, $J_{HF}$=52.2 Hz), 4.31 (ddd, 1H, $J_{HH}$=5.8, 4.7, $J_{HF}$=15.4 Hz), 4.11-4.09 (m, 1H), 3.82-3.79 (m, 1H), 3.39 (ddd, 1H, $J_{HH}$=12.1, 5.6, 1.5 Hz), 1.64 (br, 1H), 1.11 (s, 9H); $^{13}$C NMR (126 Hz, CDCl$_3$) δ 168.3, 161.8, 149.0, 140.5, 135.7, 135.2, 132.8, 132.3, 131.3, 130.5, 130.4, 130.3, 129.2, 128.02, 127.96, 102.4, 91.8 (d, $J_{CF}$=91.8 Hz), 89.5 (d, $J_{CF}$=33.6 Hz), 69.5 (d, $J_{CF}$=69.5 Hz), 60.3, 26.8.

Synthesis of Compound 6a

Anhydrous solution of compound 4a (6.5 g, 11.0 mmol) was added IBX (7.7 g, 27.6 mmol) and stirred for 2 hours at 85° C. After cooling the mixture in an ice bath, the precipitate in the solution was filtered off through celite. Collected eluent was evaporated, co-evaporated with anhydrous CH$_3$CN three times under argon atmosphere, and obtained compound 5a as a white foam was used without further purification. In a separate flask, anhydrous CH$_2$Cl$_2$ (25 mL) solution containing CBr$_4$ (7.3 g, 22.1 mmol) was added PPh$_3$ (11.6 g, 44.2 mmol) at 0° C. and stirred for 0.5 h at 0° C. To this solution, anhydrous CH$_2$Cl$_2$ solution (25 mL) of compound 5a was added dropwise (10 min) at 0° C. and stirred for 2 h at 0° C. After diluting with CH$_2$Cl$_2$, the organic solution was washed by aq. sat. NH$_4$Cl, dried over MgSO$_4$, filtered, and evaporated. Obtained material was dissolved into minimum amount of diethyl ether and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 9:1 to 1:1) yielding compound 6a as a white foam (4.3 g, 52%). 1H NMR (500 MHz, CDCl$_3$) δ 7.68-7.84 (m, 2H), 7.70-7.65 (m, 3H), 7.60-7.58 (m, 2H), 7.52-7.49 (m, 2H), 7.42-7.36 (m, 4H), 7.31-7.28 (m, 2H), 7.09 (d, 1H, J=8.2 Hz), 6.25 (d, 11H, J=8.9 Hz), 5.75 (dd, 1H, $J_{HF}$=8.24 Hz), 5.49 (dd, 1H, $J_{HF}$=21.4 Hz), 4.77 (t, 11H, $J_{HH}$=8.5 Hz, $J_{HF}$=8.5 Hz), 4.38 (dd, 1H, $J_{HH}$=4.1 Hz, $J_{HF}$=52.1 Hz), 4.25 (ddd, 1H, $J_{HH}$=8.1, 4.9 Hz, $J_{HF}$=19.4 Hz), 1.10 (s, 9H); $^{13}$C NMR (126 Hz, CDCl$_3$) δ 167.9, 161.6, 148.3, 141.4, 135.8, 134.7 (d, $J_{C-Br}$=139.0 Hz), 132.5, 132.2, 131.1, 130.5, 130.3, 130.2, 129.2, 127.9, 102.7, 97.3, 93.3 (d, $J_{CF}$=39.1 Hz), 91.5 (d, $J_{CF}$=190.7 Hz), 82.4, 73.9 (d, $J_{CF}$=16.4 Hz), 26.7.

Synthesis of Compound 7a-E and 7a-Z

Anhydrous solution of compound 6a (4.2 g, 5.66 mmol) in DMF (25 mL) was added dimethylphosphite (2.09 mL, 22.6 mmol) and triethylamine (1.58 mL, 11.3 mmol) at 0° C., and then stirred overnight at room temperature. After the solution was diluted with ethyl acetate, the organic solution was washed with aq. sat. NH$_4$Cl and brine. Then the organic solution was dried over MgSO$_4$, filtered and evaporated. Obtained crude material was purified repeatedly by silica gel column chromatography (hexane/ethyl acetate, 9:1 to 1:1) until all pure isomeric compound were collected separately, giving compound 7a-E (1.95 g, 52%); $^1$H NMR (500 MHz, CDCl$_3$) δ 7.87-7.85 (m, 2H), 7.89-7.85 (m, 3H), 7.61-7.59 (m, 2H), 7.52-7.48 (m, 2H), 7.45-7.32 (m, 6H), 7.08 (d, 1H, $J_{HH}$=8.2), 6.49 (d, 1H, $J_{HH}$=13.7), 5.99 (dd, 1H, $J_{HH}$=13.7 Hz, 8.1 Hz), 5.75 (d, 1H, $J_{HH}$=8.2), 5.63 (d, 1H, $J_{HF}$=19.8 Hz), 4.43 (dd, 1H, $J_{HF}$=52.6 Hz, $J_{HH}$=4.3 Hz), 4.42 (t, 1H, $J_{HH}$=8.0 Hz), 4.07 (ddd, $J_{HH}$=7.8, 4.7 Hz, $J_{HF}$=19.5 Hz), 1.08 (s, 9H); $^{13}$C NMR (126 Hz, CDCl$_3$) δ 148.4, 140.4, 135.8, 135.7, 135.3, 133.3, 132.3, 132.4, 132.1, 131.1, 130.5, 130.4, 130.3, 129.2, 127.95, 127.93, 112.4, 102.7, 91.7 (d, $J_{CF}$=36.3 Hz), 91.6 (d, $J_{CF}$=191.6 Hz), 82.8, 73.9 (d, $J_{CF}$=16.4 Hz), 26.7, 19.1; and 7a-Z (0.58 g, 15%); $^1$H NMR (500 MHz, CDCl$_3$) δ 7.87-7.85 (m, 2H), 7.68-7.65 (m, 3H), 7.61-7.59 (m, 2H), 7.52-7.48 (m, 2H), 7.42-7.39 (m, 2H), 7.34-7.29 (m, 4H), 7.12 (d, 1H, $J_{HH}$=8.2 Hz), 6.51 (d, 1H, $J_{HH}$=7.4 Hz), 5.96 (dd, 1H, $J_{HH}$=8.4 Hz, 7.4 Hz), 5.75 (d, 1H, $J_{HH}$=8.2 Hz), 5.57 (dd, 1H, $J_{HH}$=1.2 Hz, $J_{HF}$=20.6 Hz), 5.04 (dd, 1H, $J_{HH}$=8.2 Hz), 4.48 ($J_{HH}$=3.5 Hz, $J_{HF}$=53.1 Hz), 4.24 (ddd, 1H, $J_{HH}$=7.8, 4.9 Hz, $J_{HF}$=18.6 Hz), 1.09 (s, 9H); $^{13}$C NMR (126 Hz, CDCl$_3$) δ 168.0, 161.7, 148.4, 141.4, 135.9, 135.8, 135.2, 132.6, 132.5, 131.2, 130.6, 130.5, 130.2, 130.1, 129.2, 127.8, 127.7, 114.5, 102.6, 93.0 (d, $J_{CF}$=37.2 Hz), 91.6 (d, $J_{CF}$=191.6 Hz), 80.3, 74.3 (d, $J_{CF}$=16.4 Hz), 26.7, 19.1.

Synthesis of Compound 9a

Anhydrous compound 7a-E (1.95 g, 2.94 mmol) and Pd(OAc)$_2$ (125 mg, 0.59 mmol) and [1,1'-Bis(diphenylphosphino)ferrocene]dichloropalladium (II) (652 mg, 1.18 mmol) were purged with argon, and then dissolved into anhydrous THF (50 mL). After adding propylene oxide (2.06 mL, 29.4 mmol), compound 8a (2.07 g, 3.24 mmol) was added in one portion and stirred at for 4 h at 70° C. After removing solvent under reduced pressure, the crude mixture was purified by silica gel column chromatography (hexane/ethyl acetate, 50:50 to 0:100) and obtained fractions containing compound 9a were further purified by silica gel column chromatography (CH$_2$Cl$_2$-MeOH, 0% to 5%) yielding compound 9a as a mixture of diastereo-isomers (2.04 g, 57%); $^{31}$P NMR (202 MHz, CDCl$_3$) δ 18.3.

Synthesis of Compound 10a

Compound 9a (2.0 g, 1.64 mmol) in anhydrous THF (22.5 mL) was added 1.0 M TBAF-THF (2.5 mL, 2.5 mmol) and stirred at ambient temperature for 30 minutes. After diluting with CH$_2$Cl$_2$ (120 mL), the organic layer was washed with brine, dried over MgSO$_4$, filtered, and then evaporated. Obtained crude material was purified by silica gel column chromatography (1% TEA-CH$_2$Cl$_2$/MeOH, 0% to 6%) yielding compound 10a (1.52 g, 94%); $^{31}$P NMR (202 MHz, CDCl$_3$) δ 19.0, 18.7.

Synthesis of Compound 11a

Compound 10a (589.7 mg, 0.6 mmol) was rendered anhydrous by repeated co-evaporation with anhydrous CH$_3$CN and then dissolved into anhydrous CH$_2$Cl$_2$ (6.0 mL). To this solution N,N-diisopropylethylamine (0.31 mL, 1.8 mmol) and 2-cyanoethyl N,N-diisopropylchlorophosphoramidite (0.16 mL, 0.72 mmol) were added at 0° C. After stirring for 30 min at 0° C., the reaction mixture was diluted with excess $CH_2Cl_2$. The organic layer was repeatedly washed with aq. sat. $NaHCO_3$, dried over $MgSO_4$, filtered, and evaporated. The obtained crude material was purified by silica gel column chromatography (1% TEA-$CH_2Cl_2$/MeOH, from 100% to 4%) yielding compound 11a as a white foam (570 mg, 80%); $^{31}$P NMR (202 MHz, $CDCl_3$) δ 150.3, 151.2, 151.1, 151.0, 18.72, 18.65, 18.55, 18.3.

Synthesis of Compound 4b

Anhydrous solution of compound 3b (1.35 g, 2.0 mmol) in pyridine (10 mL) was added DIPEA (0.63 mL, 3.6 mmol) and benzoyl chloride (0.35 mL, 3.0 mmol), and stirred for 3 hours at room temperature. After diluting with excess $CH_2Cl_2$, the organic solution was washed with aq. sat. $NaHCO_3$ and brine. After drying over $MgSO_4$, filtered and evaporating, obtained crude material was used for the next reaction without further purification. Obtained crude material containing compound 3b was added 3% trichloroacetic acid in $CH_2Cl_2$ (25 mL) and triethylsilane (1 mL, 6.26 mmol), and stirred for 1 hour at room temperature. After the reaction mixture was diluted with $CH_2Cl_2$, the solution was washed with sat. $NaHCO_3$aq. three times, dried over $MgSO_4$, filtered, then evaporated. Obtained crude material was purified by silica gel column chromatography (hexane/ethyl acetate, 4:1 to 1:4) yielding pure compound 4b (596.7 mg, 63% in 2 steps); $^1$H NMR (500 MHz, DMSO-d6) δ 8.13 (d, 1H, $J_{HH}$=8.2 Hz), 7.95 (d, 2H, $J_{HH}$=7.3 Hz), 7.81 (t, 1H, $J_{HH}$=7.5 Hz), 7.69-7.68 (m, 2H), 7.64-7.59 (m, 4H), 7.49-7.42 (m, 6H), 5.93 (d, 1H, $J_{HH}$=4.6 Hz), 5.26 (t, 1H, $J_{HH}$=4.6 Hz), 4.36 (dd, 1H, $J_{HH}$=4.6, 4.6 Hz), 4.02-4.00 (m, 1H), 3.65-3.61 (m, 1H), 3.54 (dd, 1H, $J_{HH}$=4.6, 4.6 Hz), 3.09 (s, 3H), 1.03 (s, 9H); $^{13}$C NMR (126 Hz, DMSO-d6) 169.8, 162.1, 149.5, 141.3, 136.1, 135.9, 135.8, 133.4, 133.2, 131.5, 130.7, 130.52, 130.48, 130.0, 128.4, 128.3, 102.1, 86.7, 85.6, 82.8, 79.7, 70.8, 60.2, 57.8, 27.2, 19.4; HRMS (ESI) m/z calcd for $C_{33}H_{35}N_2O_7Si^-$ [M–H]$^-$ m/z 599.2219, found m/z 599.2258.

Synthesis of Compound 6b

Anhydrous solution of compound 4b (300.4 mg, 0.5 mmol) in $CH_3CN$ (5 mL) was added IBX (350 mg, 1.3 mmol) and stirred for 2 hours at 85° C. After cooling the solution at 0° C., the precipitate was filtered off by celite-filtration. Obtained eluent containing compound 5b was evaporated, rendered anhydrous by repeated co-evaporation with anhydrous $CH_3CN$, and used for the next reaction without further purification. Separatory prepared anhydrous solution of $CBr_4$ (331.6 mg, 1.0 mmol) in $CH_2Cl_2$ (5.0 mL) was added triphenylphosphine (524.6 mg, 2.0 mmol) at 0° C. in one portion and stirred at 0° C. for 30 minutes. To this solution, compound 5b in anhydrous $CH_2Cl_2$ (1.5 mL) was added dropwise (10 min) at 0° C. and stirred for 2 h at 0° C. The solution was then diluted with $CH_2Cl_2$ and washed with sat. $NaHCO_3$aq. and brine. After the organic solution was dried over $MgSO_4$, filtered and evaporated, obtained crude material was purified by silica gel column chromatography (hexane/ethyl acetate, 9:1 to 4:6) yielding compound 6b (210.9 mg, 56%); $^1$H NMR (500 MHz, $CDCl_3$) δ 7.88 (d, 2H, $J_{HH}$=7.3 Hz), 7.70-7.62 (5H, m), 7.51-7.38 (m, 9H), 7.08 (d, 1H, $J_{HH}$=8.2 Hz), 6.26 (d, 1H, $J_{HH}$=8.6 Hz), 5.75 (d, 1H, $J_{HH}$=8.2 Hz), 5.68 (d, 1H, $J_{HH}$=0.8 Hz), 4.84 (dd, 1H, $J_{HH}$=8.6 Hz, 8.6 Hz), 3.86 (dd, 1H, $J_{HH}$=7.5 Hz, 5.0 Hz), 3.30 (s, 3H), 3.18 (br, 1H), 1.11 (s, 9H); $^{13}$C NMR (126 Hz, $CDCl_3$) 168.3, 161.7, 148.6, 138.9, 135.9, 135.8, 134.3, 132.6, 132.4, 131.2, 130.5, 130.4, 130.3, 129.2, 128.0, 127.9, 102.4, 97.5, 90.0, 82.44, 82.39, 74.4, 58.2, 26.7, 19.1; HRMS (ESI) m/z calcd for $C_{34}H_{33}Br_2N_2O_6Si^-$ [M–H]$^-$ m/z 751.0480 [M–H]$^-$, found m/z 753.6495.

Synthesis of 7b-E and 7b-Z

Anhydrous solution of compound 6b (6.11 g, 8.1 mmol) in DMF (35 mL) was added dimethylphosphite (2.97 mL, 34.0 mmol) and triethylamine (2.26 mL, 17.0 mmol) at 0° C., and then stirred overnight at room temperature. After the solution was diluted with ethyl acetate, the organic solution was washed with sat. $NH_4Cl$ aq. and brine. Then the organic solution was dried over $MgSO_4$, filtered and evaporated, and obtained crude material was purified repeatedly by silica gel column chromatography (hexane/ethyl acetate, 9:1 to 1:1) until all pure isomeric compound were collected separately, giving compound 7b-E (3.0 g, 55%); $^1$H NMR (500 MHz, $CDCl_3$) δ 7.89-7.87 (m, 2H), 7.70-7.62 (m, 5H), 7.51-7.39 (m, 8H), 7.10 (d, 1H, $J_{HH}$=8.3 Hz), 6.47 (dd, 1H, $J_{HH}$=13.6, 0.8 Hz), 6.01 (dd, 1H, $J_{HH}$=13.6, 7.9 Hz), 5.76-5.74 (m, 2H), 4.51 (dd, 1H, $J_{HH}$=7.8, 7.8 Hz), 7.36 (dd, 1H, $J_{HH}$=7.8 Hz, 4.9 Hz), 3.34 (s, 3H), 3.17 (dd, 1H, $J_{HH}$=4.7, 1.2 Hz), 1.09 (s, 9H); $^{13}$C NMR (126 Hz, $CDCl_3$) δ 168.3, 161.7, 148.7, 138.4, 135.9, 135.8, 135.3, 133.8, 132.6, 132.4, 131.2, 130.5, 130.4, 130.3, 129.2, 128.0, 127.9, 112.1, 102.3, 88.9, 82.8, 82.6, 77.2, 74.2, 58.1, 26.8, 19.1; and 7b-Z (1.23 g, 22%); $^1$H NMR (500 MHz, $CDCl_3$) δ 7.89-7.87 (m, 2H), 7.72-7.70 (m, 2H), 7.68-7.63 (m, 3H), 7.51-7.44 (m, 4H), 7.41-7.37 (m, 4H), 7.16 (d, 1H, J—8.2 Hz), 6.53 (dd, 1H, $J_{HH}$=7.4, 0.6 Hz), 6.03 (dd, 1H, $J_{HH}$=8.5, 7.4 Hz), 5.75-5.73 (m, 2H), 5.12 (t, 1H, $J_{HH}$=8.1 Hz), 3.93 (dd, 1H, $J_{HH}$=6.9, 5.0 Hz), 3.32 (br, 1H), 3.26 (s, 3H), 1.10 (s, 9H); $^{13}$C NMR (126 Hz, $CDCl_3$) δ 168.3, 161.8, 148.7, 139.3, 135.91, 135.85, 135.22, 132.74, 132.71, 131.2, 130.8, 130.5, 130.23, 130.16, 129.2, 127.78, 127.75, 114.6, 102.2, 90.1, 82.4, 80.6, 77.2, 74.8, 58.1, 26.8, 19.2.

Synthesis of Compound 8b

Anhydrous 5'-O-DMTr-2'-deoxy-2'-fluoro-3'-[methyl-N,N-(diisopropyl)amino] phosphor-amidite (4.26 g, 6.0 mmol) was dissolved in 0.45 M 1H-tetrazole/$CH_3CN$ solution (27 mL, 12 mmol) and stirred for 30 minutes at room temperature. To this solution, $H_2O$ (3.6 mL) was added and stirred for 30 minutes at room temperature. After diluting with ethyl acetate, the organic solution was washed with brine six times, dried over $MgSO_4$, filtered and then evaporated. Obtained compound 8b with a slight amount of impurity was used for the next reaction without further purification; $^{31}$P NMR ($CDCl_3$, 202 MHz) δ 8.92, 8.28.

Synthesis of Compound 9b

Anhydrous compound 7b-E (2.84 g, 4.20 mmol) and $Pd(OAc)_2$ (188.6 mg, 0.84 mmol) and [1,1'-Bis(diphenylphosphino)ferrocene]dichloropalladium (II) (931.4 mg, 1.68 mmol) were purged with argon, and then dissolved into anhydrous THF (50 mL). After adding propylene oxide (2.94 mL, 42.0 mmol), compound 9b (3.16 g, 5.04 mmol) was added in one portion and stirred at for 4 hours at 70° C. After removing solvent under reduced pressure, the crude mixture was purified by silica gel column chromatography (hexane-ethyl acetate, 50:50 to 0:100) and obtained fractions containing compound 9b were further purified by silica gel column chromatography (1% TEA-$CH_2Cl_2$/MeOH, 0% to 5%) yielding compound 9b as a mixture of diastereoisomers (3.3 g, 64%); $^{31}$P NMR (202 MHz, $CDCl_3$) δ 19.31, 18.72.

Synthesis of Compound 10b

Compound 9b (3.3 g, 2.70 mmol) in anhydrous THF (36.5 mL) was added 1.0 M TBAF-THF (4.05 mL, 4.05 mmol) and stirred at ambient temperature for 30 minutes. After diluting with $CH_2Cl_2$ (150 mL), the organic layer was washed with brine, dried over $MgSO_4$, filtered, and then evaporated. Obtained crude material was purified by silica gel column chromatography (1% TEA-$CH_2Cl_2$/MeOH, 0% to 8%) yielding compound 10b (1.25 g, 47%); $^{31}$P NMR (202 MHz, $CDCl_3$) δ 19.8, 19.1.

Synthesis of Compound 11b

Compound 10b (393.2 mg, 0.4 mmol) was rendered anhydrous by repeated co-evaporation with anhydrous $CH_3CN$ and then dissolved into anhydrous $CH_2Cl_2$ (4.0 mL). To this solution N,N-diisopropylethylamine (0.21 mL, 1.2 mmol) and 2-cyanoethyl N,N-diisopropylchlorophosphoramidite (0.11 mL, 0.48 mmol) were added at 0° C. After stirring for 30 min at 0° C., the reaction mixture was diluted with excess $CH_2Cl_2$. The organic layer was repeatedly washed with aq. sat. $NaHCO_3$, dried over $MgSO_4$, filtered, and evaporated. The obtained crude material was purified by silica gel column chromatography (1% TEA-$CH_2Cl_2$/MeOH, from 100% to 4%) yielding compound 11b as a white foam (319.6 mg, 68%); $^{31}$P NMR (202 MHz, $CDCl_3$) δ 150.7, 150.4, 150.3, 19.9, 19.5, 19.4, 18.8.

Figure 22:
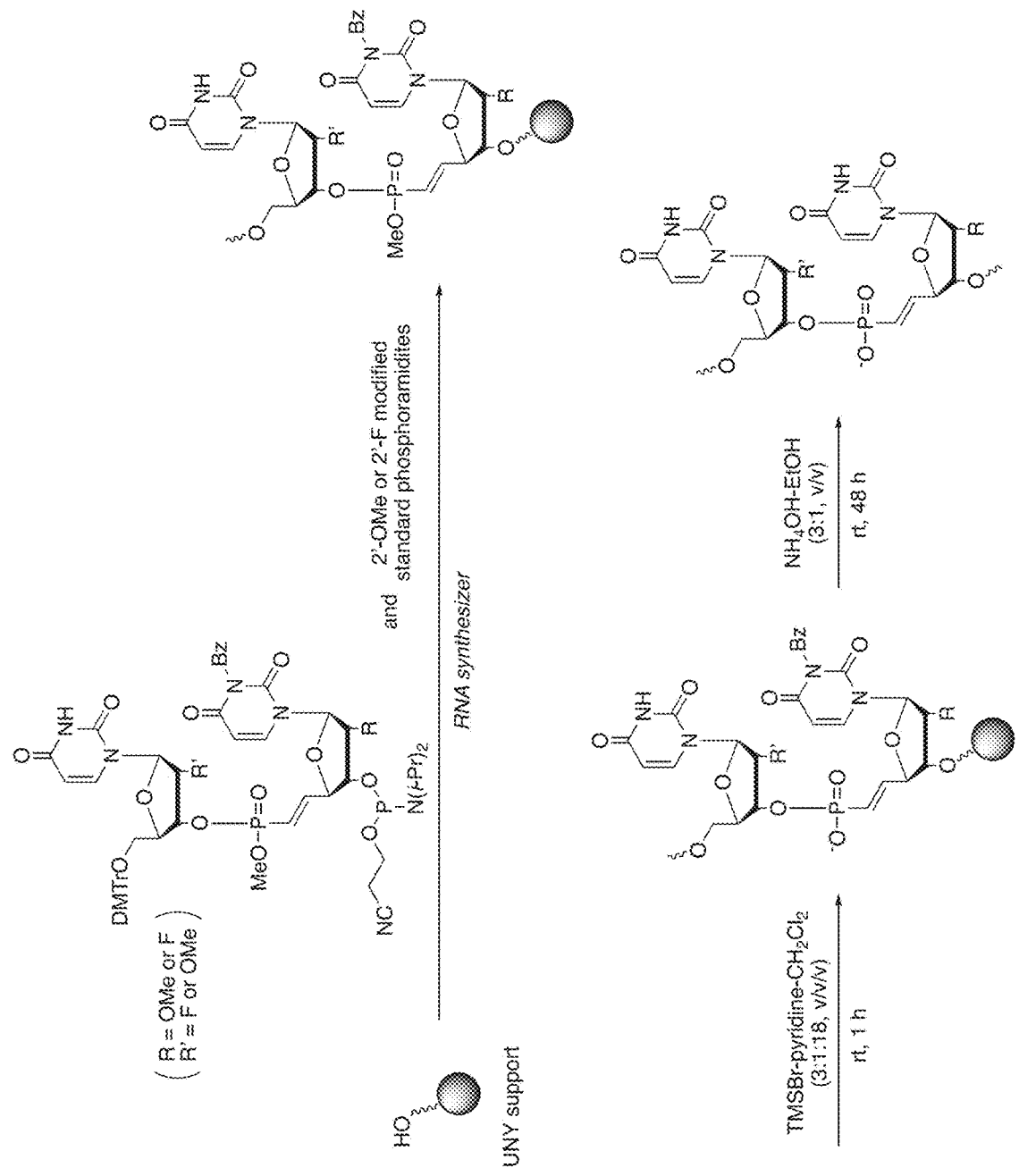
FIG. 22 depicts a method for preparing oligonucleotides having a VP-modified intersubunit linkage.
Figure 28A:
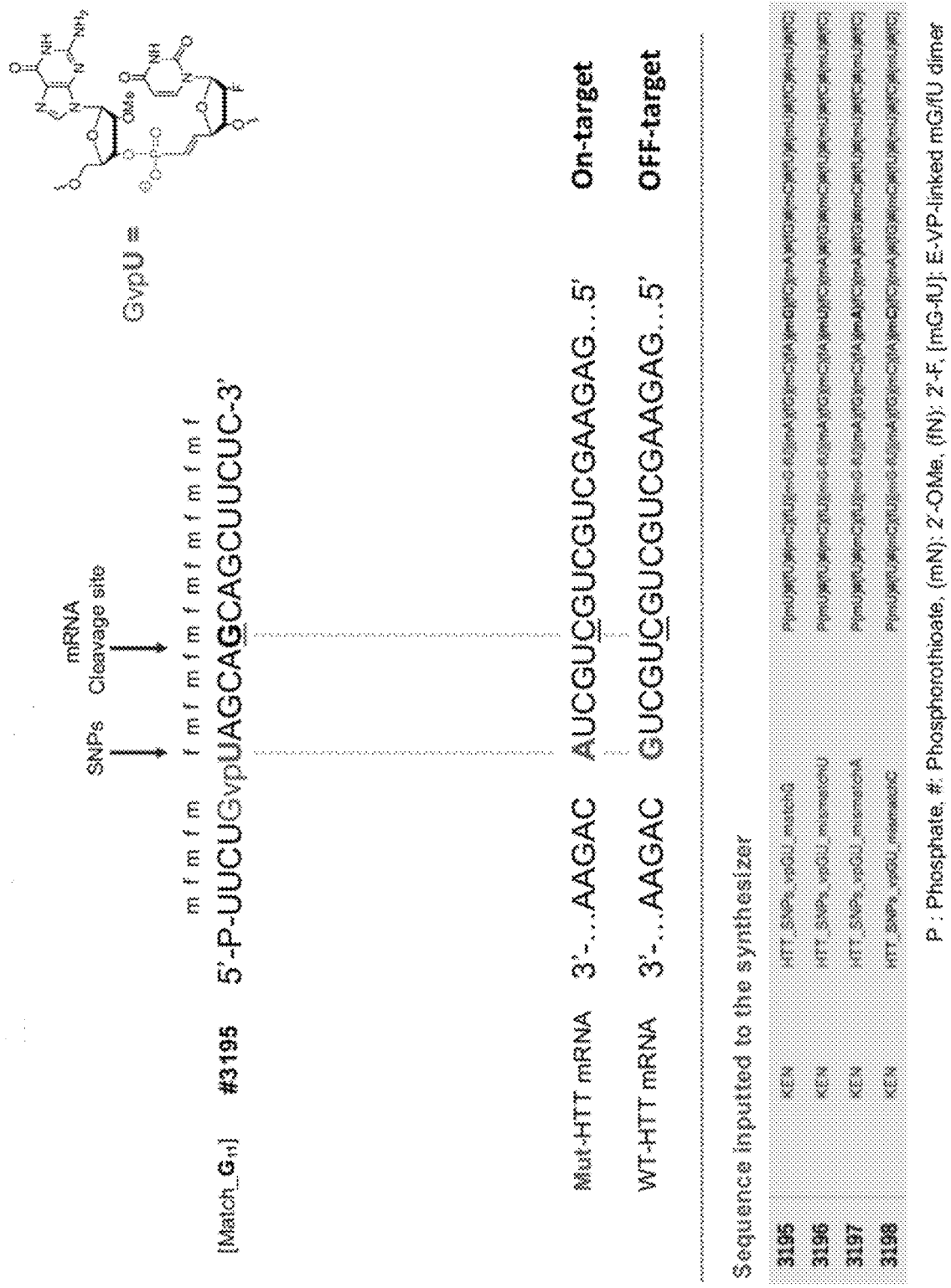
FIGS. 28A and 28B depict VP-modified sequences prepared by a synthesizer.
Figure 28B:
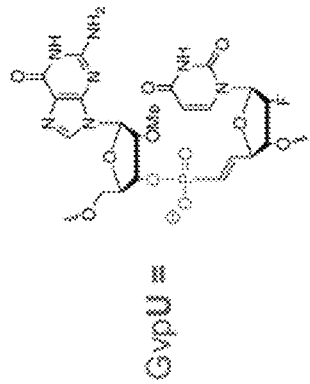

Example 8: Solid Support-Mediated Synthesis of Vinyl Phosphonate-Modified Oligonucleotides A representative synthesis of an oligonucleotide having a vinyl phosphinate modified intersubunit linkages is illustrated in FIG. 22. Examples of VP-modified sequences that were synthesized can be found in FIGS. 28A and 28B.

Synthesis of Inter-Nucleotide (E)-Vinyl Phosphonate Modified RNA Oligonucleotides.

The synthesis RNA oligonucleotides having one vinyl phosphonate linkage was performed on MerMade 12 automated RNA synthesizer (BioAutomation) using 0.1 M anhydrous $CH_3CN$ solution of 2'-modified (2'-fluoro, 2'-O-methyl) phosphonamidite and vinylphosphonate-linked dimer phosphoramidites. For the solid support, UnyLinker support (ChemGenes) was used. The synthesis was conducted by standard 1.0 μmol scale RNA phosphoramidite synthesis cycle, which consists of (i) detritylation, (ii) coupling, (iii) capping, and (iv) iodine oxidation. 5-(Benzylthio)-1H-tetrazole in anhydrous $CH_3CN$ was used for phosphoramidite activating reagent, and 3% dichloroacetic acid in $CH_2Cl_2$ was used for detritylation. 16% N-methylimidazole in tetrahydrofurane (Cap A) and 80:10:10 (v/v/v) tetrhydrofurane-$Ac_2O$-2,6-lutidine (Cap B) were used for capping reaction. 0.02 M 12 in THF-pyridine-$H_2O$ (7:2:1, v/v/v) was used for oxidation and 0.1 M 3-[(Dimethylaminomethylidene)amino]-3H-1,2,4-dithiazole3-thione in pyridine:$CH_3CN$ (9:1, v/v) was used for sulfurizing. For 5'-terminal phosphorylation, bis(2-cyanoethyl)-N,N-diisopropyl phosphoramidite was used. For the 3'-cholesterol modified RNA oligonucleotide synthesis, cholesterol 3'-lcaa CPG 500 Å (ChemGenes) was used, and RNA synthesis was conducted in the same condition as the condition used for VP-modified RNAs. After the chemical chain elongation, deprotection and cleavage from the solid support were conducted by $NH_4OH$-EtOH (3:1, v/v) for 48 hours at 26° C. In the case of vinyl phosphonate modified RNA, RNA on solid support was first treated with TMSBr-pyridine-$CH_2Cl_2$ (3:1:18, v/v/v) for 1 h at ambient temperature in RNA synthesis column. Solid support was then washed by water (1 mL×3), $CH_3CN$ (1 mL×3) and $CH_2Cl_2$ (1 mL×3) by flowing solution thorough synthesis column, and then dried under vacuum. After transferring the solid support to screw-capped sample tube, base treatment by $NH_4OH$-EtOH (3:1, v/v) for 48 h at 26° C. was conducted. Crude RNA oligonucleotide without cholesterol conjugate was purified by standard anion exchange HPLC, whereas RNAs with cholesterol-conjugate were purified by reversed-phase HPLC. Obtained all purified RNAs were desalted by Sephadex G-25 (GE Healthcare) and characterized by electrospray ionization mass spectrometry (ESI-MS) analysis.

Example 9: Silencing Efficacy

Figure 23:
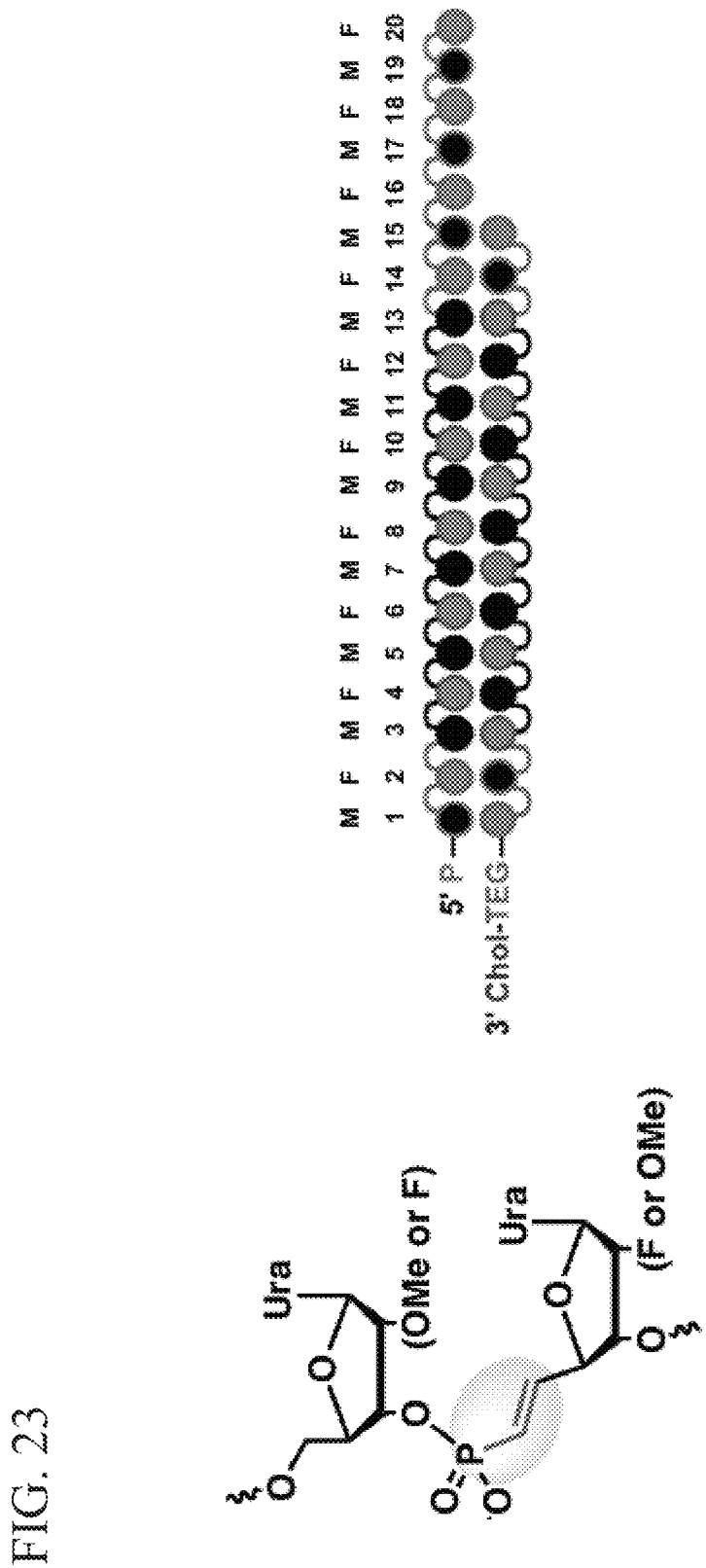
FIG. 23 is a pictoral representation of a VP-modified RNA according to certain exemplary embodiments.
Figure 24:
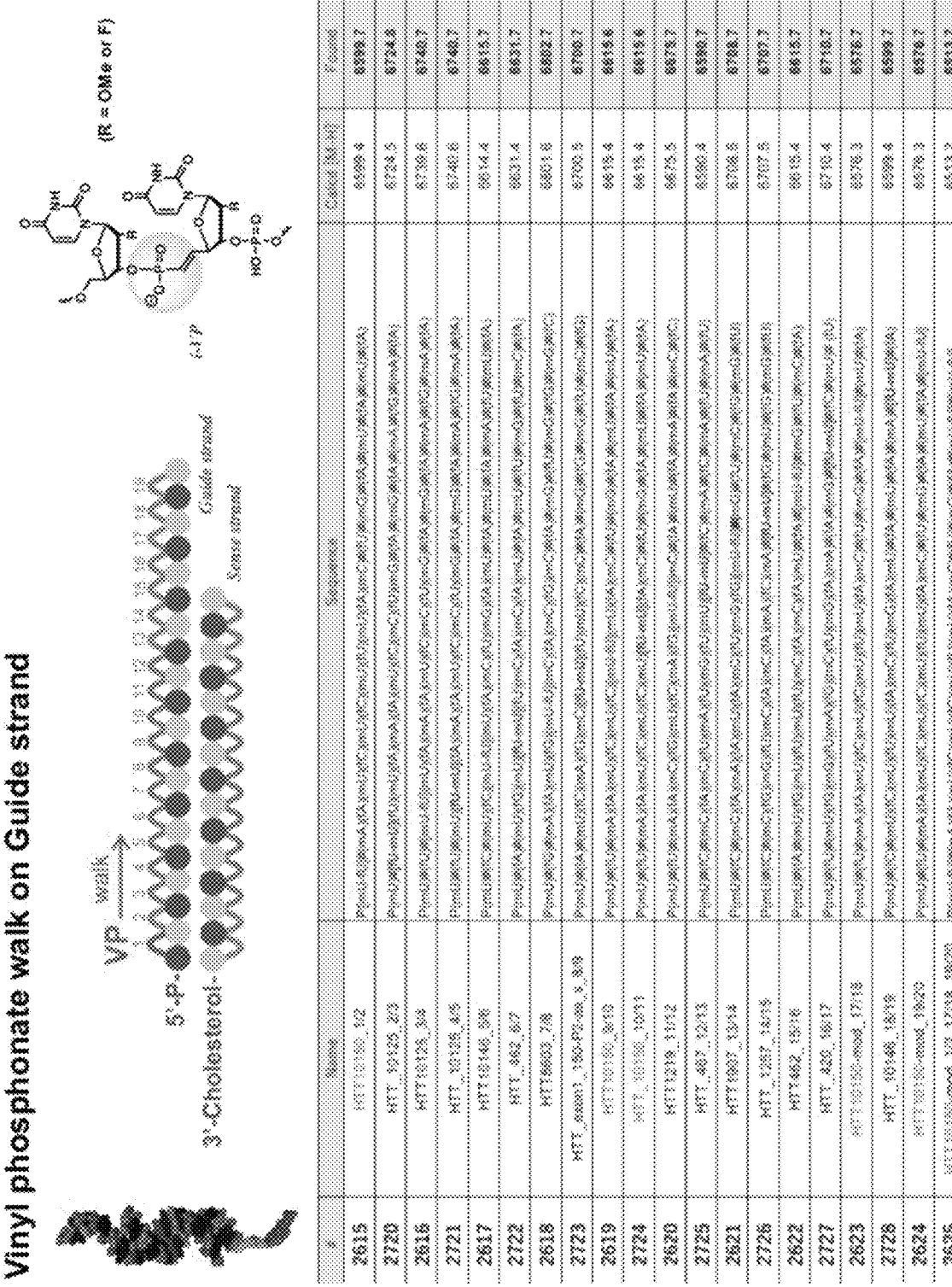
FIG. 24 illustrates the sequences of VP-modified oligonucleotides synthesized according to certain exemplary embodiments.
Figure 25:
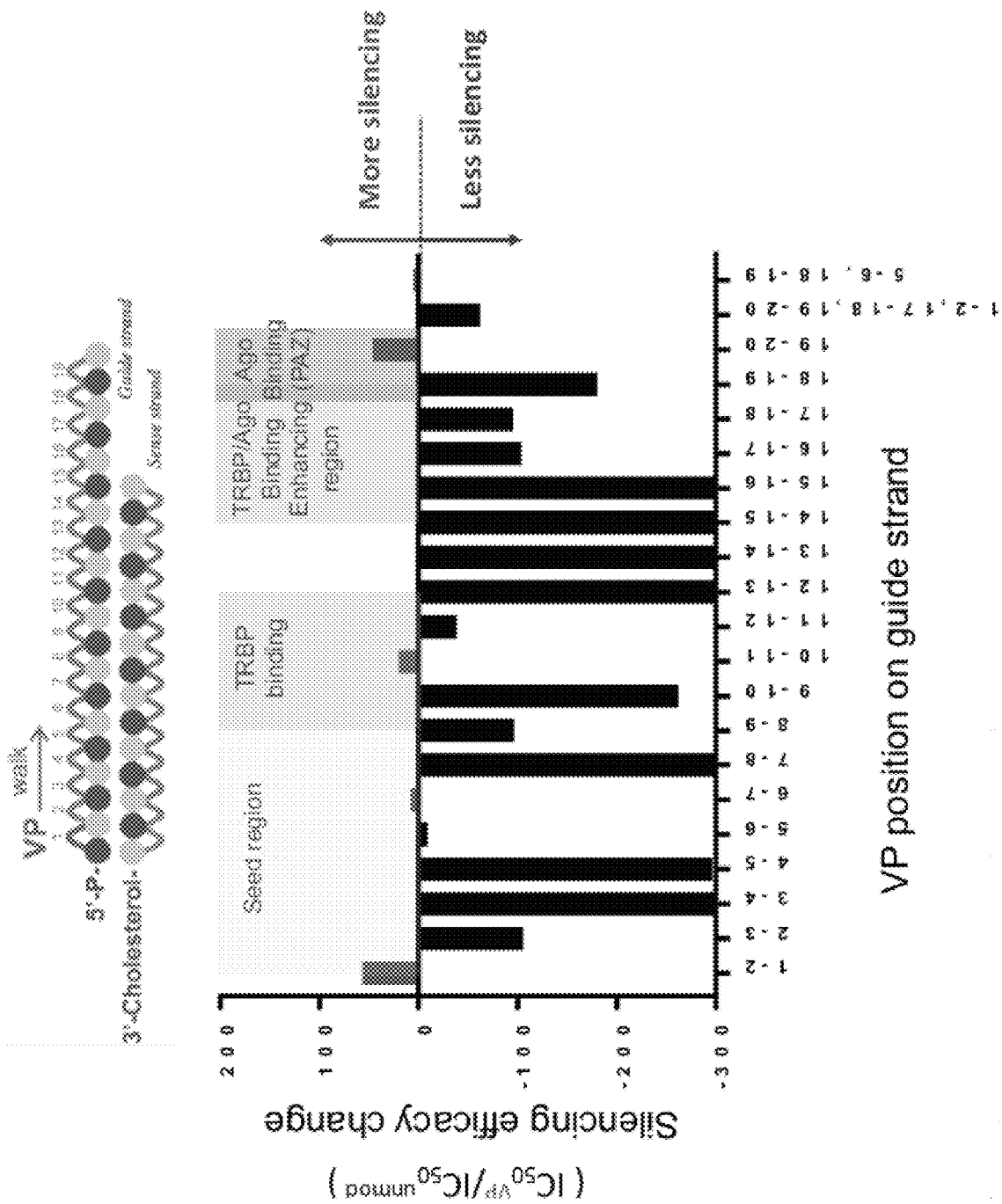
FIG. 25 is a summary of a comparative study of siRNA efficacy.

FIGS. 23 and 24 provide visual representations of the VP-modified siRNA studied herein. FIG. 25 exemplifies the effect that one or more vinyl phosphonate modifications in an intersubunit linkage at varying positions on the guide strand has on silencing. As can be seen from the data in FIG. 25, RISC is very sensitive to VP modification, and having a mismatch base pair at various positions can disrupt siRNA potency.

Figure 26:
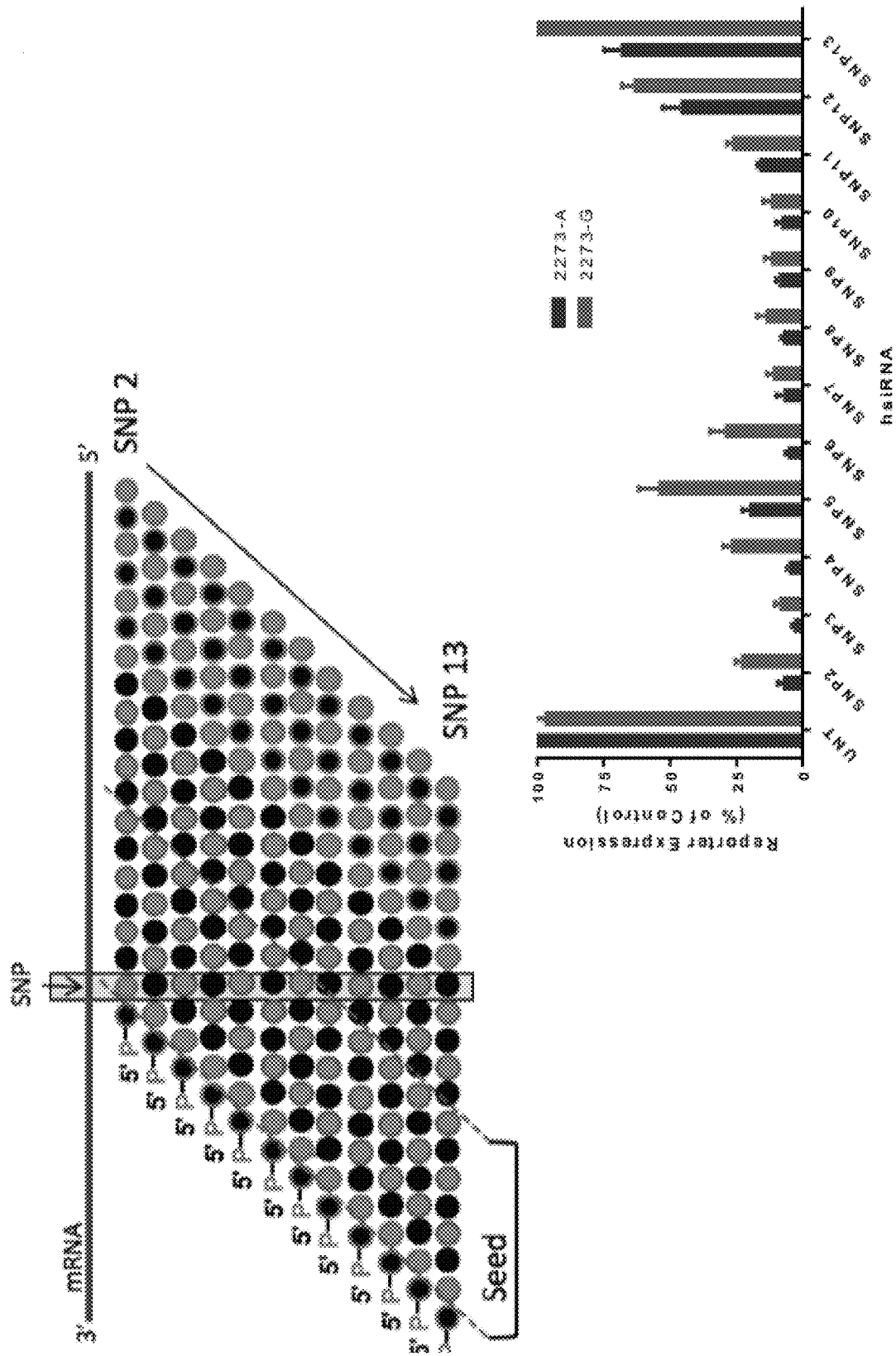
FIG. 26 is a schematic of hsiRNA antisense scaffolds aligned to HTT sequence surrounding SNP site rs362273 wherein the green box depicts the position of the SNP site.
Figure 27B:
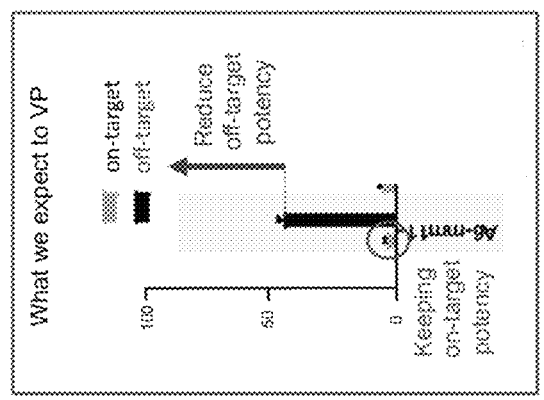
Figure 30:
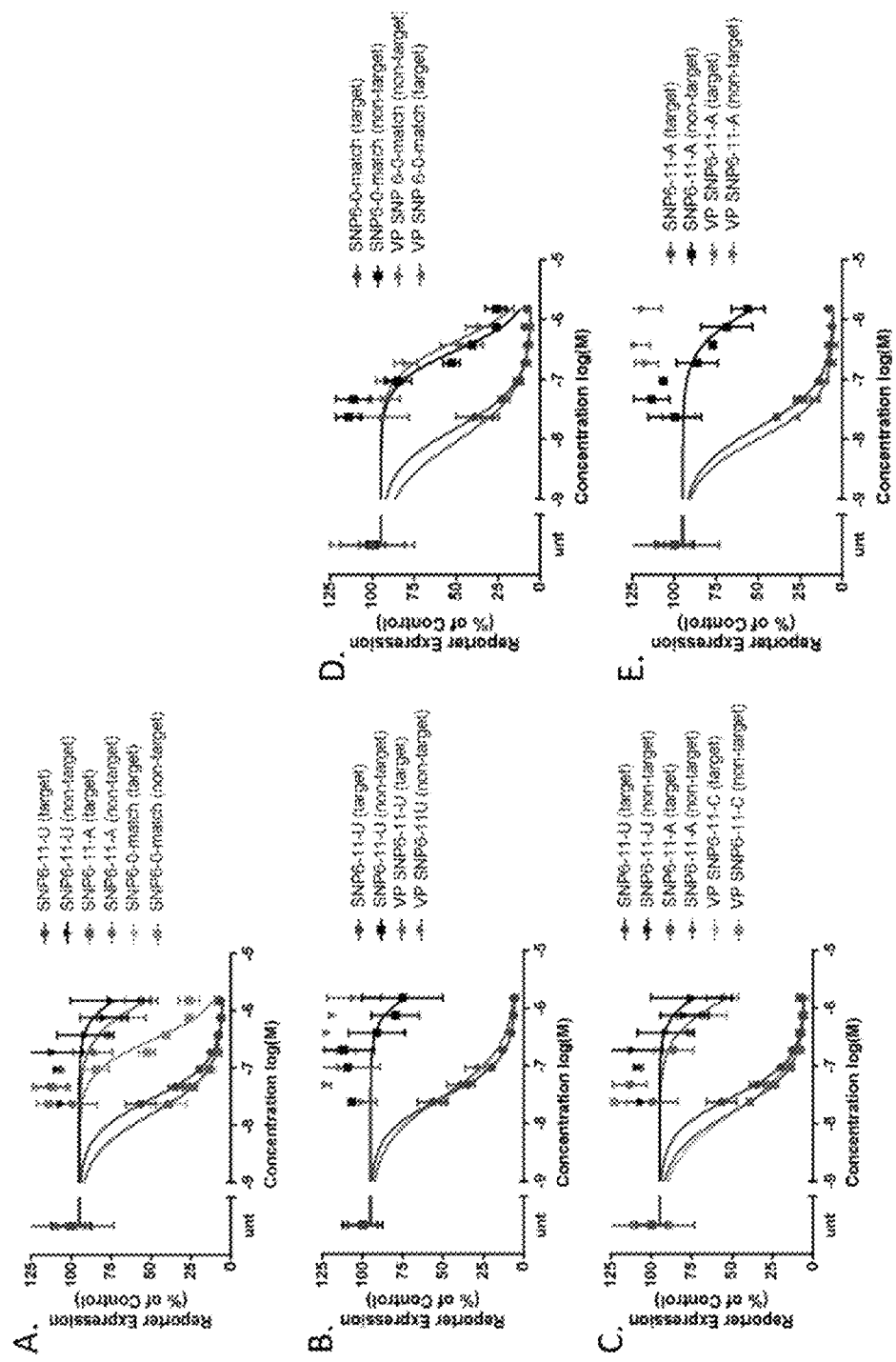
FIG. 30 demonstrates the effect a VP-modified linkage has on target/non-target discrimination of SNP-selective siRNAs.

FIGS. 26, 27A, and 27B also illustrate the ability of VP-modified siRNA to silence the mutant allele. As can be seen by FIGS. 27A and 27B, adding a mismatch in the siRNA sequence could improve allelic discrimination without affecting mutant allele silencing. FIG. 30 demonstrates that the introduction of a VP-modified linkage next to the SNP site significantly enhanced target/non-target discrimination of SNP-selective siRNAs. Compounds containing primary (position 6) and secondary (position 11) SNPs were synthesized with or without a VP-modification between positions 5 and 6. As can be seen in FIG. 30, the presence of a VP-modification had no impact on "on target" activity, but fully eliminated any detectable silencing for non-target mRNAs. The method for generating the data in FIGS. 25, 26, 27A, and 27B is described below.

hsiRNA Passive Delivery.

Cells were plated in Dulbecco's Modified Eagle's Medium containing 6% FBS at 8,000 cells per well in 96-well cell culture plates. hsiRNAs were diluted to twice the final concentration in OptiMEM (Carlsbad, CA; 31985-088), and 50 μL diluted hsiRNAs were added to 50 μL of cells, resulting in 3% FBS final. Cells were incubated for 72 hours at 37° C. and 5% $CO_2$. The maximal dose in the in vitro dose response assays was 1.5 μM compound.

Method for Quantitative Analysis of Target mRNA.

mRNA was quantified from cells using the QuantiGene 2.0 assay kit (Affymetrix, QS0011). Cells were lysed in 250 μL diluted lysis mixture composed of one part lysis mixture (Affymetrix, 13228), two parts $H_2O$ and 0.167 μg/μL proteinase K (Affymetrix, QS0103) for 30 min at 55° C. Cell lysates were mixed thoroughly, and 40 μL of each lysate was added per well of a capture plate with 20 μL diluted lysis mixture without proteinase K. Probe sets for human HTT and HPRT (Affymetrix; #SA-50339, SA-10030) were diluted and used according to the manufacturer's recommended protocol. Datasets were normalized to HPRT.

Method for Creating Bar Graph.

Data were analyzed using GraphPad Prism 7 software (GraphPad Software, Inc., San Diego, CA). Concentration-dependent $IC_{50}$ curves were fitted using a log(inhibitor) versus response—variable slope (four parameters). For each cell treatment plate, the level of knockdown at each dose was normalized to the mean of the control group (untreated group). The lower limit of the curve was set to less than 5, and the upper limit of the curve was set to greater than 95. To create the bar graph, the percent difference was calculated by subtracting the $IC_{50}$ value for each compound from the $IC_{50}$ value for each corresponding control compound, dividing by the $IC_{50}$ value for the control compound, and multiplying by 100. If the percent difference was less than −500%, the percent difference was artificially set to −500%. The lower limit of the graph was cut at −300%.

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Figure 39:
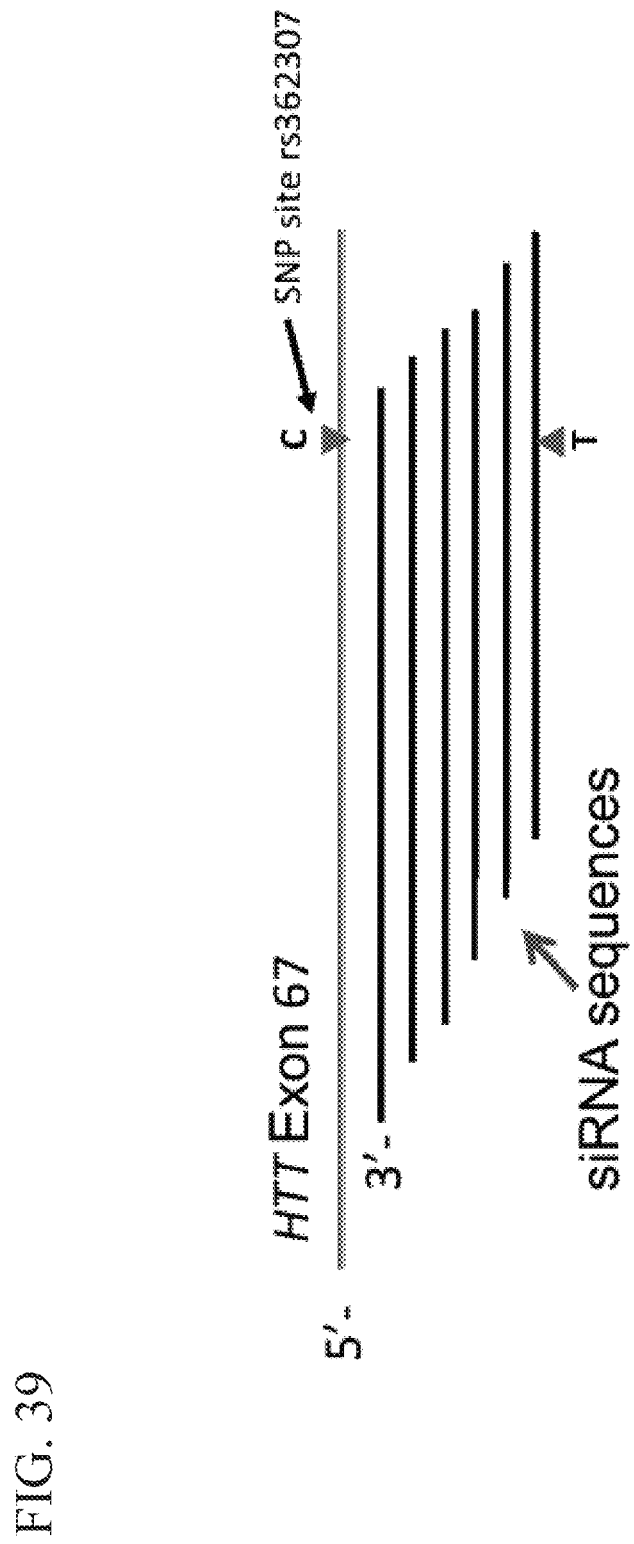
FIG. 39 is a schematic of hsiRNA antisense scaffolds aligned to HTT sequence surrounding alternative SNP site rs362273.
Figure 40:
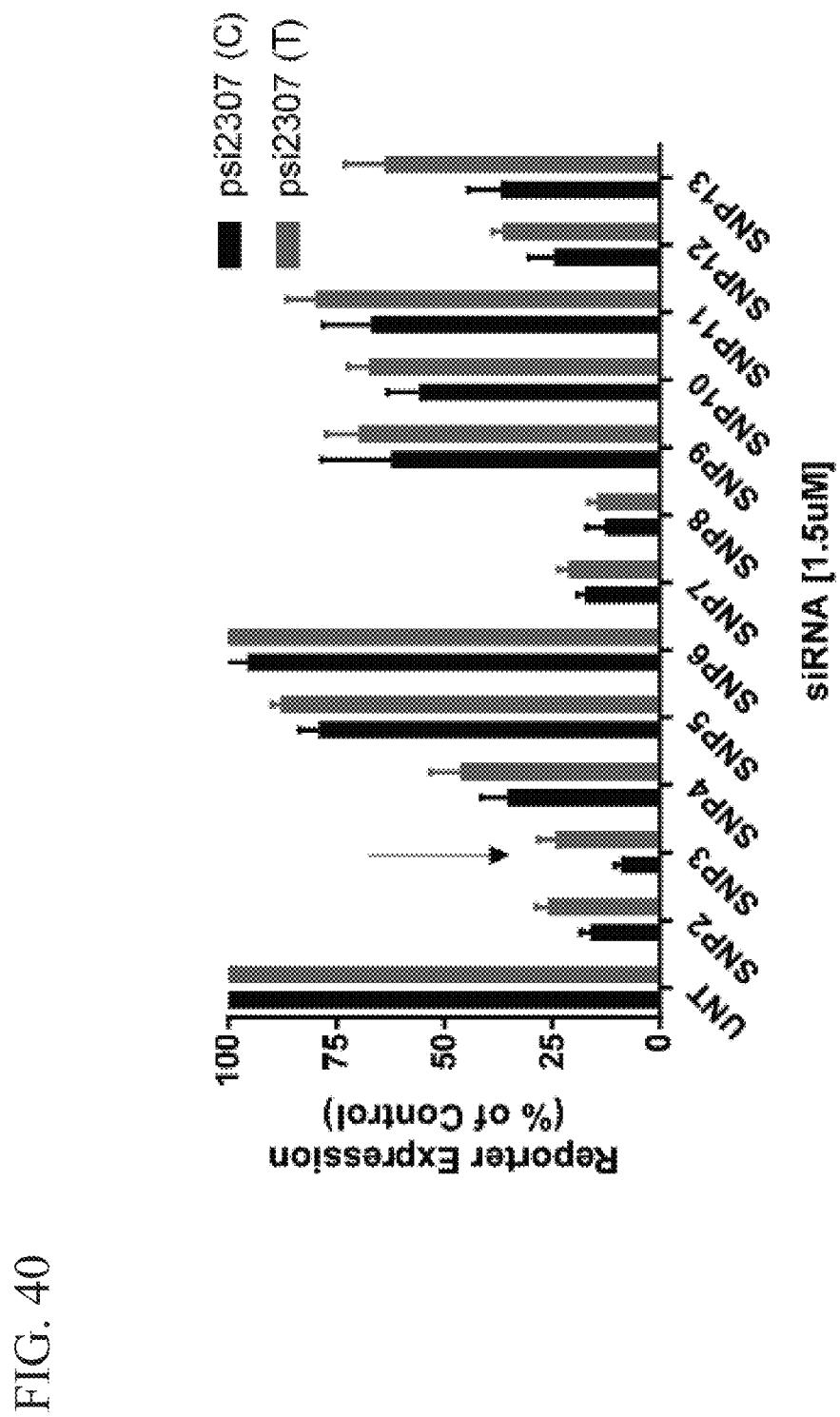
FIG. 40 depicts bar graphs showing luciferase activity following a psiCHECK reporter plasmid assay in HeLa cells transfected with the hsiRNAs of FIG. 39. The number following "SNP" represents the position of the SNP in the siRNA.
Figure 41:
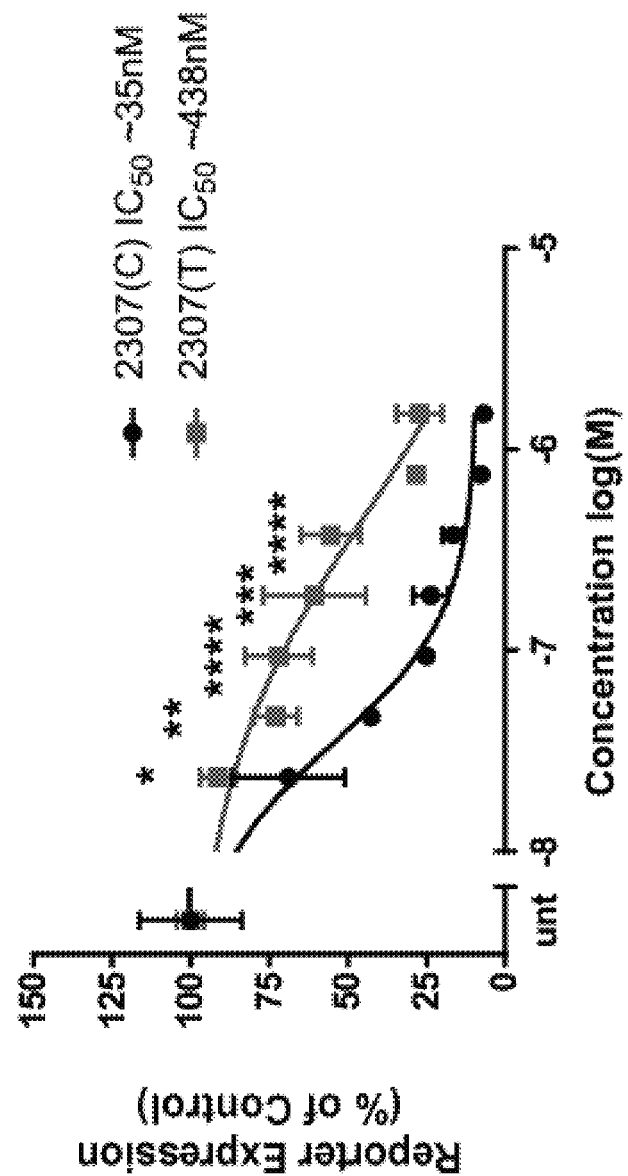
FIG. 41 depicts dose response curves comparing silencing effects for oligonucleotides of FIG. 39 targeting C or T at the SNP3 site.

Example 10: Primary Screen Yields Multiple Efficacious siRNA Sequences for SNP rs362307 Heterozygosity siRNAs designed to be complimentary to the HTT mRNA containing an alternative mutant SNP (rs362307) (FIG. 39) were all screened with reporter plasmids containing the target region for the SNP of interest (FIG. 40). HeLa cells transfected with one of two reporter plasmids were reverse transfected with 1.5 uM hsiRNAs by passive uptake, and treated for 72 hours. The number following SNP represents the position of the SNP in the siRNA. It was expected that this SNP would be more difficult to target based on the high G/C content of the region around it. It appears that placing the SNP in position 3 provided the most SNP discrimination, without losing efficacy against the mutant allele, showing that the best SNP position is sequence-specific (FIG. 41). This primary screening process may thus be carried out for selecting the best SNP position for any SNP.

Figure 42:
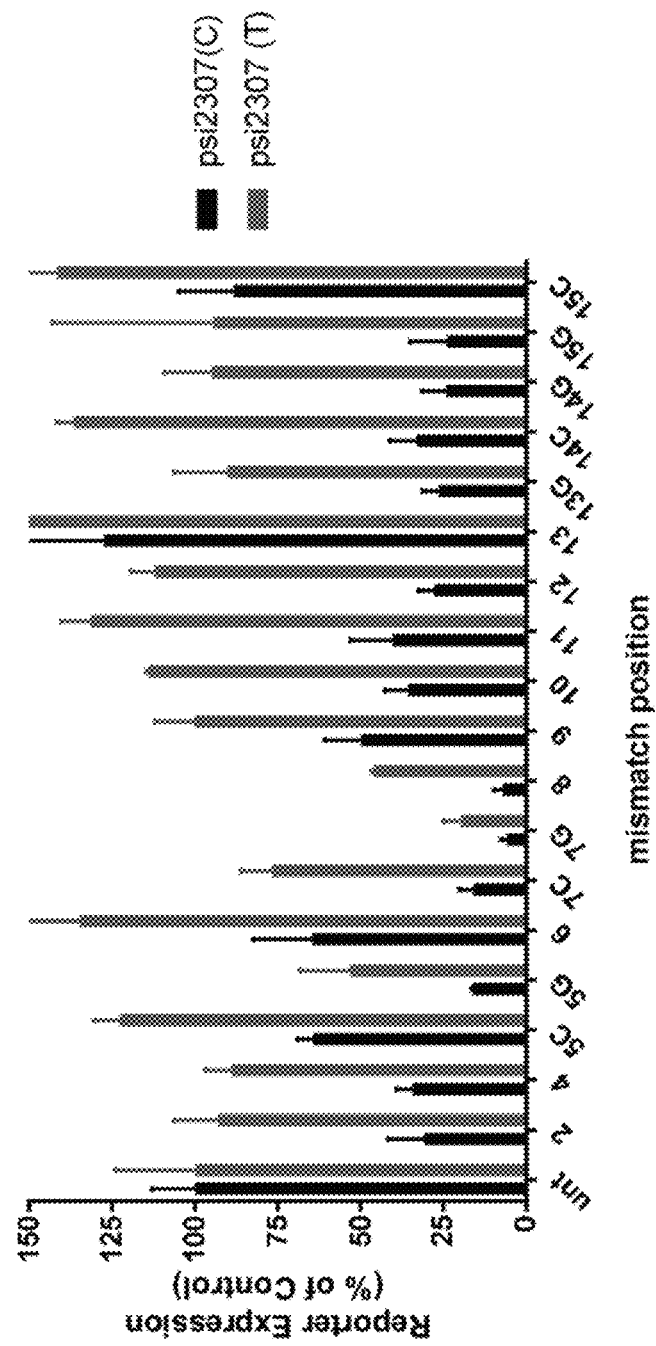
FIG. 42 depicts bar graphs showing luciferase activity following a psiCHECK reporter plasmid assay in HeLa cells transfected with hsiRNAs of FIG. 39 which were modified to feature a second mismatch at varying positions.

Example 11: When Applied to SNP rs362307, a Secondary Mismatch Continues to Improve Allelic Discrimination As reported in FIG. 42, primary screen of new sequences with mismatches introduced into all possible positions yields multiple efficacious hsiRNAs with increased SNP discrimination at position rs362307 as well. Introducing a mismatch at position 7 and 8 appeared to increase selectivity while preserving target silencing efficacy. Other secondary mismatches provided excellent discrimination, but less activity overall.

Example 12: Measuring SNP Discrimination in Sequences Including an SNP

To measure SNP discrimination by each of the sequences disclosed in Tables 5-7 (i.e., each hsiRNA having a particular SNP position nucleotide and mismatch (MM) position nucleotide combination), psiCHECK reporter plasmids containing either a wild-type region of htt or the same region of htt with the SNP of the sequence are prepared and tested using a dual-luciferase. HeLa cells transfected with one of two reporter plasmids are reverse transfected with hsiRNAs by passive uptake, and treated for 72 hours. Luciferase activities are measured in the assays with or without the additional mismatch, and are then plotted in dose response curves and compared to reveal sequences yielding the best results in terms of discrimination and efficacy of silencing.

Example 13: Synthesis of a Phosphinate-Modified Intersubunit Linkage

Figure 44A:
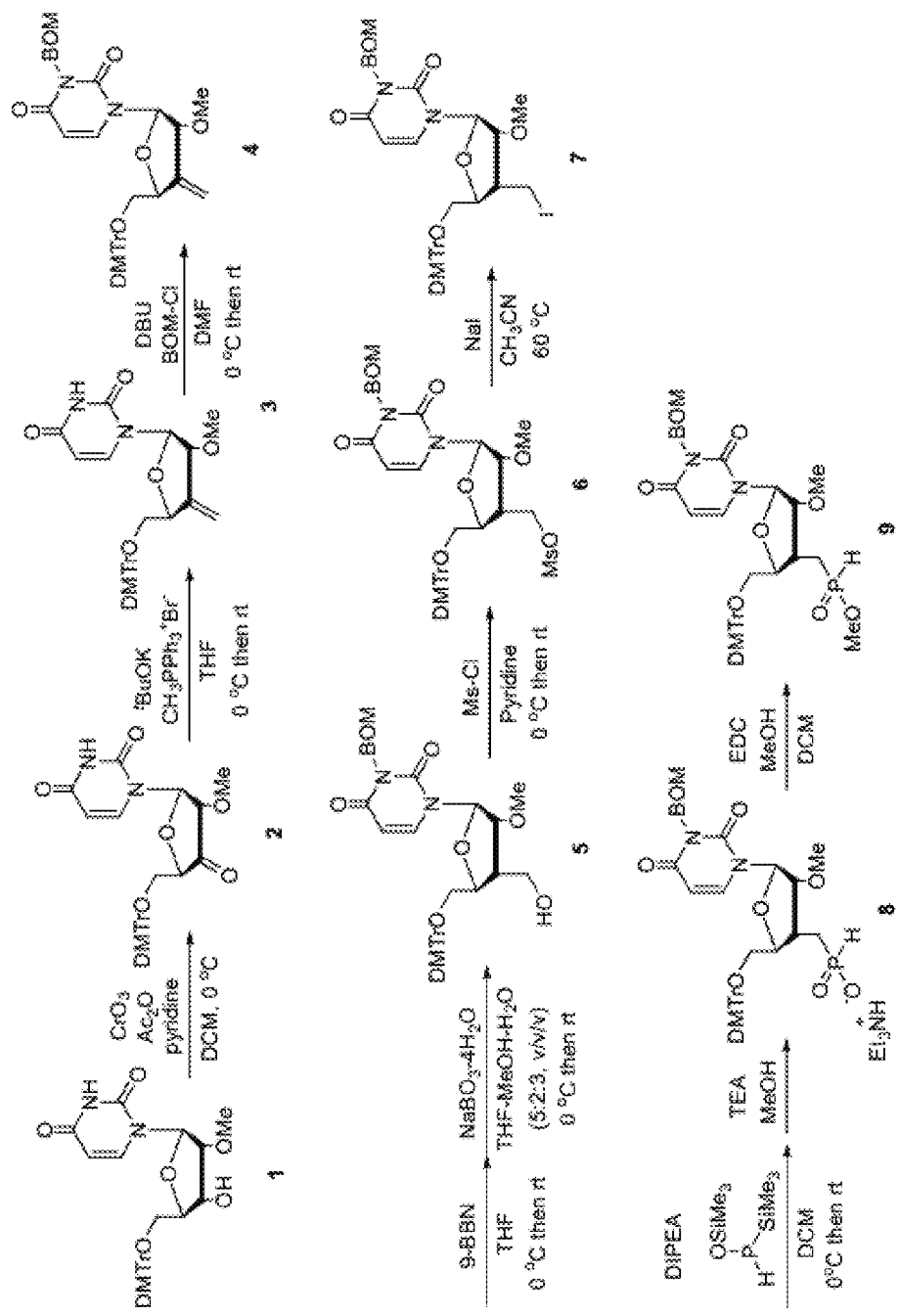
FIG. 44A shows a representative example for preparing a monomer for the modified phosphinate-containing oligonucleotides provided herein.
Figure 44B:
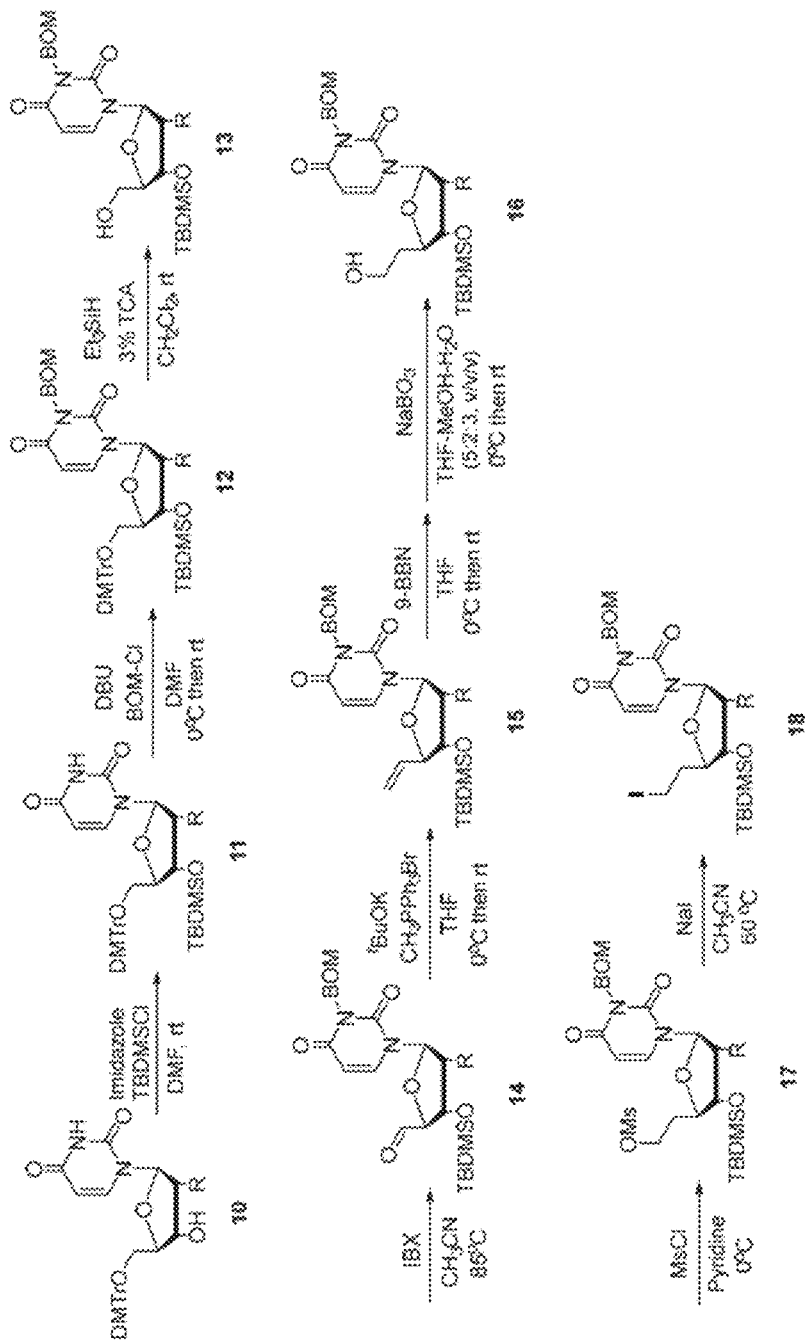
FIG. 44B shows a representative example for preparing another monomer for the modified phosphinate-containing oligonucleotides provided herein.
Figure 44C:
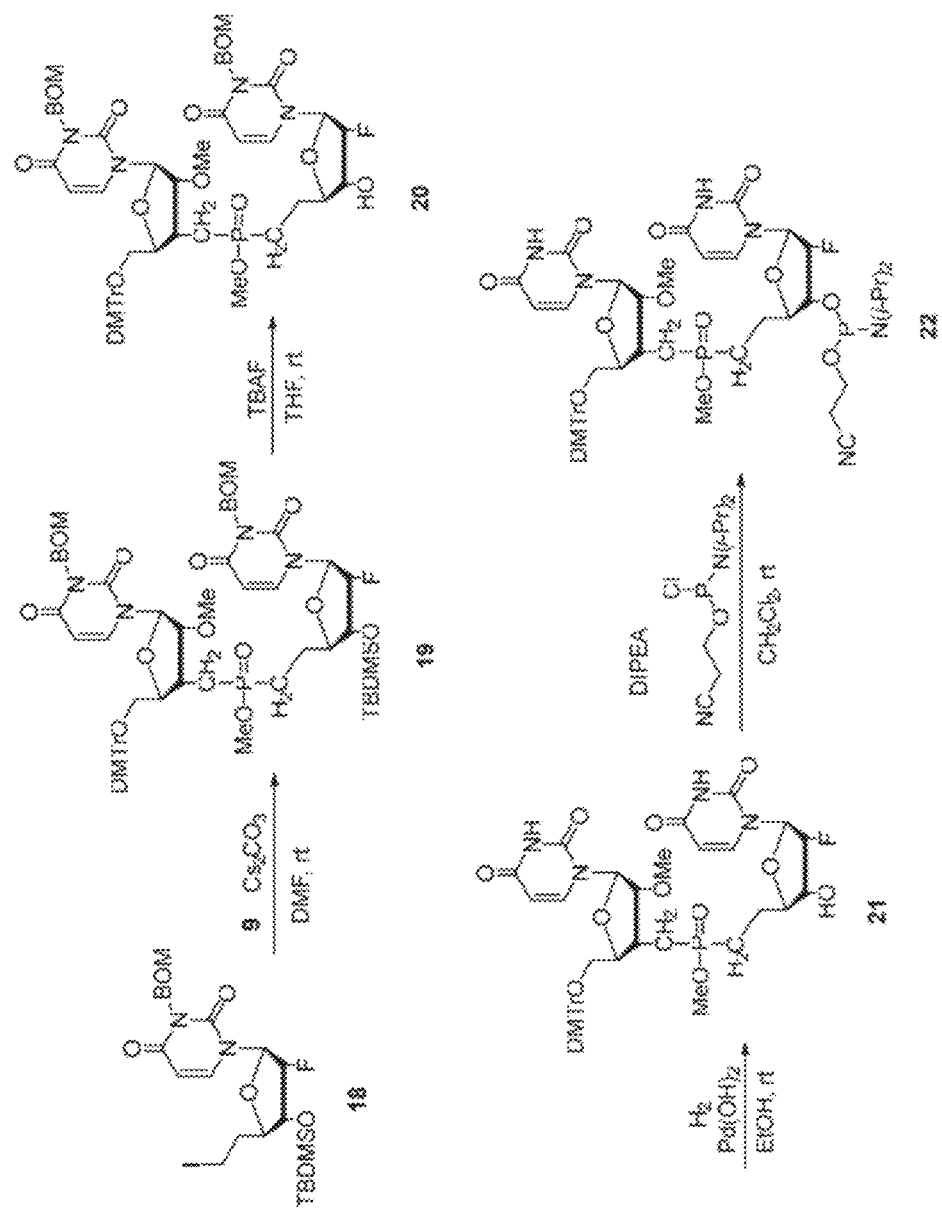
FIG. 44C shows a representative example for preparing a modified phosphinate-containing oligonucleotides provided herein.

A method for preparing a phosphinate-modified intersubunit linkage is summarized in FIGS. 44A-44C. This method involves Jones oxidation from a free alcohol to the corresponding ketone followed by a Wittig olefination to achieve the exomethylene moiety shown in intermediate compound 3. Protecting of the amide with BOM followed by hydroboration-oxidation results in the free alcohol intermediate 5. Mesylation followed by a modified Finkelstein reaction produces the iodinated intermediate 7, which then undergoes further functionalization to achieve the methyl phosphinate monomer 9.

To achieve monomer 18, various protection and deprotection steps are employed to achieve intermediate 13. IBX oxidation produces the corresponding ketone followed by Wittig olefination to access the methylene. Once again, hydroboration-oxidation followed by mesylation and Finkelstein reaction results in monomer 18.

Combining monomers 9 and 18 under basic conditions produces phosphinate-linked dimer 19. Acid-mediated and Pearlman's catalyzed deprotection followed by further phosphanamine functionalization results in dimer 22.

Example 14: Altering 2'-OMe/2'-F Content to Modify Efficacy and Discrimination By altering the 2'-O-methyl/fluoro backbone modification pattern around the SNP and mismatch site, efficacy and discrimination of the siRNA was modified (FIG. 48A-48D). Heavy 2'-fluorination adjacent to the SNP position improved target binding, but decreased target discrimination. Subsequently adding heavy 2'-O-methylation around the mismatch rescued discrimination lost due to fluorination. Although the original chemical modification pattern described supra was beneficial for in vivo study, the technique described in this example can be used to fine-tune SNP-targeting compounds described herein, and to identify additional new SNP-targeting compounds.

The invention claimed is:

1. An siRNA molecule comprising:
a sense strand having complementarity to a target gene; and an antisense strand having complementarity to the sense strand,
wherein the antisense strand comprises a nucleic acid comprising:
(a) a 5' end and a 3' end;
(b) a seed region that is complementary to a region of a gene comprising an allelic polymorphism;
(c) a single nucleotide polymorphism (SNP) position nucleotide at a position within the seed region, wherein the SNP position nucleotide is complementary to the allelic polymorphism;
(d) a mismatch (MM) position nucleotide that is a mismatch with a nucleotide in the gene; and
(e) at least one sugar-modified nucleotide (X) on either side of the SNP position nucleotide, wherein each X is located within four, three, or two nucleotides from the SNP position nucleotide; or
(f) at least one sugar-modified nucleotide (Y) on either side of the MM position nucleotide, wherein each Y is located within four, three or two nucleotides from the MM position nucleotide.

2. The siRNA molecule of claim 1, wherein:
the sense strand has a length of from 13 nucleotides or nucleotide analogs to 17 nucleotides or nucleotide analogs.

3. The siRNA molecule of claim 1, wherein the antisense strand has a length of from 18 nucleotides or nucleotide analogs to 22 nucleotides or nucleotide analogs.

4. The siRNA molecule of claim 1, wherein the sense strand has a length of 15 nucleotides or nucleotide analogs and the antisense strand has a length of 20 nucleotides or nucleotide analogs.

5. The siRNA molecule of claim 1, wherein the sense strand has a length of 16 nucleotides or nucleotide analogs and the antisense strand has a length of 20 nucleotides or nucleotide analogs.

6. A branched oligonucleotide comprising two or more siRNA molecules covalently bound to one another, wherein each siRNA molecule is, independently, an siRNA molecule of claim 1.

7. The branched oligonucleotide of claim 6, wherein the branched oligonucleotide comprises two siRNA molecules covalently bound to one another.

8. The branched oligonucleotide of claim 6, wherein the siRNA molecules are covalently bound to one another by way of a linker.

9. A double-stranded nucleic acid comprising:
(a) a first strand of nucleotides comprising:
(i) a 5' end and a 3' end;
(ii) a seed region that is complementary to a region of a gene comprising an allelic polymorphism;
(iii) a single nucleotide polymorphism (SNP) position nucleotide at a position within the seed region, wherein the SNP position nucleotide is complementary to the allelic polymorphism;
(iv) a mismatch (MM) position nucleotide that is not complementary to a nucleotide in the gene; and
(v) at least one sugar-modified nucleotide located on either side of the SNP position nucleotide, on either side of the MM position nucleotide, or a combination thereof; wherein each sugar-modified nucleotide is located within four, three, or two nucleotides from the SNP position nucleotide or from the MM position nucleotide, respectively;
(b) a second strand of nucleotides that is complementary to the first strand of nucleotides.

10. The double-stranded nucleic acid of claim 9, wherein:
the sugar-modified nucleotide comprises a modification selected from the group consisting of 2'-O-methyl(2'-OMe), 2'-fluoro (2'-F), 2'-ribo, 2'-deoxyribo, 2'-F-4'-thioarabino(2'-F-ANA), 2'-O-(2-methoxyethyl) (2'-MOE), 4'-S-RNA, locked nucleic acid (LNA), 4'-S-F-ANA, 2'-O-allyl, 2'-O-ethylamine, 2'-O-cyanoethyl-RNA(CNet-RNA), tricyclo-DNA, cyclohexenyl nucleic acid (CeNA), arabino nucleic acid (ANA), hexitol nucleic acid (HNA), and a combination thereof.

11. The double-stranded nucleic acid of claim 9, wherein:
the sugar-modified nucleotide is positioned immediately 5' to the SNP position nucleotide, immediately 3' to the SNP position nucleotide, or a mixture thereof; or
the sugar-modified nucleotide is positioned immediately 5' to the MM position nucleotide, immediately 3' to the MM position nucleotide, or a mixture thereof.

12. The double-stranded nucleic acid of claim 9, wherein the SNP position nucleotide is present from position 2 to position 6 from the 5' end of the first strand of nucleotides.

13. The double-stranded nucleic acid of claim 9, wherein:
the MM position nucleotide is located 2-11 nucleotides from the SNP position nucleotide of the first strand of nucleotides; or
the MM position nucleotide is located 2-6 nucleotides from the SNP position nucleotide of the first strand of nucleotides.

14. The double-stranded nucleic acid of claim 9, wherein the sugar-modified nucleotides comprise identical nucleotide sugar modifications, different nucleotide sur modifications, or a mixture thereof.

15. The double-stranded nucleic acid of claim 9, wherein:
the first strand has a length of from 13-17 nucleotides; or
the second strand has a length of from 18-22 nucleotides.

16. The double-stranded nucleic acid of claim 9, wherein:
the first strand has a length of 15 nucleotides and the second strand has a length of 20 nucleotides; or
the first strand has a length of 16 nucleotides and the second strand has a length of 20 nucleotides.

17. The double-stranded nucleic acid of claim 9, wherein the first strand has 3-7 more nucleotides than the second strand.

18. A branched oligonucleotide comprising two or more siRNA molecules covalently bound to one another, wherein each siRNA molecule comprises a double-stranded nucleic acid comprising:
(a) a first strand of nucleotides comprising:
  (i) a 5' end, a 3' end;
  (ii) a seed region that is complementary to a region of a gene comprising an allelic polymorphism;
  (iii) a single nucleotide polymorphism (SNP) position nucleotide at a position within the seed region, wherein the SNP position nucleotide is complementary to the allelic polymorphism;
  (iv) a mismatch (MM) position nucleotide that not complementary to a nucleotide in the gene; and
  (v) at least one sur-modified nucleotide located on either side of the SNP position nucleotide, on either side of the MM position nucleotide, or a combination thereof; wherein each sugar-modified nucleotide is located within four, three, or two nucleotides from the SNP position nucleotide or from the MM position nucleotide, respectively;
(b) a second strand of nucleotides that is complementary to the first strand of nucleotides.

19. The branched oligonucleotide of claim 18, wherein the branched oligonucleotide comprises two siRNA molecules covalently bound to one another.

20. The branched oligonucleotide of claim 18, wherein the siRNA molecules are covalently bound to one another by way of a linker.

* * * * *

SEQUENCE LISTING

<160> NUMBER OF SEQ ID NOS: 386

<210> SEQ ID NO 1
<211> LENGTH: 41
<212> TYPE: DNA
<213> ORGANISM: Homo sapiens

<400> SEQUENCE: 1
gttaagagat ggggacagta mttcaacgct agaagaacac a    41

<210> SEQ ID NO 2
<211> LENGTH: 41
<212> TYPE: DNA
<213> ORGANISM: Homo sapiens

<400> SEQUENCE: 2
agccacgaga agctgctgct rcagatcaac cccgagcggg a                                41

<210> SEQ ID NO 3
<211> LENGTH: 41
<212> TYPE: DNA
<213> ORGANISM: Homo sapiens

<400> SEQUENCE: 3
ccggagcctt tggaagtctg ygccttgtg ccctgcctcc a                                 41

<210> SEQ ID NO 4
<211> LENGTH: 41
<212> TYPE: DNA
<213> ORGANISM: Homo sapiens

<400> SEQUENCE: 4
cagcccgagc tgcctgcaga rccggcggcc tactggagca a                                41

<210> SEQ ID NO 5
<211> LENGTH: 41
<212> TYPE: DNA
<213> ORGANISM: Homo sapiens

<400> SEQUENCE: 5
cccacgcctg ctccctcatc yactgtgtgc acttcatcct g                                41

<210> SEQ ID NO 6
<211> LENGTH: 41
<212> TYPE: DNA
<213> ORGANISM: Homo sapiens

<400> SEQUENCE: 6
gggttggagc cctgcacggc rtcctctatg tgctggagtg c                                41

<210> SEQ ID NO 7
<211> LENGTH: 41
<212> TYPE: DNA
<213> ORGANISM: Homo sapiens

<400> SEQUENCE: 7
ctgctggttg ttgccaggtt rcagctgctc ttgcatctgg g                                41

<210> SEQ ID NO 8
<211> LENGTH: 41
<212> TYPE: DNA
<213> ORGANISM: Homo sapiens

<400> SEQUENCE: 8
tcctccctcc tgcaggctgg stgttggccc ctstgctgtc c                                41

<210> SEQ ID NO 9
<211> LENGTH: 41
<212> TYPE: DNA
<213> ORGANISM: Homo sapiens

<400> SEQUENCE: 9

```
gatttgggag ctctgcttgc ygactggctg tgagacgagg c                    41
```

<210> SEQ ID NO 10
<211> LENGTH: 41
<212> TYPE: DNA
<213> ORGANISM: Homo sapiens

<400> SEQUENCE: 10

```
gaaaagtttg gagggtttct ycgctcagcc ttggatgttc t                    41
```

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11

```
uucuguagca ucagcuucuc                                            20
```

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

```
uuagcaucag cuucucgugg                                            20
```

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
uuguaguagc agcuucucgu                                            20
```

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14

```
uuguagcugc agcuucucgu                                            20
```

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

```
uuguagcagc agcuacucgu                                            20
```

<210> SEQ ID NO 16

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uucuauagca gcagcuucuc                                                       20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uucuguauca gcagcuucuc                                                       20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uucuguagca ucagcuucuc                                                       20

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uucuguagca gcaucuucuc                                                       20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uucuguagca gcagcaucuc                                                       20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ucgcggacuu ccaaaggcuc                                                       20

<210> SEQ ID NO 22
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ucgcaggcuu ccaaaggcuc                                              20

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucgcagauuu ccaaaggcuc                                              20

<210> SEQ ID NO 24
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
agaagcugcu gcuaa                                                   15

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aagcugcugc uacaa                                                   15

<210> SEQ ID NO 26
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aagcugcugc uacaa                                                   15

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aagcugcugc uacaa                                                   15

<210> SEQ ID NO 28
<211> LENGTH: 15
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 28
gcugcugcua cagaa                                                          15

<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gcugcugcua cagaa                                                          15

<210> SEQ ID NO 30
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gcugcugcua cagaa                                                          15

<210> SEQ ID NO 31
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gcugcugcua cagaa                                                          15

<210> SEQ ID NO 32
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gcugcugcua cagaa                                                          15

<210> SEQ ID NO 33
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uuuggaaguc cgcga                                                          15

<210> SEQ ID NO 34
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 34
uuuggaagcc ugcga                                                      15

<210> SEQ ID NO 35
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuuggaaauc ugcga                                                      15

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuagcaucag cuucucgugg                                                 20

<210> SEQ ID NO 37
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuguaguagc agcuucucgu                                                 20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuguagcugc agcuucucgu                                                 20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uuguagcagc agcuacucgu                                                 20

<210> SEQ ID NO 40
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 40
uucuauagca gcagcuucuc                                                    20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uucuguauca gcagcuucuc                                                    20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uucuguagca ucagcuucuc                                                    20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uucuguagca gcaucuucuc                                                    20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uucuguagca gcagcaucuc                                                    20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ucgcggacuu ccaaaggcuc                                                    20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 46
ucgcaggcuu ccaaaggcuc                                          20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ucgcagauuu ccaaaggcuc                                          20

<210> SEQ ID NO 48
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
agaagcugcu gcuaa                                               15

<210> SEQ ID NO 49
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aagcugcugc uacaa                                               15

<210> SEQ ID NO 50
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aagcugcugc uacaa                                               15

<210> SEQ ID NO 51
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aagcugcugc uacaa                                               15

<210> SEQ ID NO 52
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 52
gcugcugcua cagaa                                                15

<210> SEQ ID NO 53
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gcugcugcua cagaa                                                15

<210> SEQ ID NO 54
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gcugcugcua cagaa                                                15

<210> SEQ ID NO 55
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gcugcugcua cagaa                                                15

<210> SEQ ID NO 56
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gcugcugcua cagaa                                                15

<210> SEQ ID NO 57
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uuuggaaguc cgcga                                                15

<210> SEQ ID NO 58
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 58
uuuggaagcc ugcga                                                      15

<210> SEQ ID NO 59
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuuggaaauc ugcga                                                      15

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ucagcaucag cuucucgugg                                                 20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uugcaguagc agcuucucgu                                                 20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uugcagcugc agcuucucgu                                                 20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uugcagcagc agcuacucgu                                                 20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
```
uucuacagca gcagcuucuc            20

<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uucugcauca gcagcuucuc            20

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uucugcagca ucagcuucuc            20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uucugcagca gcaucuucuc            20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ucacggacuu ccaaaggcuc            20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ucacaggcuu ccaaaggcuc            20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70

```
ucacagauuu ccaaaggcuc                                                   20

<210> SEQ ID NO 71
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
agaagcugcu gcuga                                                        15

<210> SEQ ID NO 72
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aagcugcugc ugcaa                                                        15

<210> SEQ ID NO 73
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aagcugcugc ugcaa                                                        15

<210> SEQ ID NO 74
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aagcugcugc ugcaa                                                        15

<210> SEQ ID NO 75
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gcugcugcug cagaa                                                        15

<210> SEQ ID NO 76
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gcugcugcug cagaa                                                        15
```

<210> SEQ ID NO 77
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gcugcugcug cagaa                                              15

<210> SEQ ID NO 78
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcugcugcug cagaa                                              15

<210> SEQ ID NO 79
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuuggaaguc cguga                                              15

<210> SEQ ID NO 80
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uuuggaagcc uguga                                              15

<210> SEQ ID NO 81
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uuuggaaauc uguga                                              15

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tcgaagccac gagaagctgc tgctacagat caaccccgag cggga             45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggcctcccgc tcggggttga tctgtagcag cagcttctcg tggct           45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcgaagccac gagaagctgc tgctgcagat caaccccgag cggga           45

<210> SEQ ID NO 85
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ggcctcccgc tcggggttga tctgcagcag cagcttctcg tggct           45

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uuggcagcag cuucucgugg                                        20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uuugcagcag cuucucgugg                                        20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uucgcagcag cuucucgugg                                        20

```
<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uuaucagcag cuucucgugg                                                    20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uuaguagcag cuucucgugg                                                    20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uuagcugcag cuucucgugg                                                    20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uuagcaucag cuucucgugg                                                    20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uuagcaguag cuucucgugg                                                    20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uuagcagcug cuucucgugg                                                    20

<210> SEQ ID NO 95
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uuagcagcau cuucucgugg                                                   20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uuagcagcag uuucucgugg                                                   20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uuagcagcag caucucgugg                                                   20

<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuagcagcag cuacucgugg                                                   20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uuagcagcag cuuucgugg                                                    20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uuagcagcag cuucacgugg                                                   20

<210> SEQ ID NO 101
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuagcagcag cuucuugugg                                                    20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uaguagcagc agcuucucgu                                                    20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuuuagcagc agcuucucgu                                                    20

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uuauagcagc agcuucucgu                                                    20

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uugucgcagc agcuucucgu                                                    20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uuguggcagc agcuucucgu                                                    20

<210> SEQ ID NO 107
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 107
uuguaucagc agcuucucgu                                                     20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uuguaguagc agcuucucgu                                                     20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uuguagcugc agcuucucgu                                                     20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uuguagcauc agcuucucgu                                                     20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uuguagcagu agcuucucgu                                                     20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uuguagcagc ugcuucucgu                                                     20

<210> SEQ ID NO 113
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 113
uuguagcagc aucuucucgu                                               20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
uuguagcagc aguuucucgu                                               20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuguagcagc agcaucucgu                                               20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uuguagcagc agcuacucgu                                               20

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uuguagcagc agcuuuucgu                                               20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uacuguagca gcagcuucuc                                               20

<210> SEQ ID NO 119
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 119
uuuuguagca gcagcuucuc                                                   20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uucaguagca gcagcuucuc                                                   20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uucuuuagca gcagcuucuc                                                   20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uucuauagca gcagcuucuc                                                   20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uucugucgca gcagcuucuc                                                   20

<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uucuguggca gcagcuucuc                                                   20

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 125
uucuguauca gcagcuucuc                                                20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uucuguagua gcagcuucuc                                                20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uucuguagcu gcagcuucuc                                                20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uucuguagca ucagcuucuc                                                20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uucuguagca guagcuucuc                                                20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uucuguagca gcugcuucuc                                                20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uucuguagca gcaucuucuc                                                  20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
uucuguagca gcaguuucuc                                                  20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uucuguagca gcagcaucuc                                                  20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uuagcaucag cuucucgugg                                                  20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uuguaguagc agcuucucgu                                                  20

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uuguagcugc agcuucucgu                                                  20

<210> SEQ ID NO 137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 137
uuguagcagc agcuacucgu                                          20

<210> SEQ ID NO 138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uucuauagca gcagcuucuc                                          20

<210> SEQ ID NO 139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uucuguauca gcagcuucuc                                          20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uucuguagca ucagcuucuc                                          20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uucuguagca gcaucuucuc                                          20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uucuguagca gcagcaucuc                                          20

<210> SEQ ID NO 143
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
```
agaagcugcu gcuaa                                              15

<210> SEQ ID NO 144
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
aagcugcugc uacaa                                              15

<210> SEQ ID NO 145
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
aagcugcugc uacaa                                              15

<210> SEQ ID NO 146
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
aagcugcugc uacaa                                              15

<210> SEQ ID NO 147
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcugcugcua cagaa                                              15

<210> SEQ ID NO 148
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gcugcugcua cagaa                                              15

<210> SEQ ID NO 149
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149

```
gcugcugcua cagaa                                                15

<210> SEQ ID NO 150
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gcugcugcua cagaa                                                15

<210> SEQ ID NO 151
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcugcugcua cagaa                                                15

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uucuguagca ucagcuucuc                                           20

<210> SEQ ID NO 153
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcugcugcua cagaa                                                15

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
uuaaucucuu uacugauaua                                           20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuuuuaaauc cugagaagaa                                           20
```

```
<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uuuuuaaauc cugagaagaa                                                    20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uuuuuaaauc cugagaagaa                                                    20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ucucuuuacu gauauaauua                                                    20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uauguuuuca cauauuguca                                                    20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ugaauguuca cgcagugggc                                                    20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uaucagcuuu uccagggucg                                                    20
```

<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uuaaucucuu uacugauaua                                                     20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uuaaucucuu uacugauaua                                                     20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uuaacgucag uucauaaacc                                                     20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uccacuaugu uuucacauau                                                     20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
uccaaauacu gguugucggu                                                     20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uccggucaca acauuguggu                                                     20

```
<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
uauguuuuca cauauuguca                                                     20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uuugguagcu gaaaguucuu                                                     20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uuaaucucuu uacugauuua                                                     20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ucucuuuacu gauauaauua                                                     20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uuaaucucuu uacugauauu                                                     20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uuaaucucuu uacugauuuu                                                     20

<210> SEQ ID NO 174
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uacuguagca gcagcuucuc                                               20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuuuguagca gcagcuucuc                                               20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uucaguagca gcagcuucuc                                               20

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uucuuuagca gcagcuucuc                                               20

<210> SEQ ID NO 178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uucuauagca gcagcuucuc                                               20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uucugucgca gcagcuucuc                                               20

<210> SEQ ID NO 180
<211> LENGTH: 20
```

-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uucuguggca gcagcuucuc                                               20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uucuguauca gcagcuucuc                                               20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uucuguagua gcagcuucuc                                               20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uucuguagcu gcagcuucuc                                               20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uucuguagca ucagcuucuc                                               20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uucuguagca guagcuucuc                                               20

<210> SEQ ID NO 186
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 186
uucuguagca gcugcuucuc                                                    20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uucuguagca gcaucuucuc                                                    20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uucuguagca gcaguuucuc                                                    20

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
uucuguagca gcagcaucuc                                                    20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uucuguagca gcagcuucuc                                                    20

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gagaagcugc ugcugcuaca gaa                                                23

<210> SEQ ID NO 192
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 192
gagaagcugc ugcugcugca gaa                                              23

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uucuguagca gcagcuucuc                                                  20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uucuguagca ucagcuucuc                                                  20

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uucuguagca acagcuucuc                                                  20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uucuguagca ccagcuucuc                                                  20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uucuguagca gcagcuucuc                                                  20

<210> SEQ ID NO 198
<211> LENGTH: 20
<212> TYPE: RNA
<213> ORGANISM: Artificial Sequence
<220> FEATURE:
```

<223> OTHER INFORMATION: Description of Artificial Sequence: Synthetic
    oligonucleotide

<400> SEQUENCE: 198
uucuguagca ucagcuucuc                                              20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 199
uucuguagca acagcuucuc                                              20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 200
uucuguagca ccagcuucuc                                              20

<210> SEQ ID NO 201
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 201
gagaagcugc ugcugcuaca gaa                                          23

<210> SEQ ID NO 202
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 202
gagaagcugc ugcugcugca gaa                                          23

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 203
uucuguagca gcagcuucuc                                              20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 204
uucuguagca ucagcuucuc                                                  20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uucuguagca acagcuucuc                                                  20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uucuguagca ccagcuucuc                                                  20

<210> SEQ ID NO 207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuaaucucuu uacugauaua                                                  20

<210> SEQ ID NO 208
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
aauuagagaa augac                                                       15

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uuuuggauaa acugguagcc                                                  20

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 210
uuuuggauaa acugguagcc                                              20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uuuuggauaa acugguagcc                                              20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uuuuggauaa acugguagcc                                              20

<210> SEQ ID NO 213
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ccaguuuauc caaaa                                                   15

<210> SEQ ID NO 214
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccaguuuauc caaaa                                                   15

<210> SEQ ID NO 215
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ccaguuuauc caaaa                                                   15

<210> SEQ ID NO 216
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 216
ccaguuuauc caaaa                                                      15

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uuagcagcag cuucucgugg                                                 20

<210> SEQ ID NO 218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uguagcagca gcuucucgug                                                 20

<210> SEQ ID NO 219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uuguagcagc agcuucucgu                                                 20

<210> SEQ ID NO 220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ucuguagcag cagcuucucg                                                 20

<210> SEQ ID NO 221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uucuguagca gcagcuucuc                                                 20

<210> SEQ ID NO 222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
```
uaucuguagc agcagcuucu 20

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ugaucuguag cagcagcuuc 20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uugaucugua gcagcagcuu 20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
uuugaucugu agcagcagcu 20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
uguugaucug uagcagcagc 20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ugguugaucu guagcagcag 20

<210> SEQ ID NO 228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
uggguugauc uguagcagca                                              20

<210> SEQ ID NO 229
<211> LENGTH: 105
<212> TYPE: DNA
<213> ORGANISM: Homo sapiens
<220> FEATURE:
<221> NAME/KEY: misc_feature
<222> LOCATION: (1)..(105)
<223> OTHER INFORMATION: This sequence may encompass 8-35 'cag'
      repeating units

<400> SEQUENCE: 229
cagcagcagc agcagcagca gcagcagcag cagcagcagc agcagcagca gcagcagcag    60
cagcagcagc agcagcagca gcagcagcag cagcagcagc agcag                   105

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uuagcaucag cuucucgugg                                              20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uuguaguagc agcuucucgu                                              20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uuguagcugc agcuucucgu                                              20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uuguagcagc agcuacucgu                                              20

<210> SEQ ID NO 234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
uucuauagca gcagcuucuc                                               20

<210> SEQ ID NO 235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uucuguauca gcagcuucuc                                               20

<210> SEQ ID NO 236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uucuguagca ucagcuucuc                                               20

<210> SEQ ID NO 237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uucuguagca gcaucuucuc                                               20

<210> SEQ ID NO 238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uucuguagca gcagcaucuc                                               20

<210> SEQ ID NO 239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ucgcggacuu ccaaaggcuc                                               20

<210> SEQ ID NO 240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 240
ucgcaggcuu ccaaaggcuc                                              20

<210> SEQ ID NO 241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ucgcagauuu ccaaaggcuc                                              20

<210> SEQ ID NO 242
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
agaagcugcu gcuaa                                                   15

<210> SEQ ID NO 243
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
aagcugcugc uacaa                                                   15

<210> SEQ ID NO 244
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcugcugcua cagaa                                                   15

<210> SEQ ID NO 245
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uuuggaaguc cgcga                                                   15

<210> SEQ ID NO 246
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
```
uuuggaagcc ugcga                                                15

<210> SEQ ID NO 247
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uuuggaaauc ugcga                                                15

<210> SEQ ID NO 248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
ucagcaucag cuucucgugg                                           20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uugcaguagc agcuucucgu                                           20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
uugcagcugc agcuucucgu                                           20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uugcagcagc agcuacucgu                                           20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
uucuacagca gcagcuucuc                    20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uucugcauca gcagcuucuc                    20

<210> SEQ ID NO 254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uucugcagca ucagcuucuc                    20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uucugcagca gcaucuucuc                    20

<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ucacggacuu ccaaaggcuc                    20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
ucacaggcuu ccaaaggcuc                    20

<210> SEQ ID NO 258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
ucacagauuu ccaaaggcuc                    20

<210> SEQ ID NO 259
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
agaagcugcu gcuga                                                    15

<210> SEQ ID NO 260
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aagcugcugc ugcaa                                                    15

<210> SEQ ID NO 261
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gcugcugcug cagaa                                                    15

<210> SEQ ID NO 262
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
uuuggaaguc cguga                                                    15

<210> SEQ ID NO 263
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
uuuggaagcc uguga                                                    15

<210> SEQ ID NO 264
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uuuggaaauc uguga                                                    15

<210> SEQ ID NO 265
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tcgaagccac gagaagctgc tgctacagat caaccccgag cggga         45

<210> SEQ ID NO 266
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ggcctcccgc tcggggttga tctgtagcag cagcttctcg tggct         45

<210> SEQ ID NO 267
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tcgaagccac gagaagctgc tgctgcagat caaccccgag cggga         45

<210> SEQ ID NO 268
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ggcctcccgc tcggggttga tctgcagcag cagcttctcg tggct         45

<210> SEQ ID NO 269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
uuggcagcag cuucucgugg         20

<210> SEQ ID NO 270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uuugcagcag cuucucgugg         20

```
<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uucgcagcag cuucucgugg                                           20

<210> SEQ ID NO 272
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
uugucagcag cuucucgugg                                           20

<210> SEQ ID NO 273
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
uugguagcag cuucucgugg                                           20

<210> SEQ ID NO 274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
uuggcugcag cuucucgugg                                           20

<210> SEQ ID NO 275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
uugguaucag cuucucgugg                                           20

<210> SEQ ID NO 276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
uuggcaguag cuucucgugg                                           20

<210> SEQ ID NO 277
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
uuggccgcug cuucucgugg                                               20

<210> SEQ ID NO 278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
uuggccgcau cuucucgugg                                               20

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
uuggccgcag uuucucgugg                                               20

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uuggccgcag caucucgugg                                               20

<210> SEQ ID NO 281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
uuggccgcag cuacucgugg                                               20

<210> SEQ ID NO 282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uuggccgcag cuuucgugg                                                20

<210> SEQ ID NO 283
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
uuggccgcag cuucacgugg                                               20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
uuggccgcag cuucuugugg                                               20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
uaguagcagc agcuucucgu                                               20

<210> SEQ ID NO 286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
uuuuagcagc agcuucucgu                                               20

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
uuauagcagc agcuucucgu                                               20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uugucgcagc agcuucucgu                                               20

<210> SEQ ID NO 289
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 289
uuguggcagc agcuucucgu                                                   20

<210> SEQ ID NO 290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
uuguaucagc agcuucucgu                                                   20

<210> SEQ ID NO 291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
uuguaguagc agcuucucgu                                                   20

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
uuguagcugc agcuucucgu                                                   20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uuguagcauc agcuucucgu                                                   20

<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uuguagcagu agcuucucgu                                                   20

<210> SEQ ID NO 295
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 295
uuguagcagc ugcuucucgu                                                  20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
uuguagcagc aucuucucgu                                                  20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
uuguagcagc aguuucucgu                                                  20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uuguagcagc agcaucucgu                                                  20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uuguagcagc agcuacucgu                                                  20

<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
uuguagcagc agcuuucgu                                                   20

<210> SEQ ID NO 301
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 301
uacuguagca gcagcuucuc                                                     20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uuuuguagca gcagcuucuc                                                     20

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uucaguagca gcagcuucuc                                                     20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uucuuuagca gcagcuucuc                                                     20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uucuauagca gcagcuucuc                                                     20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
uucugucgca gcagcuucuc                                                     20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 307
uucuguggca gcagcuucuc        20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uucuguauca gcagcuucuc        20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uucuguagua gcagcuucuc        20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uucuguagcu gcagcuucuc        20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
uucuguagca ucagcuucuc        20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uucuguagca guagcuucuc        20

<210> SEQ ID NO 313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uucuguagca gcugcuucuc					20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uucuguagca gcaucuucuc					20

<210> SEQ ID NO 315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
uucuguagca gcaguuucuc					20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uucuguagca gcagcaucuc					20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
uuagcaucag cuucucgugg					20

<210> SEQ ID NO 318
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
agaagcugcu gcuaa					15

<210> SEQ ID NO 319
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 319
aagcugcugc uacaa                                                          15

<210> SEQ ID NO 320
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
gcugcugcua cagaa                                                          15

<210> SEQ ID NO 321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uucuguagca ucagcuucuc                                                     20

<210> SEQ ID NO 322
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
gcugcugcua cagaa                                                          15

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uuaaucucuu uacugauaua                                                     20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uuuuuaaauc cugagaagaa                                                     20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
```
uuuuuaaauc cugagaagaa                                          20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uuuuuaaauc cugagaagaa                                          20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ucucuuuacu gauauaauua                                          20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
uaucuuuuca cauauuguca                                          20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
ugaauguuca cgcagugggc                                          20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uaucagcuuu uccagggucg                                          20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331

```
uuaaucucuu uacugauaua                                        20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
uuaaucucuu uacugauaua                                        20

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uuaacgucag uucauaaacc                                        20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uccacuaugu uuucacauau                                        20

<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
uccaaauacu gguugucggu                                        20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
uccggucaca acauuguggu                                        20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uauguuuuca cauauuguca                                        20
```

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
uuugguagcu gaaaguucuu                                              20

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
uuaaucucuu uacugauuua                                              20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
ucucuuuacu gauauaauua                                              20

<210> SEQ ID NO 341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uuaaucucuu uacugauauu                                              20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uuaaucucuu uacugauuuu                                              20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uacuguagca gcagcuucuc                                              20

```
<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uuuuguagca gcagcuucuc                                                    20

<210> SEQ ID NO 345
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
uucaguagca gcagcuucuc                                                    20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uucuuuagca gcagcuucuc                                                    20

<210> SEQ ID NO 347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
uucugucgca gcagcuucuc                                                    20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uucuguggca gcagcuucuc                                                    20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
uucuguagua gcagcuucuc                                                    20
```

```
<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uucuguagcu gcagcuucuc                                                  20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uucugucgca guagcuucuc                                                  20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uucuguagca gcugcuucuc                                                  20

<210> SEQ ID NO 353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uucuguagca gcaguuucuc                                                  20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uucuguagca gcagcuucuc                                                  20

<210> SEQ ID NO 355
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
gagaagcugc ugcugcuaca gaa                                              23

<210> SEQ ID NO 356
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
gagaagcugc ugcugcugca gaa                                              23

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
uucuguagca gcagcuucuc                                                  20

<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
uucuguagca ucagcuucuc                                                  20

<210> SEQ ID NO 359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
uucuguagca acagcuucuc                                                  20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uucuguagca ccagcuucuc                                                  20

<210> SEQ ID NO 361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
uucuguagca gcagcuucuc                                                  20

<210> SEQ ID NO 362
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
uucuguagca ucagcuucuc                                                    20

<210> SEQ ID NO 363
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
uucuguagca acagcuucuc                                                    20

<210> SEQ ID NO 364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
uucuguagca ccagcuucuc                                                    20

<210> SEQ ID NO 365
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uuaaucucuu uacugauaua                                                    20

<210> SEQ ID NO 366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uuuuggauaa acugguagcc                                                    20

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uuuuggauaa acugguagcc                                                    20

<210> SEQ ID NO 368
<211> LENGTH: 20
<212> TYPE: RNA
```

<213> ORGANISM: Artificial Sequence
<220> FEATURE:
<223> OTHER INFORMATION: Description of Artificial Sequence: Synthetic
     oligonucleotide

<400> SEQUENCE: 368
uuuuggauaa acugguagcc                                              20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 369
uuuuggauaa acugguagcc                                              20

<210> SEQ ID NO 370
<211> LENGTH: 15
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 370
ccaguuuauc caaaa                                                   15

<210> SEQ ID NO 371
<211> LENGTH: 15
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 371
ccaguuuauc caaaa                                                   15

<210> SEQ ID NO 372
<211> LENGTH: 15
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 372
ccaguuuauc caaaa                                                   15

<210> SEQ ID NO 373
<211> LENGTH: 15
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 373
ccaguuuauc caaaa                                                   15

<210> SEQ ID NO 374
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 374
uuagcagcag cuucucgugg                                                      20

<210> SEQ ID NO 375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
uguagcagca gcuucucgug                                                      20

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uuguagcagc agcuucucgu                                                      20

<210> SEQ ID NO 377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ucuguagcag cagcuucucg                                                      20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
uucuguagca gcagcuucuc                                                      20

<210> SEQ ID NO 379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
uaucuguagc agcagcuucu                                                      20

<210> SEQ ID NO 380
<211> LENGTH: 20
<212> TYPE: RNA
<213> ORGANISM: Artificial Sequence
<220> FEATURE:
```

<223> OTHER INFORMATION: Description of Artificial Sequence: Synthetic
    oligonucleotide

<400> SEQUENCE: 380
ugaucuguag cagcagcuuc                                                   20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 381
uugaucugua gcagcagcuu                                                   20

<210> SEQ ID NO 382
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 382
uuugaucugu agcagcagcu                                                   20

<210> SEQ ID NO 383
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 383
uguugaucug uagcagcagc                                                   20

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 384
ugguugaucu guagcagcag                                                   20

<210> SEQ ID NO 385
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 385
uggguugauc uguagcagca                                                   20

<210> SEQ ID NO 386
<211> LENGTH: 15
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 386
caguaaagag auuaa                                                            15
```